(12) United States Patent
Green et al.

(10) Patent No.: US 11,371,081 B2
(45) Date of Patent: Jun. 28, 2022

(54) PORTABLE, LOW-COST PATHOGEN DETECTION AND STRAIN IDENTIFICATION PLATFORM

(71) Applicants: ARIZONA BOARD OF REGENTS ON BEHALF OF ARIZONA STATE UNIVERSITY, Scottsdale, AZ (US); PRESIDENT AND FELLOWS OF HARVARD COLLEGE, Cambridge, MA (US); MASSACHUSETTS INSTITUTE OF TECHNOLOGY, Cambridge, MA (US)

(72) Inventors: Alexander Green, Scottsdale, AZ (US); Dana Braff, Cambridge, MA (US); Melissa K. Takahashi, Cambridge, MA (US); Keith Pardee, Toronto (CA); James J. Collins, Cambridge, MA (US); Guillaume Lambert, Ithaca, NY (US); Thomas Ferrante, Cambridge, MA (US)

(73) Assignees: ARIZONA BOARD OF REGENTS ON BEHALF OF ARIZONA STATE UNIVERSITY, Scottsdale, AZ (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 402 days.

(21) Appl. No.: 16/303,937

(22) PCT Filed: May 25, 2017

(86) PCT No.: PCT/US2017/034545
§ 371 (c)(1),
(2) Date: Nov. 21, 2018

(87) PCT Pub. No.: WO2017/205668
PCT Pub. Date: Nov. 30, 2017

(65) Prior Publication Data
US 2020/0080137 A1   Mar. 12, 2020

Related U.S. Application Data

(60) Provisional application No. 62/403,778, filed on Oct. 4, 2016, provisional application No. 62/341,221, filed on May 25, 2016.

(51) Int. Cl.
*C12Q 1/6827* (2018.01)
*C12Q 1/6816* (2018.01)
*C12Q 1/70* (2006.01)

(52) U.S. Cl.
CPC ......... *C12Q 1/6827* (2013.01); *C12Q 1/6816* (2013.01); *C12Q 1/701* (2013.01)

(58) Field of Classification Search
None
See application file for complete search history.

(56) References Cited

U.S. PATENT DOCUMENTS

| | | |
|---|---|---|
| 10,550,440 B2 | 2/2020 | Green |
| 2012/0003630 A1 | 1/2012 | Collins |
| 2015/0275203 A1 | 10/2015 | Green |
| 2019/0185856 A1 | 6/2019 | Green |
| 2019/0218624 A1 | 7/2019 | Green |
| 2019/0256898 A1 | 8/2019 | Green |
| 2019/0276901 A1 | 9/2019 | Green |
| 2019/0285620 A1 | 9/2019 | Green |
| 2019/0382746 A1 | 12/2019 | Green |
| 2020/0071777 A1 | 3/2020 | Green |

FOREIGN PATENT DOCUMENTS

| | | | |
|---|---|---|---|
| WO | WO 2015/089465 | * | 6/2015 |
| WO | 2016/077350 | | 5/2016 |
| WO | 2017147585 A1 | | 8/2017 |
| WO | 2018026762 A1 | | 2/2018 |
| WO | 2018026765 A1 | | 2/2018 |
| WO | 2018027177 A1 | | 2/2018 |
| WO | 2018075502 A1 | | 4/2018 |
| WO | 2018093898 A1 | | 5/2018 |
| WO | 2018112350 A1 | | 6/2018 |
| WO | 2018187687 A1 | | 10/2018 |

OTHER PUBLICATIONS

Pardee (Cell 165, 1255-1266 May 19, 2016).*
Wu (Journal of Clinical Microbiology vol. 39, No. Aug. 8, 2001 pp. 2794-2798).*
Pardee (Cell 159, 940-954 Nov. 6, 2014).*
The International Search Report and Written Opinion for International Patent Application No. PCT/US2017/034545 dated Oct. 17, 2017.
Pardee et al. 'Rapid, Low-Cost Detection of Zika Virus Using Programmable Biomolecular Components' May 19, 2016, Cell, vol. 165, No. 5, pp. 1255-1266; summary; p. 1256, first column, first paragraph, second paragraph; p. 1258, second column, first paragraph; p. 1260, second column, first paragraph, third paragraph; p. 1261, second column, first paragraph; p. 1264, first column, fourth paragraph, second column, second paragraph http://dx.doi.org/10.1016/j.cell.2016.04.059.

(Continued)

*Primary Examiner* — Amanda Haney
(74) *Attorney, Agent, or Firm* — Quarles & Brady LLP

(57) ABSTRACT

Methods for detecting the presence of a pathogen infection are described. In particular, this document provides a method of detecting target nucleic acids, such as pathogen-specific RNA, in a biological sample obtained from a subject, where the method comprises using one or more toehold switch sensors and an isothermal amplification step to detect the target nucleic acid. Methods specific for detecting and identify the presence of a virus such as Zika virus are also provided.

13 Claims, 17 Drawing Sheets

Specification includes a Sequence Listing.

(56) References Cited

OTHER PUBLICATIONS

Green et al. 'Toehold Switches: De-Novo-Designed Regulators of Gene Expression' 2014, Cell vol. 159, No. 4, pp. 925-939; summary; p. 928, first column, third paragraph. http://dx.doi.org/10.1016/j.cell.2014.10.002.
Antunes, P., et al. (2015). Quantification of NS1 dengue biomarker in serum via optomagnetic nanocluster detection. Sci. Rep. 5, 16145.
Barzon, L., et al. (2016). Isolation of infectious Zika vims from saliva and prolonged viral RNA shedding in a traveller returning from the Dominican Republic to Italy, Jan. 2016. Euro Surveill. 21, 30159.
Belhaj, K., et al. "Plant genome editing made easy: targeted mutagenesis in model and crop plants using the CRISPR/Cas system." Plant methods 9.1 (2013): 39.
Bogdanove, A.J., et al. "TAL effectors: customizable proteins for DNA targeting." Science 333.6051 (2011): 1843-1846.
Bogoch, I.I., et al. (2016). Anticipating the international spread of Zika virus from Brazil. Lancet 387, 335-336.
Calvet, G., et al. (2016). Detection and sequencing of Zika virus from amniotic fluid of fetuses with microcephaly in Brazil: a case study. Lancet Infect. Dis. Published online Feb. 17, 2016. http://dx.doi.org/10.1016/S1473-3099(16) 00095-5.
Carlson, D.F., et al. "Efficient TALEN-mediated gene knockout in livestock." Proceedings of the National Academy of Sciences 109. 43 (2012): 17382-17387.
Casper, E.T., et al. (2007). A handheld NASBA analyzer for the field detection and quantification of Karenia brevis. Harmful Algae 6, 112-118.
Cordray, M.S., et al. (2012). Emerging nucleic acid- based tests for point-of-care detection of malaria. Am. J. Trop. Med. Hyg. 87, 223-230.
Crannell, Z.A., et al. (2014). Equipment-free incubation of recombinase polymerase amplification reactions using body heat. PLoS ONE 9, e112146.
Campos, RdM., (2016). Prolonged detection of Zika virus RNA in urine samples during the ongoing Zika virus epidemic in Brazil. J. Clin. Virol. 77, 69-70.
Deiman, B., et al. (2002). Characteristics and applications of nucleic acid sequence-based amplification (NASBA). Mol. Biotechnol. 20, 163-179.
Doench, J.G., et al. (2014). Rational design of highly active sgRNAs for CRISPR Cas9-mediated gene inactivation. Nat. Biotechnol. 32, 1262-1267.
Enfissi, A., et al. (2016). Zika vims genome from the Americas. Lancet Lond. Engl. 387, 227-228.
Faria, N.R., et al. (2016). Zika vims in the Americas: Early epidemiological and genetic findings. Science.
Gaj, T., et al. "ZFN, TALEN, and CRISPR/Cas-based methods for genome engineering." Trends in biotechnology 31.7 (2013): 397-405.
Galindo-Fraga, A., et al. (2015). Zika virus: A new epidemic on our doorstep. Rev. Invest. Cli'n. 67, 329-332.
GENBANK Accession No. AF326573. Feb. 12, 2004.
GENBANK Accession No. AY632535. Nov. 23, 2010.
GENBANK Accession No. KF268950. Dec. 21, 2015.
GENBANK Accession No. KJ776791. Aug. 31, 2016.
GENBANK Accession No. KM204118. Mar. 8, 2016.
GENBANK Accession No. KM204119. Mar. 8, 2016.
GENBANK Accession No. KU312312. Jan. 13, 2016.
Geurts, A.M., et al. "Knockout rats via embryo microinjection of zinc-finger nucleases." Science 325.5939 (2009): 433-433.
Gibson, D.G., et al. (2009). Enzymatic assembly of DNA molecules up to several hundred kilobases. Nat. Methods 6, 343-345.
Gootenberg, J.S., et al. "Nucleic acid detection with CRISPR-Cas13a/C2c2." Science 356.6336 (2017): 438-442.
Gourinat, A.-C., et al. (2015). Detection of Zika virus in urine. Emerg. Infect. Dis. 21, 84-86.
Guatelli, J.C., et al. (1990). Isothermal, in vitro amplification of nucleic acids by a multienzyme reaction modeled after retroviral replication. Proc. Natl. Acad. Sci. USA 87, 1874-1878.
Haddow, A.D., et al. (2012). Genetic characterization of Zika virus strains: geographic expansion of the Asian lineage. PLoS Negl. Trop. Dis. 6, e1477.
Haft, D.H., et al. "A guild of 45 CRISPR-associated (Cas) protein families and multiple CRISPR/Cas subtypes exist in prokaryotic genomes." PLoS computational biology 1.6 (2005): e60.
Humbert, O. et al. "Targeted gene therapies: tools, applications, optimization." Critical reviews in biochemistry and molecular biology 47.3 (2012): 264-281.
Jinek, M., et al. "A programmable dual-RNA-guided DNA endonuclease in adaptive bacterial immunity." science 337.6096 (2012): 816-821.
Kim, E., et al. "Precision genome engineering with programmable DNA-nicking enzymes." Genome research 22.7 (2012): 1327-1333.
Kim, H. et al. "A guide to genome engineering with programmable nucleases." Nature Reviews Genetics 15.5 (2014): 321.
Kotula, J.W., et al. (2014). Programmable bacteria detect and record an environmental signal in the mammalian gut. Proc. Natl. Acad. Sci. USA 111, 4838-4843.
Lambeth, C.R., et al. (2005). Flow cytometry-based assay for titrating dengue virus. J. Clin. Microbiol. 43, 3267-3272.
Lanciotti, R.S., et al. (2008). Genetic and serologic properties of Zika virus associated with an epidemic, Yap State, Micronesia, 2007. Emerg. Infect. Dis. 14, 1232-1239.
Liu, W., et al. "Polymerase Spiral Reaction (PSR): A novel isothermal nucleic acid amplification method." Scientific reports 5 (2015): 12723.
Lu, T.K., et al. (2013). Advancing bacteriophage-based microbial diagnostics with synthetic biology. Trends Biotechnol. 31, 325-327.
Mlakar, J., et al. (2016). Zika Virus Associated with Microcephaly. N. Engl. J. Med. 374, 951-958.
Oehler, E., et al. (2014). Zika virus infection complicated by Guillain-Barre syndrome-case report, French Polynesia, Dec. 2013. Euro Surveill. 19, 20720.
Pardee, K., et al. (2014). Paper-based synthetic gene networks. Cell 159, 940-954.
Ran, F.A., et al. "Double nicking by RNA-guided CRISPR Cas9 for enhanced genome editing specificity." Cell 154.6 (2013): 1380-1389.
Rohrman, B.A., et al. (2012). A lateral flow assay for quantitative detection of amplified HIV-1 RNA. PLoS ONE 7, e45611.
Schrader, C., et al. (2012). PCR inhibitors—occurrence, properties and removal. J. Appl. Microbiol. 113, 1014-1026.
Silva, G., et al. "Meganucleases and other tools for targeted genome engineering: perspectives and challenges for gene therapy." Current gene therapy 11.1 (2011): 11-27.
Slomovic, S., et al. (2015). Synthetic biology devices for in vitro and in vivo diagnostics. Proc. Natl. Acad. Sci. USA 112, 14429-14435.
Smith, D.W., et al. (2016). Zika virus and Guillain-Barre syndrome: another viral cause to add to the list. Lancet 387, 1486-1488.
Sozhamannan, S., et al. (2015). Evaluation of Signature Erosion in Ebola Virus Due to Genomic Drift and Its Impact on the Performance of Diagnostic Assays. Viruses 7, 3130-3154.
Stefan, C.P., et al. (2016). Development of real-time reverse transcriptase qPCR assays for the detection of Punta Toro virus and Pichinde virus. Virol. J. 13, 54.
Takasu, Y., et al. "Targeted mutagenesis in the silkworm Bombyx mori using zinc finger nuclease mRNA injection." Insect biochemistry and molecular biology 40.10 (2010): 759-765.
Tappe, D., et al. (2014). First case of laboratory-confirmed Zika virus infection imported into Europe, Nov. 2013. Euro Surveill. 19, 20685.
U.S. Appl. No. 16/322,719, Green et al., filed Feb. 1, 2019.
U.S. Appl. No. 16/468,846, Green, filed Jun. 12, 2019.
U.S. Appl. No. 16/603,338, Green et al., filed Oct. 7, 2019.
Ulrich, R.M., et al. (2010). Detection and quantification of Karenia mikimotoi using real-time nucleic acid sequence-based amplification with internal conlrol RNA (IC- NASBA). Harmful Algae 9, 116-122.

(56) References Cited

OTHER PUBLICATIONS

Urnov, F.D., et al. "Genome editing with engineered zinc finger nucleases." Nature Reviews Genetics 11.9 (2010): 636.
Victora, C.G., et al. (2016). Microcephaly in Brazil: how to interpret reported numbers? Lancet 387, 621-624. WHO (2016).
Vijaya Satya, R., et al. (2010). A high-throughput pipeline for the design of real-time PCR signatures. BMC Bioinformatics 11, 340.
Watanabe, T., et al. "Non-transgenic genome modifications in a hemimetabolous insect using zinc-finger and TAL effector nucleases." Nature communications 3 (2012): 1017.
World Health Organization. WHO to fast-track availability of diagnostics for Zika virus. http://www.who.int/medicines/news/fast_track_diagnostics_zika/en/.
Yen, C.-W., et al. (2015). Multicolored silver nanoparticles for multiplexed disease diagnostics: distinguishing dengue, yellow fever, and Ebola viruses. Lab Chip 15, 1638-1641.
Zadeh, J.N., et al. (2011). Nucleic acid sequence design via efficient ensemble defect optimization. J. Comput. Chem. 32, 439-452.
Zadeh, J.N., et al. (2011). NUPACK: Analysis and design of nucleic acid systems. J. Comput. Chem. 32, 170-173.
Zammarchi, L., et al. (2015). Zika virus infections imported to Italy: clinical, immunological and virological findings, and public health implications. J. Clin. Virol. 63, 32-35.
Zika Experimental Science Team. (2016). ZIKV-001: Infection of three rhesus macaques with French Polynesian Zika virus. https://zika.labkey.com/project/OConnor/ZIKV-001/begin.view. 2016.

\* cited by examiner

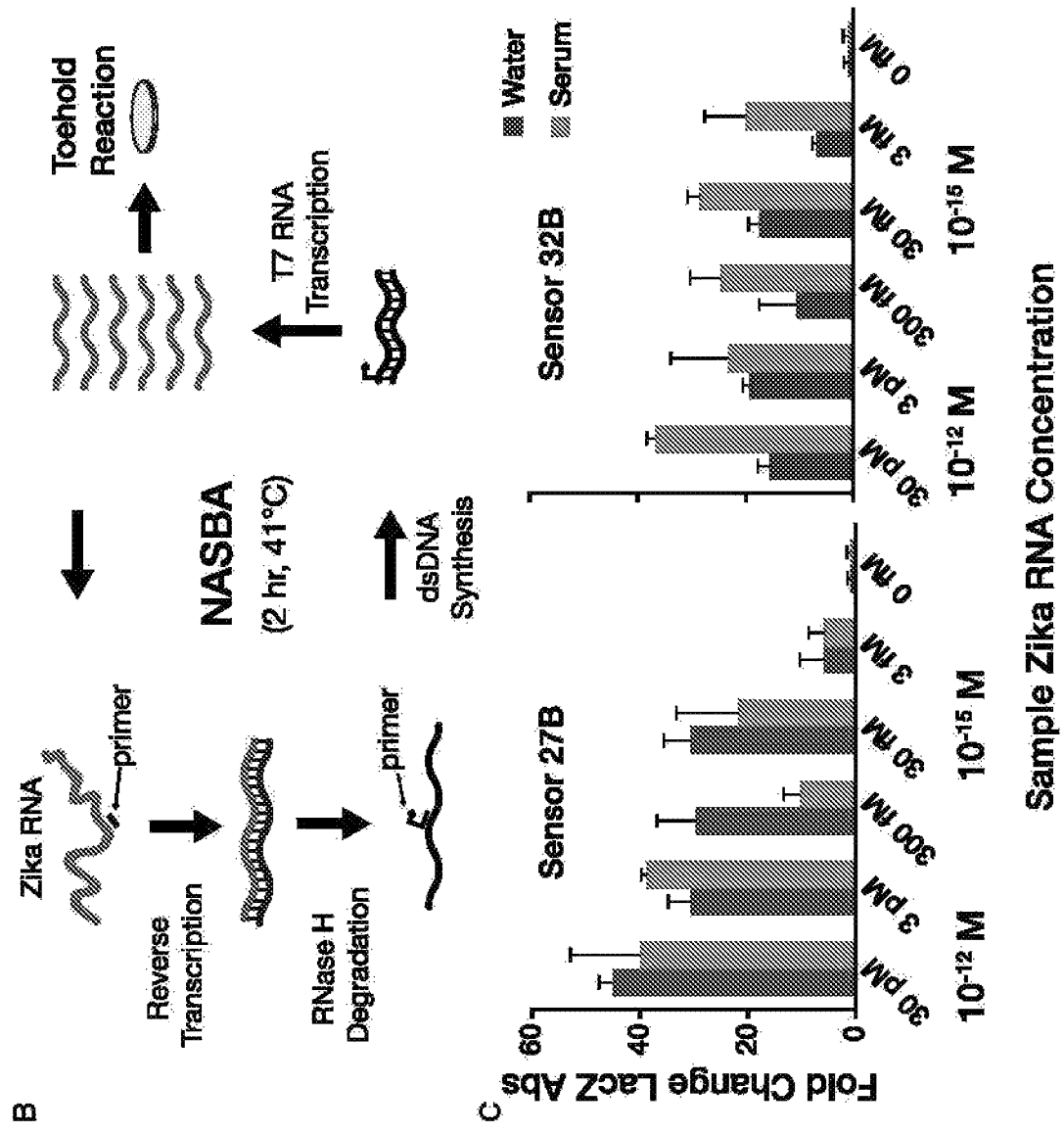
FIGS. 3A-3C, CONTINUED

```
Zika27     1   TGGTGACATG CGCTAAGTTT GCATGCTCCA AGAAAATGAC CGGGAAGAGC
Dengue27   1   TATTGACGTG TGCCAAGTTC AAGTGTGTGA CAAACTAGA AGGAAAGATA Zika27     51  ATGCAGCCAG AGAATCTGGA GTACGGGATA ATGCTGTCAG TTCA---TGG
Dengue27   51  GTTCAATATG AAAACCTAAA ATATCAGTG ATAGTCACTG TCCACAGTGG Zika27     101 CTCCCACGCAC AGTGGGATGA TCGTTAATGA CACAGGACAT GAAACTGATG
Dengue27   101 GGACCAGCAC CAGGTGGGAA ACCGAGAGT-- ACAGAACAT GGAACAATTG Zika27     151 AGAATAGAGC GAAGTTGAAG ATAACGCCCA ATTCACCAAG AGCCGAAGCC
Dengue27   151 CGAC------A ------- TAACACCTC AAGCTCGCAC GTCGGAAATA Zika27     201 AGCCTGGGGG CGGTTTGGAAG CCTAGGACTT GATTGTGAAC CGAAGGACAGG
Dengue27   201 CAGCTGACCG ACTACGGAGC CCTCACATTG GACTGCTCAC CTAGAACAGG Zika27     251 CCTTGACTTT TCAGATTTGT ATTACTTGAAC TATGAATAAC AAGCACTGGC
Dengue27   251

Zika27     301 TGGTTCACAA GGAGTGGTTC CACGACAATTC CATTACCTTG GCACGCTGGG
Dengue27   301
```

B

```
Zika32     1   AGCTGGAGTG TTGTTTGGTA TGGGCAAAGG GATGCCATTC TACGCATGGG
Dengue32   1   GGCAGCAGTA TGATGGGAC TTGACAAGGG ATGGCCAATA TCGAAGATGG Zika32     51  ACTTTGGAGT CCCGGTCTGCTA ATGATAGGTT GCTACTCACA ATTAACACCC
Dengue32   51  ACATAGGAGT TCCACTCTC GCCTTAGGGT GCTATTCCCA GGTGAACCCA Zika32     101 CTGACCCTAA TAGTGGCCAT CAGTTTGCTC GTGGCGCACT ACATG-TACT
Dengue32   101 TTGACACTGA CAGGGGGGT GTGATGTTA GTGCTCATT ATGCCATAAT Zika32     151 TGATCCCAGG GCTGCAGGCA GCAGCTGCGC GTGCTGCCCA GAAGAGAACC
Dengue32   151 TGGACC-AGG ACTGCAAGCA AAGGCCACTA GAGAAGCTCA AAAGAGGAC Zika32     201 GCAGCTGGCA TCATGAAGAA CCCTGTTGTG GATGGGATAG TGGTGACTGA
Dengue32   201 GCGGGCCGGAA TAATGAAAA TCCAACCGTA GACGGGAATTG TTGCAATAGA Zika32     251 CATTGACACA ATGACAATTG ACCCCAAGT ACCCCCAAGT CGAGAAAAAG ATGGGACAGG
Dengue32   251 CTTGGATCCT GTGGTTTATG ATACAAAATT TGAAAAACAG CTAGGCCAAA Zika32     301 ---TGCTACT CATAGCAGTA GCGGTCTCGA GCGGCATA    338
Dengue32   301 TAATGTTACT GATA CTTTG TACATCAC-A GATCCTC-    338
```

FIGS. 5A-5C, CONTINUED
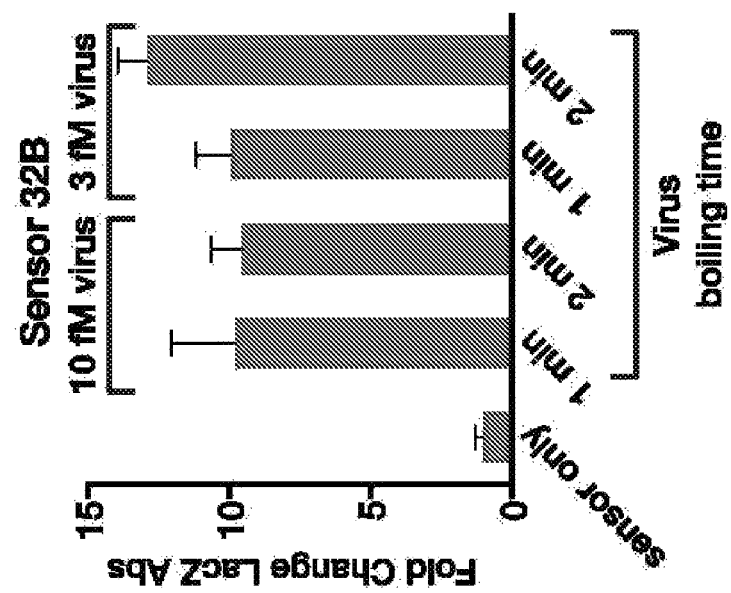
C

FIGS. 7A-7C
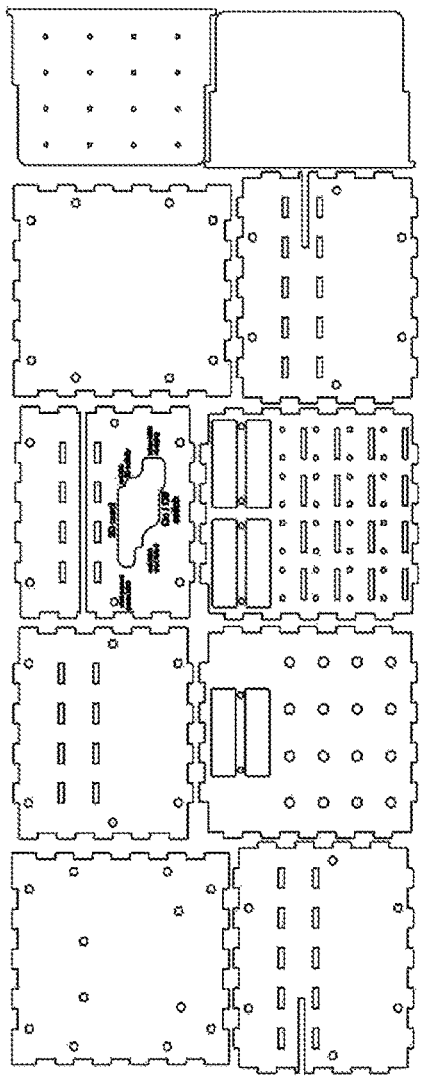
A.
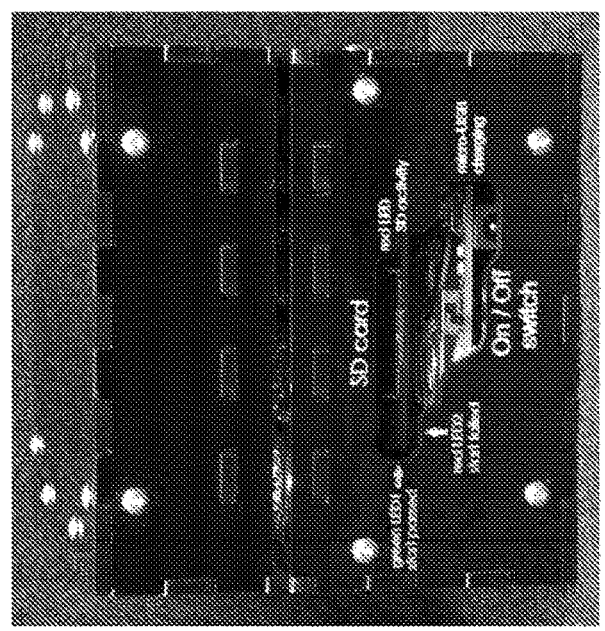
B.

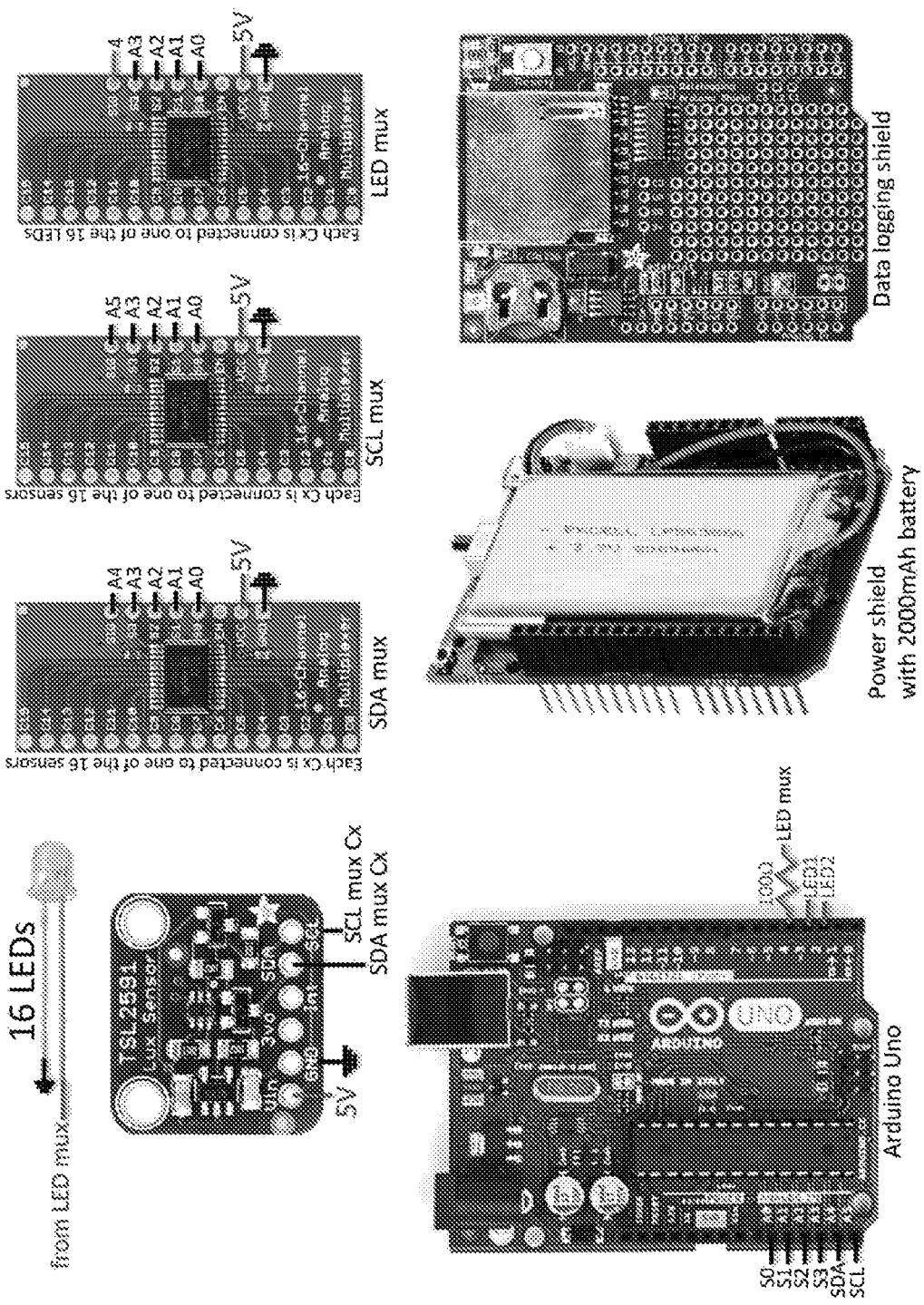
FIGS. 7A-7C, CONTINUED

FIG. 11
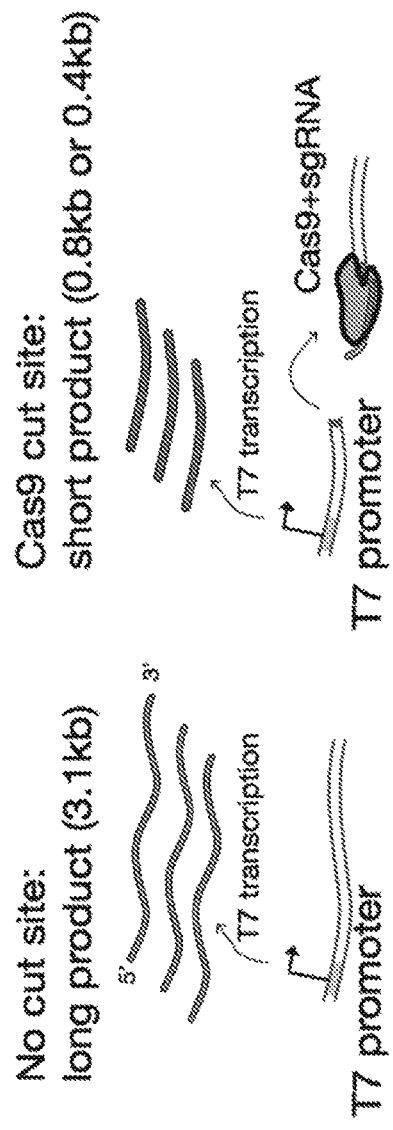
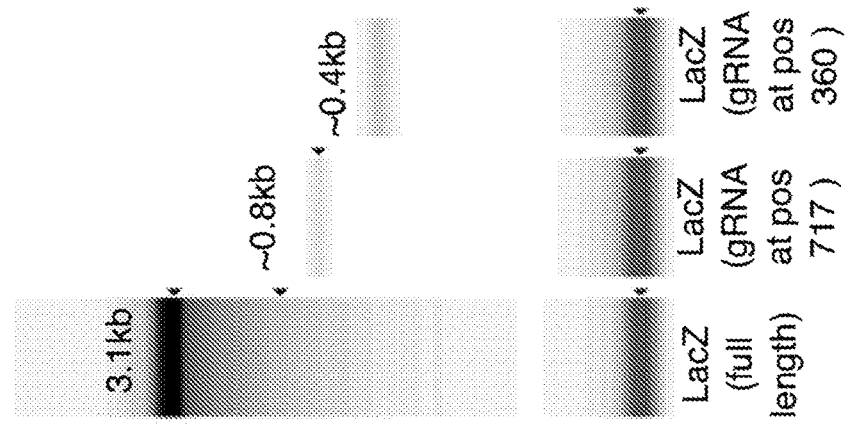

PORTABLE, LOW-COST PATHOGEN DETECTION AND STRAIN IDENTIFICATION PLATFORM

CROSS-REFERENCE TO RELATED APPLICATIONS

This application represents the national stage entry of PCT International Application No. PCT/US2017/034545, filed on May 25, 2017, and claims the benefit of U.S. Provisional Patent Application No. 62/341,221, filed on May 25, 2016, and U.S. Provisional Patent Application No. 62/403,778, filed on Oct. 4, 2016, each of which is incorporated by reference it its entirety as if fully set forth herein.

STATEMENT REGARDING FEDERALLY SPONSORED RESEARCH OR DEVELOPMENT

Not applicable.

SEQUENCE LISTING

The instant application contains a Sequence Listing which has been submitted electronically in ASCII format and is hereby incorporated by reference in its entirety. Said ASCII copy, created on May 25, 2017, is named 112624_00851_SL.txt and is 217,680 bytes in size.

BACKGROUND

Synthetic biology is an emerging discipline that has great potential to respond to global pandemics. The increasing ability of synthetic biologists to repurpose and engineer natural biological components for practical applications has led to new opportunities for molecular diagnostics.

In the case of viral outbreaks, standard serological approaches such as antibody detection have limited diagnostic value due to cross-reactivity in patients that have previously been infected by other flaviviruses circulating in the region. As a result, accurate diagnosis requires nucleic acid-based detection methods, such as PCR and isothermal nucleic acid amplification. However, such techniques are expensive, require technical expertise to run and interpret, and use equipment that is incompatible with use in remote and low-resource locations where surveillance and containment are critically needed. Accordingly, there remains a need in the art for improved methods and devices for rapid detection of target nucleic acids, including pathogen-specific nucleic acids for infection detection and for accurate strain identification.

BRIEF SUMMARY

In a first aspect, provided herein is a method of detecting a target nucleic acid in a sample. In some cases, the method comprises or consists essentially of the steps of: (a) obtaining nucleic acid from a biological sample obtained from a subject; (b) amplifying the nucleic acid using isothermal amplification; (c) contacting the amplified nucleic acid to a toehold switch, wherein the toehold switch encodes a reporter protein and comprises one or more single-stranded toehold sequence domains that are complementary to a target nucleic acid or the reverse complement thereof, wherein the contacting occurs under conditions that allow translation of the coding domain in the presence of the target nucleic acid but not in the absence of the target nucleic acid, and detecting the reporter protein as an indicator that the target nucleic acid is present in the amplified nucleic acid of the subject; and (d) identifying the target nucleic acid as containing a target protospacer adjacent motif (PAM), wherein identifying comprises: (i) amplifying nucleic acid obtained from the biological sample using a reverse primer designed to append the trigger sequence of one or more toehold switch sequence domains; (ii) contacting the amplified nucleic acid of (i) to CRISPR/Cas under conditions that allow for sequence-specific cleavage of the contacted nucleic acid by CRISPR/Cas when the target PAM is present in the amplified nucleic acid; and (iii) detecting activation of the toehold switch, wherein activation does not occur in the event of CRISPR/Cas-mediated sequence-specific cleavage, thereby indicating the presence of the target PAM. The toehold switch can comprise one or more single-stranded toehold sequence domains, a fully or partially double-stranded stem domain comprising an initiation codon, a loop domain comprising a ribosome binding site, and a coding domain. The toehold and stem domains can be complementary in sequence to a naturally occurring RNA. The loop domain can be complementary in sequence to a non-naturally occurring RNA. The target nucleic acid can be an RNA specific to a pathogen. The pathogen is selected from the group consisting of a virus, bacterium, fungus, and parasite. In some cases, the pathogen is a virus. The virus can be Zika virus. The virus can an American Zika variant (GenBank: KU312312). The virus strain can be an African Zika variant (GenBank: KF268950). The toehold switch can comprise an E. coli lacZ gene encoding β-galactosidase. Detecting activation of the one or more toehold switch sensors can comprise performing a LacZ-based colorimetric assay. Isothermal amplification can be selected from the group consisting of NASBA (nucleic acid sequence-based amplification), loop-mediated isothermal amplification (LAMP), recombinase polymerase amplification (RPA), and helicase-dependent amplification (HDA). The biological sample can be selected from the group consisting of blood, serum, urine, saliva, tissue, cell, and organ, or a fraction or portion thereof.

In another aspect, provided herein is a method of detecting a target nucleic acid in a sample. In some cases, the method comprises or consists essentially of: (a) obtaining RNA from a biological sample obtained from a subject; (b) amplifying the RNA using isothermal amplification; (c) contacting the amplified RNA to a toehold switch, wherein the toehold switch encodes a reporter protein and comprises one or more single-stranded toehold sequence domains that are complementary to a target RNA or the reverse complement thereof, wherein the contacting occurs under conditions that allow translation of the coding domain in the presence of the target RNA but not in the absence of the target RNA, and detecting the reporter protein as an indicator that the target RNA is present in the amplified RNA of the subject; and (d) identifying the target RNA as containing a target protospacer adjacent motif (PAM), wherein identifying comprises: (i) amplifying RNA obtained from the biological sample using a reverse primer designed to append the trigger sequence of one or more toehold switch sequence domains; (ii) contacting the amplified RNA of (i) to CRISPR/Cas under conditions that allow for sequence-specific cleavage of the contacted RNA by CRISPR/Cas when the target PAM is present in the amplified RNA; and (iii) detecting activation of the toehold switch, wherein activation does not occur in the event of CRISPR/Cas-mediated sequence-specific cleavage, thereby indicating the presence of the target nucleic acid. The toehold switch can comprise one or more single-stranded toehold sequence domains, a fully or partially double-stranded stem domain comprising an initiation codon, a loop domain comprising a ribosome binding site, and a coding domain. The toehold and stem domains can be complementary in sequence to a naturally occurring RNA. The loop domain can be complementary in sequence to a non-naturally occurring RNA. The target nucleic acid can be an RNA specific to a pathogen. The pathogen can be selected from the group consisting of a virus, bacterium, fungus, and parasite. In some cases, the pathogen is a virus. The virus can be Zika virus. The virus can be an American Zika variant (GenBank: KU312312). The virus can be an African Zika variant (GenBank: KF268950). The toehold switch can comprise an *E. coli* lacZ gene encoding β-galactosidase. Detecting activation of the one or more toehold switch sensors can comprise performing a LacZ-based colorimetric assay. Isothermal amplification can be selected from the group consisting of NASBA (nucleic acid sequence-based amplification), loop-mediated isothermal amplification (LAMP), recombinase polymerase amplification (RPA), and helicase-dependent amplification (HDA). The biological sample is selected from the group consisting of blood, serum, urine, saliva, tissue, cell, and organ, or a fraction or portion thereof.

In a further aspect, provided herein is a method of detecting presence of virus in a sample. The method can comprise or consist essentially of the steps of: (a) obtaining RNA from a biological sample obtained from a subject; (b) amplifying the RNA using isothermal amplification; (c) contacting the amplified RNA to a toehold switch, wherein the toehold switch encodes a reporter protein and comprises one or more single-stranded toehold sequence domains that are complementary to an endogenous virus RNA sequence or the reverse complement thereof, wherein the contacting occurs under conditions that allow translation of the coding domain in the presence of the endogenous virus RNA but not in the absence of the endogenous virus RNA, and detecting the reporter protein as an indicator that the endogenous virus RNA is present in the amplified RNA of the subject. The virus can be Zika virus. The toehold switch can comprise one or more Zika genome-specific single-stranded toehold sequence domains, a thermodynamically stable double-stranded stem domain, a loop domain comprising a ribosome binding site, and a coding domain. The loop domain can be complementary in sequence to a naturally occurring RNA. The loop domain can be complementary in sequence to a non-naturally occurring RNA. The loop domain can be 11 nucleotides or 12 nucleotides. The toehold switch can comprise an *E. coli* lacZ gene encoding β-galactosidase. Isothermal amplification can be selected from the group consisting of NASBA (nucleic acid sequence-based amplification), loop-mediated isothermal amplification (LAMP), recombinase polymerase amplification (RPA), and helicase-dependent amplification (HDA).

In another aspect, provided herein is a device for identifying a pathogen, comprising a preserved paper test article, wherein a methods described herein is performed using the preserved paper test article. The paper test article can be preserved by freeze-drying.

In another aspect, provided herein is a kit for detecting a pathogen, comprising one or more of a device as described herein and an electronic optical reader.

In a further aspect, provided herein is a method of genotyping a nucleic acid molecule. The method can comprise or consist essentially of contacting the nucleic acid molecule with: a programmable nuclease; and a sgRNA, wherein the combination of the nuclease and sgRNA can specifically bind to at least one sequence variant of the nucleic acid molecule; and detecting the presence or absence of a cut in the nucleic acid molecule generated by the nuclease. In some cases, the method further comprises a first step of performing reverse transcription on a RNA molecule and performing 2nd strand DNA synthesis with a toehold primer to generate the nucleic acid molecule; and wherein the detecting step comprises: transcribing an RNA from the nucleic acid molecule after contacting it with the nuclease, using a primer which initiates transcription from a location distal of the sequence variation site with respect to the location of the toehold primer sequence; and contacting a sensor with the RNA resulting from step a) and detecting the presence or absence of sensor activation; wherein the sensor is activated if the nuclease is not able to cut the nucleic acid molecule in step a). The presence of a cut can indicate that the nucleic acid molecule has a sequence variant to which the sgRNA and nuclease can specifically bind. The presence of a cut can indicate that the nucleic acid molecule has a sequence variant to which the nuclease specifically binds. The programmable nuclease can be Cas. The sequence variant can occur at a PAM site. The nucleic acid molecule can be of human, animal, prokaryotic, eukaryotic, pathogenic, or synthetic origin. The nucleic acid molecule can be of viral origin. The viral nucleic acid molecule can be a Zika virus nucleic acid molecule. The sequence variant being detected can differentiate at least one of the African, American, and Asian Zika strains from the others. The sequence variant can be selected from Table 2. The sequence variant being detected can differentiate the African and American Zika virus strains. The sequence variant can be the SNP occurring at site 7330 of the African (GenBank: KF268950) and American (GenBank: KU312312) Zika strains. The sgRNA can have the sequence of SEQ ID NO: 1.

In another aspect, provided herein is a composition comprising a sgRNA which can specifically bind to a sequence flanking at least one sequence variant selected from Table 2, wherein the sequence variation occurs at a CRISPR/Cas PAM binding site. The sgRNA can comprise SEQ ID NO: 1. The sgRNA can be selected from Table 2.

In a further aspect, provided herein is a composition comprising a CRISPR/Cas nuclease and a sgRNA that specifically binds to a sequence flanking at least one sequence variant occurring in a population. The population can be a viral population. The viral population can be a Zika virus population. The variant can be selected from Table 2. The sgRNA can be selected from Table 2. The sgRNA can comprise SEQ ID NO: 1.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein:

FIGS. 5A-5C present sequence alignments and RNA extraction optimization data. (A and B) Sequence alignments of Zika virus and Dengue virus genomic regions targeted by sensors (A) 27B (SEQ ID NOS 777 and 778, respectively) and (B) 32B (SEQ ID NOS 779 and 780, respectively). Red boxes indicates sequences targeted by the respective toehold switches, red and blue boxes indicate the NASBA-amplified regions, and the remaining sequence indicates natural flanking RNA sequences from each virus. The entire Zika 32 sequence shown here was cloned into lentivirus to make proxy Zika virus. (C) Effect of boiling time on RNA extraction. Lentivirus was packaged with the Zika virus RNA fragment corresponding to sensor 32B. Virus was diluted to 10 and 3 fM target RNA in 7% human serum. Twenty-five μL of virus was heated to 95° C. for 1 and 2 minutes. One μL was then used to initiate NASBA-mediated RNA amplification. A 1:7 dilution of 2 hours NASBA reactions in water was then used to rehydrate freeze-dried, paper-based reactions. Fold change was calculated from absorbance (570 nm) after 60 minutes at 37° C. Error bars represent SD of three replicates.

FIGS. 7A-7C present an exemplary portable electronic optical reader. (A) Line drawings used to cut the housing for the electronic reader from black acrylic using a laser cutter. (B) Image of the 16-reaction reader from the front. Chip containing paper-based sensors slides into the slot illuminated by the green light. Reader dimensions: 106 mm wide×116 mm deep×96 mm high. (C) Components and circuit design used to assemble the electronic optical reader.

FIG. 11 depicts a schematic of NASBA-CRISPR Cleavage (NASBACC).

Figure 1:
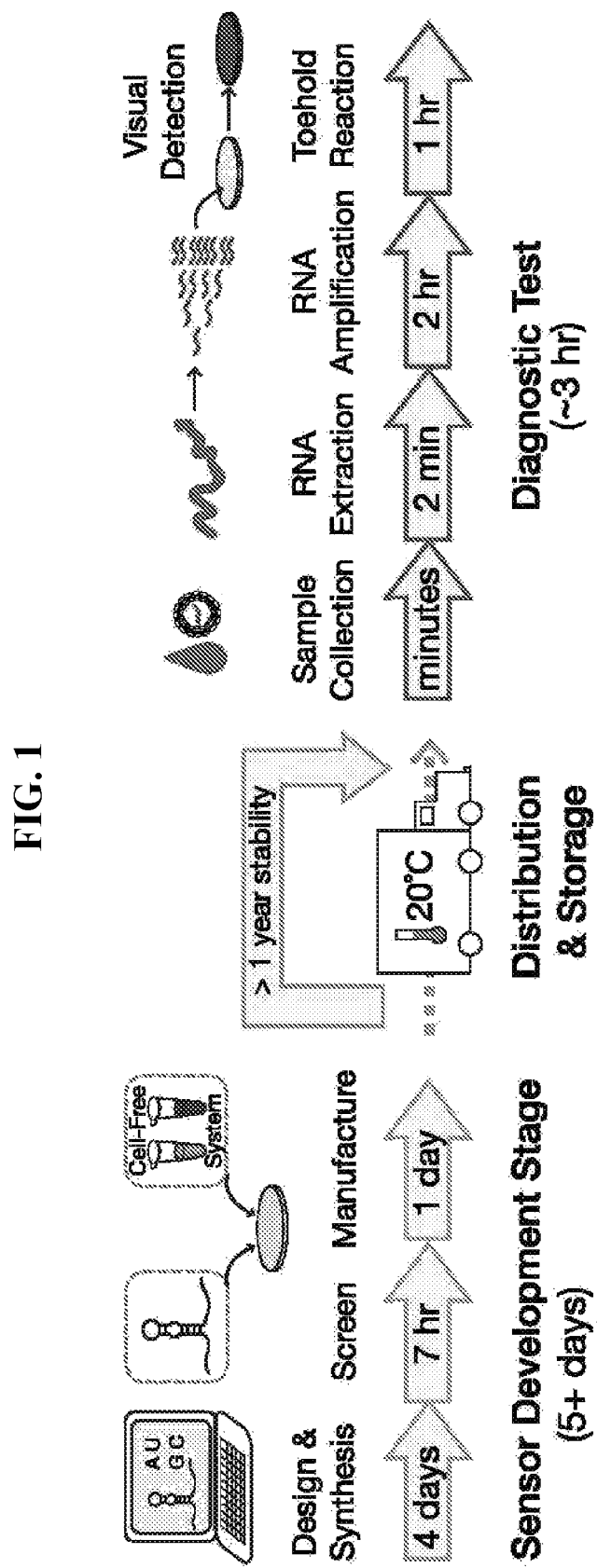
FIG. 1 presents an exemplary workflow for rapid prototyping of paper-based, biomolecular sensors. Using sequence information from online databases, primers for isothermal RNA amplification and toehold switch-based RNA sensors were designed in silico using purpose-built algorithms. Once synthesized, the resulting sequence-specific toehold sensors can be assembled and validated in less than 7 hours (hrs.). In under a day, validated sensors can be embedded into paper and freeze-dried along with a cell-free transcription and translation system to be deployed in the field as stable diagnostics. For the diagnostic test, extracted RNA is isothermally amplified via NASBA and used to rehydrate the freeze-dried paper sensors. The detection of the appropriate trigger RNA is indicated by a color change in the paper disc from yellow to purple.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and compositions provided herein are based at least in part on the Inventors' development of a diagnostic platform utilizing engineered biomolecular, nucleic acid-based sensors and CRISPR-based technology that permits rapid, specific, and low-cost detection of viral nucleic acids at clinically relevant concentrations. In particular, the inventors developed engineered biomolecular sensors for the specific detection of pathogen genomes such as viral RNA genomes.

Without being bound to any particular theory or mechanism of action, it is believed that the inventors addressed limitations in the practical deployment of nucleic acid-based molecular diagnostics by combining isothermal RNA amplification with toehold switch sensors on a freeze-dried, paper-based platform. By automating the amplification primer and sensor design process using in silico algorithms, the methods described herein provide clinically relevant sensitivity, discriminating between pathogen genotypes with single-base resolution.

Accordingly, in a first aspect, provided herein is a method of detecting a target nucleic acid in a biological sample obtained from a subject. As described herein, the method comprises or consists essentially of (a) obtaining nucleic acid (e.g., DNA, RNA) from a biological sample containing or suspected of containing a target nucleotide sequence; (b) amplifying the nucleic acid using a primer designed to hybridize to the target nucleotide sequence; (c) contacting the amplified nucleic acid to a toehold switch, where the riboregulator encodes a reporter protein and comprises one or more toehold sequence domains that are complementary to the target nucleotide sequence, where the contacting occurs under conditions that allow translation of the coding domain in the presence of the target nucleic acid but not in the absence of the target nucleic acid, and detecting the reporter protein as an indicator that the target nucleic acid is present in the amplified nucleic acid of the subject.

In certain embodiments, the target nucleotide sequence is a nucleic acid from a pathogen, where the biological sample contains or is suspected of containing the pathogen. Accordingly, the methods provided herein are useful to detect any pathogen or infectious agent. Pathogens and infectious agents may comprise viruses, (e.g., single stranded RNA viruses, single stranded DNA viruses, Zika virus, HIV, hepatitis A, B, and C virus, HSV, CMV EBV, HPV), parasites (e.g., protozoan and metazoan pathogens such as *Plasmodia* species, *Leishmania* species, *Schistosoma* species, *Trypanosoma* species), bacteria (e.g., *Mycobacteria*, in particular, *M. tuberculosis, Salmonella, Streptococci, E. coli, Staphylococci*), fungi (e.g., *Candida* species, *Aspergillus* species), *Pneumocystis carinii*, and prions. In certain embodiments, the pathogen is a virus, and the methods can be used to detect any virus. In other embodiments, the pathogens that are detected are bacteria, fungi, or parasites. An advantage of the methods and systems described herein is that they can be applied for the detection and identification of essentially any nucleic acid-containing organism. Accordingly, the pathogen or infectious agent can be virtually any pathogen or infectious agent for which genetic information (e.g., gene sequences) is available. In other cases, the target nucleic acid is human in origin. In such cases, the methods can be employed to detect one or more target nucleic acids in a biological sample such as a biological sample obtained for forensic analysis, for genotyping, and the like.

In such cases, the methods provided herein can further comprise identifying the pathogen detected in the biological sample. For example, the method can further comprise (i) amplifying RNA obtained from the biological sample; (ii) contacting the amplified RNA of (i) to a nuclease under conditions that allow for sequence-specific cleavage of the contacted RNA by the nuclease when a pathogen strain-specific protospacer adjacent motif (PAM) is present; and (iii) detecting activation of a toehold switch, where activation does not occur in the event of nuclease-mediated sequence-specific cleavage, thereby indicating the presence of the pathogen strain-specific PAM. In other cases, DNA is obtained from the biological sample and amplified as described above.

Other target nucleotide sequences include, without limitation, DNA or RNA sequences that can identify a species (e.g., ribosomal RNAs or DNAs); DNA or RNA sequences that are associated with a particular genetic condition (e.g., where the target comprises a single nucleotide polymorphism (SNP) for which PAM identification is advantageous, including, without limitation, BRCA1/BRCA2 mutations, cystic fibrosis, Duchenne muscular dystrophy, hemochromatosis); DNA or RNA sequences for identifying a particular person with high certainty (e.g., identifying a suspect in a criminal investigation; identifying a "high value target" in a military operation).

For forensic applications, the target nucleotide sequence can be a DNA or RNA sequence associated with one or more particular identifiable features (e.g., skin color, hair color, eye color). In such cases, a biological sample can be assayed to detect a target nucleic acid of an unknown subject or for comparison to samples from known individuals. For applications related to pathogen detection, detection of particular RNA sequences is advantageous for determining, for example, the life cycle stage of a pathogen associated with an infection. By way of example, particular target nucleic acids can be detected to detect the presence of malaria parasite *Plasmodium falciparum* and to determine whether the parasite is in a life cycle phase in which it can reproduce and, thus, transmit infection. Other applications for which the methods provided herein include, without limitation, profiling species in an environment (e.g., water); profiling species in an human or animal microbiome; food safety applications (e.g., detecting the presence of a pathogenic species, determining or confirming food source/origin such as type of animal or crop plant); obtaining patient expression profiles (e.g., detecting expression of a gene or panel of genes (e.g., biomarkers) to monitor the patient's response to a therapeutic regimen, to select a therapeutic regimen suitable for the patient, or to detect exposure of the patient to a toxin or environmental agent that affects expression of the gene or panel of genes; and molecular encryption applications such as marking certain products (e.g., high value products) using nucleic acid barcodes.

The nucleic acid molecule can be, e.g., an RNA, a DNA, an mRNA, and/or a genomic nucleic acid. In some embodiments of any of the aspects, the nucleic acid molecule can be human, animal, prokaryotic, eukaryotic, or pathogenic in origin. In some embodiments of any of the aspects, the nucleic acid molecule can be of viral origin. Nucleic acids and/or other moieties of the invention may be isolated. As used herein, "isolated" means separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Biological samples appropriate for use according to the methods provided herein include, without limitation, blood, serum, urine, saliva, tissues, cells, and organs, or portions thereof.

Since the methods of the present invention provide single-base discrimination, the methods are particularly suited to distinguishing between genomes of a pathogen strain (e.g., to distinguish between pathogen strains) and/or identifying the presence of nucleic acids specific to a particular pathogen. As described herein, the methods incorporate isothermal RNA amplification and the sequence-specific nuclease activity of a CRISPR/Cas system. "Clustered Regularly Interspaced Palindromic Repeats (CRISPRs)/CRISPR associated (Cas)" systems have been employed for targeted genome editing applications across many species. CRISPR systems belong to different classes, with different repeat patterns, sets of genes, and species ranges. The number of Cas genes at a given CRISPR locus can vary between species. The terms "Cas gene" and "CRISPR-associated (Cas) gene" are used interchangeably herein. A comprehensive review of the Cas protein family is presented in Haft et al. (2005) Computational Biology, *PLoS Comput. Biol.* 1:e60 (doi:10.1371/journal.pcbi.0010060). At least 41 CRISPR-associated (Cas) gene families have been described.

Without being bound to any particular theory or mechanism of action, Cas enzymes recognize a strain-specific protospacer adjacent motif (PAM) sequence. In one embodiment, in the case of the enzyme Cas9 the PAM sequence is NGG, where N can be any DNA base. Thus, a single base mutation, such as one that changes the sequence AGG to AAG, abolishes the PAM site and prevents Cas nuclease-based cleavage. As used herein, the term "protospacer" refers to the portion of a crRNA (or sgRNA) that is complementary to the genomic DNA target sequence. Generally, protospacers are usually 20 nucleotides in length. Referring to FIG. 8, the methods provided herein can employ pathogen strain-specific "NGG" protospacer adjacent motif (PAM) sequences and isothermal RNA amplification using primers having specificity to the toehold switch domain. In such cases, the amplified DNA will undergo Cas-mediated cleavage only if the appropriate strain-specific PAM sequence is present. The truncated RNA, generated through transcription of the cleaved DNA product, is unable to activate the toehold switch. In the absence of the PAM sequence, the full-length RNA product containing the toehold switch domain is generated, allowing for nucleic acid-based sensor activation. Trigger RNA is only amplified from DNA that is not cut by Cas, thereby allowing for strain-specific detection using the toehold switch. With respect to distinguishing between Zika virus strains, analysis of the sequences of the American Zika variant (GenBank: KU312312) and an African Zika variant (GenBank: KF268950) revealed over 600 sites at which a PAM site was present in one strain and not the other. Since both viruses have genomes of ~10.5 kb in length, PAM sites that can be used to identify viruses in a strain-specific manner occur approximately every 17 bases within the genomes of the two closely related strains and thus provide considerable opportunities for strain identification according to the methods provided herein.

Figures 2A, 2B, 2C, 2D:
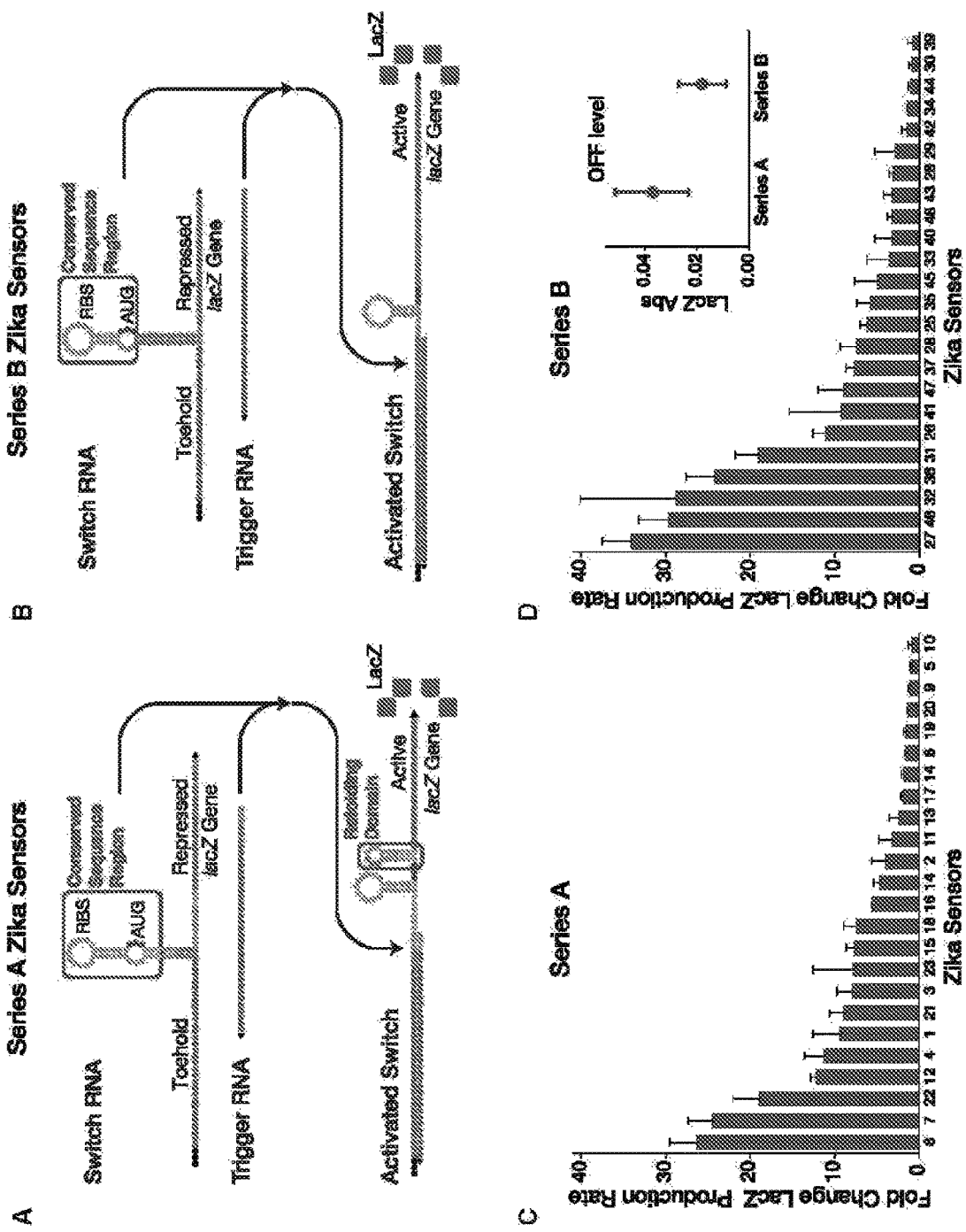
FIGS. 2A-2D demonstrate rapid prototyping of 48 paper-based RNA toehold sensors for Zika virus detection. (A) Series A toehold switch sensor schematic. The sensor design from Green et al., Cell 159:925-939 (2014) was modified with a shortened 11-nucleotide (nt) loop sequence to reduce leakage of output gene expression. (B) Series B toehold switch sensor schematic. Based on the same Zika genomic region as the A series, these sensors include a 12-nt loop and lack the refolding domain. These modifications were made to further reduce LacZ reporter leakage in the OFF state. (C) Maximum fold change in the rate of LacZ production for the Series A Zika virus RNA sensors during the first 90 minutes (min) at 37° C. Fold change of LacZ production rate is determined from the slope of absorbance at 570 nm over time (sensor alone versus sensor with 3,000 nM RNA trigger). Sensors are ordered according to fold change. (D) Maximum fold change in the rate of LacZ production for the Series B Zika virus RNA sensors during the first 90 min at 37° C. Error bars represent SD from three replicates. Inset: average LacZ absorbance of the OFF states at 60 min indicates an overall reduction in LacZ reporter leakage for the Series B sensors. Error bars represent SD across the 24 sensors.

As used herein, the term "toehold switch" generally refers to a nucleic acid-based regulator of gene expression, configured to repress or activate translation of an open reading frame and thus production of a protein. Toehold switches, which are a type of prokaryotic riboregulator, activate gene expression in response to cognate RNAs with essentially arbitrary sequences. Gene regulation is achieved through the presence of a regulatory nucleic acid element (the cis-repressive RNA or crRNA) within the 5' untranslated region (5' UTR) of an mRNA molecule. The cis-repressive nucleic acid element (crRNA) forms a hairpin structure comprising a stem domain and a loop domain through complementary base pairing. The hairpin structure blocks access to the mRNA transcript by the ribosome, thereby preventing translation. In some embodiments, the stem domain of the hairpin structure sequesters the ribosome binding site (RBS). In some embodiments, including for example embodiments involving eukaryotic cells, the stem domain of the hairpin structure is positioned upstream of the start (or initiation) codon, within the 5' UTR of an mRNA. In some cases, riboregulators comprise synthetic (engineered) molecules. In other cases, toehold switches comprise endogenous, naturally occurring RNAs or regions thereof. See, for example, U.S. 2015/0275203. The stem domain can be as small as 12 bps, but in some cases will be longer than 12 bps, including 13, 14, 15, 16, 17, 18, 19, 20, or more base pairs in length. In some cases, the loop domain is complementary to a naturally occurring RNA. In other cases, the loop domain is complementary to a non-naturally occurring RNA. The toehold domain can be 5, 6, 7, 8, 9, 10, 11, 12, 13, 14, 15, 16, 17, 18, 19, 20, or more nucleotides in length. Referring to FIGS. 2A and 2B, an exemplary toehold switch domain comprises an 11-nt or 12-nt loop domain.

The toehold switch further comprises a fully or partially double-stranded stem domain comprising an initiation codon, a loop domain comprising a ribosome binding site (RBS), and a coding domain. The unpaired region upstream of the RBS in a toehold switch can be shortened or lengthened to modulate protein output and, in turn, device dynamic range. In some cases, the toehold and stem domains are complementary in sequence to a naturally occurring RNA. In other cases, the sequence detected can also be the complement of the naturally occurring RNA. For example, after isothermal amplification, it is possible to transcribe the antisense of the RNA rather than the sense.

The toehold switch can further comprise a thermodynamically stable double-stranded stem domain, a loop domain comprising a ribosome binding site, and a coding domain. In some cases, the loop domain is complementary in sequence to a naturally occurring Zika virus RNA. In other cases, the loop domain is complementary in sequence to a non-naturally occurring RNA. Preferably, the loop domain is 11 nucleotides or 12 nucleotides in length. In some cases, the length of loop domains can be increased or decreased, for example, to alter reaction thermodynamics.

As shown in FIGS. 2A and 2B, the toehold switch can be operably linked to a reporter element (e.g., an *E. coli* lacZ reporter element encoding β-galactosidase) that is 3' to the hairpin structure. As used herein, the term "operably linked" refers to a relationship between two nucleic acid sequences wherein the production or expression of one of the nucleic acid sequences is controlled by, regulated by, modulated by, etc., the other nucleic acid sequence. Reporter proteins appropriate for the methods provided herein include, without limitation, enzymatic reporters (e.g., β-galactosidase, alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

Any isothermal amplification protocol can be used according to the methods provided herein. Exemplary types of isothermal amplification include, without limitation, nucleic acid sequence-based amplification (NASBA), loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), and polymerase spiral reaction (PSR available at nature.com/articles/srep12723 on the World Wide Web). In some cases, a forward primer is used to introduce a T7 promoter site into the resulting DNA template to enable transcription of amplified RNA products via T7 RNA polymerase. In other cases, a reverse primer is used to add a trigger sequence of a toehold sequence domain.

As used herein, "nuclease" refers to an enzyme capable of cleaving the phosphodiester bonds between the nucleotide subunits of nucleic acids. Nucleases can be site-specific, i.e. site-specific nucleases cleave DNA bonds only after specifically binding to a particular sequence. Therefore, nucleases specific for a given target can be readily selected by one of skill in the art. Nucleases often cleave both strands of dsDNA molecule within several bases of each other, resulting in a double-stranded break (DSB). Exemplary nucleases include, but are not limited to Cas9; Cas13; meganucleases; TALENs; zinc finger nucleases; FokI cleavage domain; RNA-guided engineered nucleases; Cas-derived nucleases;

homing endonucleases (e.g. I-AniI, I-CreI, and I-SceI) and the like. In some embodiments of any of the aspects, the nuclease is an endonuclease. As used herein, "endonuclease" refers to an enzyme capable of cleaving the phosphodiester bonds between the nucleotide subunits of nucleic acids within a polynucleotide, e.g., cleaving a phosphodiester bond that is not either the 5' or 3' most bond present in the polynucleotide. In other embodiments of any of the aspects, the nuclease is a meganuclease. As used herein, "meganuclease" refers to endonucleases, which have a large recognition sequence (e.g., dsDNA sequences of 12-40 bp). Due to the size of the recognition sequences, meganucleases are particularly specific. Meganuclease specificity can be engineered. In some embodiments of any of the aspects, the meganuclease can be a LAGLIDADG homing endonuclease (SEQ ID NO: 2).

In some embodiments, the nuclease can be an engineered nuclease. As used herein, the terms "engineered" and "genetically engineered" are used interchangeably and refer to the aspect of having been manipulated by the hand of man. For example, a nuclease is considered to be "engineered" when the sequence of the nuclease is manipulated by the hand of man to differ from the sequence of the nuclease as it exists in nature. As is common practice and is understood by those in the art, progeny and copies of an engineered polynucleotide and/or polypeptide are typically still referred to as "engineered" even though the actual manipulation was performed on a prior entity. Methods of engineering nucleases to achieve a desired sequence specificity are known in the art and are described, e.g., in Kim and Kim. Nature Reviews Genetics 2014 15:321-334; Kim et al. Genome Res. 2012 22:1327-1333; Belhaj et al. Plant Methods 2013 9:39; Urnov et al. Nat Rev Genet 2010 11:636-646; Bogdanove et al. Science 2011 333:1843-6; Jinek et al. Science 2012 337:816-821; Silva et al. Curr Gene Ther 2011 11:11-27; Ran et al. Cell 2013 154:1380-9; Carlson et al. PNAS 212 109:17382-7, Guerts et al. Science 2009 325: 433-3; Takasu et al. Insect Biochem Mol Biol 2010 40:759-765; and Watanabe et al. Nat. Commun. 2012 3; each of which is incorporated by reference herein in its entirety.

In some embodiments, the nuclease is a programmable nuclease. As used herein "programmable nuclease" refers to a nuclease that has been engineered to create a double-stranded break (DSB) or nick at a nucleic acid sequence that the native nuclease would not act upon, e.g. the sequence specificity of the nuclease has been altered. As described herein, programmable nucleases can be used to genotype a nucleic acid and/or determine the sequence of a nucleic acid. In particular, programmable nucleases can differentiate between point mutations or SNPs, e.g., SNPs that occur in a PAM site. In one aspect of any of the embodiments, described herein is a method of genotyping a nucleic acid molecule, the method comprising: a) contacting the nucleic acid molecule with: a programmable nuclease; and a single guide ("sgRNA") which can specifically bind to at least one sequence variant of the nucleic acid molecule; and b) detecting the presence or absence of a cut in the nucleic acid molecule generated by the nuclease. In one aspect of any of the embodiments, described herein is a method of genotyping a nucleic acid molecule, the method comprising: a) contacting the nucleic acid molecule with: a programmable nuclease; and a sgRNA wherein the combination of the nuclease and sgRNA can specifically bind to at least one sequence variant of the nucleic acid molecule; and b) detecting the presence or absence of a cut in the nucleic acid molecule generated by the nuclease. In some embodiments of any of the aspects, the presence of a cut indicates that the nucleic acid molecule has a sequence variant for which the sgRNA is specific. In some embodiments of any of the aspects, the presence of a cut indicates that the nucleic acid molecule has a sequence variant to which the nuclease specifically binds. In some embodiments of any of the aspects, the presence of a cut indicates that the nucleic acid molecule has a sequence variant for which the sgRNA is specific and has a sequence variant to which the nuclease specifically binds. In some embodiments of any of the aspects, the presence of a cut indicates that the nucleic acid molecule has a sequence variant to which the sgRNA and nuclease can specifically bind.

By way of non-limiting example, the programmable nuclease can be Cas9; Cas13, a Cas nickase mutant; TALEN; ZFNs; Cpf1; and/or SaCas9. In some embodiments of any of the aspects, the programmable nuclease is Cas9. In some embodiments, the programmable nuclease is Cas9. In some embodiments of any of the aspects, the programmable nuclease is S. pyogenes Cas9 or a variant thereof, e.g., New England Biolabs #M0386 (Ipswich, Mass.). When Cas9 nuclease (or Cas9-derived nuclease) is selected for use, the nuclease will generate a cut and/or nick where the guide RNA hybridizes to the nucleic acid molecule.

In order for a Cas nuclease to recognize and cleave a target nucleic acid molecule, a CRISPR targeting RNA ("crRNA") and trans-activating crRNA ("tracrRNA") must be present. crRNAs hybridize with tracrRNA to form a hybrid guide RNA ("gRNA") which then associates with the Cas9 nuclease. Alternatively, the gRNA can be provided as a single contiguous RNA, and forms a single guide RNA ("sgRNA"). Once the sgRNA is complexed with Cas, the complex can bind to a target nucleic acid molecule. The sgRNA binds specifically to a complementary target sequence via a target-specific sequence in the crRNA portion (e.g., the spacer sequence), while Cas itself binds to a protospacer adjacent motif (CRISPR/Cas protospacer-adjacent motif; PAM). The Cas nuclease then mediates cleavage of the target nucleic acid to create a double-stranded break within the sequence bound by the sgRNA. Different Cas enzymes have different PAM recognition sequences. For example, S. pyogenes Cas9 requires a NGG PAM sequence while other CRISPR/Cas systems have been described in other prokaryotic species, which recognize a different PAM sequence (e.g., CCN, TCN, TTC, AWG, CC, NNAGNN, NGG, NGGNG).

In some embodiments of any of the aspects, the sgRNA is provided as a single continuous nucleic acid molecule. In some embodiments of any of the aspects, a hybrid gRNA is provided as a set of hybridized molecules, e.g., a crRNA and tracrRNA.

In embodiments in which the nuclease to which the amplified DNA or RNA is contacted is a Cas nuclease, a method of detecting a viral nucleic acid comprises or consists essentially of: (a) obtaining DNA or RNA from a biological sample obtained from a subject; (b) amplifying the DNA or RNA using a primer designed to append a trigger sequence of one or more toehold sequence domains; (c) contacting the amplified DNA or RNA to a toehold switch, where the riboregulator encodes a reporter protein and comprises one or more toehold sequence domains, where the contacting occurs under conditions that allow translation of the coding domain in the presence of the endogenous virus DNA or RNA but not in the absence of the endogenous virus DNA or RNA, and detecting the reporter protein as an indicator that the endogenous virus DNA or RNA is present in the amplified DNA or RNA of the subject; and (d) identifying the strain of virus, where identifying comprises: (i) amplifying DNA or RNA from the biological sample; (ii) contacting the amplified DNA or RNA of (i) to Cas (e.g., Cas9, Cas13) under conditions that allow for sequence-specific cleavage of the contacted RNA by Cas (e.g., Cas9, Cas13) when a virus strain-specific protospacer adjacent motif (PAM) is present; and (iii) detecting activation of the toehold switch, where activation does not occur in the event of Cas-mediated sequence-specific cleavage, thereby indicating the presence of the virus strain-specific PAM. For example, the methods provided herein can be used to distinguish between viral strains, e.g., where one strain comprises a PAM site while the second strain comprises a SNP that eliminates the PAM site, such an American Zika variant (GenBank: KU312312) and an African Zika variant (GenBank: KF268950), and also between other flavivirus strains. See, FIGS. 5A-5B. In such cases the toehold switch comprises one or more Zika genome-specific single-stranded toehold sequence domains. Exemplary sequences of toehold switches suitable for use for Zika RNA detection are provided in Table 8.

In some cases, the one or more toehold sequence domains are complementary to an endogenous virus DNA or RNA sequence. In such cases, where the toehold switch recognizes an endogenous RNA sequence, there is no requirement for a primer that appends a toehold sequence domain.

With respect to the amplification step, the target sequence for a toehold switch is in some cases added via an amplification primer for the NASBACC process. In other cases, a toehold switch that detects an endogenous pathogen DNA or RNA sequence is used.

In another aspect, provided herein is a method of detecting Zika virus in a sample. The methods can comprises, or consist essentially of, (a) obtaining RNA from a biological sample obtained from a subject; (b) amplifying the RNA using isothermal amplification; and (c) contacting the amplified RNA to a riboregulator, wherein the riboregulator encodes a reporter protein and comprises one or more toehold domains that is complementary to a Zika virus RNA, wherein the contacting occurs under conditions that allow translation of the coding domain in the presence of the Zika virus RNA but not in the absence of the Zika virus RNA, and detecting the reporter protein as an indicator that the Zika virus RNA is present in the amplified RNA of the subject.

In some cases, it may be advantageous to adapt the methods described herein for high-throughput, reproducible, and rapid detection, for example in a clinical setting. When riboregulator output is coupled to a reporter element, such as a LacZ reporter element, the riboregulator acts as a genetically encodable sensor and detectable probe for endogenous DNA or RNA (e.g., endogenous pathogen DNA, endogenous pathogen RNA) in a sample. For example, such toehold switches can be provided in a device configured for rapid, reproducible detection in a clinical setting. In some cases, the device comprises a preserved paper test article, upon which any step(s) of the method provided herein can be performed. In preferred embodiments, the paper test article is preserved by freeze-drying. The reporter element can be a reporter protein, e.g., a polypeptide with an easily assayed enzymatic activity or detectable signal that is naturally absent from the host cell. Exemplary but non-limiting reporter proteins include lacZ, catalase, xylE, GFP, RFP, YFP, CFP, neomycin phosphotransferase, luciferase, mCherry, and derivatives or variants thereof. In some embodiments of any of the aspects, the reporter protein is suitable for use in a colorimetric assay. Examples of genes encoding fluorescent proteins that may be used in accordance with the invention include, without limitation, those proteins provided in U.S. Patent Application No. 2012/0003630 (see Table 59 therein), incorporated herein by reference.

In some cases, the device is used with a portable electronic reader. In this manner, the electronic reader serves as companion technology that provides robust and quantitative measurements of device outputs. As shown in FIGS. 7A-7C, an exemplary electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between an LED light source (570 nm) and electronic sensors. Using onboard electronics, samples can be read at a rate of 29 reads per minute. Accordingly, the portable electronic reader provides low-noise measurements of changes associated with the reporter element including changes in light transmission due to LacZ-mediated color change.

As used herein, "sequence variations" can refer to substitutions, insertions, deletions, duplications, and/or rearrangements. Sequence variations of a locus occurring in a population are referred to as alleles. Sequence variations can be present in (and therefore, detected in) the gDNA and/or mRNA of a gene. In some embodiments of any of the aspects, the sequence variation is a point mutation, e.g. a single nucleotide polymorphism (SNP). As used herein, a "point mutation" refers to the identity of the nucleotide present at a site of a mutation in the mutant copy of a genomic locus (including insertions and deletions), i.e., it refers to an alteration in the sequence of a nucleotide at a single base position from the wild type sequence. A SNP (single nucleotide polymorphism) is one type of point mutation that occurs at the same genomic locus between different individual subjects or entities in a population or different strains in a species. SNPs can be allelic. At least four alleles of a SNP locus are possible, although SNPs that vary only between two nucleotides at the target site are not uncommon.

In some embodiments of any of the aspects, the target nucleic acid is a Zika virus nucleic acid molecule, e.g., a Zika virus genomic molecule or a molecule transcribed from the Zika virus genome.

The methods described herein can permit identification of the species of virus present in a sample (e.g., a sample obtained from a subject), and/or permit identification of the strain of a virus present in a sample based upon sequence variations found between species and/or strains. Such information can be used to direct treatment, e.g., different strains of Zika virus are known to cause different symptoms and secondary conditions at varying frequencies. In some embodiments of any of the aspects, the sequence variant being detected differentiates at least one of the African, American, and Asian Zika strains from the others. Exemplary sequence variants that differentiate these strains are provided in Table 5.

In certain embodiments, provided herein is a method for genotyping a nucleic acid molecule. The method can comprise or consist essentially of contacting the nucleic acid molecule with a programmable nuclease and a sgRNA, where the combination of the nuclease and sgRNA can specifically bind to at least one sequence variant of the nucleic acid molecule; and detecting the presence or absence of a cut in the nucleic acid molecule generated by the nuclease. In some cases, the method further comprises a first step of performing reverse transcription on a RNA molecule and performing 2nd strand DNA synthesis with a toehold primer to generate the nucleic acid molecule. In such cases, the detecting step comprises: (i) transcribing an RNA from the nucleic acid molecule after contacting it with the nuclease, using a primer which initiates transcription from a location distal of the sequence variation site with respect to the location of the toehold primer sequence; and (ii) contacting a sensor with the RNA resulting from step (a) and detecting the presence or absence of sensor activation; wherein the sensor is activated if the nuclease is not able to cut the nucleic acid molecule in step (a). As used herein, the term "toehold primer" refers to an oligonucleotide primer configured to add a detectable tag or label sequence, where the tag or label sequence is detectable by a downstream nucleic acid sensor.

Primers and sgRNAs can readily be designed for a given variant according to the principles described herein. Cas9 selectively cleaves DNA only in the presence of an NGG protospacer adjacent motif (PAM). As demonstrated herein, e.g. in Example 1, numerous strain-specific PAM sites exist. The reverse transcription primer is designed to specifically bind near the selected PAM site such that reverse transcription proceeds towards the PAM site. The sgRNA and/or guide RNA is then designed to specifically bind to a sequence located between the PAM site and the sequence to which the reverse transcription primer specifically binds. Tools for designing primers and sgRNAs are known in the art. For example, a primer sequence can be selected to have a desired $T_M$ (melting temperature) using any of a number of widely available algorithms (e.g., OLIGO™ (Molecular Biology Insights Inc. Colorado) primer design software and VENTRO NTI™ (Invitrogen, Inc. California) primer design software and programs available on the internet, including Primer3 and Oligo Calculator). Algorithms are also widely available for sgRNA design (e.g., several online tools (e.g., The Broad Institute's sgRNA Design tool, CRISPR Design or CHOPCHOP, which are available on the internet). Methods of making primers and other nucleic acid sequences (e.g., oligonucleotides, sgRNAs) are well known in the art, and numerous commercial sources offer oligonucleotide synthesis services suitable for providing molecules according to the methods and compositions described herein, e.g. INVITROGEN™ Custom DNA Oligos; Life Technologies; Grand Island, N.Y. or custom DNA Oligos from IDT; Coralville, Iowa).

In some embodiments of any of the aspects, the sequence variant being detected differentiates the African and American Zika virus strains. In some embodiments of any of the aspects, the sequence variant is the SNP occurring at site 7330 of the African (GenBank: KF268950) and American (GenBank: KU312312) Zika strains. In some embodiments of any of the aspects, the sgRNA has the sequence of SEQ ID NO: 1. In some embodiments of any of the aspects, the method differentiates the African and American Zika virus strains by detecting the presence or absence of the SNP occurring at site 7330 of the African (GenBank: KF268950) and American (GenBank: KU312312) Zika strains, and the sgRNA has the sequence of SEQ ID NO:1.

Articles of Manufacture

In another aspect, the present invention provides articles of manufacture useful for detecting a virus or identifying a virus strain. In preferred embodiments, the article of manufacture is a kit for detecting a virus, where the kit comprises a plurality of preserved paper test articles and an electronic optical reader. Optionally, a kit can further include instructions for performing the virus detection and/or strain identification methods provided herein.

In some aspects of any of the embodiments, described herein is a composition comprising a Cas nuclease and a sgRNA which can specifically bind to at least one sequence variant occurring in a population. In some aspects of any of the embodiments, described herein is a composition comprising a Cas9 nuclease and a sgRNA which can specifically bind to at least one sequence variant occurring in a population, wherein the sequence variation occurs at the Cas9 PAM binding site.

In some aspects of any of the embodiments, described herein is a composition comprising a Cas nuclease and a sgRNA which can specifically bind to at least one sequence variant occurring in a viral population. In some aspects of any of the embodiments, described herein is a composition comprising a Cas9 nuclease and a sgRNA which can specifically bind to at least one sequence variant occurring in a viral population, wherein the sequence variation occurs at the Cas9 PAM binding site.

In some aspects of any of the embodiments, described herein is a composition comprising a Cas nuclease and a sgRNA which can specifically bind to at least one sequence variant occurring in a Zika virus population. In some aspects of any of the embodiments, described herein is a composition comprising a Cas9 nuclease and a sgRNA which can specifically bind to at least one sequence variant occurring in a Zika virus population, wherein the sequence variation occurs at the Cas9 PAM binding site.

In some aspects of any of the embodiments, described herein is a composition comprising a Cas nuclease and a sgRNA which can specifically bind to at least one sequence variant selected from Table 10. In some aspects of any of the embodiments, described herein is a composition comprising a Cas9 nuclease and a sgRNA which can specifically bind to at least one sequence variant selected from Table 5, wherein the sequence variation occurs at the Cas9 PAM binding site.

In some aspects of any of the embodiments, described herein is a composition comprising a Cas9 nuclease and a sgRNA comprising SEQ ID NO:1. In some aspects of any of the embodiments, described herein is a composition comprising a Cas9 nuclease and a sgRNA comprising SEQ ID NO:1, wherein the sequence variation occurs at the Cas9 PAM binding site. In some embodiments of any of the aspects, the sgRNA consists of SEQ ID NO:1.

In some aspects of any of the embodiments, described herein is a sgRNA which can specifically bind to a sequence flanking at least one sequence variant selected from Table 5, wherein the sequence variation occurs at a Cas9 PAM binding site. In some aspects of any of the embodiments, described herein is a composition a sgRNA comprising SEQ ID NO:1. In some aspects of any of the embodiments, described herein is a composition a sgRNA consisting of SEQ ID NO:1.

Methods for sgRNA selection and design are described elsewhere herein. In some embodiments of any of the aspects, a sgRNA which can specifically bind to a sequence flanking a given sequence variant can comprise a 20 nt sequence complementary to a sequence found from 1-30 nucleotides from the sequence variation. In some embodiments of any of the aspects, a sgRNA which can specifically bind to a sequence flanking a given sequence variant can comprise a 20 nt sequence complementary to a sequence found from 1-25 nucleotides from the sequence variation. In some aspects of any of the embodiments, a sgRNA which can specifically bind to a sequence flanking a given sequence variant can comprise a 20 nt sequence complementary to a sequence found from 1-20 nucleotides from the sequence variation.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein, "about" means within 5% of a stated concentration range or within 5% of a stated time frame.

It should also be understood that, unless clearly indicated to the contrary, in any methods claimed herein that include more than one step or act, the order of the steps or acts of the method is not necessarily limited to the order in which the steps or acts of the method are recited.

Having now described the invention, the same will be illustrated with reference to certain examples, which are included herein for illustration purposes only, and which are not intended to be limiting of the invention.

EXAMPLES

Reference is now made to the following examples, which together with the above descriptions illustrate the invention in a non-limiting fashion.

Example 1: Rapid, Low-Cost Detection of Zika Virus Using Programmable Biomolecular Components Materials and Methods In Silico Sensor Design and DNA Synthesis:

A set of 48 toehold switch sensors and corresponding NASBA primers were generated using an integrated in silico design algorithm.

Figures 3A, 3B, 3C:
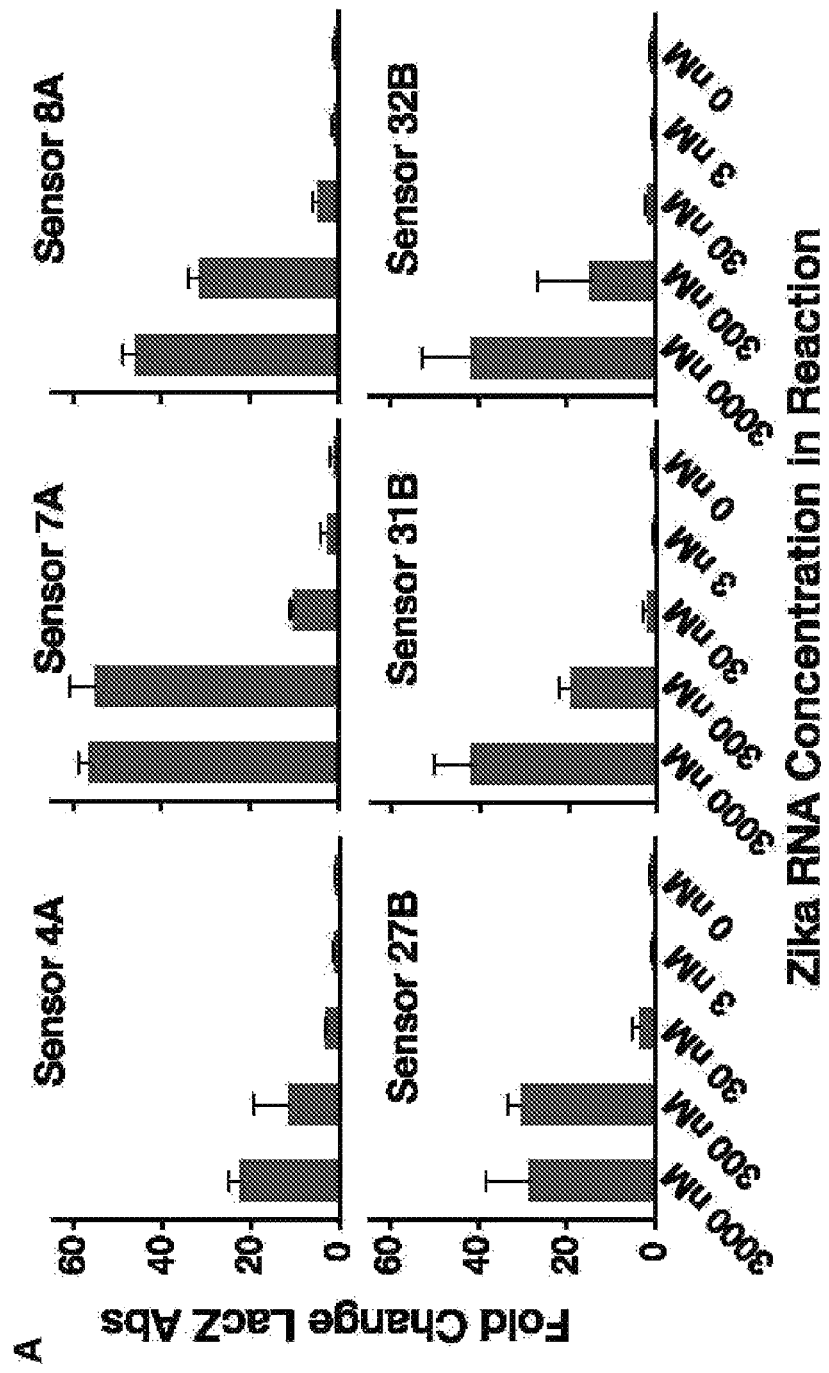
FIGS. 3A-3C demonstrate detection of femtomolar (fM) concentrations of Zika virus RNA fragments. (A) Sensitivity of six of the best performing Series A and B sensors without RNA amplification. Fold change is calculated from absorbance (570 nm) after 30 minutes at 37° C. Error bars represent SD from three replicates. (B) A schematic of NASBA (nucleic acid sequence based amplification)-mediated RNA amplification. (C) Zika RNA fragments diluted in water or 7% human serum were amplified using NASBA with input concentrations ranging from 30 pM down to 3 fM. A 1:7 dilution of the NASBA reaction in water was then used to rehydrate freeze-dried, paper-based reactions containing sensors 27B and 32B. Fold change is calculated as described in (A) after 30 minutes at 37° C.

DNA Sensor Assembly:

Toehold switch constructs were amplified from DNA templates (Integrated DNA Technologies) and ligated to the lacZ reporter gene via PCR. Plasmids were constructed for characterization of the top six toehold switches (FIG. 3A). The DNA templates were amplified using PCR and inserted into pET system parent plasmids (EMD Millipore) using Gibson assembly (Gibson et al., 2009) with 30 bp overlap regions. Plasmids for sensors 27B and 32B are available through Addgene (plasmid numbers: 75006-75011).

Cell-Free Reactions:

Details of RNA sensor validation are described in Pardee et al. (2014). Briefly, amplified sensor DNA was column purified and tested on paper discs (2 mm) containing freeze-dried, cell-free reactions (NEB, PURExpress) in the presence or absence of trigger RNA coding for a complementary region of the Zika virus genome (128-178 nts). The cell-free reactions consisted of: NEB Solution A (40%) and B (30%), chlorophenol red-b-D-galactopyranoside (Sigma, 0.6 mg/ml), RNase inhibitor (Roche, 03335402001; 0.5%), and linear DNA constructs encoding the toehold sensors (0.33 nM). The paper discs (Whatman, 1442-042) were blocked in 5% BSA overnight prior to use. Trigger RNA was produced using T7 RNAP-based transcription (Epicenter ASF3257) from linear DNA templates. Paper-based reactions (1.8 µl) were incubated at 37° C. using either our companion electronic reader inside a humidified chamber or a plate reader (BioTek Neo). For the in-house reader, paper discs were placed into 2 mm holes in a removable acrylic chip; for the plate reader, paper discs were placed into black, clear bottom 384-well plates (Corning 3544).

NASBA:

For NASBA reactions, the trigger elements (128-178 nts) were extended by 100 nts on the 5' and 3' ends with the relevant Zika genome sequence to provide suitable template RNAs. RNA amplicons were spiked into 7% human serum (Sigma H4522) where indicated. Reaction Buffer (Life Sciences NECB-24; 33.5%), Nucleotide Mix (Life Sciences NECN-24; 16.5%), RNase inhibitor (Roche, 03335402001; 0.5%), 12.5 mM of each NASBA primer (2%), nuclease free water (2.5%), and RNA amplicon (20%) were assembled at 4° C. and incubated at 65° C. for 2 min, followed by a 10 min incubation at 41° C. Enzyme Mix (Life Sciences NEC-1-24; 25%) was then added to the reaction (for a final volume of 5 and the mixture was incubated at 41° C. for 2 hr. unless noted otherwise. For output reads with paper-based toeholds, the NASBA reactions were diluted 1:7 in water. See Table 2 for primer sequences.

Lentivirus Preparation and Processing:

HEK293FT cells (Life Technologies, R70007) used for virus packaging were cultured in DMEM supplemented with 10% FBS, 1% penicillin-streptomycin, and 4 mM GlutaMAX (ThermoFisher Scientific). 12 hr. prior to transfection, $6.5 \times 10^6$ cells were seeded in a 10 cm dish. 7.5 mg psPAX2, 2.5 mg pMD2.G, and 10 mg pSB700 modified to include a Zika or Dengue RNA fragment were transfected using the HeBS—CaCl$_2$ method. Media was changed 12 hr. post-transfection. 27 hr. after changing media, viral supernatant was harvested and filtered using a 0.45 mm syringe filter. Viral supernatant was then purified with ViraBind Lentivirus Purification Kit (Cell Biolabs VPK-104) and buffer exchanged into 1×PBS with Lenti-X Concentrator (Clontech, 631231). Viral RNA concentration was quantified using QuickTiter Lentivirus Quantification Kit (VPK-112). Virus samples were spiked into 7% human serum at a final volume of 25 μl. Samples were heated to 95° C. for 1 and 2 min and used as input to NASBA.

Zika Virus Preparation and Processing:

100 μl of Zika virus isolate (MR 766) was utilized for infection of 106 Vero cells in 4 ml of media (DMEM supplemented with 2% fetal calf serum [FCS] and penicillin-streptomycin). The supernatant was removed after 2 hr. of incubation at 37° C. and replaced with fresh media (DMEM, 10% FCS) for 48 hr. of infection. Cell debris was removed by centrifugation at 1,500 rcf for 10 min, and aliquots of the virus were stored at −80° C. until use. The virus was buffer exchanged into 1×PBS with Lenti-X Concentrator (Clontech, 631231). Viral RNA concentrations were determined from virus purified with the QIAamp Viral RNA Mini Kit (QIAGEN 52904) and confirmed with qRT-PCR. The titer of the Zika virus used was $6.7 \times 10^7$ infectious units per milliliter (Lambeth et al., 2005). Virus samples were spiked into 7% human serum at a final volume of 30 μl. Samples were heated to 95° C. for 2 min and used as input to NASBA. NASBA primers were re-designed to accommodate the MR 766 strain sequence.

Dengue Orthogonality:

Genomic RNA from three Dengue serotypes was purified using the QIAamp Viral RNA Mini Kit (QIAGEN 52904). Dengue 1 (GenBank: KM204119), Dengue 2 (GenBank: KM204118), Dengue 4 (GenBank: AF326573). NASBA reactions using the sensor 32B primer set were performed on 30 pM RNA for 2 hr. NASBA reactions were diluted 1:7 in water and used to rehydrate freeze-dried, paper-based reactions containing sensor 32B.

Electric Optical Reader:

The portable device consists of four layers housed within a laser-cut acrylic box fastened together with metal screws and mounting brackets (FIG. 7; McMaster-Carr, 8505K14, 98164A061; Digi-Key, 36-621-ND). The top layer holds a multiplexer (Sparkfun, BOB-09056), solderable breadboard (Sparkfun, PRT-12702), friction lock connectors (Digi-Key, A31001-ND, A19473-ND) and 16 LEDs (Digi-Key, 754-1262-ND). The LEDs have a very narrow viewing angle and an emission of 570 nm to match the absorbance maximum of the chlorophenol red product from the LacZ reaction. The LEDs were placed in close proximity to the chip in the middle layer, which holds 16 paper disks within 2 mm apertures. The apertures prevented transmission of stray light and were coaxial with the LEDs in the top layer and the array of 16 TSL2591 sensors (Adafruit, 1980) in the third layer below, which also contained two solderable breadboards and connectors as above. The bottom layer contains the Arduino Uno with an attached Power Shield (Adafruit, 2708) connected to a rechargeable 2,000 mAh lithium ion battery (Adafruit, 2011) on which a datalogging shield (Adafruit, 1141) was stacked with connectors (Digi-Key, A30954-ND, A19476) and a 4 GB SD/MicroSD Card (Adafruit, 102). To prevent crosstalk between reads, reactions were read in series by sequentially activating each LED and sensor pair. The read frequency and pattern of the reader can be easily adjusted by modifying and uploading alternative sketches to the Arduino. The raw data (which is the median of 29 100 ms, 4283 gain reads per minute) was saved to the SD card along with the date and time of the run, integration time and gain settings. The data were processed with the MATLAB script and graphed in Prism. A diagram of the circuit and an overview of the laser cut parts can be found in FIG. 7, and laser cutting patterns, the Arduino sketch, and MATLAB script are in Appendix A.

Calculation of Fold Change:

The calculation of fold change for plate reader data was done by first subtracting the background absorbance measured from paper-based reactions that did not contain sensor DNA or trigger RNA. These normalized values were smoothed to reduce measurement noise using a three-point average of the time point and the data collected 10 min before and after. The minimum value of each well was then adjusted to zero. For data presented in FIGS. 3, 6, and 10, fold change was calculated from these zero adjusted values by dividing the wells at each time point by the average signal from the corresponding sensor-alone control wells. For our initial sensor screen (FIG. 2), we used a more sensitive measure of fold change based on the difference in the rate of color change between control and RNA trigger wells. This was done by calculating the rate of change in normalized absorbance (570 nm) values using slope; where, at each 10 min time point, the rate was calculated using $S_n = (T_{n+1} - T_n)/10$, where T is the normalized data at a time point ($T_n$) and the time point 10 min later ($T_{n+1}$), and $S_n$ is the slope reported for $T_n$. Fold change was then calculated as above. MATLAB script to analyze data collected on a plate reader is provided in Appendix A.

NASBA-CRISPR Cleavage (NASBACC):

Reactions were performed in a 5 μl volume containing (NASBA buffer), 1 μl of a 250 nM Cas9 nuclease (NEB, M0386), and 250 nM purified gRNA (GeneArt precision gRNA synthesis kit, ThermoFisher Scientific, A29377) mix, 3 nM NASBACC primers, and 0.4 units of RNase inhibitor (NEB, M0314). The forward NASBACC primer is composed of the reverse complement of the trigger H sequence (5'-GTT TGA ATG AAT TGT AGG CTT GTT ATA GTT ATG TTT-3' (SEQ ID NO: 3)) and the forward binding sequence of the (region 32) NASBA primers. The reverse NASBACC primer contains the T7 promoter sequence (5'-CTA ATA CGA CTC ACT ATA GG-3' (SEQ ID NO: 4)) followed by the reverse binding sequence of the (region 32) NASBA primers. The assembled reaction was incubated at 37° C. for 2 to 6 hours. For toehold activation assay on freeze-dried paper, NASBACC reactions were diluted 1:10 in nuclease-free water.

Zika Virus Stock Production for Macaque Infection:

ZIKV strain H/PF/2013 (GenBank accession number: KJ776791), originally isolated from a 51-year-old female in France returning from French Polynesia with a single round of amplification on Vero cells, was obtained from Xavier de Lamballerie (European Virus Archive, Marseille France). Virus stocks were prepared by inoculation onto a confluent monolayer of C6/36 mosquito cells. A single harvest of virus with a titer of $1.26 \times 10^6$ PFU/ml for the Asian-lineage (equivalent to $1.43 \times 10^9$ vRNA copies/ml) was used.

Viremic Plasma Processing:

All Indian-origin rhesus macaque monkeys from which plasma was isolated were cared for by the staff at the Wisconsin National Primate Research Center (WNPRC) in accordance with the regulations and guidelines outlined in the Animal Welfare Act and the Guide for the Care and Use of Laboratory Animals and the recommendations of the Weatherall report. This study was approved by the University of Wisconsin-Madison Graduate School Institutional Animal Care and Use Committee (Animal Care and Use Protocol Number G005401). For all procedures (i.e., physical examination, virus inoculation, blood and swab collection), animals were anesthetized with an intramuscular dose of ketamine (10 ml/kg). Blood samples were obtained using a vacutainer system or needle and syringe from the femoral or saphenous vein. For processing, plasma was diluted 1:10 in nuclease free water, heated to 95° C. for 2 min, and immediately added to a NASBA reaction. NASBA was run for 3 hr.

Zika Virus Challenge of Macaques, Plasma Collection, and Processing:

The virus stock was thawed, diluted in PBS to the appropriate concentration for each challenge, and loaded into a 1 ml syringe that was kept on ice until challenge. Animals were anesthetized as described above, and 1 ml of inocula was administered subcutaneously over the cranial dorsum. At the conclusion of the procedure, animals were closely monitored by veterinary and animal care staff for adverse reactions and signs of disease. Fresh plasma and PBMC were isolated from EDTA-treated whole blood by Ficoll density centrifugation at 1860 rcf for 30 min. The plasma layer was collected and centrifuged for an additional 8 min at 670 rcf to remove residual cells. The supernatant plasma was then filtered over a 0.45 µm syringe filter. Collected plasma was diluted 1:10 in nuclease free water. Diluted samples were heated to 95° C. for two minutes and immediately added to a NASBA reaction as described above. NASBA was run for three hours.

qRT-PCR to Determine Macaque Plasma Viral Loads:

Viral RNA was extracted from 300 µl of plasma using the Viral Total Nucleic Acid Purification Kit (Promega) on a Maxwell 16 MDx instrument. Viral RNA was quantified by qRT-PCR using the primers and probe designed by Lanciotti et al. (2008). The RT-PCR was performed using the SuperScript III Platinum one-step quantitative RT-PCR system (Invitrogen) on the LightCycler 480 instrument (Roche Diagnostics). Primers and probe were used at final concentrations of 600 nm and 100 nm, respectively, along with 150 ng random primers (Promega). Cycling conditions were as follows: 37° C. for 15 min, 50° C. for 30 min, and 95° C. for 2 min, followed by 50 cycles of 95° C. for 15 seconds and 60° C. for 1 min. Virus concentration was determined by interpolation onto an internal standard curve composed of seven 10-fold serial dilutions of a synthetic ZIKV RNA fragment based on the Asian lineage.

Results

In Silico Toehold Switch Design:

Toehold switch sensors are programmable synthetic ribo-regulators that control the translation of a gene via the binding of a trans-acting trigger RNA. The switches contain a hairpin structure that blocks gene translation in cis by sequestration of the ribosome binding site (RBS) and start codon. Upon a switch binding to a complementary trigger RNA, sequestration of the RBS and start codon is relieved, activating gene translation (FIGS. 2A-2B) (Green et al., 2014). To allow for colorimetric detection of trigger RNA sequences, the sensors can be designed to regulate translation of the enzyme LacZ, which mediates a color change by converting a yellow substrate (chlorophenol red-b-D-galactopyranoside) to a purple product (chlorophenol red).

Toehold switch sensors for sequence-based detection of Zika virus were generated using an expanded version of the previously developed in silico design algorithm (Green et al., 2014). The modified algorithm screened the genome of the Zika strain prevalent in the Americas (Genbank: KU312312) for regions compatible with RNA amplification and toehold switch activation. The selected Zika genome regions were then computationally filtered to eliminate potential homology to the human transcriptome and to a panel of related viruses, including Dengue and Chikungunya. A total of 24 unique regions of the Zika genome compatible with downstream sensing efforts were identified.

Two toehold switches, each utilizing a different design scheme, were designed for each region, resulting in a total of 48 sensors. The first design scheme, termed the A series, utilizes a modification to the original toehold switch (Green et al., 2014) that reduces the size of the loop domain from 18 nts to 11 nts (FIG. 2A) to discourage loop-mediated docking of the ribosome and therefore reduce leakage in the OFF state. The second design scheme, termed the B series, features a 12-nt loop and incorporates a more thermodynamically stable stem in order to lower OFF state gene expression (FIG. 2B).

Rapid In Vitro Sensor Assembly and Screening:

In vitro assembly and initial screening of all 48 sensors took place in a 7 hr. time period, with low costs associated with sensor development (DNA input $20 USD/sensor) and testing ($0.10-$1/test). All 48 sensors and 24 targeted genomic regions were assembled in-house using in vitro protocols. Toehold switches were constructed by ligating the sensors (~130 nt) to a LacZ reporter element in a single 2 hr. PCR-based step. Sensor performance screening to assess each sensor against its respective trigger RNA element (Zika genome fragment) was completed using low volume, cell-free transcription and translation reactions on paper. We found that 25 (52%) of the 48 sensors produce a fold change of five or greater in the presence of the appropriate trigger element (128-178 nucleotide regions of the Zika genome; FIGS. 2C, 2D). The top-ranked sensors exhibited activation as high as 34-fold over sensor alone (sensor 27B) and were activated in as quickly as 20 minutes after incubation at 37° C. (sensors 7A and 8A). For all sensors, maximum fold change occurred within the first 90 min. Averaging the LacZ output from sensors not exposed to trigger RNA confirmed that the low background design of the series B toehold switch sensors successfully reduced signal leakage (FIG. 2D, inset).

Figures 4A, 4B, 4C, 4D, 4E, 4F:
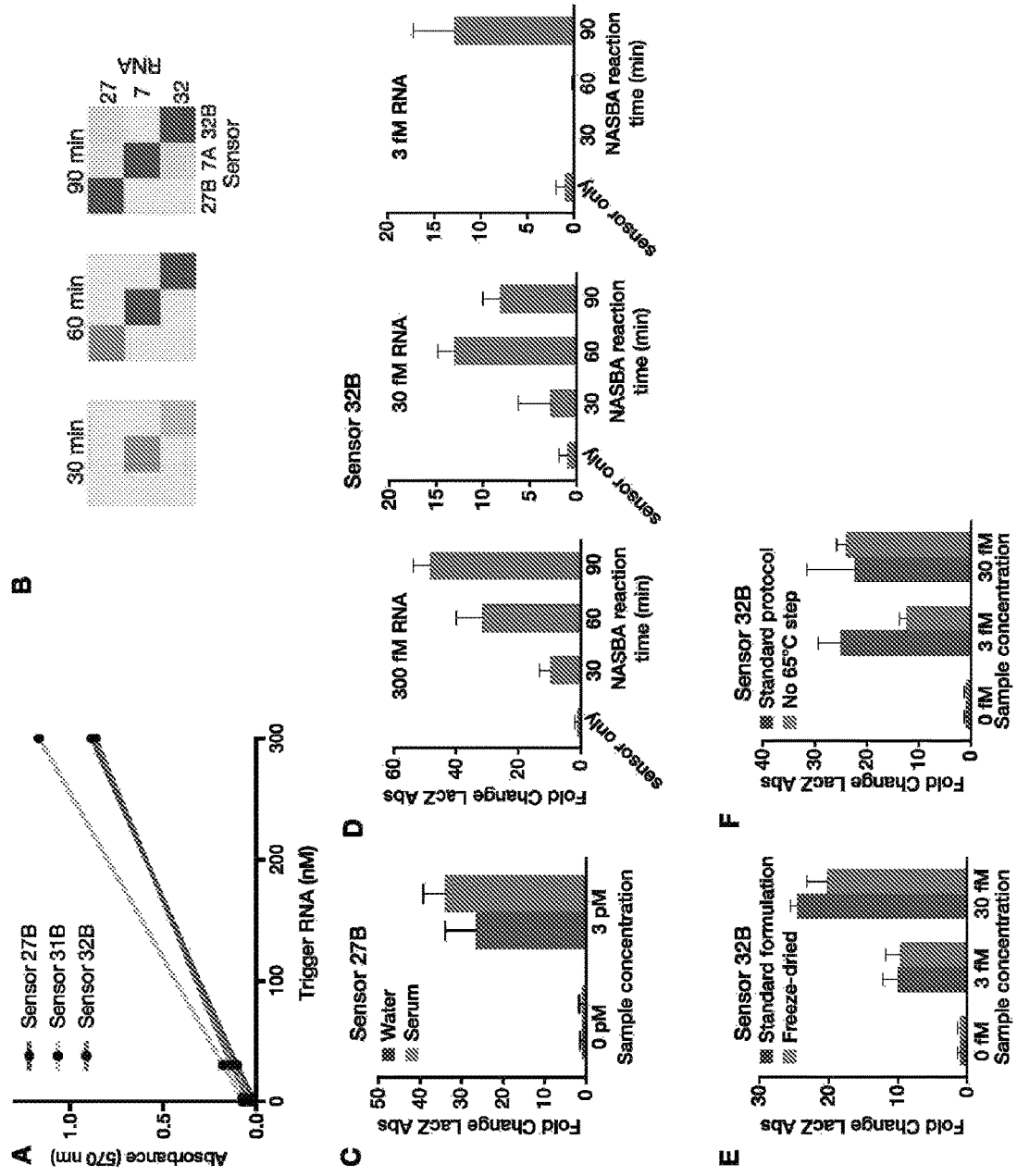
FIGS. 4A-4F demonstrate sensor specificity and sensitivity. (A) Linear response of sensors 27B, 31B and 32B to corresponding RNA trigger at 0 nM, 3 nM, 30 nM and 300 nM. Each point represents the mean of triplicate data taken at 60 min. (B) Orthogonality of sensors 27B, 7A and 32B to treatments of 3000 nM of trigger RNA from each of the three sensors. The absorbance output (570 nm) of the sensors at each time point was converted to a ratio of the maximum absorbance of respective sensor at the 90 min time point and plotted as a heat map. Yellow indicates no sensor activation and purple indicates maximum sensor activation. (C) Reproducibility of NASBA reactions. Samples of Zika RNA in water or 7% human serum were amplified in three independent 2 hr. NASBA reactions. Each NASBA reaction was diluted 1:7 in water and used to rehydrate three freeze-dried, paper-based reactions containing sensor 27B for a total of nine replicates. Fold change was calculated from absorbance (570 nm) after 30 minutes at 37° C. Error bars represent SD from nine replicates for the 3 pM sample and three replicates for the 0 pM sample. (D) Effect of NASBA reaction time on sensitivity. Samples of Zika RNA in 7% human serum were amplified in NASBA reactions for 30, 60, and 90 minutes. Diluted NASBA reactions (1:7) were tested with sensor 32B. Fold change was calculated as above. Error bars represent SD of three replicates. (E) NASBA with freeze-dried reagents. Samples of Zika RNA in 7% human serum were amplified by NASBA reagents in the standard formulation and by reagents freeze-dried in-house. Fold change and error bars were calculated as above after 60 minutes. (F) Removing the 65° C. step from NASBA protocol. Samples of Zika RNA in 7% human serum incubated at 95° C. for two minutes, mimicking viral lysis, and then amplified by NASBA according to the standard procedure without the 65° C. step. Fold change and error bars were calculated as above after 60 minutes.

Assessing and Improving Zika Virus Sensor Sensitivity:

We selected top performing sensors from both the A and B series for trigger RNA titration experiments and found that all chosen sensors were activated with as little as 30 nM of trigger RNA (FIG. 3A). The sensors displayed a linear response to RNA concentration, providing semi-quantitative information on input trigger RNA values (FIG. 4A). Additionally, our top three sensors were highly orthogonal to each other when challenged with a high dose of trigger RNA from off-target Zika sequences (3,000 nM) (FIG. 4B).

Though the sensors displayed specificity for their respective Zika RNA trigger, they were unable to detect clinically relevant RNA concentrations. Zika viral loads have been documented as high as $202 \times 10^6$ copies/ml (365 fM) in urine (Gourinat et al., 2015). However, viral loads in saliva and serum are reportedly even lower, with $3 \times 10^6$ copies/ml (4.9 fM) (Barzon et al., 2016) documented in patient saliva and $2.5 \times 10^6$ copies/ml (4.1 fM) (Zika Experimental Science Team, 2016) and $7.2 \times 10^5$ copies/ml (1.2 fM) (Lanciotti et al., 2008) in primate and patient serum, respectively. Accordingly, to increase the sensitivity of our diagnostic platform, we incorporated an isothermal RNA amplification technique known as NASBA (nucleic acid sequence-based amplification) into our workflow (FIG. 1).

NASBA is a promising candidate for use with our diagnostic scheme because it is known to be extremely sensitive and has a proven track record in field-based diagnostic applications (Cordray and Richards-Kortum, 2012). The amplification process begins with reverse transcription of a target RNA that is mediated by a sequence-specific reverse primer to create an RNA/DNA duplex. RNase H then degrades the RNA template, allowing a forward primer containing the T7 promoter to bind and initiate elongation of the complementary strand, generating a double-stranded DNA product. T7-mediated transcription of the DNA template then creates copies of the target RNA sequence. Importantly, each new target RNA can be detected by the toehold switch sensors and also serve as starting material for further amplification cycles. NASBA requires an initial heating step (65° C.), followed by isothermal amplification at 41° C. (FIG. 3B) (Guatelli et al., 1990).

NASBA was performed on trigger RNA corresponding to Zika genomic regions for sensors 27B and 32B. Trigger RNAs were spiked into either water or human serum (7%) to more closely mimic clinical samples. NASBA reactions were run for 2 hr. and then applied to freeze-dried, paper-based sensors. We saw detection with Zika sensors from NASBA reactions initiated with as little as 3 fM of trigger RNA (FIG. 3C), a value within the range of reported patient viral loads. Zika sensor detection of NASBA-amplified trigger RNA proved to be reliable on samples spiked into either serum or water (FIG. 4C). Additionally, for reactions initialized with high concentrations of trigger RNA (>300 fM), NASBA reaction times could be reduced to as little as 30 minutes (FIG. 4D). NASBA reagents are compatible with freeze-drying (FIG. 4E) and could therefore be easily deployed and utilized alongside our paper-based sensors. We also demonstrated that NASBA can be run in the absence of the initial heating step (65° C.) (FIG. 4F), further reducing the technical and power requirements for deployment.

Field-Ready Diagnostic Platform:

To move our experiments toward conditions more representative of those found in clinics worldwide, we focused on three key efforts: (1) testing sensor specificity against related viruses that share clinical symptoms, partial homology, and geographic range with Zika virus; (2) building a second-generation portable, battery-powered reader to provide lab-quality results in low resource environments; and (3) developing a low-cost and tractable method for viral RNA extraction.

Figures 6A, 6B, 6C, 6D:
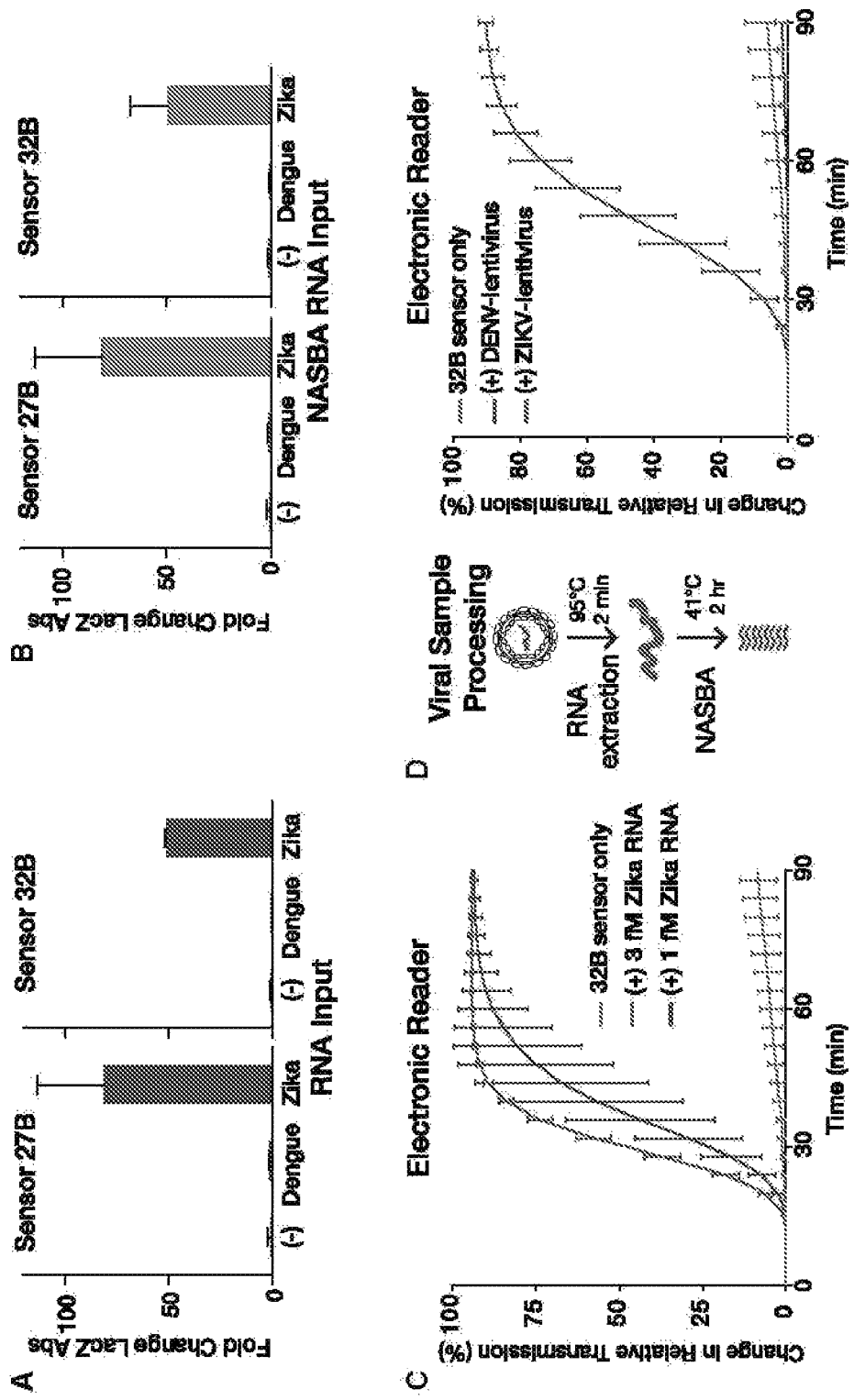
FIGS. 6A-6D present data collected during development of a field-ready diagnostic platform. (A) Sequence specificity of Zika virus sensors 27B and 32B. Sensors were challenged with 3,000 nM of RNA corresponding to target sequences from the Zika virus or the homologous region of the Dengue virus. Fold change is calculated from absorbance (570 nm) at 60 minutes after rehydration and incubation of freeze dried, paper-based reactions at 37° C. Error bars represent SD from three replicates. (B) Zika virus sensors 27B and 32B were tested for specificity using NASBA reaction products derived from 300 fM input RNA corresponding to target genomic regions of the Zika or Dengue viruses in 7% human serum. Fold change was calculated as in (A). (C) Using the portable electronic reader, time-course data were collected for Zika virus sensor 32B in the presence of RNA amplified from 1 fM or 3 fM inputs of trigger RNA in 7% human serum. To increase sensitivity, NASBA reactions were run for 2.5 hours. Graphs plot the relative absorbance of 570 nm wavelength light compared to background, which was collected every minute from freeze-dried, cell-free reactions embedded into paper. (D) Incorporating viral sample processing into the diagnostic workflow. Lentivirus was packaged with Zika RNA or homologous Dengue RNA fragments targeted by sensor 32B. Three femtomolar of virus was spiked into 7% human serum and heated to 95° C. for 2 minutes to extract viral RNA. The boiled lysate was used to initiate NASBA-mediated RNA amplification. A 1:7 dilution of the 2 hours NASBA reaction in water was then used to rehydrate freeze-dried paper-based reactions. Time-course data were collected on the portable electronic reader as in (C).

Although our sensor design algorithm screened for Zika genomic sequences that are mostly distinct from those of related viruses, the targeted Zika sequences do share substantial similarity (51%-59%) with their Dengue virus counterparts (FIGS. 5A-5B). To test the Zika sensors for possible cross-reactivity, we exposed the sensors to regions of the Dengue genome that share a degree of homology with regions targeted in the Zika genome. Sensors 27B and 32B were treated with high concentrations of RNA amplicons (3,000 nM) from either Zika or Dengue genomic regions. As seen in FIG. 6A, Dengue RNA sequences failed to activate the toehold switch sensors. We also tested our NASBA primer sets for specificity to their targeted Zika sequences by applying the NASBA-mediated amplification and paper-based detection scheme to 300 fM inputs of the Dengue and Zika RNA in human serum (7%). Again, no response to the Dengue RNA sequences was observed, demonstrating robust sequence specificity in our amplification and detection scheme (FIG. 6B).

As part of our efforts to advance the paper-based sensor platform toward field-ready diagnostics, we designed a second generation portable electronic reader to serve as an accessible, low-cost companion technology that provides robust and quantitative measurements of sensor outputs. The electronic reader was assembled using readily available consumer components, open-source code, and laser-cut acrylic housing, with a total cost of just under $250 (FIG. 7 and Table 3). The reader is powered by a lithium ion battery (18.5 hr.) that can be re-charged via micro USB and houses onboard data storage (4 GB) to resolve the need for an attached laptop during diagnostic reads (Pardee et al., 2014). To achieve sensitive detection of toehold switch signal output, an acrylic chip that holds the freeze-dried, paper-based reactions is placed into the reader between an LED light source (570 nm) and electronic sensors (FIG. 7B). Using onboard electronics, each sample is read 29 times per minute, providing low-noise measurements of changes in light transmission due to LacZ-mediated color change.

To demonstrate the utility of the companion reader, we monitored detection of 1 fM and 3 fM of Zika RNA amplicons that had been amplified in NASBA reactions for 2.5 hr. The reader detected significant signal from both samples, which are within the reported range of Zika virus in patient serum (1.2 fM) and urine (365 fM) (Gourinat et al., 2015; Lanciotti et al., 2008), after just over 20 min (FIG. 6C).

Our next challenge was to develop a technique to release RNA from the viral capsid using simple methodology compatible with low-resource environments. To this end, we tested the efficacy of boiling viral samples to break down the capsid. For initial development, we engineered lentivirus, which is also an RNA virus, to encapsulate the regions of either the Zika or Dengue genomes that correspond to the sensor 32B target sequence (FIG. 5B). These proxy Zika and Dengue viruses were spiked into human serum (7%) at a final concentration of 3 fM and heated to 95° C. for either 1 or 2 min. The resulting lysates were then immediately used to initiate NASBA reactions, in order to simulate what might be recovered from a patient sample. Boiling the viral samples for one minute was sufficient to release detectable amounts of RNA in our amplification and toehold switch detection scheme (FIG. 5C). NASBA reactions from 2 min boiled samples were also monitored for sensor activation on the portable electronic reader. We detected strong sensor activation in less than 30 minutes from 3 fM of lentivirus carrying Zika RNA. We were also able to demonstrate clear discrimination between lentiviruses containing Zika and Dengue RNA sequences (FIG. 6D).

Figures 8A, 8B, 8C, 8D, 8E:
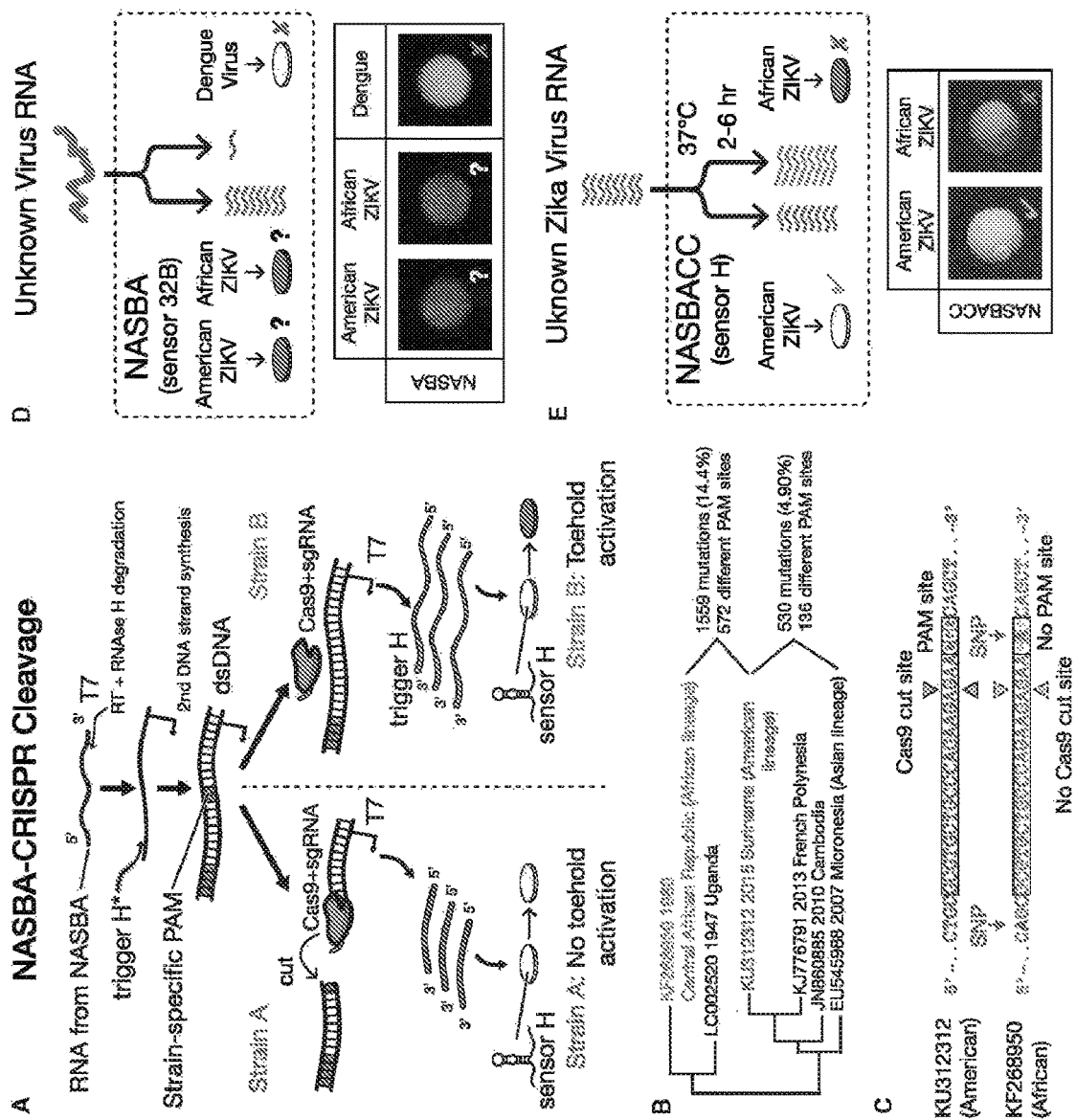
FIGS. 8A-8E illustrate an exemplary protocol for strain differentiation at single-base resolution. (A) Schematic representation of NASBA-CRISPR Cleavage (NASBACC)-genotyping following a positive Zika diagnosis. A synthetic trigger sequence is appended to a NASBA-amplified RNA fragment through reverse transcription. The presence of a strain-specific PAM leads to the production of either truncated or full-length trigger RNA, which differentially activates a toehold switch (sensor H) (Pardee et al., 2014). (B) The probability that a non-biased single nucleotide polymorphism (SNP) between two strains can be discriminated by CRISPR/Cas9 is 48% (Table S4). Hence, genetic drift between the American and African or Asian strains, while relatively small (14.4% and 4.9% sequence dissimilarity, respectively), has created hundreds of strain-specific PAM sites. (C) A SNP between African (GenBank: KF268950) and American (GenBank: KU312312) strains at site 7330 (SEQ ID NOS 782 and 781, respectively) disrupts an existing PAM site, allowing for Cas9-mediated DNA cleavage only in the American strain. (D) Sensor 32B can distinguish between Dengue and Zika RNA sequences but cannot discriminate between American and African Zika strains. Paper discs containing sensor 32B were rehydrated with 300 nM trigger RNA corresponding to sequences from American-Zika, African-Zika, or Dengue. Colorimetric outputs: a purple color indicates the activation of LacZ expression from the toehold switch, and a yellow color indicates the toehold switch remained inactive. (E) NASBACC can discriminate between American- and African-lineages of Zika virus. Paper discs containing sensor H were rehydrated with a 1:10 dilution of NASBACC reactions initiated with 0.05 µl of a 300 nM RNA sample. In this case, an inactive toehold switch leads to a positive identification of the American Zika strain.

NASBA-CRISPR Cleavage Assay to Discriminate Between Zika Strains:

During epidemic outbreaks, it is often valuable to monitor pathogen lineage and geographic spread. In some cases, genetic variants may be responsible for different clinical manifestations of infection. For example, the Zika strain found in Brazil has been uniquely connected with higher incidences of fetal microcephaly and Guillain-Barré syndrome (Calvet et al., 2016; Mlakar et al., 2016). To allow for strain-specific detection and tracking, we developed an assay that provides single-base discrimination in a manner that is compatible with our freeze-dried sensor platform. Our assay, which we term NASBA-CRISPR Cleavage (NASBACC), leverages the sequence-specific nuclease activity of CRISPR/Cas9 to discriminate between viral lineages (FIG. 8A). To do this, NASBACC exploits the ability of Cas9 to selectively cleave DNA only in the presence of an NGG protospacer adjacent motif (PAM). Since any non-biased mutation has a 48% probability of either creating a new PAM site or destroying an existing one (Table 4), there are many strain-specific PAM sites that can be used for lineage discrimination (FIGS. 8B-8C). In the NASBACC detection scheme, RNA sequences undergo NASBA amplification utilizing a reverse primer designed to append the trigger sequence of a synthetic toehold switch (sensor H, FIG. 8A) (Pardee et al., 2014). In the presence of the appropriate PAM sequence and guide RNA target site, the double-stranded DNA that is synthesized as part of the NASBA reaction undergoes Cas9-mediated cleavage, resulting in a truncated RNA product that is unable to activate the sensor H toehold switch. In the absence of the PAM sequence, the full-length RNA product containing the sensor H trigger sequence is generated, allowing for sensor H activation. Trigger RNA is only amplified from DNA that is not cut by Cas9, thereby allowing for strain-specific detection using toehold sensor H.

Using the paper-based system, sensor 32B was able to distinguish between Zika and Dengue RNA sequences. However, this sensor could not discriminate between the African (GenBank: KF268950) and American (GenBank: KU312312) Zika variants (FIG. 8D), a feature that may be useful in certain diagnostic applications. To address this, we applied our NASBACC detection scheme to discriminate between the African and American Zika strains. Due to a single-base difference in the trigger regions of these two strains, a PAM site only exists in the American-lineage sequence (FIG. 8C). Thus, only the American strain sequence was cleaved by Cas9, which led to amplification of truncated RNA that did not activate the sensor H toehold switch (FIG. 8E). Conversely, the African strain sequence does not contain the PAM site and was not cleaved by Cas9, which resulted in amplification of full-length RNA that activated the sensor H toehold switch. Incorporating NASBACC into our diagnostic workflow can provide precise genotypic information within a few hours. As with the other biomolecular elements of this workflow, Cas9 is compatible with lyophilization and could be used in the field (FIG. 9).

Figures 10A, 10B, 10C, 10D:
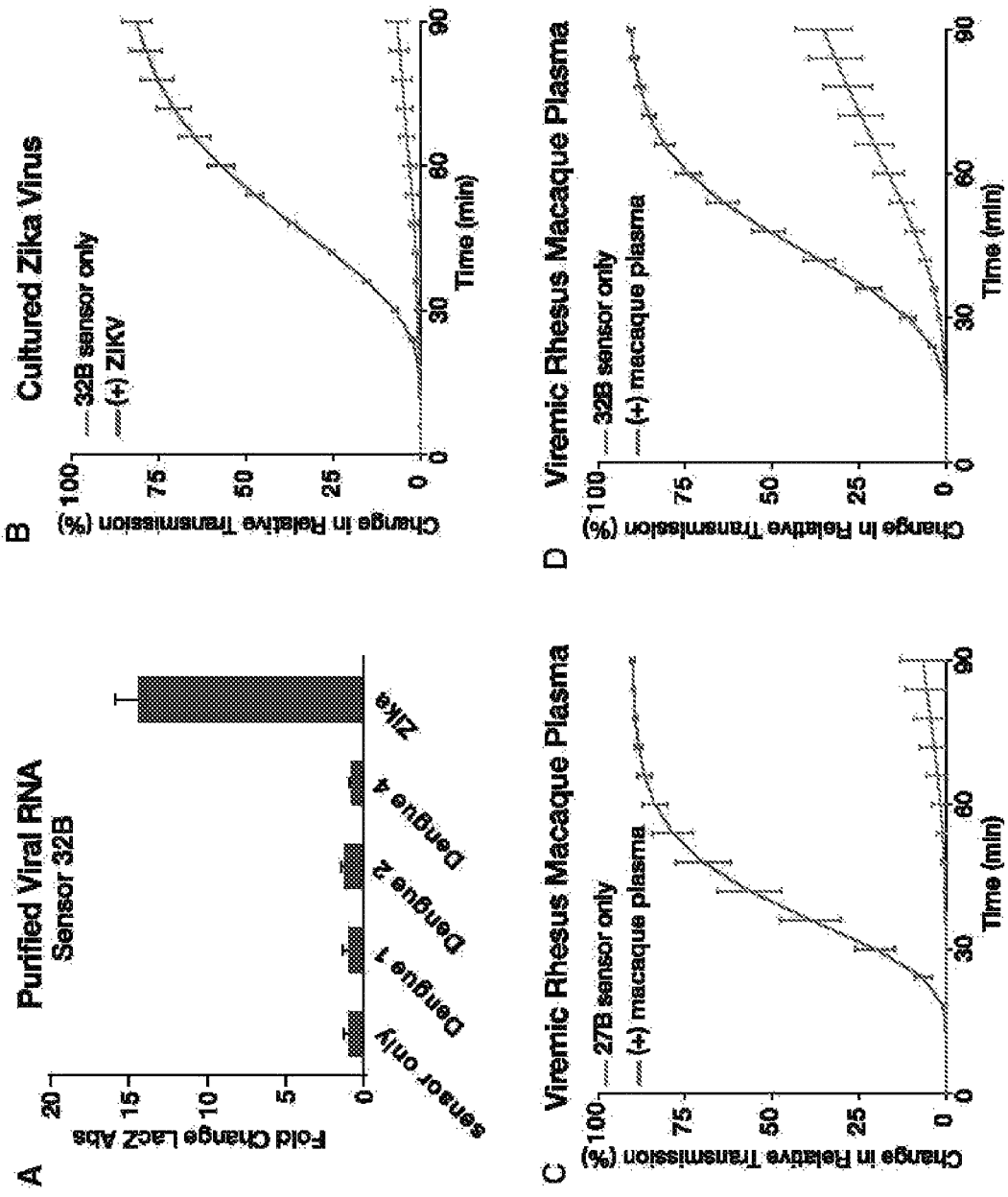
FIGS. 10A-10D are graphs data from assays validating diagnostic workflow on live Zika virus samples. (A) Specificity of sensor 32B against purified genomic RNA. Sensor 32B was tested for specificity using NASBA reaction products performed on 30 fM RNA purified from Zika virus and three different Dengue virus serotypes. Fold change is calculated from absorbance (570 nm) at 60 minutes (min) after rehydration and incubation of freeze-dried, paper-based reactions at 37° C. Error bars represent SD from three replicates. (B) Detection of live Zika virus. Ten femtomolar (fM) of laboratory-cultured Zika virus was spiked into human serum (7%), heated to 95° C. for 2 min, and used to initiate NASBA-mediated RNA amplification. A 1:7 dilution of the 3 hour (hr.) NASBA reaction in water was then used to rehydrate freeze-dried, paper-based reactions. Time-course data were collected on the portable electronic reader. Graph plots the relative absorbance of 570 nm wavelength light compared to background. Error bars represent SD from three replicates. (C and D) Detection of Zika virus in viremic rhesus macaque plasma using sensors 27B and 32B. Plasma containing 2.8 fM of Zika virus was diluted 1:10 in nuclease free water, heated to 95° C. for 2 minutes, and used to initiate NASBA-mediated RNA amplification. 3 hr. NASBA reactions were monitored on the portable electronic reader as in (B).

Diagnostic Workflow Validation with Active Zika Virus:

We next sought to validate our sensor platform with live Zika virus. First, we verified that our amplification and detection scheme could successfully detect full-length genomic RNA purified from Zika virus (Uganda strain MR 766) (FIG. 10A). We designed new NASBA primers to accommodate sequence differences between the Uganda Zika strain (GenBank: AY632535) and the American Zika strain (GenBank: KU312312) that our sensors and primers had originally been designed to detect. Computational analysis suggested that Uganda-lineage Zika RNA would activate sensor 32B despite two base mismatches in the toehold region, and this was confirmed experimentally (FIG. 10A). We also demonstrated sensor orthogonality to full length genomic Dengue RNA isolated from three different Dengue serotypes using these methods (FIG. 10A).

Once we confirmed that the sensors behaved as expected on full-length genomic RNA, we sought to validate the sample preparation scheme and diagnostic workflow from start to finish. Active Zika virus was cultured in the laboratory and spiked into human serum (7%) at a final concentration of 10 fM, to mimic a clinical sample. The viral sample was then heated to 95° C. for 2 min, and the resulting lysate was subjected to NASBA amplification for three hours. Sensor activation from the NASBA-amplified viral sample was monitored on the portable electronic reader. We successfully detected activation of sensor 32B from a diagnostic workflow initiated with live Zika virus (FIG. 10B).

For the final validation of our system, we acquired and tested plasma samples from a viremic macaque infected with Zika virus (GenBank: KJ776791) (Zika Experimental Science Team, 2016). The macaque was found to have a plasma viral load of $1.7 \times 10^6$ copies/ml (2.8 fM) by a standard qRT-PCR protocol, which was within the detection limits of our platform as tested on synthetic RNA amplicons (FIG. 6C). The viremic plasma was diluted 1:10 in water to reduce known inhibitory effects of plasma on downstream reactions and was then taken through our sample processing and diagnostic workflow. The sample was heated to 95° C. for 2 min and then amplified via NASBA for 3 hr. Paper-based reactions were monitored on the portable electronic reader and showed strong activation with both sensors 27B and 32B in less than 30 min (FIGS. 10C-10D).

In Silico Strategy for Toehold Switch Sensor and NASBA Primer Design.

An integrated in silico strategy was developed for generating optimal NASBA primers and toehold switches for detection of Zika. Mirroring the procedure used for running the paper-based diagnostic assay, a set of optimal primers was initially generated for the NASBA reaction and then a series of toehold switch designs screened for activity on the RNA transcripts produced by NASBA was developed.

Identification of Optimal NASBA Primers for Zika Amplification.

A set of potential primer pairs with favorable characteristics for NASBA reactions as described by Deiman et al. (Deiman et al., 2002) was generated. The Zika genome was analyzed to identify all potential forward and reverse priming sites that had the following characteristics:

GC content between 40-60%
Template hybridization regions of 20- to 24-nts and with DNA melting temperatures above 41° C.
No consecutive runs of four or more nucleotides
An A base at the final 3' nucleotide
Minimal DNA primer internal secondary structure, including the T7 promoter region
Minimal DNA primer dimer formation probability
Higher GC content in the 6-nts at the 5' end of the primer that hybridized to the template
Higher AT content in the 6-nts at the 3' end of the primer All subsequences from the Zika genome that did not satisfy requirements 1 to 4 were immediately eliminated from consideration. The remaining primers were then analyzed for characteristics 5-8 and the deviation from optimal 50% GC content, with each parameter converted into a numerical score. The forward NASBA primers, which append the T7 promoter site to NASBA DNA intermediate, were modeled with this T7 promoter site present. Accordingly, the prefix sequence AATTCTAATACGACTCACTATAGGGAGAAGG (SEQ ID NO: 5) (T7 promoter sequence underlined) was appended to the 5' end of each forward primer. The resulting scores were combined and used to estimate the overall favorability of every potential primer in the Zika genome. Following this initial screen, the top 2% of all the potential primers were then compared to the rest of the Zika genome to determine the longest contiguous region of the primer that matched more than one site in the genome. This comparison provided a coarse check of primer specificity in advance of more detailed primer specificity screening conducted later in the design process. The length of this contiguous region for each primer was then incorporated into a final score for each primer.

The first stage of screening resulted in a set of forward and reverse primers to provide optimal characteristics for binding to the target genome; however, it did not consider other important effects on NASBA efficiency, namely the length and secondary structure of the amplicon produced by NASBA. To consider these amplicon-related effects, the binding sites for each primer on the genome were identified and, if more than one primer acted at the same site, the primer awarded the highest favorability score was selected.

A set of potential forward and reverse primer pairs was constructed based on the recommended amplicon lengths for successful NASBA reactions. Although NASBA is known to work best with amplicons having lengths between approximately 120-nts to 250-nts (Deiman et al., 2002), this rapid screening approach initially employs synthetic DNA strands as templates for transcribing the target RNA. Since the length of these DNA oligos (IDT Ultramers) is currently limited to 200-nts including the T7 promoter site, primer pairs were instead examined for amplicons ranging from 120- to 176-nts in length. After applying all the above constraints on primer and amplicon sequences, a set of 4351 potential NASBA primer pairs remained. The RNA amplicons generated for each of these primers pairs were then assessed for their secondary structure. NASBA reactions are known to be more effective when applied to templates having low secondary structure. Consequently, the degree of amplicon single-strandedness was examined using the NUPACK ensemble defect function (Zadeh et al., 2011a, 2011b).

Next, each of the potential NASBA primers were then coarsely screened for sequence similarities with 11 viruses known to be closely related to Zika: Dengue virus 1, Dengue virus 2, Dengue virus 3, Dengue virus 4, West Nile virus, St. Louis encephalitis virus, yellow fever virus, Powassan virus, Semliki Forest virus, O'nyong'nyong virus, and Chikungunya virus. Sequence similarities were estimated by determining the maximum contiguous sequence in the primer that was found in any of the 11 related viruses. More stringent specificity screening was carried out in later stages as described below.

After all the above screening procedures, the final NASBA primer pairs were sorted by quality after taking into account the favorability scores of each primer, the secondary structure of the amplicon, and the potential for non-specific binding with other viruses.

Identification of Optimal Toehold Switches for NASBA Products.

Out of the 4351 NASBA amplicons, the top 1025 were selected as potential targets for toehold switches. The in silico design process for these toehold switches followed closely that previously used for designing mRNA sensors in vivo (Green et al., 2014) and on paper (Pardee et al., 2014). Briefly, toehold switch mRNA sensors were designed that hybridized to the NASBA amplicon at 1-nt increments. This sliding window encompassed the internal region of the NASBA product outside of the primer binding sites. This internal region was selected to avoid any potential for sensor activation or competitive binding by residual NASBA primers. The resulting toehold switches were analyzed for secondary structure and toehold availability, and screened to eliminate any sensors with unwanted in-frame stop codons in the output gene sequence. The target transcript itself was again assayed for single-strandedness and availability of the sensor binding sites. The above factors were incorporated into a sensor design score as described previously (Green et al., 2014). The highest scoring toehold switch sensor for each amplicon was then passed on to the final selection stage.

Final Design Selection Process.

After the above screening and design stages, the set of 1025 NASBA primer pairs was assembled with corresponding optimized toehold switch sensors. The top overall designs were selected by combining the favorability scores obtained from the NASBA and toehold switch evaluation steps. The primer and sensor sequences from these top designs were then tested for specificity against the human transcriptome and the same panel of closely related viral genomes listed above using NCBI/Primer-BLAST. Moreover, they were screened for specificity within the Zika genome itself. Ultimately, the top 24 designs that survived the Primer-BLAST specificity stage were selected for testing using our rapid in vitro screening approach.

Modifying the Toehold Switch Sensor Design for Decreased Signal Leakage.

Detailed studies of the toehold switch design parameters (Green et al., 2014) and thermodynamic considerations suggested two simple strategies for decreasing leakage from the toehold switches: reducing the size of the loop containing the ribosome binding site (RBS) in the sensor, and further stabilization of the sensor stem. Both these strategies were applied in the Zika-specific toehold switches.

The ON and OFF state signals from the toehold switches increase as the size of the loop in the switch RNA increases. This effect is likely due to two factors: increased accessibility of the RBS to the ribosome, which promotes translation in the presence or absence of the target RNA; and entropic effects that discourage stem formation as the loop becomes longer. Conversely, decreasing the size of the loop is associated with lower leakage, albeit with a decrease in ON state activity. Stabilizing the switch RNA stem by adding additional base pairs or by eliminating the downstream refolding domain (Green et al., 2014) increases the free energy required to unwind the sensor stem and thus encourages decreased signal leakage.

In accordance with above factors, two different types of toehold switches were tested aiming to lower leakage. The first type of sensor, referred to as the A series, are nearly identical to those previously used for mRNA sensing (Green et al., 2014; Pardee et al., 2014), except their loop domain has been reduced from 18-nts to 11-nts. These A sensors retained the downstream refolding domain to encourage sensor triggering and they all have the same sequence at the top of the sensor stem-loop (GUUAUAGUUAUGAACAGAGGAGACAUAA-CAUGAAC (SEQ ID NO: 6)) as illustrated in FIG. 3A.

The second type of sensor, referred to as the B series, possesses a stem that has been lengthened by one base pair overall and a loop region that is only 12-nts. Importantly, the B sensors also lack the downstream refolding domain to further stabilize the OFF state. The parental toehold switch for the B sensors exhibited extremely low leakage in preliminary measurements in paper-based reactions and provided a sizeable ON/OFF ratio of ~600-fold regulating GFP expression in E. coli. These B sensors all featured the same conserved sequence (GGACUUUAGAACAGAG-GAGAUAAAGAUG (SEQ ID NO: 7)) at the top of their stem-loops as illustrated in FIG. 2B.

Considerations of Sequence Information in Design of the Biomolecular Diagnostics Evolutionary drift. At the time we began our experiments, few complete genomes for the Zika virus had been reported. In fact, the first complete genome of the strain circulating in the Americas was only published on January 7 in The Lancet (Enfissi et al., 2016). However, previous comparisons of Zika strains do provide information on the degree of evolutionary drift for the virus. Haddow et al. found that a Zika strain isolated in Malaysia in 1966 differed by only 4.3% in nucleotide sequence from isolates obtained Micronesia and Cambodia in 2007 and 2010, respectively (Haddow et al., 2012). Authors also found ≤11.7% nucleotide sequence difference between African and Asian virus lineages, which they argued provided sufficient conserved sequence for genetic tests for both lineages. More recent studies have shown the rate of mutation of Zika is ~10-3 nucleotide changes/site/year, which is relatively high among flaviviruses, but a manageable rate for our diagnostic assay (Faria et al., 2016).

Specificity of the NASBA/toehold switch isothermal assay. Since the experiments are performed at mostly 41° C. and 37° C., melting-temperature-dependent tuning of primer specificity is not possible in our assays. The benefit of this temperature limitation is that our NASBA and toehold switch detection schemes are able to tolerate mismatches and compensate for variability in the sequence of the target RNA molecules. The binding between the toehold switch 32B, our highest performing sensor, and RNAs from homologous regions in Zika strains isolated from Africa (Uganda, Nigeria, Senegal) and Asia (Malaysia, Cambodia, French Polynesia) were analyzed. All these strains are predicted to fully activate the toehold sensors even with up to 4-nt (11%) mismatches.

Compensating for evolutionary drift. The above analysis is borne out in data showing that sensor 32B can detect the target sequence from both the American and African strains of the virus (FIG. 8E). This flexibility in sequence detection is balanced with the three combined layers of specificity in our biomolecular approach. This includes the extensive in silico screening of NASBA primers and toehold switch sequences to limit cross-reactivity with off-target sequences and the single-base discrimination of NASBACC. The net result is a programmable platform that can be manufactured to produce diagnostics with both high sequence specificity and the capacity to manage sequence diversity as pathogens evolve. It is also worth mentioning that, in addition to increasing specificity, NASBACC can be used to remove non-specific sequences from samples as well as aid in the discovery mutations in the target regions.

Integration with signature erosion analysis tools. Software such as BioVelocity (Sozhamannan et al., 2015) and TOPSI (Vijaya Satya et al., 2010) are adept at determining conserved sequence regions across multiple genomes and eliminating those shared with other pathogens or humans. Using these valuable tools, a set of specific sites for NASBA priming and toehold switch binding can be generated and then subjected to the same screening by toehold secondary structure and NASBA primer characteristics described in this work.

Freeze-Dried NASBA.

For freeze-dried NASBA experiments, Enzyme Mix was lyophilized separately from the other components. The solution containing reaction buffer, nucleotide mix, RNase inhibitor, and primers was reconstituted in 15% DMSO, while the Enzyme Mix was reconstituted in nuclease-free water.

Freeze-Dried CRISPR/Cas9 Nuclease Assay.

Reactions were performed in a 30 j·tl volume of 1×Cas9 Nuclease Reaction Buffer (NEB #M03865) containing 30 nM of guide RNA (gRNA), 30 nM of Cas9 Nuclease (*S. pyogenes*, NEB #M03865), and 3 nM of substrate DNA (pAG_TS1_KS001 plasmid). Six gRNA sequences targeting the lacZ gene (Doench et al., 2014) inserted into plasmid pAG_TS1_KS001 were used for the CRISPR/Cas9 freeze-dried assay. All components except substrate DNA were first combined in a 27 µl reaction volume and incubated for 10 minutes at 25° C. to allow Cas9+gRNA to form duplexes. For fresh reactions, 3 µl of a 30 nM solution of substrate DNA was added to the solution. For freeze-dried reactions, the 27 µl solution was lyophilized overnight and reconstituted with 30 j·tl of a solution containing 3 nM of substrate DNA. After the addition of substrate DNA, the solution was incubated for 1 h at 37 C and run on a 1% agarose gel for fragment analysis.

Care and Use of Macaques at the Wisconsin National Primate Research Center.

All Indian-origin rhesus macaque monkeys from which plasma was isolated were cared for by the staff at the Wisconsin National Primate Research Center (WNPRC) in accordance with the regulations and guidelines outlined in the Animal Welfare Act and the Guide for the Care and Use of Laboratory Animals and the recommendations of the Weatherall report. This study was approved by the University of Wisconsin-Madison Graduate School Institutional Animal Care and Use Committee (Animal Care and Use Protocol Number G005401). For all procedures (i.e., physical examination, virus inoculation, blood and swab collection), animals were anesthetized with an intramuscular dose of ketamine (10 ml/kg). Blood samples were obtained using a vacutainer system or needle and syringe from the femoral or saphenous vein.

Zika Virus Stock Production for Macaque Infection.

ZIKV strain H/PF/2013 (GenBank accession number: KJ776791), originally isolated from a 51-year-old female in France returning from French Polynesia with a single round of amplification on Vero cells, was obtained from Xavier de Lamballerie (European Virus Archive, Marseille France). Virus stocks were prepared by inoculation onto a confluent monolayer of C6/36 mosquito cells. A single harvest of virus with a titer of $1.26 \times 10^6$ PFU/ml for the Asian-lineage (equivalent to $1.43 \times 10^9$ vRNA copies/ml) was used.

Zika Virus Challenge of Macaques, Plasma Collection and Processing.

The virus stock was thawed, diluted in PBS to the appropriate concentration for each challenge, and loaded into a 1 ml syringe that was kept on ice until challenge. Animals were anesthetized as described above, and 1 ml of inocula was administered subcutaneously over the cranial dorsum. At the conclusion of the procedure, animals were closely monitored by veterinary and animal care staff for adverse reactions and signs of disease. Fresh plasma and PBMC were isolated from EDTA-treated whole blood by Ficoll density centrifugation at 1860 rcf for 30 min. The plasma layer was collected and centrifuged for an additional 8 min at 670 rcf to remove residual cells. The supernatant plasma was then filtered over a 0.45 µm syringe filter. Collected plasma was diluted 1:10 in nuclease free water. Diluted samples were heated to 95 C for two minutes and immediately added to a NASBA reaction as described above. NASBA was run for three hours.

Example 2

Cas9 Interferes with T7-Mediated RNA Production.

RNA can be produced in vitro from a DNA template containing the T7 promoter sequence (5'-TAATACGACT-CACTATAGGG-3' (SEQ ID NO: 768)). If the DNA template has viable CRISPR-Cas9 target sites, addition of Cas9+gRNA complex to the in vitro RNA production reaction leads to the production of truncated RNA product.

In FIG. 11, RNA was produced from a DNA template using NEB's HiScribe™ T7 Quick High Yield RNA Synthesis Kit. In lane 1, Cas9 without a gRNA was added to the reaction. In lanes 2 and 3, Cas9+gRNA that target the LacZ gene at positions 717 (gRNA: cttcagcctccagtacagcg (SEQ ID NO: 769)) and 360 (gRNA: gttcccacggagaatccgac (SEQ ID NO: 770)) was added to the reaction. Truncated RNA products were produced in lanes 2&3, and full-length RNA only in lane 1. Traces were generated using a BioAnalyzer (Agilent).

Cas9 can be Freeze-Dried and Remain Active.

It was next tested whether guide RNA targeting the LacZ sequence contained in the LacZ gene would remain active after being freeze-dried. In particular, a reaction containing Cas9+gRNA complex in Cas9 buffer (NEB #m0386) was freeze dried and re-hydrated with a solution containing 3 nM of template DNA. The template DNA is a supercoiled plasmid containing the LacZ gene.

Figures 9A, 9B:
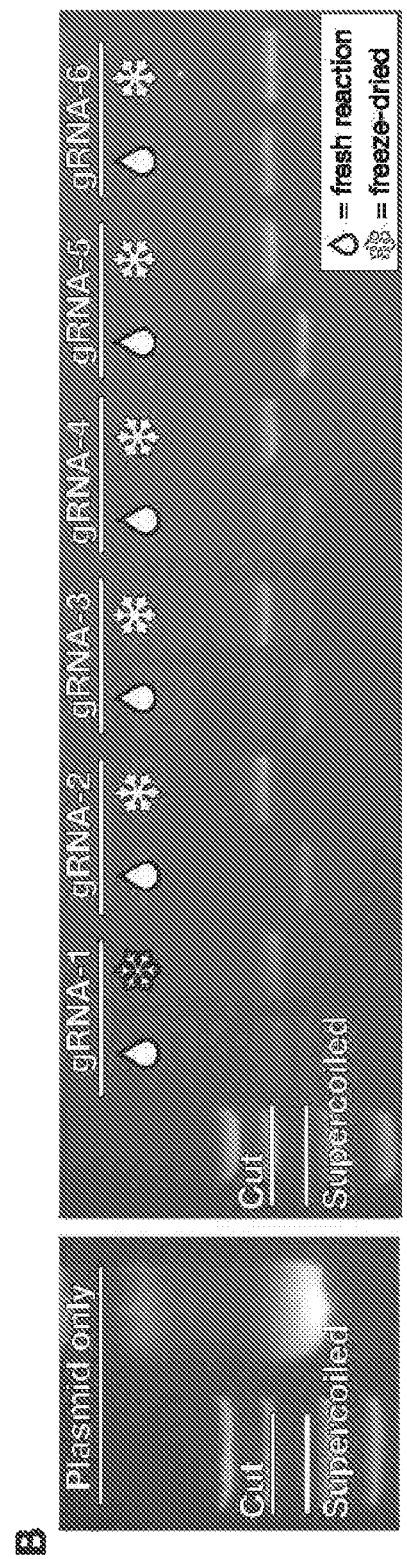
FIGS. 9A-9B present data from a CRISPR nuclease assay using fresh and freeze-dried reactions. (A) Sequence information and location of the gRNA used to target the lacZ gene (SEQ ID NOS 783-788, respectively, in order of appearance). Each sequence was selected for maximum activity using the Doench et al. scoring algorithm (Doench et al., 2014). (B) Gel showing the length of supercoiled versus cut DNA following the in vitro digestion of a lacZ-containing plasmid for fresh and freeze-dried reactions. Note that the activity of some gRNA/Cas9 combinations is improved under freeze-dried conditions.

In FIGS. 9A-9B, the sequence of 6 gRNA is listed and the gel image resulting nuclease reaction is shown. Nuclease activity was maintained for all gRNA target sequences, and some gRNA (#1, 2, 3, 4, 5) showed increase activity following the freeze-drying process).

Cas9 without Guide RNA does not Interfere with NASBA.

The presence of Cas9 nuclease alone does not interfere with NASBA reactions. The non-reactivity of NASBA reactions to Cas9 nucleases was demonstrated by adding Cas9 nuclease and Cas9 buffer to a NASBA reaction. Since the stability of thermal Cas9 has not been demonstrated above 37° C., the NASBA reaction was performed at 37° C.

Figure 12:
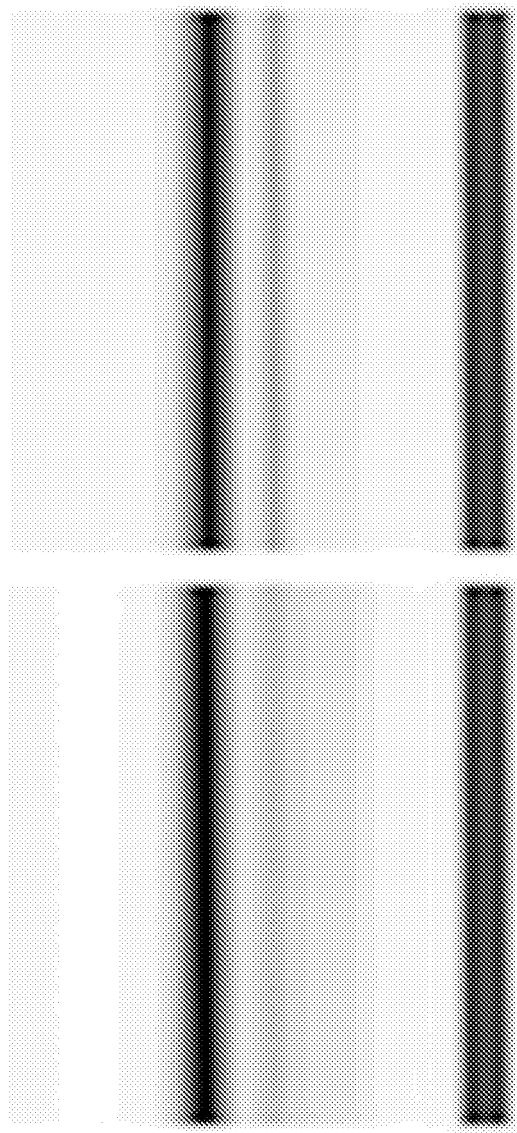
FIG. 12 demonstrates that Cas9 without guide RNA does not interfere with NASBA.

FIG. 12 shows the RNA product from a NASBA reaction (left) and a NASBA reaction with added Cas9, Cas9 buffer, but with no guide RNA (right). Both RNA produces are of the same quality/length. Traces were generated using a BioAnalyzer (Agilent).

Cas9 with a gRNA Targeting a Site Lacking a PAM Site does not Interfere with NASBA.

A key aspect of this invention is that a single base mutation affecting a PAM site will present Cas9 from binding/cleaving template DNA. To demonstrate this, a guide RNA with the 20-bp spacer sequence neg4-noGG (neg4-noGG TTTCAAGAATGGAAAACATC (SEQ ID NO: 771)) was designed to be homologous a region of the American strain (GenBank: KU312312) of Zika RNA, but at a location that lacks a PAM site (ATG): neg4-noNGG, Loc=2621 of GenBank: KU312312, sequence:

```
                                       (SEQ ID NO: 772)
gegggatctcctagTTTCAAGAATGGAAAACATCATGtggagatcagta gaa.
```

For comparison, another guide RNA sequence with the spacer sequence pos4 (pos4: GATCTCCTCTGTTT-CAAGAA (SEQ ID NO: 773)) was designed near a PAM site (TGG) to cut the template DNA and interfere with NASBA amplification: pos4, Loc=2610 of GenBank: KU312312, sequence:

```
                                       (SEQ ID NO: 774)
agatggtatctgcggGATCTCCTCTGTTTCAAGAATGGaaaacatcatg tgga.
```

Figure 13:
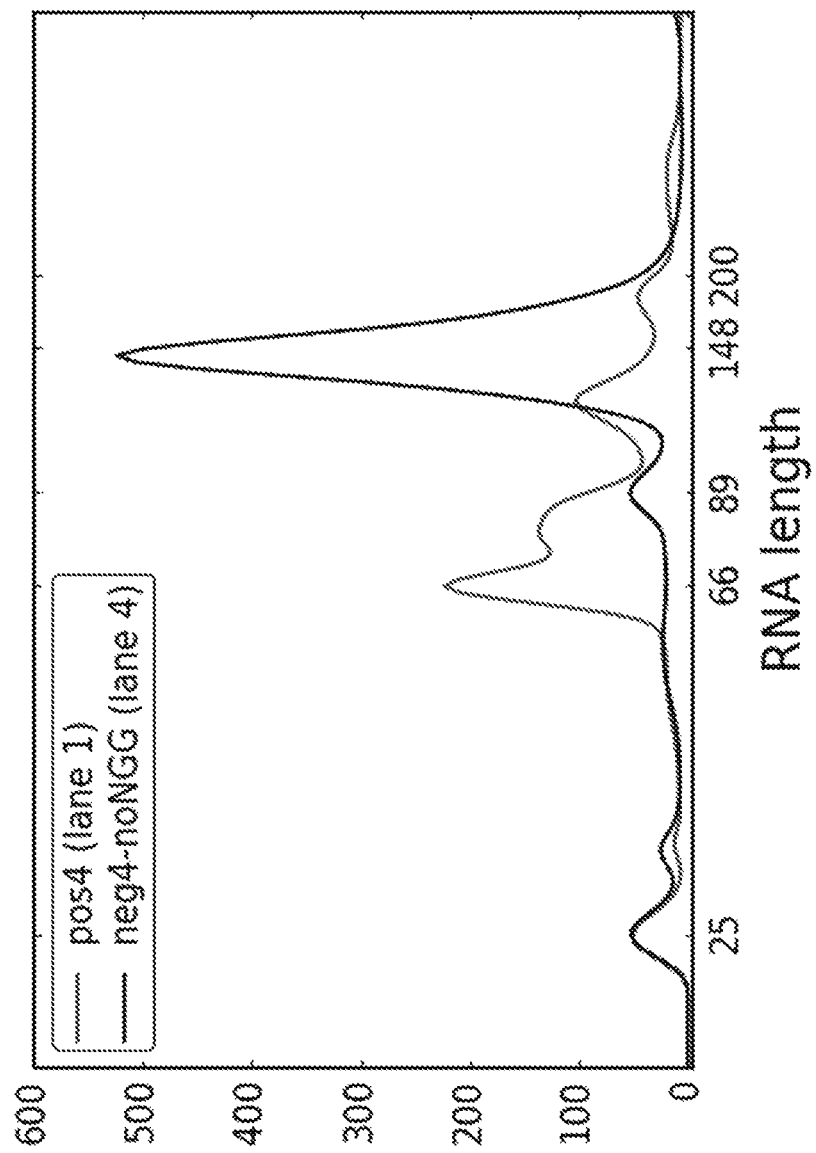
FIG. 13 demonstrates that Cas9 with a gRNA targeting a site lacking a PAM site does not interfere with NASBA.

FIG. 13 depicts the resulting RNA tract of the NASBA amplification reaction as quantified on a BioAnalyzer. The "pos4" gRNA cuts the intermediate template DNA and results in a shorter RNA product compared with the "neg4-noNGG" gRNA (66 bp vs. 148 bp).

Cas9 with a gRNA that Targets Reverse-Transcribed RNA Interferes with NASBA.

This is demonstrated in FIGS. 8A-8E.

Cas9 can Interfere with NASBA Amplification when Using Low Reverse Transcription (RT) Primers Concentration of 3 nM or Less.

The amount of template DNA that is generated during the reverse-transcription step of a NASBA reaction has to remain low. Using the conditions detailed above herein (250 nM final concentration of Cas9+gRNA), it was found that the amount of reverse transcription primer present in the NASBA has to be 3 nM or lower in order to efficiently cleave any intermediate template DNA generated during a NASBA reaction. A final concentration of 1 nM is preferable.

Figure 14:
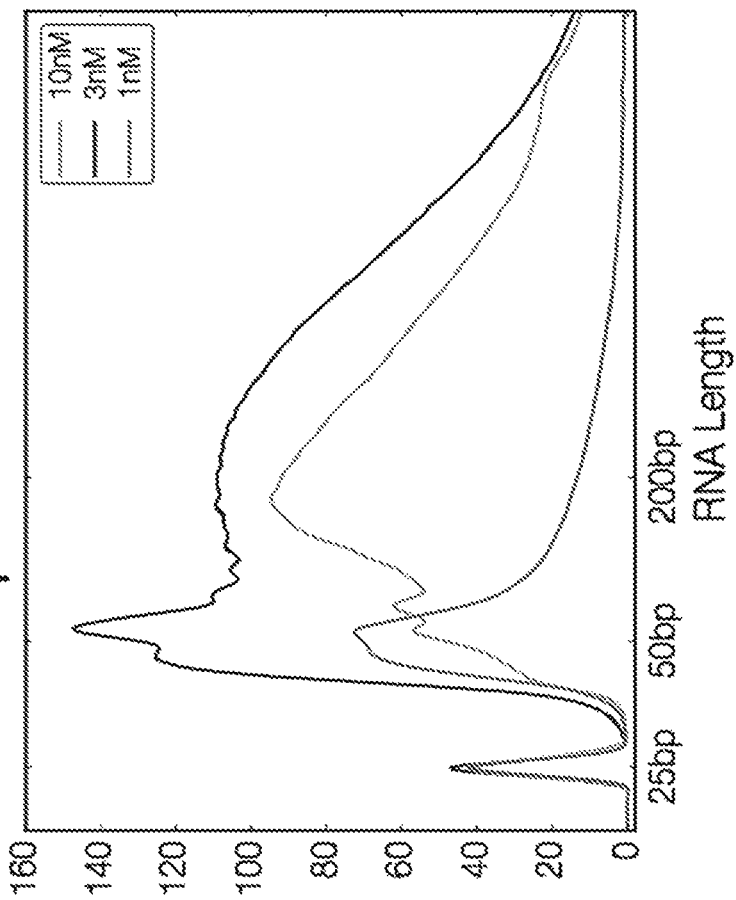
FIG. 14 depicts a graph of the effect of primer concentration on NASBACC.

FIG. 14 depicts the RNA product generated from three reactions containing 1 nM, 3 nM, or 10 nM of NASBA primers. The guide RNA with the spacer sequence TGGAGTCCCGCTGCTAATGA (SEQ ID NO: 775) was designed to target the African strain (GenBank: KF268950) of the Zika virus. The expected size following a successful Cas9 cleavage is 50 base pairs (bp). The full-length, uncut RNA is 200 bp. 8gRNA, Loc=7208 of (GenBank: KF268950)

```
Sequence:
                                       (SEQ ID NO: 776)
ttatgcatgggacttTGGAGTCCCGCTGCTAATGATGGgttgctactca caat
```

Table Showing the PAM Site Creation/Annihilation Following a Random Mutation (Table 4).

This table shows all the possible outcomes of a random mutation, where a PAM site can be created or annihilated.

Algorithm to Detect Diverging PAM Sites Between Two Strains.

List of PAM sites that differ between the American-African strains (572, FIGS. 8A-8E): see Table 5. Each gRNA sequence in Table 5 provides the 30-nt region immediately 5' to the PAM sequence in the last column. To generate the full sgRNA sequence used, the 20 bases adjacent to the 3' end of each gRNA sequence column are identified, and the following sequence is appended to the 3' end of that 20-base sequence (an example is shown in paragraph 000145):

```
                                       (SEQ ID NO: 789)
5'-GTTTTAGAGCTAGAAATAGCAAGTTAAAATAAGGCTAGTCCGTTATC

AACTTGAAAAAGTGGCACCGAGTCGGTGCTTTT-3'.

sgRNA sequence: Region 8 (8gRNA) + crRNA/tracrRNA
                                       (SEQ ID NO: 1)
TGGAGTCCCGCTGCTAATGAGTTTTAGAGCTAGAAATAGCAAGTTAAAAT

AAGGCTAGTCCGTTATCAACTTGAAAAAGTGGCACCGAGTCGGTGCTTTT.
```

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

TABLE 2

Sequences of NASBA Primers Used for Zika RNA Amplification

| Toehold Switch Sensor | | NASBA Primers for Zika Virus from the Americas (KU312312) | | | SEQ ID NO: |
|---|---|---|---|---|---|
| A Series | B series | Forward | SEQ ID NO: | Reverse | |
| 1A | 25B | AATTCTAATACGACTCACTATAGGGAGAAGGCAGTGATCTAGGCTACTGGA | 8 | GCCCAGCTAAAGACTTGGGTATGA | 32 |
| 2A | 26B | AATTCTAATACGACTCACTATAGGGAGAAGGGTGCCAGAGTTGTGTGTACA | 9 | CATCCAGTGATCCTCGTTCA | 33 |
| 3A | 27B | AATTCTAATACGACTCACTATAGGGAGAAGGGCACAGTGGGATGATCGTTA | 10 | CCTGTCCTCGGTTCACAATCAA | 34 |
| 4A | 28B | AATTCTAATACGACTCACTATAGGGAGAAGGCGGGATCTCCTCTGTTTCAA | 11 | AATCTCTGTGGACCTCTCCA | 35 |
| 5A | 29B | AATTCTAATACGACTCACTATAGGGAGAAGGCCATCACTGGGTCTCATCAA | 12 | GAGGCCAACAATTCCGACACTA | 36 |
| 6A | 30B | AATTCTAATACGACTCACTATAGGGAGAAGGAATGCTGTCAGTTCATGGCTCCCA | 13 | CTGTCCTCGGTTCACAATCA | 37 |
| 7A | 31B | AATTCTAATACGACTCACTATAGGGAGAAGGATGGTCTCTTCCTGGTTGTGGA | 14 | CCAGAACCTTGGATCGTTCA | 38 |
| 8A | 32B | AATTCTAATACGACTCACTATAGGGAGAAGGGACCCTAATAGTGGCCATCA | 15 | CCATCCACAACAGGGTTCTTCA | 39 |
| 9A | 33B | AATTCTAATACGACTCACTATAGGGAGAAGGGTTTGGTATGGGCAAAGGGA | 16 | CAGCCCTGGGATCAAGTACATGTA | 40 |
| 10A | 34B | AATTCTAATACGACTCACTATAGGGAGAAGGGCCATCTATGCTGCCTTGACAA | 17 | GCCCATACCAAACAACACTCCA | 41 |
| 11A | 35B | AATTCTAATACGACTCACTATAGGGAGAAGGGTGATTCTGCTCATGGTGCA | 18 | GCTTAGCCAGGTCACTCATTGA | 42 |
| 12A | 36B | AATTCTAATACGACTCACTATAGGGAGAAGGGTTTGTTCCAAGCGTGAGGA | 19 | AAGTTGGCGCCCATCTCTGAAA | 43 |
| 13A | 37B | AATTCTAATACGACTCACTATAGGGAGAAGGAGATCAACCACTGCAAGCGGAA | 20 | GTTCTTTCCTGGGCCTTATCTCA | 44 |
| 14A | 38B | AATTCTAATACGACTCACTATAGGGAGAAGGAGTGGTTCCACGACATTCCA | 21 | CCTTCTTGACTCCCTAGAACCA | 45 |
| 15A | 39B | AATTCTAATACGACTCACTATAGGGAGAAGGTGGACGCCAGAGTTTGTTCAGA | 22 | ATCTCTCTGTCATGTGTCCTGGCA | 46 |
| 16A | 40B | AATTCTAATACGACTCACTATAGGGAGAAGGGCCGGAATAACCTACACAGA | 23 | TCTGAACAAACTCTGGCGTCCA | 47 |
| 17A | 41B | AATTCTAATACGACTCACTATAGGGAGAAGGGGCTACTGGATTGAGAGTGAGA | 24 | GCCCAGCTAAAGACTTGGGTATGA | 48 |
| 18A | 42B | AATTCTAATACGACTCACTATAGGGAGAAGGCAGCCAGAATTGCATGTGTCCTCA | 25 | TGTTCTCTCCAACCATCCGA | 49 |
| 19A | 43B | AATTCTAATACGACTCACTATAGGGAGAAGGGGAGCGGACAAGTTGTCACTTA | 26 | GCTCTGCAACCAGTTAGTCA | 50 |
| 20A | 44B | AATTCTAATACGACTCACTATAGGGAGAAGGGTGCTCGGTGGACTTCTCAAAGAA | 27 | ATCTTCCCAGGCTTGCTTGA | 51 |
| 21A | 45B | AATTCTAATACGACTCACTATAGGGAGAAGGAGTGGTGCAACTCATTCGGA | 28 | TGCCATTCGTTTGAGCCTATCCA | 52 |
| 22A | 46B | AATTCTAATACGACTCACTATAGGGAGAAGGCAATACCAGAGAGGGCTACA | 29 | GCAGTGGTTGATCTCAGAGA | 53 |

TABLE 2 -continued

Sequences of NASBA Primers Used for Zika RNA Amplification

| | | | | | |
|---|---|---|---|---|---|
| 23A | 47B | AATTCTAATACGACTCACTATAGGGAGAAGGAGTAGGTCTTCTGGGCTTGA | 30 | CGCAGGTCAATGTCCATTGAGA | 54 |
| 24A | 48B | AATTCTAATACGACTCACTATAGGGAGAAGGGCTCAAACGAATGGCAGTCA | 31 | CCACTCTTGTGTGTCCTTCCTA | 55 |

| Toehold Switch Sensor | | NASBA Primers for MR 766 Zika Virus (AY632535) | |
|---|---|---|---|
| A Series | B series | Forward | Reverse |
| 1A | 25B | | |
| 2A | 26B | | |
| 3A | 27B | AATTCTAATACGACTCACTATAGGGAGAAGGGCACAGTGGGATGATCGTTA (SEQ ID NO: 56) | CCTGTCCTCGGTTCACAATCAA (SEQ ID NO: 58) |
| 4A | 28B | | |
| 5A | 29B | | |
| 6A | 30B | | |
| 7A | 31B | | |
| 8A | 32B | AATTCTAATACGACTCACTATAGGGAGAAGGACTCTGATAGTAGCTATCA (SEQ ID NO: 57) | CCATCCACAACGGGATTCTTCA (SEQ ID NO: 59) |
| 9A | 33B | | |
| 10A | 34B | | |
| 11A | 35B | | |
| 12A | 36B | | |
| 13A | 37B | | |
| 14A | 38B | | |
| 15A | 39B | | |
| 16A | 40B | | |
| 17A | 41B | | |
| 18A | 42B | | |
| 19A | 43B | | |
| 20A | 44B | | |
| 21A | 45B | | |
| 22A | 46B | | |
| 23A | 47B | | |
| 24A | 48B | | |

TABLE 3

Exemplary Materials for Portable Electronic Reader
total $: 244.238

| Vendor | quantity | price | total price | item # | description |
|---|---|---|---|---|---|
| Adafruit | 1 | 24.95 | 24.95 | 50 | Arduino Uno R3 (Atmega328 - assembled) |
| Adafruit | 1 | 19.95 | 19.95 | 2078 | Adafruit PowerBoost 500 Shield - Rechargeable 5 V Power Shield |
| Adafruit | 1 | 12.5 | 12.5 | 2011 | Lithium Ion Battery - 3.7 v 2000 mAh |

TABLE 3-continued

Exemplary Materials for Portable Electronic Reader
total $: 244.238

| Vendor | quantity | price | total price | item # | description |
|---|---|---|---|---|---|
| Adafruit | 1 | 19.95 | 19.95 | 1141 | Adafruit Assembled Data Logging shield for Arduino |
| Adafruit | 1 | 7.95 | 7.95 | 102 | SD/MicroSD Memory Card (4 GB SDHC) |
| Adafruit | 16 | 6.26 | 100.16 | 1980 | Adafruit TSL2591 High Dynamic Range Digital Light Sensor |
| Sparkfun | 3 | 2.8 | 8.4 | PRT-12702 | SparkFun Solderable Breadboard - Mini |
| Digi-Key | 2 | 0.49 | 0.98 | A19473-ND | CONN HEADER VERT 9POS.100 TIN |
| Digi-Key | 2 | 0.643 | 1.286 | A19476-ND | CONN HEADER VERT 13POS.100 TIN |
| Digi-Key | 2 | 1.21 | 2.42 | A31001-ND | CONN RECEPT 9POS 28AWG MTA100 |
| Digi-Key | 2 | 1.93 | 3.86 | A30954-ND | CONN RECEPT 13POS 28AWG MTA100 |
| Digi-Key | 20 | 0.2246 | 4.492 | 36-621-ND | BRACKET RT ANG MOUNT 4-40 STEEL, for reader assembly |
| McMaster-Carr | 1 | 2.36 | 2.36 | 90760A005 | Zinc Plated Steel Narrow Hex Nut 4-40 Thread Size, 3/16" Wide, 1/16" High, for reader assembly |
| McMaster-Carr | 1 | 6.74 | 6.74 | 8505K11 | Black Acrylic, for reader |
| McMaster-Carr | 2 | 8.04 | 16.08 | 92095A453 | M2 screws, for attaching sensors |
| McMaster-Carr | 1 | 1.04 | 1.04 | 90592A004 | M2 nuts, for attaching sensors |
| Inventables | 1 | 4.84 | 4.84 | 23876-35 | Clear acrylic, for bottom half of cassette |
| Inventables | 1 | 6.28 | 6.28 | 24112-04 | Black acrylic, for top half of cassette |

TABLE 4

Probabilities of PAM Site Disruption From Single Point Mutations

A. Summary of the effect of single point mutations

12 PAM sites
4 double PAM sites
32 PAM site created
12 double PAM site created
32 PAM site destroyed
12 double PAM site destroyed
4 PAM site inverted
Each mutation has a 23% probability (44/192) of creating a new PAM site, a 23% probability (44/192) of destroying and existing PAM site, and a 2% probability (4/192) of inverting the orientation of an existing PAM site. Overall, any given point mutations has a 48% probability (92/192) of disrupting an existing PAM site.

B. Detailed list of all single point mutations on every 3-bp sequences.

| | | Center letter: A Last | | | | | | | Center letter: C Last | | | | | |
|---|---|---|---|---|---|---|---|---|---|---|---|---|---|---|
| First | A | | C | | G | | T | First | A | | C | | G | | T |
| A | AAA | ACA | AAC | ACC | AAG | ACG | AAT | ACT | A | ACA | ACA | ACC | AAC | ACG | AAG | ACT | AAT |
| | | AGA | | AGC | | AGG | | AGT | | | AGA | | AGC | | AGG | | AGT |
| | | ATA | | ATC | | ATG | | ATT | | | ATA | | ATC | | ATG | | ATT |
| C | CAA | CCA | CAC | CCC | CAG | CCG | CAT | CCT | C | CCA | CAA | CCC | CAC | CCG | CAG | CCT | CAT |
| | | CGA | | CGC | | CGG | | CGT | | | CGA | | CGC | | CGG | | CGT |
| | | CTA | | CTC | | CTG | | CTT | | | CTA | | CTC | | CTG | | CTT |
| G | GAA | GCA | GAC | GCC | GAG | GCG | GAT | GCT | G | GCA | GAA | GCC | GAC | GCG | GAG | GCT | GAT |
| | | GGA | | GGC | | GGG | | GGT | | | GGA | | GGC | | GGG | | GGT |
| | | GTA | | GTC | | GTG | | GTT | | | GTA | | GTC | | GTG | | GTT |
| T | TAA | TCA | TAC | TCC | TAG | TCG | TAT | TCT | T | TCA | TAA | TCC | TAC | TCG | TAG | TCT | TAT |
| | | TGA | | TGC | | TGG | | TGT | | | TGA | | TGC | | TGG | | TGT |
| | | TTA | | TTC | | TTG | | TTT | | | TTA | | TTC | | TTG | | TTT |

| | | Center letter: G Last | | | | | | | Center letter: T Last | | | | | |
|---|---|---|---|---|---|---|---|---|---|---|---|---|---|---|
| First | A | | C | | G | | T | First | A | | C | | G | | T |
| A | AGA | AAA | AGC | AAC | AGG | AAG | AGT | AAT | A | ATA | AAA | ATC | AAC | ATG | AAG | ATT | AAT |
| | | ACA | | ACC | | ACG | | ACT | | | ACA | | ACC | | ACG | | ACT |
| | | ATA | | ATC | | ATG | | ATT | | | AGA | | AGC | | AGG | | AGT |
| C | CGA | CAA | CGC | CAC | CGG | CAG | CGT | CAT | C | CTA | CAA | CTC | CAC | CTG | CAG | CTT | CAT |
| | | CCA | | CCC | | CCG | | CCT | | | CCA | | CCC | | CCG | | CCT |
| | | CTA | | CTC | | CTG | | CTT | | | CGA | | CGC | | CGG | | CGT |
| G | GGA | GAA | GGC | GAC | GGG | GAG | GGT | GAT | G | GTA | GAA | GTC | GAC | GTG | GAG | GTT | GAT |
| | | GCA | | GCC | | GCG | | GCT | | | GCA | | GCC | | GCG | | GCT |
| | | GTA | | GTC | | GTG | | GTT | | | GGA | | GGC | | GGG | | GGT |

TABLE 4-continued

Probabilities of PAM Site Disruption From Single Point Mutations

| T | TGA | TAA | TGC | TAC | TGG | TAG | TGT | TAT | T | TTA | TAA | TTC | TAC | TTG | TAG | TTT | TAT |
|---|---|---|---|---|---|---|---|---|---|---|---|---|---|---|---|---|---|
| | | TCA | | TCC | | TCG | | TCT | | | TCA | | TCC | | TCG | | TCT |
| | | TTA | | TTC | | TTG | | TTT | | | TGA | | TGC | | TGG | | TGT |

TABLE 5

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| African | 302 | -1 | TTTTTCCCCACAGAACCCCATCTGTTGATG | 60 | AGG |
| African | 406 | 1 | ATGTTGAGAATAATCAATGCTAGGAAGGAG | 61 | AGG |
| African | 433 | -1 | TAGTCAGCAGGAGACCAATGATTCCGATGC | 62 | TGG |
| African | 469 | -1 | CACTTCCACGTCTGGTAATCTCCGCTGCCA | 63 | TGG |
| African | 487 | -1 | CCAAGTACATGTAGTATGCACTTCCACGTC | 64 | TGG |
| African | 517 | 1 | CGTGGAAGTGCATACTACATGTACTTGGAC | 65 | AGG |
| African | 547 | -1 | GGCATTTGTTAACTCCCAAGTTGGTAGCAA | 66 | AGG |
| African | 578 | -1 | CACATGTGCCCGAGATCCATGATCTGTACA | 67 | TGG |
| African | 595 | 1 | AACAAATGCCATGTACAGATCATGGATCTC | 68 | GGG |
| African | 839 | -1 | TTCCTAAATATCCAGTTTTCAACCTTGATC | 69 | AGG |
| African | 842 | 1 | AATCAAGAGAATACACGAAGCACCTGATCA | 70 | AGG |
| African | 871 | 1 | AAGGTTGAAAACTGGATATTTAGGAACCCC | 71 | GGG |
| African | 874 | -1 | AGGCAATGGCAACAGCTGCGAGCGCAAACC | 72 | CGG |
| African | 904 | -1 | CTTTTTGGCTCGTCGAGCTTCCCAAAAGCC | 73 | AGG |
| African | 1036 | -1 | AACCTCCATGTTCCAAGACGACATCAACCC | 74 | AGG |
| African | 1075 | -1 | TGTCAACTGTTGGCTTGTCCTGTGCCATAA | 75 | CGG |
| African | 1121 | 1 | CAACAGTTGACATAGAGTTGGTCACGACAA | 76 | CGG |
| African | 1141 | -1 | TTGATGCCTCATAACAGTAGGATCTTACCT | 77 | CGG |
| African | 1243 | -1 | TGTCCACCAATGTTCTTTTGCACACATATT | 78 | GGG |
| African | 1244 | -1 | CTGTCCACCAATGTTCTTTTGCACACATAT | 79 | TGG |
| African | 1262 | 1 | CAGACACCCAATATGTGTGCAAAAGAACAT | 80 | TGG |
| African | 1285 | 1 | AGAACATTGGTGGACAGAGGTTGGGGAAAT | 81 | GGG |
| African | 1330 | -1 | TCCCAGTCATCTTCTTGGAACACGTGAACT | 82 | TGG |
| African | 1478 | 1 | ATGAAACTGACGAAAACAGAGCGAAAGTCG | 83 | AGG |
| African | 1562 | 1 | TAGGACTTGATTGTGAACCAAGGACAGGCC | 84 | TGG |
| African | 1594 | -1 | CTTTGTGCACCAACCAGTGCTTGTTGTTCA | 85 | TGG |
| African | 1643 | -1 | CCGGTATCTGCCCCAGCATGCCAAGGCAAT | 86 | GGG |
| African | 1691 | 1 | CAGATACCGGAACTCCACACTGGAACAACA | 87 | AGG |
| African | 1694 | 1 | ATACCGGAACTCCACACTGGAACAACAAGG | 88 | AGG |
| African | 1723 | -1 | CTAGAACAACGACGGTTTGCCTCTTGGCGT | 89 | GGG |
| African | 1724 | -1 | CCTAGAACAACGACGGTTTGCCTCTTGGCG | 90 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| African | 1741 | -1 | CGGCTCCTTCCTGGCTCCCTAGAACAACGA | 91 | CGG |
| African | 1757 | 1 | AGAGGCAAACCGTCGTTGTTCTAGGGAGCC | 92 | AGG |
| African | 1760 | -1 | CCAGCAAGAGCCGTGTGAACGGCTCCTTCC | 93 | TGG |
| African | 1771 | -1 | CCTCCAGAGCTCCAGCAAGAGCCGTGTGAA | 94 | CGG |
| African | 1837 | -1 | TGTCCATTTTTAAGCGGCATTTCAAATGGC | 95 | CGG |
| African | 1853 | -1 | CCCTTCAATCTAAGCTTGTCCATTTTTAAG | 96 | CGG |
| African | 1906 | -1 | CAGCTGGGACCTTGGTAAATGTGAACGCTG | 97 | CGG |
| African | 1922 | 1 | CCTTGTGCACCGCAGCGTTCACATTTACCA | 98 | AGG |
| African | 1993 | -1 | TGTCCACCGCCATCTGGGCTGGGACCTTGC | 99 | AGG |
| African | 2003 | -1 | AGGGTCTGCATGTCCACCGCCATCTGGGCT | 100 | GGG |
| African | 2008 | -1 | GGGTCAGGGTCTGCATGTCCACCGCCATCT | 101 | GGG |
| African | 2032 | -1 | TGGCGGTTATCAGCCTCCCGACTGGGGTCA | 102 | GGG |
| African | 2033 | -1 | TTGGCGGTTATCAGCCTCCCGACTGGGGTC | 103 | AGG |
| African | 2062 | -1 | AATTCTCAGTGCTTTCAGTAATCACAGGGT | 104 | TGG |
| African | 2117 | -1 | CCTATGACAATGTAAGAATCCCCAAATGGT | 105 | GGG |
| African | 2210 | 1 | GGAGTGGTAGCACCATCGGAAAAGCATTTG | 106 | AGG |
| African | 2248 | 1 | GTGAGAGGTGCCAAGAGAATGGCAGTTCTG | 107 | GGG |
| African | 2249 | 1 | TGAGAGGTGCCAAGAGAATGGCAGTTCTGG | 108 | GGG |
| African | 2278 | 1 | GGGGATACAGCCTGGGACTTCGGATCAGTC | 109 | GGG |
| African | 2279 | 1 | GGGATACAGCCTGGGACTTCGGATCAGTCG | 110 | GGG |
| African | 2318 | -1 | AACAGTGATTTGAAAGCTGCTCCAAAAATC | 111 | TGG |
| African | 2378 | -1 | AAACCCAACCACACCAGCAGCGTGCCTATG | 112 | AGG |
| African | 2390 | 1 | GGTTCTCACAGATCCTCATAGGCACGCTGC | 113 | TGG |
| African | 2428 | -1 | CTCCCCCCAGGGCCAAGCATGTGAGGGAGA | 114 | TGG |
| African | 2447 | 1 | ATGGATCCATCTCCCTCACATGCTTGGCCC | 115 | TGG |
| African | 2471 | -1 | CACCCCACGTCAGCAGAGACAGCCGTGGAG | 116 | AGG |
| African | 2474 | 1 | CCCTGGGGGGAGTGATGATCTTCCTCTCCA | 117 | CGG |
| African | 2537 | 1 | ACTTCTCAAAAAGAGAAACGAGATGTGGCA | 118 | CGG |
| African | 2630 | 1 | CCCCCCGCAGATTGGCAGCAGCAGTCAAGC | 119 | AGG |
| African | 2642 | 1 | TGGCAGCAGCAGTCAAGCAGGCTTGGGAAG | 120 | AGG |
| African | 2644 | 1 | GCAGCAGCAGTCAAGCAGGCTTGGGAAGAG | 121 | GGG |
| African | 2668 | -1 | ATTTCCACATGATGTTTTCCATTCTTGAAA | 122 | CGG |
| African | 2699 | 1 | CAAGAATGGAAAACATCATGTGGAAATCAG | 123 | TGG |
| African | 2792 | -1 | AGCTCATTCACAGGCACTGGCAATCTTTGT | 124 | GGG |
| African | 2864 | 1 | AAGCCTGGGGGAAATCATATTTTGTCAGAG | 125 | CGG |
| African | 2878 | -1 | GTGTGTCACCATCGACAACAAAACTGTTGT | 126 | TGG |
| African | 2981 | -1 | TCTTCTCTAACCTTGAGCCAAACACTGGTG | 127 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| African | 2986 | -1 | AGTAGTCTTCTCTAACCTTGAGCCAAACAC | 128 | TGG |
| African | 3032 | -1 | TTTCCCTTAACAGCTGTTCCTATGACGGCT | 129 | GGG |
| African | 3070 | -1 | TTTCAATCCAGTAGCCCAGGTCACTGTGGG | 130 | CGG |
| African | 3073 | -1 | CACTTTCAATCCAGTAGCCCAGGTCACTGT | 131 | GGG |
| African | 3074 | -1 | TCACTTTCAATCCAGTAGCCCAGGTCACTG | 132 | TGG |
| African | 3080 | 1 | TTAAGGGAAAGGAGGCCGCCCACAGTGACC | 133 | TGG |
| African | 3083 | -1 | TCATTCTTTTCACTTTCAATCCAGTAGCCC | 134 | AGG |
| African | 3251 | -1 | GCTTGAGTTCTGTAACCCTCTCTAGTGTTG | 135 | TGG |
| African | 3317 | -1 | TGAACCTTGGTGCCTGGACATTCCTCAAAC | 136 | CGG |
| African | 3340 | -1 | TAGTTCCGCATGTCTCCTCCACGTGAACCT | 137 | TGG |
| African | 3542 | 1 | AGAGCAACTTAGTGAGGTCAATGGTGACAG | 138 | CGG |
| African | 3556 | -1 | GCACTCCAAGAGAGAAGTGGTCCATGTGAT | 139 | CGG |
| African | 3668 | 1 | TCATTATGAGCACATCAATGGCAGTGCTGG | 140 | TGG |
| African | 3676 | -1 | AGTCACTCATTAAAAATCCTCCCAGGATCA | 141 | TGG |
| African | 3764 | 1 | CCTTCGCAGAAATGAACACTGGAGGAGATG | 142 | TGG |
| African | 3779 | 1 | ACACTGGAGGAGATGTGGCTCACTTGGCAT | 143 | TGG |
| African | 3811 | -1 | AATTAGCTCTGAAAATAAAGGAGACCAGCA | 144 | AGG |
| African | 3823 | -1 | CACGAGGTGTCCAATTAGCTCTGAAAATAA | 145 | AGG |
| African | 3872 | -1 | GAGATTGCAGTTTGCAAAAGACACGAAGCC | 146 | AGG |
| African | 3929 | -1 | GCCAACCAGGCCAAAGCAAATCCATTGACG | 147 | AGG |
| African | 3976 | -1 | TTGCCAGAGCAATGTTGTCAGTGCGTGGCA | 148 | CGG |
| African | 4058 | 1 | CCCGAGGTACACTGCTCGTGGCATGGAGAG | 149 | CGG |
| African | 4099 | -1 | GGTTCTTCTTCACACTACCTTTCCCTTTCA | 150 | GGG |
| African | 4102 | 1 | TGTGGAGGGTTTATGCTCCTCTCCCTGAAA | 151 | GGG |
| African | 4130 | -1 | GCAGTCAATCCCAAGGCCATGACAAATGGC | 152 | AGG |
| African | 4409 | 1 | TTGAAAGAGCAGGTGACATCACATGGGAAA | 153 | AGG |
| African | 4639 | -1 | TGGTCTCTCCTTTTTTCACTTCTTTGGGAG | 154 | CGG |
| African | 4672 | 1 | AAAGAAGTGAAAAAAGGAGAGACCACAGAT | 155 | GGG |
| African | 4673 | 1 | AAGAAGTGAAAAAAGGAGAGACCACAGATG | 156 | GGG |
| African | 4696 | -1 | CTCCAACCTGTGTTGAACCCAGCAGTCTGC | 157 | GGG |
| African | 4697 | -1 | ACTCCAACCTGTGTTGAACCCAGCAGTCTG | 158 | CGG |
| African | 4703 | 1 | GGGTATACAGAGTGATGACCCGCAGACTGC | 159 | TGG |
| African | 4715 | 1 | TGATGACCCGCAGACTGCTGGGTTCAACAC | 160 | AGG |
| African | 4754 | -1 | GCAGCTCCTTTTGTGACGTGCCACATGGTG | 161 | TGG |
| African | 4786 | 1 | ATGTGGCACGTCACAAAAGGAGCTGCACTG | 162 | AGG |
| African | 4819 | 1 | AGCGGTGAAGGGAGACTTGATCCATACTGG | 163 | GGG |

TABLE 5 -continued

Suitable sites in the African, Asian, and American Zika virus genomes for CRISPR complex cleavage. American-African NASBACC genotyping

| Target Strain | Position | strand | gRNA-sequence | SEQ ID NO: | PAM-site |
|---|---|---|---|---|---|
| African | 4820 | 1 | GCGGTGAAGGGAGACTTGATCCATACTGGG | 164 | GGG |
| African | 4852 | 1 | GATGTCAAGCAGGACTTAGTGTCATACTGT | 165 | GGG |
| African | 4865 | 1 | ACTTAGTGTCATACTGTGGGCCTTGGAAGT | 166 | TGG |
| African | 4924 | 1 | GTGCAGCTCTTGGCAGTACCCCCCGGAGAG | 167 | AGG |
| African | 4925 | 1 | TGCAGCTCTTGGCAGTACCCCCCGGAGAGA | 168 | GGG |
| African | 4933 | -1 | TGAATATTCCAGGCAGAGTCTGAATGTTTC | 169 | TGG |
| African | 5008 | -1 | TGTCTAGGATCGGGGATCCTGAAGTTCCTG | 170 | CGG |
| African | 5026 | -1 | CTATCACTCTTCCGCATTTGTCTAGGATCG | 171 | GGG |
| African | 5027 | -1 | CCTATCACTCTTCCGCATTTGTCTAGGATC | 172 | GGG |
| African | 5111 | 1 | AGAATGGAAGCTATGTTAGTGCCATAACCC | 173 | AGG |
| African | 5126 | 1 | TTAGTGCCATAACCCAGGGAAAGAGGGAGG | 174 | AGG |
| African | 5135 | 1 | TAACCCAGGGAAAGAGGGAGGAGGAGACTC | 175 | CGG |
| African | 5158 | -1 | GGACAGTTAGCTGCTTCTTCTTCAGCATCG | 176 | AGG |
| African | 5186 | 1 | CGATGCTGAAGAAGAAGCAGCTAACTGTCC | 177 | TGG |
| African | 5189 | -1 | CTAGTCTTTCCGGCTCCTGGATGCAGATCC | 178 | AGG |
| African | 5209 | -1 | CTATTTCAGGAAGAACTCTCCTAGTCTTTC | 179 | CGG |
| African | 5276 | 1 | CCATAAAAAAGAGACTCCGCACAGTGATTT | 180 | TGG |
| African | 5330 | 1 | CTGAGATGGAGGAAGCCTTGAGAGGACTTC | 181 | CGG |
| African | 5371 | 1 | ATGACAACAGCAGTTAACGTCACCCACTCT | 182 | GGG |
| African | 5416 | -1 | TAGGGACTCTGATGGGTTGTAATAGGCGTG | 183 | AGG |
| African | 5423 | -1 | TTGTAATTAGGGACTCTGATGGGTTGTAAT | 184 | AGG |
| African | 5434 | -1 | TGATGTAGAGATTGTAATTAGGGACTCTGA | 185 | TGG |
| African | 5489 | -1 | GATATGTATCCTCTTGCAGCTATACTTGAG | 186 | GGG |
| African | 5678 | -1 | CTTGGAACGAACCAAACTGTTTTCCCAGAA | 187 | TGG |
| African | 5680 | 1 | TCAGGCTTTGATTGGGTGACAGACCATTCT | 188 | GGG |
| African | 5737 | -1 | GTATGACCCGCTTTCCAGCCTTTGTCAGAC | 189 | AGG |
| African | 5773 | 1 | AAGGCTGGAAAGCGGGTCATACAACTCAGC | 190 | AGG |
| African | 5875 | 1 | TCAGAGATGGGCGCGAATTTCAAAGCTGAC | 191 | CGG |
| African | 5876 | 1 | CAGAGATGGGCGCGAATTTCAAAGCTGACC | 192 | GGG |
| African | 5941 | 1 | ATACTTGATGGTGAGAGAGTCATCTTGGCT | 193 | GGG |
| African | 6005 | -1 | CCATACATGTACTCATCTCCAGGTTTGTTA | 194 | GGG |
| African | 6055 | -1 | TTGCTTCAAGCCAGTGTGCATGGTCTTCAT | 195 | CGG |
| African | 6136 | 1 | CTCCAGGATGGCCTCATAGCCTCGCTCTAC | 196 | CGG |
| African | 6140 | -1 | TCAATGGCAGCTACCTTATCGGCCTCAGGC | 197 | CGG |
| African | 6152 | 1 | TAGCCTCGCTCTACCGGCCTGAGGCCGATA | 198 | AGG |
| African | 6236 | -1 | GATGCAACCTGATAGGCTAGCCAAACGGGA | 199 | AGG |
| African | 6403 | 1 | AGAGTGCTCAAACCAAGATGGATGGATGCG | 200 | AGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| African | 6404 | 1 | GAGTGCTCAAACCAAGATGGATGGATGCGA | 201 | GGG |
| African | 6418 | -1 | ATTCTTTGAACGACTTCAGGGCAGCATGAT | 202 | CGG |
| African | 6457 | -1 | CCATTACTCCTAAAGCCACTCCTCTTTTCC | 203 | CGG |
| African | 6485 | 1 | GGAAAAGAGGAGTGGCTTTAGGAGTAATGG | 204 | AGG |
| African | 6520 | 1 | CTGGGAACATTGCCAGGACACATGACAGAG | 205 | AGG |
| African | 6587 | 1 | TGCGAGCAGAGACTGGAAGCAGGCCTTACA | 206 | AGG |
| African | 6661 | 1 | CTCTTAGGCTTGTTGGGAACAGTTTCGTTG | 207 | GGG |
| African | 6829 | -1 | TGTCCTGGGGAGATCTTTGCTTCTCTGGCT | 208 | CGG |
| African | 6881 | 1 | AGGACAACCAGATGGCAATCATCATCATGG | 209 | TGG |
| African | 6887 | 1 | ACCAGATGGCAATCATCATCATGGTGGCAG | 210 | TGG |
| African | 6989 | 1 | TAATGGGAAGGAGAGAAGAAGGAGTAACTA | 211 | TGG |
| African | 7033 | -1 | TGAGAGTTGTCAGTGCGGCATAGATAGCCC | 212 | AGG |
| African | 7048 | -1 | GGACGGCTGGGGTGATGAGAGTTGTCAGTG | 213 | CGG |
| African | 7082 | 1 | CAACTCTCATCACCCCAGCCGTCCAACACG | 214 | CGG |
| African | 7206 | 1 | AT-GGGACTTTGGAGTCCCGCTGCTAATGA | 215 | TGG |
| African | 7358 | -1 | CAATGTCAGTTACCACTATTCCATCCACAA | 216 | CGG |
| African | 7526 | -1 | ATTTGTTTGGAGAACCTTCCCACAAGGTGG | 217 | AGG |
| African | 7580 | -1 | GGTAACTTCCTCTGAAGATGTTGCACAGTG | 218 | AGG |
| African | 7611 | -1 | GTCACTGTATAAATAAGAGAAGCGCCTGCC | 219 | AGG |
| African | 7656 | -1 | TCTCCCGTTCCACCTCCACGTCTCTTGACT | 220 | AGG |
| African | 7677 | 1 | CTGGCCTAGTCAAGAGACGTGGAGGTGGAA | 221 | CGG |
| African | 7716 | -1 | GAGTAGAACTCCAGGGCCGACATCTGATTC | 222 | AGG |
| African | 7779 | 1 | AAAAGTCAGGCATCACTGAAGTGTGTAGAG | 223 | AGG |
| African | 7817 | -1 | CGCTTCCCCGGGATACAGCATGTCCTCCTG | 224 | TGG |
| African | 7835 | 1 | GGAGTGGCCACAGGAGGACATGCTGTATCC | 225 | CGG |
| African | 7836 | 1 | GAGTGGCCACAGGAGGACATGCTGTATCCC | 226 | GGG |
| African | 7890 | -1 | CTGCCACATCCGAGGTCAACAACCTTTCCA | 227 | TGG |
| African | 7908 | -1 | TAATAGCTCCAACCCCTCTGCCACATCCG | 228 | AGG |
| African | 7959 | 1 | GCTATTATGCCGCCACCATCCGGAAAGTGC | 229 | AGG |
| African | 7962 | 1 | ATTATGCCGCCACCATCCGGAAAGTGCAGG | 230 | AGG |
| African | 7980 | 1 | GGAAAGTGCAGGAGGTGAAAGGATACACAA | 231 | AGG |
| African | 7994 | -1 | AGCTTTGCACCAGCATGGGTTCTTCATGAC | 232 | CGG |
| African | 8081 | -1 | CTATGTCACACAGCAAGGTATCACACGGCT | 233 | CGG |
| African | 8096 | -1 | TAGATGATGACTCACCTATGTCACACAGCA | 234 | AGG |
| African | 8157 | -1 | TCAAGCCAGTCCCCCACCATAGAGAGCACT | 235 | CGG |
| African | 8193 | 1 | CTATGGTGGGGACTGGCTTGAGAAAAGAC | 236 | CGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| African | 8195 | 1 | ATGGTGGGGACTGGCTTGAGAAAAGACCG | 237 | GGG |
| African | 8196 | 1 | TGGTGGGGACTGGCTTGAGAAAAGACCGG | 238 | GGG |
| African | 8211 | 1 | TTGAGAAAAGACCGGGGCCTTCTGTATAA | 239 | AGG |
| African | 8262 | -1 | CTGACTAATCCTCCCCATACCTACGTTGC | 240 | AGG |
| African | 8315 | -1 | TTGCTCCAGAGACCCAATACATCTCATGTG | 241 | TGG |
| African | 8391 | -1 | ACTGGCCTCCTGGGACCATCCATGCGTCCC | 242 | AGG |
| African | 8445 | -1 | CAGCTTGCCACAGCTCGTGTGCCCGAGCCG | 243 | AGG |
| African | 8448 | 1 | TGAAATATGAGGAAGATGTGAACCTCGGCT | 244 | CGG |
| African | 8493 | 1 | TGGCAAGCTGTGCTGAAGCTCCCAACATGA | 245 | AGG |
| African | 8585 | -1 | CTTGTGTGGGGCTTCGTAGCTCCCATGGT | 246 | AGG |
| African | 8588 | 1 | AACCATCCATACAGGACATGGGCCTACCAT | 247 | GGG |
| African | 8630 | -1 | TTGACAGGAGTCTAACAACCCCATTCACGA | 248 | GGG |
| African | 8631 | -1 | TTTGACAGGAGTCTAACAACCCCATTCACG | 249 | AGG |
| African | 8724 | -1 | GTGTCCACTTTTTCTTTGAAGACTCTTTGT | 250 | TGG |
| African | 8756 | -1 | GGCGAGTGCCTTCTTGGGGATCTGGCACCC | 251 | TGG |
| African | 8787 | -1 | CACAGCCAGGAAGAGACCATGTTCATTGCC | 252 | TGG |
| African | 8817 | 1 | CAATGAACATGGTCTCTTCCTGGCTGTGGA | 253 | AGG |
| African | 8823 | 1 | ACATGGTCTCTTCCTGGCTGTGGAAGGAGT | 254 | TGG |
| African | 8825 | 1 | ATGGTCTCTTCCTGGCTGTGGAAGGAGTTG | 255 | GGG |
| African | 8895 | 1 | TCATCAACAAGGTGCGCAGCAATGCAGCAC | 256 | TGG |
| African | 8931 | 1 | CAATATTTGAAGAGGAAAAAGAATGGAAGA | 257 | CGG |
| African | 8939 | -1 | CCCAAAACCTTGGATCATTCACAGCCTCCA | 258 | CGG |
| African | 8940 | 1 | AAGAGGAAAAAGAATGGAAGACGGCCGTGG | 259 | AGG |
| African | 9105 | 1 | AAGGCAGCCGCGCCATCTGGTACATGTGGT | 260 | TGG |
| African | 9116 | -1 | AGAATCCAAGGGCTTCAAACTCCAAGAATC | 261 | TGG |
| African | 9120 | 1 | TCTGGTACATGTGGTTGGGAGCCAGATTCT | 262 | TGG |
| African | 9159 | -1 | CCACCTCCTGAGTTTTCTCTTCCCATCCAA | 263 | TGG |
| African | 9239 | 1 | AGACTTGGATACATTCTAGAAGAAATGAAT | 264 | CGG |
| African | 9240 | 1 | GACTTGGATACATTCTAGAAGAAATGAATC | 265 | GGG |
| African | 9278 | -1 | CAAACTTACTAATGCGGGTGTCCCAGCCAG | 266 | CGG |
| African | 9326 | -1 | TGTGCCCTTCCTCCATTTGGTTGGTAATTA | 267 | AGG |
| African | 9342 | 1 | AGAATGAAGCCTTAATTACCAACCAAATGG | 268 | AGG |
| African | 9424 | 1 | CAAAGTGGTGAAGGTCCTCAGACCAGCTGA | 269 | AGG |
| African | 9459 | 1 | GGAAAACAGTTATGGACATCATTTCAAGAC | 270 | AGG |
| African | 9494 | -1 | CCACTAAGTTGGTAAATGTGTTGAGAGCAT | 271 | AGG |
| African | 9537 | -1 | ATCTCTAACACTTCCTCAGCCTCCATATTC | 272 | CGG |
| African | 9595 | -1 | ATTGCACTGCAACCATCTGGTCACTTTCTC | 273 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| African | 9747 | 1 | ATGACATGGGAAAAGTTAGGAAAGACACAC | 274 | AGG |
| African | 9795 | -1 | TGCAGCTTGTTGAAATGGTGGGAGCAGAAC | 275 | GGG |
| African | 9855 | -1 | CGGCCAATCAATTCATCTTGGTGGCGGCAA | 276 | GGG |
| African | 9932 | -1 | GCCACATCTGTGCATATGATTTTGCTAGAC | 277 | AGG |
| African | 10014 | 1 | ACCTTCGACTGATGGCCAATGCTATTTGTT | 278 | CGG |
| African | 10046 | -1 | CCTTTCCGTGGATTGACCAGGTGGTTCTCC | 279 | CGG |
| African | 10092 | 1 | TCCACGGAAAGGGAGAATGGATGACTACTG | 280 | AGG |
| African | 10146 | 1 | GAGTGTGGATTGAGGAGAACGACCATATGG | 281 | AGG |
| African | 10185 | -1 | CACCATAAGTCCTCCCTTTTTCCCAGATAG | 282 | GGG |
| African | 10200 | 1 | GGACAGACATCCCCTATCTGGGAAAAGGG | 283 | AGG |
| African | 10223 | -1 | CCCAAGTGGTGCGGGGCCTGTGCCCTATAA | 284 | GGG |
| African | 10224 | -1 | GCCCAAGTGGTGCGGGGCCTGTGCCCTATA | 285 | AGG |
| African | 10232 | 1 | GACTTATGGTGTGGATCCCTTATAGGGCAC | 286 | AGG |
| African | 10241 | -1 | TGTCTTTGATGTTCTCAGCCCAAGTGGTGC | 287 | GGG |
| African | 10242 | -1 | GTGTCTTTGATGTTCTCAGCCCAAGTGGTG | 288 | CGG |
| African | 10332 | 1 | AAGAAAAATACATGGACTACTTATCCACCC | 289 | AGG |
| African | 10341 | -1 | CCAGGTGTGGACCCTTCCTCACCCAAGTAG | 290 | CGG |
| African | 10350 | 1 | ACTTATCCACCCAGGTCCGCTACTTGGGTG | 291 | AGG |
| American | 188 | 1 | AACGCGGAGTAGCCCGTGTGAGCCCCTTTG | 292 | GGG |
| American | 229 | 1 | AGGCTGCCAGCCGGACTTCTGCTGGGTCAT | 293 | GGG |
| American | 275 | 1 | TCTTGGCGATTCTAGCCTTTTTGAGATTCA | 294 | CGG |
| American | 368 | 1 | TGGAAATAATAAAGAAGTTCAAGAAAGATC | 295 | TGG |
| American | 452 | -1 | ACCTCCGCTGCCATAGCTGTGGTCAGCAGG | 296 | AGG |
| American | 463 | -1 | CACGTCTAGTGACCTCCGCTGCCATAGCTG | 297 | TGG |
| American | 476 | 1 | GCCTCCTGCTGACCACAGCTATGGCAGCGG | 298 | AGG |
| American | 490 | 1 | ACAGCTATGGCAGCGGAGGTCACTAGACGT | 299 | GGG |
| American | 530 | 1 | ACTATATGTACTTGGACAGAAACGATGCTG | 300 | GGG |
| American | 552 | -1 | TATATAACACTTATTCATCCCCAATGTGGT | 301 | TGG |
| American | 559 | 1 | GGGGAGGCCATATCTTTTCCAACCACATTG | 302 | GGG |
| American | 646 | 1 | ATGAGCTATGAATGCCCTATGCTGGATGAG | 303 | GGG |
| American | 647 | 1 | TGAGCTATGAATGCCCTATGCTGGATGAGG | 304 | GGG |
| American | 719 | -1 | CTAGATCTCCGTGCTTCACCTTTTTTGTGA | 305 | TGG |
| American | 769 | -1 | ACCGCGTTTGCAGCTTCCTAGTGGAATGGG | 306 | AGG |
| American | 772 | -1 | GCGACCGCGTTTGCAGCTTCCTAGTGGAAT | 307 | GGG |
| American | 773 | -1 | TGCGACCGCGTTTGCAGCTTCCTAGTGGAA | 308 | TGG |
| American | 809 | 1 | GGAAGCTGCAAACGCGGTCGCAAACCTGGT | 309 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 1000 | 1 | TACAGCATCAGGTGCATAGGAGTCAGCAAT | 310 | AGG |
| American | 1001 | 1 | ACAGCATCAGGTGCATAGGAGTCAGCAATA | 311 | GGG |
| American | 1136 | 1 | AGCTGGTTACAACAACAGTCAGCAACATGG | 312 | CGG |
| American | 1196 | -1 | TCAAGGTAGGCTTCACCTTGTGTTGGGCAG | 313 | CGG |
| American | 1357 | -1 | ACTCCAGATTCTCTGGCTGGATGCTCTTCC | 314 | CGG |
| American | 1387 | 1 | AAGAGCATCCAGCCAGAGAATCTGGAGTAC | 315 | CGG |
| American | 1391 | -1 | TGCTGGGAGCCATGAACTGACAGCATTATC | 316 | CGG |
| American | 1507 | -1 | CTAGGCTTCCAAACCCCCCCAGGGTGGCTT | 317 | CGG |
| American | 1513 | -1 | CAAGTCCTAGGCTTCCAAACCCCCCCAGGG | 318 | TGG |
| American | 1517 | -1 | CAATCAAGTCCTAGGCTTCCAAACCCCCCC | 319 | AGG |
| American | 1519 | 1 | AATTCACCAAGAGCCGAAGCCACCCTGGGG | 320 | GGG |
| American | 1535 | -1 | AGGCCTGTCCTCGGTTCACAATCAAGTCCT | 321 | AGG |
| American | 1619 | 1 | CTATGAATAACAAGCACTGGCTGGTTCACA | 322 | AGG |
| American | 1634 | -1 | GCCCCAGCGTGCCAAGGTAATGGAATGTCG | 323 | TGG |
| American | 1712 | 1 | GGAACAACAAAGAAGCACTGGTAGAGTTCA | 324 | AGG |
| American | 1742 | 1 | AGGACGCACATGCCAAAAGGCAAACTGTCG | 325 | TGG |
| American | 1783 | -1 | CATCCATCTCAGCCTCCAGAGCTCCAGCAA | 326 | GGG |
| American | 1784 | -1 | CCATCCATCTCAGCCTCCAGAGCTCCAGCA | 327 | AGG |
| American | 1817 | 1 | GAGCTCTGGAGGCTGAGATGGATGGTGCAA | 328 | AGG |
| American | 1834 | -1 | CCATTTTCAGGCGACATTTCAAGTGGCCAG | 329 | AGG |
| American | 1856 | -1 | ACGCCCTTCAATCTAAGTTTATCCATTTTC | 330 | AGG |
| American | 1928 | 1 | GTACTGCAGCGTTCACATTCACCAAGATCC | 331 | CGG |
| American | 1945 | 1 | TTCACCAAGATCCCGGCTGAAACACTGCAC | 332 | GGG |
| American | 2068 | -1 | TCTTAGAGTTCTCAGTGCTTTCAGTGATTA | 333 | CGG |
| American | 2174 | -1 | TTTCCAATGGTGCTGCCACTCCTGTGCCAG | 334 | TGG |
| American | 2315 | -1 | AATGATTTGAAAGCTGCTCCAAAGATTTGA | 335 | TGG |
| American | 2482 | -1 | AGTCCACCGAGCACCCCACATCAGCAGAGA | 336 | CGG |
| American | 2519 | 1 | ATGTGGGGTGCTCGGTGGACTTCTCAAAGA | 337 | AGG |
| American | 2638 | -1 | CAGAGGAGATCCCGCAGATACCATCTTCCC | 338 | AGG |
| American | 2723 | 1 | GATCAGTAGAAGGGGAGCTCAACGCAATCC | 339 | TGG |
| American | 2747 | 1 | CAATCCTGGAAGAGAATGGAGTTCAACTGA | 340 | CGG |
| American | 2756 | 1 | AAGAGAATGGAGTTCAACTGACGGTCGTTG | 341 | TGG |
| American | 2806 | -1 | TCCAGCCGTGGGGCAGCTCGTTCACAGGCA | 342 | CGG |
| American | 2834 | 1 | TGCCTGTGAACGAGCTGCCCCACGGCTGGA | 343 | AGG |
| American | 2891 | 1 | GAGCAGCAAAGACAAATAACAGCTTTGTCG | 344 | TGG |
| American | 2921 | -1 | AGAAAGCTGTTCCATGCTCTATGTTTGAGT | 345 | GGG |
| American | 3175 | -1 | TCTCTTCTATTCCATCTGTCCACAATGTGT | 346 | GGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 3176 | -1 | CTCTCTTCTATTCCATCTGTCCACAATGTG | 347 | TGG |
| American | 3223 | -1 | TGTGATGGCTGAGTGGCCCAGCTAAAGACT | 348 | TGG |
| American | 3232 | 1 | AGTGATCTGATCATACCCAAGTCTTTAGCT | 349 | GGG |
| American | 3259 | -1 | GCCCTTTCATTTGGGTCCTGTAGCCCTCTC | 350 | TGG |
| American | 3268 | 1 | CTCAGCCATCACAATACCAGAGAGGGCTAC | 351 | AGG |
| American | 3277 | -1 | GCTCTTCACTGTGCCATGGCCCTTTCATTT | 352 | GGG |
| American | 3278 | -1 | AGCTCTTCACTGTGCCATGGCCCTTTCATT | 353 | TGG |
| American | 3332 | -1 | CATGTTTCCTCCACGTGGACCTTAGTGCCT | 354 | GGG |
| American | 3427 | 1 | AGCGGAAGGGTGATCGAGGAATGGTGCTGC | 355 | AGG |
| American | 3428 | 1 | GCGGAAGGGTGATCGAGGAATGGTGCTGCA | 356 | GGG |
| American | 3457 | 1 | AGGGAGTGCACAATGCCCCCACTGTCGTTC | 357 | CGG |
| American | 3458 | 1 | GGGAGTGCACAATGCCCCCACTGTCGTTCC | 358 | GGG |
| American | 3461 | -1 | TCCATTCCATACCAACAGCCATCTTTAGCC | 359 | CGG |
| American | 3577 | -1 | GCACCATGAGCAGAATCACAAGCACTCCAA | 360 | GGG |
| American | 3578 | -1 | TGCACCATGAGCAGAATCACAAGCACTCCA | 361 | AGG |
| American | 3605 | 1 | TTGGAGTGCTTGTGATTCTGCTCATGGTGC | 362 | AGG |
| American | 3707 | -1 | GTGGCACCCATCAAAATTGCAAGCTTAGCC | 363 | AGG |
| American | 3740 | 1 | AGCTTGCAATTTTGATGGGTGCCACCTTCG | 364 | CGG |
| American | 3850 | -1 | ACGAGGCCAAGGCCAGCAGCATGCTTTCAC | 365 | GGG |
| American | 3851 | -1 | CACGAGGCCAAGGCCAGCAGCATGCTTTCA | 366 | CGG |
| American | 3863 | 1 | CTAATTGGACACCCCGTGAAAGCATGCTGC | 367 | TGG |
| American | 3877 | -1 | AGGCGGAGATCGCAGTTTGCAAAAGACACG | 368 | AGG |
| American | 3904 | -1 | TGATGAGAACCATCAGGTCGCCTTCCAAGG | 369 | CGG |
| American | 3905 | 1 | CGTGTCTTTTGCAAACTGCGATCTCCGCCT | 370 | TGG |
| American | 3907 | -1 | CATTGATGAGAACCATCAGGTCGCCTTCCA | 371 | AGG |
| American | 4000 | -1 | CCAGTGGTGTCAGAGCAGCCAGGATTGCCA | 372 | AGG |
| American | 4025 | 1 | CCTTGGCAATCCTGGCTGCTCTGACACCAC | 373 | TGG |
| American | 4030 | 1 | GCAATCCTGGCTGCTCTGACACCACTGGCC | 374 | CGG |
| American | 4031 | 1 | CAATCCTGGCTGCTCTGACACCACTGGCCC | 375 | GGG |
| American | 4075 | 1 | GTGGCGTGGAGAGCAGGCCTTGCTACTTGC | 376 | GGG |
| American | 4076 | 1 | TGGCGTGGAGAGCAGGCCTTGCTACTTGCG | 377 | GGG |
| American | 4148 | -1 | GGGTCGACCAGCCTCACAGCGGTTAGTCCC | 378 | AGG |
| American | 4159 | -1 | CCACGTTGATGGGTCGACCAGCCTCACAG | 379 | CGG |
| American | 4166 | 1 | TCATGGCCCTGGGACTAACCGCTGTGAGGC | 380 | TGG |
| American | 4322 | 1 | CAGATATAGAGATGGCTGGGCCCATGGCCG | 381 | CGG |
| American | 4324 | -1 | CCACGTAACTGACAATTAGCAGACCGACCG | 382 | CGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 4441 | -1 | CACCACTCTCATCTAGCGCCACATCGAGCC | 383 | GGG |
| American | 4442 | -1 | TCACCACTCTCATCTAGCGCCACATCGAGC | 384 | CGG |
| American | 4480 | -1 | CTCTCATGGGGGGACCGTCATCCTCCACCA | 385 | GGG |
| American | 4501 | -1 | GGACCACCTTGAGTATGATCTCTCTCATGG | 386 | GGG |
| American | 4502 | -1 | AGGACCACCTTGAGTATGATCTCTCTCATG | 387 | GGG |
| American | 4643 | 1 | GTGGTGCTCTATGGGATGTGCCTGCTCCCA | 388 | AGG |
| American | 4655 | 1 | GGGATGTGCCTGCTCCCAAGGAAGTAAAAA | 389 | AGG |
| American | 4657 | 1 | GATGTGCCTGCTCCCAAGGAAGTAAAAAAG | 390 | GGG |
| American | 4658 | 1 | ATGTGCCTGCTCCCAAGGAAGTAAAAAAGG | 391 | GGG |
| American | 4741 | 1 | ACACAAGTTGGAGTGGGAGTTATGCAAGAG | 392 | GGG |
| American | 4742 | 1 | CACAAGTTGGAGTGGGAGTTATGCAAGAGG | 393 | GGG |
| American | 4783 | -1 | GATCAAGTCTCCCTTCACCGCTTCTCAGCG | 394 | CGG |
| American | 4838 | 1 | ATCCATACTGGGGAGATGTCAAGCAGGATC | 395 | TGG |
| American | 4879 | -1 | CCAAGAGCTGCACCTCGCTGTGCCCGTCCC | 396 | AGG |
| American | 4882 | 1 | GGTCCATGGAAGCTAGATGCCGCCTGGGAC | 397 | GGG |
| American | 4912 | -1 | GGATGTTCCTCGCTCTCTCTCCGGGGGGCA | 398 | CGG |
| American | 4930 | 1 | CTCTTGGCCGTGCCCCCCGGAGAGAGAGCG | 399 | AGG |
| American | 4943 | -1 | TCCTTTGTCTTAAATATTCCGGGCAGAGTC | 400 | TGG |
| American | 4954 | -1 | CAATGTCCCCATCCTTTGTCTTAAATATTC | 401 | CGG |
| American | 4985 | 1 | TATTTAAGACAAAGGATGGGACATTGGAG | 402 | CGG |
| American | 5041 | 1 | ACTTCAGGATCTCCTATCCTAGACAAGTGT | 403 | GGG |
| American | 5086 | 1 | CTTTATGGCAATGGGGTCGTGATCAAAAAT | 404 | GGG |
| American | 5116 | 1 | GGGAGTTATGTTAGTGCCATCACCCAAGGG | 405 | AGG |
| American | 5206 | 1 | CTAACTGTCTTAGACTTGCATCCTGGAGCT | 406 | GGG |
| American | 5218 | -1 | CTTCACGGACTATTTCAGGAAGAACTCTCC | 407 | TGG |
| American | 5312 | 1 | CAACCAGGGTTGTCGCTGCTGAAATGGAGG | 408 | AGG |
| American | 5321 | -1 | GTTGTCATATAACGCACTGGAAGCCCTCTA | 409 | AGG |
| American | 5323 | 1 | GTCGCTGCTGAAATGGAGGAGGCCCTTAGA | 410 | GGG |
| American | 5446 | -1 | GGGCCTCATCCATAATATACAGATTATAGT | 411 | TGG |
| American | 5468 | 1 | TCCCCAACTATAATCTGTATATTATGGATG | 412 | AGG |
| American | 5548 | -1 | TTCCTGGTGGCGTGGCGGTCATGAAGATGG | 413 | CGG |
| American | 5563 | -1 | GAAATGCGTCACGGGTTCCTGGTGGCGTGG | 414 | CGG |
| American | 5591 | 1 | CCACGCCACCAGGAACCCGTGACGCATTTC | 415 | CGG |
| American | 5623 | -1 | AGCTCCAGGCTCTCTCTGGGACTTCCACTT | 416 | CGG |
| American | 5669 | 1 | GAGCCTGGAGCTCAGGCTTTGATTGGGTGA | 417 | CGG |
| American | 5710 | 1 | GGAAAAACAGTTTGGTTTGTTCCAAGCGTG | 418 | AGG |
| American | 5801 | -1 | ACAAAGTCCCACTCTTGATGTTTTGTTTTC | 419 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 5863 | -1 | TGGAATCTATGACACGGTCAGCTTTAAAGT | 420 | TGG |
| American | 5893 | -1 | CATCAAGTATGACCGGCTTTAGGCATCTCC | 421 | TGG |
| American | 5906 | 1 | GTGTCATAGATTCCAGGAGATGCCTAAAGC | 422 | CGG |
| American | 5968 | -1 | TGCCTATGCGCCCCCTCCTCTGGGCAGCGC | 423 | TGG |
| American | 5978 | -1 | TTGGGATTCCTGCCTATGCGCCCCCTCCTC | 424 | TGG |
| American | 5980 | 1 | CCTGTCACACATGCCAGCGCTGCCCAGAGG | 425 | AGG |
| American | 5981 | 1 | CTGTCACACATGCCAGCGCTGCCCAGAGGA | 426 | GGG |
| American | 6007 | -1 | CTCCATACAGATACTCATCTCCAGGTTTGT | 427 | TGG |
| American | 6037 | 1 | AAACCTGGAGATGAGTATCTGTATGGAGGT | 428 | GGG |
| American | 6095 | -1 | ATGAGGCCATCTTGGAGGTAAATATTGTCA | 429 | AGG |
| American | 6188 | 1 | CAGCCATTGAGGGAGAGTTCAAGCTTAGGA | 430 | CGG |
| American | 6245 | 1 | TCATGAAAAGAGGAGATCTTCCTGTTTGGC | 431 | TGG |
| American | 6280 | -1 | TGCCATCAAAGCACCATCTTCTATCTGTGT | 432 | AGG |
| American | 6341 | 1 | CCAACAACACCATAATGGAAGACAGTGTGC | 433 | CGG |
| American | 6361 | -1 | TCGGTTTGAGCACTCTTTTCTCTCCGTGTC | 434 | TGG |
| American | 6388 | 1 | AGACACGGAGAGAAAAGAGTGCTCAAACCG | 435 | AGG |
| American | 6406 | -1 | ACTTCAGGGCCGCATGATCTGAACAAACTC | 436 | TGG |
| American | 6422 | 1 | GGATGGACGCCAGAGTTTGTTCAGATCATG | 437 | CGG |
| American | 6440 | 1 | GTTCAGATCATGCGGCCCTGAAGTCATTCA | 438 | AGG |
| American | 6548 | -1 | CTTCCAGTCTCTGCCCGCATGAGCACAGCG | 439 | AGG |
| American | 6559 | 1 | GAAGCCATTGACAACCTCGCTGTGCTCATG | 440 | CGG |
| American | 6560 | 1 | AAGCCATTGACAACCTCGCTGTGCTCATGC | 441 | GGG |
| American | 6595 | -1 | TCTCTAGGGTCTCCGGCAATTGGGCCGCCG | 442 | CGG |
| American | 6596 | 1 | AGACTGGAAGCAGGCCTTACAAAGCCGCGG | 443 | CGG |
| American | 6635 | 1 | TGCCGGAGACCCTAGAGACCATTATGCTTT | 444 | TGG |
| American | 6637 | 1 | CCGGAGACCCTAGAGACCATTATGCTTTTG | 445 | GGG |
| American | 6806 | -1 | TCTGGCTCAGGTATGAGCACCACCAGCAAT | 446 | AGG |
| American | 6913 | -1 | TTGTTCTCTCCAACCATCCGAGTTCATTGG | 447 | CGG |
| American | 6916 | -1 | TCTTTGTTCTCTCCAACCATCCGAGTTCAT | 448 | TGG |
| American | 6953 | -1 | CCCTCCTCTCTCCTTCCCATTAGATGGCTT | 449 | AGG |
| American | 6959 | -1 | GTTGCCCCCTCCTCTCTCCTTCCCATTAGA | 450 | TGG |
| American | 6974 | 1 | GTGACCTAAGCCATCTAATGGGAAGGAGAG | 451 | AGG |
| American | 6977 | 1 | ACCTAAGCCATCTAATGGGAAGGAGAGAGG | 452 | AGG |
| American | 6979 | 1 | CTAAGCCATCTAATGGGAAGGAGAGAGGAG | 453 | GGG |
| American | 6980 | 1 | TAAGCCATCTAATGGGAAGGAGAGAGGAGG | 454 | GGG |
| American | 6991 | -1 | GCCGCAGGTCAATGTCCATTGAGAATCCTA | 455 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 7016 | -1 | GCATAGATGGCCCAAGCTGAGGCTGGCCGC | 456 | AGG |
| American | 7039 | -1 | GGGTAATGAAAGTTGTCAAGGCAGCATAGA | 457 | TGG |
| American | 7051 | -1 | GTTGGACGGCTGGGGTAATGAAAGTTGTCA | 458 | AGG |
| American | 7096 | -1 | CCATCGCCATTAAGGAGTAGTTGTTGTATG | 459 | AGG |
| American | 7242 | -1 | TGCGCCACGAGCAAAATGATGGCCACTATT | 460 | AGG |
| American | 7253 | -1 | AGTACATGTAGTGCGCCACGAGCAAAATGA | 461 | TGG |
| American | 7289 | 1 | CTCGTGGCGCACTACATGTACTTGATCCCA | 462 | GGG |
| American | 7329 | 1 | CAGCAGCTGCGCGTGCTGCCCAGAAGAGAA | 463 | CGG |
| American | 7356 | -1 | ATGTCAGTCACCACTATTCCATCCACAACA | 464 | GGG |
| American | 7428 | 1 | TTGACCCCAAGTGGAGAAAAAGATGGGAC | 465 | AGG |
| American | 7466 | -1 | CCCCCCACCCCAGGCGGTCCGCGACAGTA | 466 | TGG |
| American | 7484 | -1 | TGATCAGGGCCCCAGCCTCCCCCCACCCCC | 467 | AGG |
| American | 7499 | 1 | TCGCGGACCGCCTGGGGGTGGGGGAGGCT | 468 | GGG |
| American | 7500 | 1 | CGCGGACCGCCTGGGGGTGGGGGAGGCTG | 469 | GGG |
| American | 7508 | -1 | CCCACAAAGTGGAAGTTGCGGCTGTGATCA | 470 | GGG |
| American | 7509 | -1 | TCCCACAAAGTGGAAGTTGCGGCTGTGATC | 471 | AGG |
| American | 7520 | -1 | TCGGAGAGCCTTCCCACAAAGTGGAAGTTG | 472 | CGG |
| American | 7595 | 1 | TCTACAGCCACTTCACTGTGTAACATTTTT | 473 | AGG |
| American | 7596 | 1 | CTACAGCCACTTCACTGTGTAACATTTTTA | 474 | GGG |
| American | 7653 | 1 | TAATCTACACAGTAACAAGAAACGCTGGCT | 475 | TGG |
| American | 7667 | 1 | ACAAGAAACGCTGGCTTGGTCAAGAGACGT | 476 | GGG |
| American | 7668 | 1 | CAAGAAACGCTGGCTTGGTCAAGAGACGTG | 477 | GGG |
| American | 7689 | 1 | AGAGACGTGGGGGTGGAACAGGAGAGACCC | 478 | TGG |
| American | 7691 | -1 | GGTTCAAGCGGGCCTTCCATTTCTCTCCCA | 479 | GGG |
| American | 7692 | -1 | TGGTTCAAGCGGGCCTTCCATTTCTCTCCC | 480 | AGG |
| American | 7704 | 1 | GAACAGGAGAGACCCTGGGAGAGAAATGGA | 481 | AGG |
| American | 7712 | -1 | AGAACTCCAGGGCCGACATCTGGTTCAAGC | 482 | GGG |
| American | 7713 | -1 | TAGAACTCCAGGGCCGACATCTGGTTCAAG | 483 | CGG |
| American | 7722 | -1 | TTGTAGGAGTAGAACTCCAGGGCCGACATC | 484 | TGG |
| American | 7748 | -1 | TGCACACCTCGGTGATGCCTGACTTTTTGT | 485 | AGG |
| American | 7767 | 1 | TCTACTCCTACAAAAAGTCAGGCATCACCG | 486 | AGG |
| American | 7769 | -1 | GGGCGCGGCGGGCCTCTTCTCTGCACACCT | 487 | CGG |
| American | 7790 | -1 | CCGTTGCCACACCGTCCTTGAGGGCGCGGC | 488 | GGG |
| American | 7791 | -1 | CCCGTTGCCACACCGTCCTTGAGGGCGCGG | 489 | CGG |
| American | 7815 | 1 | CCCGCCGCGCCCTCAAGGACGGTGTGGCAA | 490 | CGG |
| American | 7827 | -1 | CTCAGCTTTGCACTTCCTCGGGACACAGCA | 491 | TGG |
| American | 7868 | 1 | GGAAGTGCAAAGCTGAGATGGTTGGTGGAG | 492 | CGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 7869 | 1 | GAAGTGCAAAGCTGAGATGGTTGGTGGAGC | 493 | GGG |
| American | 7992 | -1 | CTTTGCACCAACACGGGTTCTTCATGACCA | 494 | GGG |
| American | 8043 | -1 | ATATGAAAGACGTCCACCCCACTCTTAAGA | 495 | CGG |
| American | 8051 | 1 | TATGGGTGGAACATAGTCCGTCTTAAGAGT | 496 | GGG |
| American | 8052 | 1 | ATGGGTGGAACATAGTCCGTCTTAAGAGTG | 497 | GGG |
| American | 8144 | 1 | TCATCATCTAGTCCTGAAGTGGAAGAAGCA | 498 | CGG |
| American | 8163 | -1 | CTTTTTTCAAGCCAATCCCCCACCATGGAG | 499 | AGG |
| American | 8168 | -1 | CTGGTCTTTTTTCAAGCCAATCCCCCACCA | 500 | TGG |
| American | 8226 | -1 | TCCAGGGTTTCCATCATAGTGCTGGTGTAT | 501 | GGG |
| American | 8253 | -1 | CCTCCCCCATACCTACGCTGCAGTCGCTCC | 502 | AGG |
| American | 8283 | 1 | AGCGACTGCAGCGTAGGTATGGGGGAGGAC | 503 | TGG |
| American | 8306 | -1 | AGACCCAGTACATCTCATGTGTAGAGTTGC | 504 | GGG |
| American | 8307 | -1 | GAGACCCAGTACATCTCATGTGTAGAGTTG | 505 | CGG |
| American | 8357 | -1 | GGAGCTGGCTCGTGGTGGACACACTTTTTA | 506 | TGG |
| American | 8382 | -1 | CTAGGCCCGTCCATGCGCCCCAAGAGGAGC | 507 | TGG |
| American | 8390 | 1 | AGTGTGTCCACCACGAGCCAGCTCCTCTTG | 508 | GGG |
| American | 8402 | 1 | ACGAGCCAGCTCCTCTTGGGGCGCATGGAC | 509 | GGG |
| American | 8430 | 1 | ACGGGCCTAGGAGGCCAGTGAAATATGAGG | 510 | AGG |
| American | 8456 | 1 | GAGGAGGATGTGAATCTCGGCTCTGGCACG | 511 | CGG |
| American | 8457 | 1 | AGGAGGATGTGAATCTCGGCTCTGGCACGC | 512 | GGG |
| American | 8511 | -1 | TCCGCGTGCTCACTGCGGATCCTTTCAATG | 513 | CGG |
| American | 8516 | 1 | AACATGAAGATCATTGGTAACCGCATTGAA | 514 | AGG |
| American | 8535 | 1 | ACCGCATTGAAAGGATCCGCAGTGAGCACG | 515 | CGG |
| American | 8568 | -1 | TAGCTTCCATGGTAAGCCCATGTCCTATAT | 516 | GGG |
| American | 8598 | 1 | ATAGGACATGGGCTTACCATGGAAGCTATG | 517 | AGG |
| American | 8627 | -1 | ACAGGAGCCTGACAACCCCGTTTATTAGAG | 518 | AGG |
| American | 8645 | 1 | TCAGCGTCCTCTCTAATAAACGGGGTTGTC | 519 | AGG |
| American | 8670 | 1 | TTGTCAGGCTCCTGTCAAAACCCTGGGATG | 520 | TGG |
| American | 8699 | -1 | TTTGCTGACCATACGGTGTGGTGTCGGTCA | 521 | TGG |
| American | 8705 | -1 | AAACTCTTTGCTGACCATACGGTGTGGTGT | 522 | CGG |
| American | 8711 | -1 | CCTTGAAAACTCTTTGCTGACCATACGGTG | 523 | TGG |
| American | 8736 | 1 | CCACACCGTATGGTCAGCAAAGAGTTTTCA | 524 | AGG |
| American | 8769 | -1 | ATGCTCATAACCTGACGAGTGCCTTCTTGG | 525 | GGG |
| American | 8897 | 1 | ATCAACAAGGTTCGTAGCAATGCAGCATTA | 526 | GGG |
| American | 8898 | 1 | TCAACAAGGTTCGTAGCAATGCAGCATTAG | 527 | GGG |
| American | 8997 | -1 | TACACACAACTCTGGCACTCTCCTCTCAGG | 528 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 9056 | 1 | AACATGATGGGAAAAAGAGAAAAGAAACAA | 529 | GGG |
| American | 9057 | 1 | ACATGATGGGAAAAAGAGAAAAGAAACAAG | 530 | GGG |
| American | 9069 | 1 | AAAGAGAAAAGAAACAAGGGGAATTTGGAA | 531 | AGG |
| American | 9075 | 1 | AAAAGAAACAAGGGGAATTTGGAAAGGCCA | 532 | AGG |
| American | 9077 | -1 | GCCACATATACCAGATGGCGCGGCTGCCCT | 533 | TGG |
| American | 9107 | 1 | GGCAGCCGCGCCATCTGGTATATGTGGCTA | 534 | GGG |
| American | 9108 | 1 | GCAGCCGCGCCATCTGGTATATGTGGCTAG | 535 | GGG |
| American | 9164 | 1 | CTTGGATTCTTGAACGAGGATCACTGGATG | 536 | GGG |
| American | 9198 | 1 | GAGAGAACTCAGGAGGTGGTGTTGAAGGGC | 537 | TGG |
| American | 9228 | -1 | CTTCCTCCTGGTATACGACTCATCTCTTCT | 538 | AGG |
| American | 9254 | 1 | CTAGAAGAGATGAGTCGTATACCAGGAGGA | 539 | AGG |
| American | 9299 | 1 | GACACTGCTGGCTGGGACACCCGCATTAGC | 540 | AGG |
| American | 9353 | 1 | CTAATCACCAACCAAATGGAGAAAGGGCAC | 541 | AGG |
| American | 9354 | 1 | TAATCACCAACCAAATGGAGAAAGGGCACA | 542 | GGG |
| American | 9362 | -1 | GGTATGTGTACTTGATTATGGCCAATGCCA | 543 | AGG |
| American | 9374 | -1 | CCACTTTGTTTTGGTATGTGTACTTGATTA | 544 | TGG |
| American | 9393 | -1 | GCTGGTCTAAGGACCTTTACCACTTTGTTT | 545 | TGG |
| American | 9467 | 1 | GTTATGGACATTATTTCGAGACAAGACCAA | 546 | AGG |
| American | 9587 | 1 | CTAGAGATGCAAGACTTGTGGCTGCTGCGG | 547 | AGG |
| American | 9632 | 1 | ACTAACTGGTTGCAGAGCAACGGATGGGAT | 548 | AGG |
| American | 9738 | 1 | GGTTCTTGAATGATATGGGAAAAGTTAGGA | 549 | AGG |
| American | 9771 | 1 | ACACACAAGAGTGGAAACCCTCAACTGGAT | 550 | GGG |
| American | 9825 | -1 | GGAACCACAATGGACCTCCCGTCCTTGAGA | 551 | TGG |
| American | 9833 | 1 | CACCACTTCAACAAGCTCCATCTCAAGGAC | 552 | GGG |
| American | 9836 | 1 | CACTTCAACAAGCTCCATCTCAAGGACGGG | 553 | AGG |
| American | 9857 | -1 | CCCGGCCAATCAGTTCATCTTGGTGGCGGC | 554 | AGG |
| American | 9881 | 1 | CCCTGCCGCCACCAAGATGAACTGATTGGC | 555 | CGG |
| American | 9882 | 1 | CCTGCCGCCACCAAGATGAACTGATTGGCC | 556 | GGG |
| American | 9903 | 1 | TGATTGGCCGGGCCCGCGTCTCTCCAGGGG | 557 | CGG |
| American | 9921 | -1 | GCATATGATTTTGCTAGGCAAGCAGTCTCC | 558 | CGG |
| American | 9936 | -1 | AGCTGCCACATTTGCGCATATGATTTTGCT | 559 | AGG |
| American | 9969 | -1 | ATCAGTCGGAGGTCCCTTCTGTGGAAATAA | 560 | AGG |
| American | 9980 | 1 | CAAATGTGGCAGCTCCTTTATTTCCACAGA | 561 | AGG |
| American | 9981 | 1 | AAATGTGGCAGCTCCTTTATTTCCACAGAA | 562 | GGG |
| American | 9993 | -1 | ACAGATGAACAAATGGCATTGGCCATCAGT | 563 | CGG |
| American | 10010 | -1 | GAACCCAGTCAACTGGCACAGATGAACAAA | 564 | TGG |
| American | 10091 | -1 | CTCTGTTCCACACCACAAGCATGTCTTCAG | 565 | TGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 10160 | -1 | AATAGGGAATGTCTGTCCATTTCGTAACTG | 566 | GGG |
| American | 10161 | -1 | AAATAGGGAATGTCTGTCCATTTCGTAACT | 567 | GGG |
| American | 10250 | -1 | TGTTGACTGTGTTTTAATGTTCTCAGCCC | 568 | AGG |
| American | 10326 | -1 | TCTTCACCCAAGTAGCGAACTTGGGTGGAT | 569 | AGG |
| Asian | 469 | -1 | CACTCCCACGTCTAGTGACCTCCACTGCCA | 570 | TGG |
| Asian | 722 | -1 | CTTCTAGATCTCCGTGCTTCACCTTTTTG | 571 | TGG |
| Asian | 839 | -1 | TTCCTGAATATCCAATTTTCGACTCTAATC | 572 | AGG |
| Asian | 904 | -1 | CTTTTTGGCTCGTTGAACTTCCCAAAAGCC | 573 | AGG |
| Asian | 1075 | -1 | TGTCGACAGCCGGTTTGTCCTGTGCCATTA | 574 | CGG |
| Asian | 1091 | 1 | GTTGTGTTACCGTAATGGCACAGGACAAAC | 575 | CGG |
| Asian | 1172 | 1 | TAAGATCCTATTGCTATGAGGCATCAATAT | 576 | CGG |
| Asian | 1472 | 1 | CAGGACATGAAACTGATGAGAATAGAGCGA | 577 | AGG |
| Asian | 1906 | -1 | CAGCCGGGATCTTGGTGAATGTGAACGCTG | 578 | CGG |
| Asian | 1993 | -1 | TGTCCACCGCCATCTGAGCTGGAACCTTGC | 579 | AGG |
| Asian | 2390 | 1 | GGTTCTCACAAATTCTCATTGGAACGTTGC | 580 | TGG |
| Asian | 2537 | 1 | ACTTCTCAAAGAAGGAAACGAGATGCGGTA | 581 | CGG |
| Asian | 2644 | 1 | GCAGCAGCAGTCAAGCAAGCCTGGGRAGAT | 582 | GGG |
| Asian | 3140 | -1 | TTTGGCCATTCACATGTTTTCATCTCGATC | 583 | AGG |
| Asian | 3712 | -1 | CAAAGGTGGCACCCATCAAAATTGCAAGCT | 584 | TGG |
| Asian | 3872 | -1 | GAGATCGCAGTTTGCAGAAGACACGAAGCC | 585 | AGG |
| Asian | 4102 | 1 | TGCGGGGGGTTCATGCTTCTCTCTCTGAAG | 586 | GGG |
| Asian | 4106 | 1 | GGGGGTTCATGCTTCTCTCTCTGAAGGGGA | 587 | AGG |
| Asian | 4130 | -1 | GCGGTGAGTCCCAAGGCCATGACAAATGGT | 588 | AGG |
| Asian | 4292 | 1 | TATGCGCGTTGGCCGGAGGGTTCGCCAAGG | 589 | CGG |
| Asian | 4454 | 1 | CTGGAAACAGTCCCCGGCTCGATGTGGCAC | 590 | TGG |
| Asian | 4754 | -1 | GCGGATCCTTTTGTGACGTGCCACATAGTG | 591 | TGG |
| Asian | 5195 | -1 | ACTCTCCTGGTTTTCCCAGCTCCAGGATGC | 592 | AGG |
| Asian | 5371 | 1 | ATGACAACAGCAGTCAATGTCACCCATTCT | 593 | GGG |
| Asian | 5569 | -1 | AGTCCGGGAATGCGTCACGGGTTCCTGGTG | 594 | GGG |
| Asian | 5570 | -1 | GAGTCCGGGAATGCGTCACGGGTTCCTGGT | 595 | GGG |
| Asian | 5594 | -1 | TCGGTGTCCATAATTGGTGAGTTGGAGTCC | 596 | GGG |
| Asian | 6347 | 1 | ACACCATAATGGAAGACAGTGTGCCGGCAG | 597 | AGG |
| Asian | 6475 | -1 | GCAATGTTCCCAGGGCTTCCATCACTCCAA | 598 | AGG |
| Asian | 6503 | 1 | TTGGAGTGATGGAAGCCCTGGGAACATTGC | 599 | CGG |
| Asian | 6887 | 1 | ACCAAATGGCAATCATCATCATGATAGCAG | 600 | TGG |
| Asian | 7082 | 1 | CAACTTTCATCACCCCAGCCGTCCAACATG | 601 | CGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| Asian | 7206 | 1 | AT-GGGACTTTGGAGTCCCGCTGCTAATGA | 602 | TGG |
| Asian | 7571 | -1 | CCCTAAAAATGTTACACAGTGAAGTGGCTG | 603 | TGG |
| Asian | 7677 | 1 | CTGGCTTGGTCAAGAGACGTGGGGGTGGAA | 604 | CGG |
| Asian | 7716 | -1 | GAGTAGAACTCTAGGGCCGACATCTGGTTC | 605 | AGG |
| Asian | 8453 | -1 | CTTCAGCGCAGCTTACCACAGCCCGCGTGC | 606 | CGG |
| Asian | 9120 | 1 | TCTGGTATATGTGGCTAGGGGCTAGATTCC | 607 | TGG |
| Asian | 9123 | -1 | TCGTTCAAGAATCCAAGGGCTTCGAACTCC | 608 | AGG |
| Asian | 9516 | 1 | TCACTTACGCTCTTAATACATTCACCAACC | 609 | TGG |
| American | 650 | 1 | GCTATGAATGCCCTATGCTGGATGAGGGGG | 610 | TGG |
| American | 1507 | -1 | CTAGGCTTCCAAACCCCCCAGGGTGGCTT | 611 | CGG |
| American | 1519 | 1 | AATTCACCAAGAGCCGAAGCCACCCTGGGG | 612 | GGG |
| American | 2068 | -1 | TCTTAGAGTTCTCAGTGCTTTCAGTGATTA | 613 | CGG |
| American | 2174 | -1 | TTTCCAATGGTGCTGCCACTCCTGTGCCAG | 614 | TGG |
| American | 2608 | -1 | AGGCTTGCTTGACTGCTGCTGCCAATCTAC | 615 | GGG |
| American | 2609 | -1 | CAGGCTTGCTTGACTGCTGCTGCCAATCTA | 616 | CGG |
| American | 2612 | 1 | ACAAGTACCATCCTGACTCCCCCCGTAGAT | 617 | TGG |
| American | 3277 | -1 | GCTCTTCACTGTGCCATGGCCCTTTCATTT | 618 | GGG |
| American | 3278 | -1 | AGCTCTTCACTGTGCCATGGCCCTTTCATT | 619 | TGG |
| American | 3569 | -1 | AGCAGAATCACAAGCACTCCAAGGGAGAAG | 620 | TGG |
| American | 3877 | -1 | AGGCGGAGATCGCAGTTTGCAAAAGACACG | 621 | AGG |
| American | 4007 | 1 | CACGCACTGATAACATCACCTTGGCAATCC | 622 | TGG |
| American | 4094 | -1 | TTCTTCACACTGCCTTTTCCCTTCAGAGAG | 623 | AGG |
| American | 4148 | -1 | GGGTCGACCAGCCTCACAGCGGTTAGTCCC | 624 | AGG |
| American | 4262 | -1 | TTGGCGAACCCTCCAGCCAATGCGCATATC | 625 | AGG |
| American | 4478 | 1 | TGGCGCTAGATGAGAGTGGTGATTTCTCCC | 626 | TGG |
| American | 4520 | 1 | ACGGTCCCCCCATGAGAGAGATCATACTCA | 627 | AGG |
| American | 4985 | 1 | TATTTAAGACAAAGGATGGGGACATTGGAG | 628 | CGG |
| American | 5312 | 1 | CAACCAGGGTTGTCGCTGCTGAAATGGAGG | 629 | AGG |
| American | 6095 | -1 | ATGAGGCCATCTTGGAGGTAAATATTGTCA | 630 | AGG |
| American | 6166 | -1 | GCTCCGTCCTAAGCTTGAACTCTCCCTCAA | 631 | TGG |
| American | 6440 | 1 | GTTCAGATCATGCGGCCCTGAAGTCATTCA | 632 | AGG |
| American | 6620 | -1 | CCCAGCAACCCCAAAAGCATAATGGTCTCT | 633 | AGG |
| American | 6878 | 1 | CCCAGGACAACCAAATGGCAATCATCATCA | 634 | TGG |
| American | 7039 | -1 | GGGTAATGAAAGTTGTCAAGGCAGCATAGA | 635 | TGG |
| American | 7051 | -1 | GTTGGACGGCTGGGGTAATGAAAGTTGTCA | 636 | AGG |
| American | 7096 | -1 | CCATCGCCATTAAGGAGTAGTTGTTGTATG | 637 | AGG |
| American | 7408 | -1 | TAGCACCTGTCCCATCTTTTTCTCCACTTG | 638 | GGG |

TABLE 5 -continued

Suitable sites in the African, Asian, and American Zika virus genomes for CRISPR complex cleavage.
American-African NASBACC genotyping

| Target Strain | Position | strand | gRNA-sequence | SEQ ID NO: | PAM-site |
|---|---|---|---|---|---|
| American | 7409 | -1 | GTAGCACCTGTCCCATCTTTTTCTCCACTT | 639 | GGG |
| American | 7520 | -1 | TCGGAGAGCCTTCCCACAAAGTGGAAGTTG | 640 | CGG |
| American | 7731 | 1 | GGAAGGCCCGCTTGAACCAGATGTCGGCCC | 641 | TGG |
| American | 7815 | 1 | CCCGCCGCGCCCTCAAGGACGGTGTGGCAA | 642 | CGG |
| American | 7868 | 1 | GGAAGTGCAAAGCTGAGATGGTTGGTGGAG | 643 | CGG |
| American | 7869 | 1 | GAAGTGCAAAGCTGAGATGGTTGGTGGAGC | 644 | GGG |
| American | 8609 | -1 | CGTTTATTAGAGAGGACGCTGACCCTTGTG | 645 | TGG |
| American | 9015 | -1 | CTTTTTCCCATCATGTTGTACACACAACTC | 646 | TGG |
| American | 9881 | 1 | CCCTGCCGCCACCAAGATGAACTGATTGGC | 647 | CGG |
| American | 9882 | 1 | CCTGCCGCCACCAAGATGAACTGATTGGCC | 648 | GGG |
| American | 10278 | 1 | GGGCTGAGAACATTAAAAACACAGTCAACA | 649 | TGG |

TABLE 6

Sequences of Toehold Switch Sensors and Corresponding Target Sequences in Zika Genome.

| Target sequence in Zika virus genome | Location in genome | A Series Sensors | | B Series Sensors | | Target RNA Fragment Used for Initial Sensor Screening | | | |
|---|---|---|---|---|---|---|---|---|---|
| | | Sensor Name | Sensor sequence | Sensor Name | Sensor sequence | Sequence | Genome Start site | Genome End site | Genome fragment length |
| UUGAGAGUGAGAAGAAUGACACAUGGAGGCUGAAGA (SEQ ID NO: 650) | 3027 | 1A | UCUUCAGCCUCCAUGUGUCAUUCUUCUCACUCUCAAGUUAUAGUUAUGAACAGAGGAGACAUAACAUGAACUUGAGAAACCAAGUUAACCUGGCGGCAGCGCAAAAG (SEQ ID NO: 674) | 25B | UCUUCAGCCUCCAUGUGUCAUUCUUCUCACUCUCAAGGACUUUAGAACAGAGGAGAUAAAGAUGUUGAGAGUGAGUAACCUGGCGGCAGCGCAAAAG (SEQ ID NO: 698) | GGGCAGUGAUCUAGGCUACUGGAUUGAGAGUGAGAAGAAUGACACAUGGAGGCUGAAGAGGCCCAUCUGAUCGAGAUGAAAACAUGUGAAUGGCCAAAGUCCCACACAUUGUGGACAGAUGGAAUAGAAGAGUGAUCUGAUCAUACCCAAGUCUUUAGCUGGGC (SEQ ID NO: 722) | 3007 | 3170 | 164 |
| AUGAUGGGAAAAAGAGAAAAGAAACAAGGGGAAUUU (SEQ ID NO: 651) | 8963 | 2A | AAAUUCCCCUUGUUUCUUUUCUCUUUUUCCCAUCAUGUAUAGUUAUGAACAGAGGAGACAUAACAUGAACAUGAUGAACCAUGUUAACCUGGCGGCAGCGCAAAAG (SEQ ID NO: 675) | 26B | AAAUUCCCCUUGUUUCUUUUCUCUUUUUCCCAUCAUGGACUUUAGAACAGAGGAGAUAAAGAUGAUGAUGGGAAAAAACCUGGCGGCAGCGCAAAAG (SEQ ID NO: 699) | GGGUGCCAGAGUUGUGUGUACAGAUGAUGGGAAAAAGAGAAAAGAAACAAGGGGAAUUUGGAAAGGCCAAGGGAAAGGCAGCCGCGCCAUCUGGUAUAUGUGGCUAGGGGCUAGAUUUCUAGAGUUCGAAGCCCUUGGAUUCUUGAACGAGGAUCACUGGAUGG (SEQ ID NO: 723) | 8941 | 9098 | 158 |

TABLE 6 -continued

Sequences of Toehold Switch Sensors and Corresponding Target Sequences in Zika Genome.

| Target sequence in Zika virus genome | Location in genome | A Series Sensors | | B Series Sensors | | Target RNA Fragment Used for Initial Sensor Screening | | | |
|---|---|---|---|---|---|---|---|---|---|
| | | Sensor Name | Sensor sequence | Sensor Name | Sensor sequence | Sequence | Genome Start site | Genome End site | Genome fragment length |
| GACACAG GACAUGA AACUGAU GAGAAUA GAGCGAA A (SEQ ID NO: 652) | 1373 | 3A | UUUCGCUCU AUUCUCAUCA GUUUCAUGU CCUGUGUCG UUAUAGUUA UGAACAGAG GAGACAUAAC AUGAACGACA CAAACGUCGU UAACCUGGC GGCAGCGCAA AAG (SEQ ID NO: 676) | 27B | UUUCGCUCU AUUCUCAUC AGUUUCAUG UCCUGUGUC GGACUUUAG AACAGAGGA GAUAAAGAU GGACACAGG ACACAACCU GGCGGCAGC GCAAAAG (SEQ ID NO: 700) | GGGCCAGCACAG UGGGAUGAUCGU UAAUGACACAGG ACAUGAAACUGA UGAGAAUAGAGC GAAAGUUGAGAU AACGCCCAAUUC ACCAAGAGCCGA AGCCACCCUGGG GGGGUUUGGAAG CCUAGGACUUGA UUGUGAACCGAG GACAGG (SEQ ID NO: 724) | 1348 | 1494 | 147 |
| UGGAAAA CAUCAUG UGGAGAU CAGUAGA AGGGGAG C (SEQ ID NO: 653) | 2610 | 4A | GCUCCCCUUC UACUGAUCU CCACAUGAUG UUUUCCAGU UAUAGUUAU GAACAGAGG AGACAUAACA UGAACUGGA AAAACCCAGU UAACCUGGC GGCAGCGCAA AAG (SEQ ID NO: 677) | 28B | GCUCCCCUU CUACUGAUC UCCACAUGA UGUUUUCCA GGACUUUAG AACAGAGGA GAUAAAGAU GUGGAAAAC AUCAAACCU GGCGGCAGC GCAAAAG (SEQ ID NO: 701) | GGGCGGGAUCUC CUCUGUUUCAAG AAUGGAAAACAU CAUGUGGAGAUC AGUAGAAGGGGA GCUCAACGCAAU CCUGGAAGAGAA UGGAGUUCAACU GACGGUCGUUGU GGGAUCUGUAAA AAACCCCAUGUG GAGAGGUCCACA GAGAUU (SEQ ID NO: 725) | 2586 | 2733 | 148 |
| GGGGAAA AAAGAGG CUAUGGA AAUAAUA AAGAAGU U (SEQ ID NO: 654) | 256 | 5A | AUUAUUUCC AUAGCCUCU UUUUUCCCC GUUAUAGUU AUGAACAGA GGAGACAUA ACAUGAACG GGGAAAACCC CGUUAACCU GGCGGCAGC GCAAAAG (SEQ ID NO: 678) | 29B | AACUUCUUU AACUUCUUU AUUAUUUCC AUAGCCUCU UUUUUCCCC GGACUUUAG AACAGAGGA GAUAAAGAU GGGGGAAAA AAGAAACCU GGCGGCAGC GCAAAAG (SEQ ID NO: 702) | GGGCCAUCACUG GGUCUCAUCAAU AGAUGGGGUUCA GUGGGGAAAAAA GAGGCUAUGGAA AUAAUAAAGAAG UUCAAGAAAGAU CUGGCUGCCAUG CUGAGAAUAAUC AAUGCUAGGAAG CGAGGCGCAGAU ACUAGUGUCGGA AUUGUUGGCCUC (SEQ ID NO: 726) | 220 | 385 | 166 |
| GAUAACG CCCAAUU CACCAAG AGCCGAA GCCACCC U (SEQ ID NO: 655) | 1414 | 6A | AGGGUGGCU UCGGCUCUU GGUGAAUUG GGCGUUAUC GUUAUAGUU AUGAACAGA GGAGACAUA ACAUGAACGA UAACAACAUC GUUAACCUG GCGGCAGCG CAAAAG (SEQ ID NO: 679) | 30B | AGGGUGGCU UCGGCUCUU GGUGAAUUG GGCGUUAUC GGACUUUAG AACAGAGGA GAUAAAGAU GGAUAACGC CCAUAACCU GGCGGCAGC GCAAAAG (SEQ ID NO: 703) | GGGAAUGCUGUC AGUUCAUGGCUC CCAGCACAGUGG GAUGAUCGUUAA UGACACAGGACA UGAAACUGAUGA GAAUAGAGCGAA AGUUGAGAUAAC GCCCAAUUCACC AAGAGCCGAAGC CACCCUGGGGGG GUUUGGAAGCCU AGGACUUGAUUG UGAACCGAGGAC AGG (SEQ ID NO: 727) | 1327 | 1494 | 168 |

TABLE 6 -continued

Sequences of Toehold Switch Sensors and Corresponding Target Sequences in Zika Genome.

| Target sequence in Zika virus genome | Location in genome | A Series Sensors | | B Series Sensors | | Target RNA Fragment Used for Initial Sensor Screening | | | |
|---|---|---|---|---|---|---|---|---|---|
| | | Sensor Name | Sensor sequence | Sensor Name | Sensor sequence | Sequence | Genome Start site | Genome End site | Genome fragment length |
| UUGAAGA GGAAAAA GAGUGGA AGACUGC AGUGGAA G (SEQ ID NO: 656) | 8841 | 7A | CUUCCACUGC AGUCUUCCAC UCUUUUUCC UCUUCAAGU UAUAGUUAU GAACAGAGG AGACAUAACA UGAACUUGA AGAACCAAGU UAACCUGGC GGCAGCGCAA AAG (SEQ ID NO: 680) | 31B | CUUCCACUG CAGUCUUCC ACUCUUUUU CCUCUUCAA GGACUUUAG AACAGAGGA GAUAAAGAU GUUGAAGAG GAAAAACCU GGCGGCAGC GCAAAAG (SEQ ID NO: 704) | GGGAGAAGGAUG GUCUCUUCCUGG UUGUGGAAAGAG CUAGGCAAACAC AAACGGCCACGA GUCUGUACCAAA GAAGAGUUCAUC AACAAGGUUCGU AGCAAUGCAGCA UUAGGGGCAAUA UUUGAAGAGGAA AAAGAGUGGAAG ACUGCAGUGGAA GCUGUGAACGAU CCAAGGUUCUGG GCUCUAGUGGAC AAGGAAAGA (SEQ ID NO: 728) | 8729 | 8920 | 192 |
| UUUUGC UCGUGGC GCACUAC AUGUACU UGAUCCC AG (SEQ ID NO: 657) | 7188 | 8A | CUGGGAUCA AGUACAUGU AGUGCGCCAC GAGCAAAAG UUAUAGUUA UGAACAGAG GAGACAUAAC AUGAACUUU UGCAACAAAG UUAACCUGG CGGCAGCGCA AAAG (SEQ ID NO: 681) | 32B | CUGGGAUCA AGUACAUGU AGUGCGCCA CGAGCAAAA GGACUUUAG AACAGAGGA GAUAAAGAU GUUUUGCUC GUGUAACCU GGCGGCAGC GCAAAAG (SEQ ID NO: 705) | GGGCUGACCCUA AUAGUGGCCAUC AUUUUGCUCGUG GCGCACUACAUG UACUUGAUCCCA GGGCUGCAGGCA GCAGCUGCGCGU GCUGCCCAGAAG AGAACGGCAGCU GGCAUCAUGAAG AACCCUGUUGUG GAUGG (SEQ ID NO: 729) | 7166 | 7299 | 134 |
| UUGCUAC UCACAAU UAACACC CCUGACC CUAAUAG U (SEQ ID NO: 658) | 7144 | 9A | GUCAGGGGU GUUAAUUGU GAGUAGCAA GUUUAUAGUU AUGAACAGA GGAGACAUA ACAUGAACU UGCUAAACCA AGUUAACCU GGCGGCAGC GCAAAAG (SEQ ID NO: 682) | 33B | ACUAUUAGG ACUAUUAGG GUCAGGGGU GUUAAUUGU GAGUAGCAA GGACUUUAG AACAGAGGA GAUAAAGAU GUUGCUACU CACUAACCU GGCGGCAGC GCAAAAG (SEQ ID NO: 706) | GGGUUUGGUAU GGGCAAAGGGAU GCCAUUCUACGC AUGGGACUUUGG AGUCCCGCUGCU AAUGAUAGGUUG CUACUCACAAUU AACACCCUGAC CCUAAUAGUGGC CAUCAUUUUGCU CGUGGCGCACUA CAUGUACUUGAU CCCAGGGCUG (SEQ ID NO: 730) | 7078 | 7228 | 151 |
| ACCACCU CAUACAA CAACUAC UCCUUAA UGGCGAU G (SEQ ID NO: 659) | 7022 | 10A | AAGGAGUAG UUGUUGUAU GAGGUGGU UUAUAGUUA UGAACAGAG GAGACAUAAC AUGAACACCA CCAACGGUG UUAACCUGG CGGCAGCGCA AAAG (SEQ ID NO: 707) | 34B | CAUCGCCAUU CAUCGCCAU UAAGGAGUA GUUGUUGUA UGAGGUGGU GGACUUUAG AACAGAGGA GAUAAAGAU GACCACCUCA UAUAACCUG GCGGCAGCG CAAAAG (SEQ ID NO: 683) | GGGCCAUCUAUG CUGCCUUGACAA CUUUCAUUACCC CAGCCGUCCAAC AUGCAGUGACCA CCUCAUACAACA ACUACUCCUUAA UGGCGAUGGCCA CGCAAGCUGGAG UGUUGUUUGGU AUGGGCAAAGGG AUGCCAUUCUAC GCAUGGGACUUU GGAGUCCCGCUG CUAAUGAUA (SEQ ID NO: 731) | 6966 | 7141 | 176 |

TABLE 6 -continued

Sequences of Toehold Switch Sensors and Corresponding Target Sequences in Zika Genome.

| Target sequence in Zika virus genome | Location in genome | A Series Sensors Sensor Name | A Series Sensors Sensor sequence | B Series Sensors Sensor Name | B Series Sensors Sensor sequence | Target RNA Fragment Used for Initial Sensor Screening Sequence | Genome Start site | Genome End site | Genome fragment length |
|---|---|---|---|---|---|---|---|---|---|
| ACCACAA AGAUCAU CAUAAGC ACAUCAA UGGCAGU G (SEQ ID NO: 660) | 3563 | 11A | CACUGCCAUU GAUGUGCUU AUGAUGAUC UUUGUGGUG UUAUAGUUA UGAACAGAG GAGACAUAAC AUGAACACCA CAAACGGUG UUAACCUGG CGGCAGCGCA AAAG (SEQ ID NO: 684) | 35B | CACUGCCAU UGAUGUGCU UAUGAUGAU CUUUGUGGU GGACUUUAG AACAGAGGA GAUAAAGAU GACCACAAA GAUAAACCU GGCGGCAGC GCAAAAG (SEQ ID NO: 708) | GGGAGAAGGGUG AUUCUGCUCAUG GUGCAGGAAGGG UUGAAGAAGAGA AUGACCACAAAG AUCAUCAUAAGC ACAUCAAUGGCA GUGCUGGUAGCU AUGAUCCUGGGA GGAUUUUCAAUG AGUGACCUGGCU AAGCUUGCAAUU UUGAUGGGUGCC ACCUUCGCGGAA AUGAACACUGGA GGAGAUGUAGC (SEQ ID NO: 732) | 3521 | 3702 | 182 |
| AGACAGA GUUCCAG AAAACAA AACAUCA AGAGUGG G (SEQ ID NO: 661) | 5721 | 12A | CCCACUCUUG AUGUUUUGU UUCUGGAA CUCUGUCUG UUAUAGUUA UGAACAGAG GAGACAUAAC AUGAACAGAC AGAACUCUG UUAACCUGG CGGCAGCGCA AAAG (SEQ ID NO: 685) | 36B | CCCACUCUU GAUGUUUUG UUUCUGGA ACUCUGUCU GGACUUUAG AACAGAGGA GAUAAAGAU GAGACAGAG UUCCAACCU GGCGGCAGC GCAAAAG (SEQ ID NO: 709) | GGGAGAAGGGUU UGUUCCAAGCGU GAGGAACGGCAA UGAGAUCGCAGC UUGUCUGACAAA GGCUGGAAAACG GGUCAUACAGCU CAGCAGAAAGAC UUUUGAGACAGA GUUCCAGAAAAC AAAACAUCAAGA GUGGGACUUUGU CGUGACAACUGA CAUUUCAGAGAU GGGCGCCAACUU UAAAGCUGACCG UGUCAUAGAUUC CAGGAGAUGCCU AAAGCCGGUCAU ACU (SEQ ID NO: 733) | 5628 | 5850 | 223 |
| UGCACAA UGCCCCC ACUGUCG UUCCGGG CUAAAGA U (SEQ ID NO: 662) | 3368 | 13A | AUCUUUAGC CCGGAACGAC AGUGGGGGC AUUGUGCAG UUAUAGUUA UGAACAGAG GAGACAUAAC AUGAACUGC ACAAACGCAG UUAACCUGG CGGCAGCGCA AAAG (SEQ ID NO: 686) | 37B | AUCUUUAGC CCGGAACGA CAGUGGGGG CAUUGUGCA GGACUUUAG AACAGAGGA GAUAAAGAU GUGCACAAU GCCGAACCU GGCGGCAGC GCAAAAG (SEQ ID NO: 710) | GGGAGAUCAACC ACUGCAAGCGGA AGGGUGAUCGAG GAAUGGUGCUGC AGGGAGUGCACA AUGCCCCACUG UCGUUCCGGGCU AAAGAUGGCUGU UGGUAUGGAAUG GAGAUAAGGCCC AGGAAAGAACCA (SEQ ID NO: 734) | 3316 | 3445 | 130 |
| GACACCG GAACUCC ACACUGG AACAACA AAGAAGC A (SEQ ID NO: 663) | 1598 | 14A | UGCUUCUUU GUUGUUCCA GUGUGGAGU UCCGGUGUC GUUAUAGUU AUGAACAGA GGAGACAUA ACAUGAACGA CACCAACGUC | 38B | UGCUUCUUU GUUGUUCCA GUGUGGAGU UCCGGUGUC GGACUUUAG AACAGAGGA GAUAAAGAU GGACACCGG AACAAACCU | GGGAGUGGUUCC ACGACAUUCCAU UACCUUGGCACG CUGGGGCAGACA CCGGAACUCCAC ACUGGAACAACA AAGAAGCACUGG UAGAGUUCAAGG ACGCACAUGCCA | 1555 | 1711 | 157 |

TABLE 6 -continued

Sequences of Toehold Switch Sensors and Corresponding Target Sequences in Zika Genome.

| Target sequence in Zika virus genome | Location in genome | A Series Sensors Sensor Name | A Series Sensors Sensor sequence | B Series Sensors Sensor Name | B Series Sensors Sensor sequence | Target RNA Fragment Used for Initial Sensor Screening Sequence | Genome Start site | Genome End site | Genome fragment length |
|---|---|---|---|---|---|---|---|---|---|
| | | | GUUAACCUG GCGGCAGCG CAAAAG (SEQ ID NO: 687) | | GGCGGCAGC GCAAAAG (SEQ ID NO: 711) | AAAGGCAAACUG UCGUGGUUCUAG GGAGUCAAGAAG GAGCAGUUCACA CG (SEQ ID NO: 735) | | | |
| GUUUGCC GCUGGGA AAGAGG AGCGGCU UUUGGA GU (SEQ ID NO: 664) | 6379 | 15A | ACUCCAAAAG CCGCUCCUCU UUUCCCAGC GGCAAACGU UAUAGUUAU GAACAGAGG AGACAUAACA UGAACGUUU GCAACAACGU UAACCUGGC GGCAGCGCAA AAG (SEQ ID NO: 688) | 39B | ACUCCAAAA GCCGCUCCU CUUUUCCCA GCGGCAAAC UGAAGUCAUUCA AGGAGUUUGCCG ACUUUAG AACAGAGGA GAUAAAGAU GGUUUGCCG CUGCAACCU GGCGGCAGC GCAAAAG (SEQ ID NO: 712) | GGGUGGACGCCA GAGUUUGUUCAG AUCAUGCGGCCC UGAAGUCAUUCA AGGAGUUUGCCG CUGGGAAAGAG GAGCGGCUUUUG GAGUGAUGGAAG CCCUGGGAACAC UGCCAGGACACA UGACAGAGAGAU (SEQ ID NO: 736) | 6330 | 6458 | 129 |
| GGCAGAA GUGUGG ACCAGAC ACGGAGA GAAAAGA GU (SEQ ID NO: 665) | 6277 | 16A | ACUCUUUUC UCUCCGUGU CUGGUCCACA CUUCUGCCG UUAUAGUUA UGAACAGAG GAGACAUAAC AUGAACGGC AGAAACGCCG UUAACCUGG CGGCAGCGCA AAAG (SEQ ID NO: 689) | 40B | ACUCUUUUC UCUCCGUGU CUGGUCCAC ACUUCUGCC GGACUUUAG AACAGAGGA GAUAAAGAU GGGCAGAAG UGUAAACCU GGCGGCAGC GCAAAAG (SEQ ID NO: 713) | GGGCUGCCGGAA UAACCUACACAG AUAGAAGAUGGU GCUUUGAUGGCA CGACCAACAACA CCAUAAUGGAAG ACAGUGUGCCGG CAGAAGUGUGGA CCAGACACGGAG AGAAAAGAGUGC UCAAACCGAGGU GGAUGGACGCCA GAGUUUGUUCAG A (SEQ ID NO: 737) | 6198 | 6351 | 154 |
| CUGAUCG AGAUGAA AACAUGU GAAUGGC CAAAGUC C (SEQ ID NO: 666) | 3071 | 17A | GGACUUUGG CCAUUCACAU GUUUUCAUC UCGAUCAGG UUAUAGUUA UGAACAGAG GAGACAUAAC AUGAACCUG AUCAACCAGG UUAACCUGG CGGCAGCGCA AAAG (SEQ ID NO: 690) | 41B | GGACUUUGG CCAUUCACA UGUUUUCAU CUCGAUCAG GGACUUUAG AACAGAGGA GAUAAAGAU GCUGAUCGA GAUGAACCU GGCGGCAGC GCAAAAG (SEQ ID NO: 714) | GGGCUACUGGAU UGAGAGUGAGAA GAAUGACACAUG GAGGCUGAAGAG GGCCCAUCUGAU CGAGAUGAACA AUGUGAAUGGCC AAAGUCCCACAC AUUGUGGACAGA UGGAAUAGAAGA GAGUGAUCUGAU CAUACCCAAGUC UUUAGCUGGGC (SEQ ID NO: 738) | 3017 | 3170 | 154 |
| GAGCCAG AAAAGCA AAGAUCU CCCCAGG ACAACCA A (SEQ ID NO: 667) | 6761 | 18A | UUGGUUGUC CUGGGGAGA UCUUUGCUU UUCUGGCUC GUUAUAGUU AUGAACAGA GGAGACAUA ACAUGAACGA GCCAAACCUC GUUAACCUG GCGGCAGCG CAAAAG (SEQ ID NO: 691) | 42B | UUGGUUGUC CUGGGGAGA UCUUUGCUU UUCUGGCUC GGACUUUAG AACAGAGGA GAUAAAGAU GGAGCCAGA AAAGAACCU GGCGGCAGC GCAAAAG (SEQ ID NO: 715) | GGGCAGCCAGAA UUGCAUGUGUCC UCAUUGUUGUGU UCCUAUUGCUGG UGGUGCUCAUAC CUGAGCCAGAAA AGCAAAGAUCUC CCCAGGACAACC AAAUGGCAAUCA UCAUCAUGUAG CAGUAGGUCUUC UGGGCUUGAUUA CCGCCAAUGAAC UCGGAUGGUUGG AGAGAACA (SEQ ID NO: 739) | 6702 | 6874 | 173 |

TABLE 6 -continued

Sequences of Toehold Switch Sensors and Corresponding Target Sequences in Zika Genome.

| Target sequence in Zika virus genome | Location in genome | A Series Sensors | | B Series Sensors | | Target RNA Fragment Used for Initial Sensor Screening | | | |
|---|---|---|---|---|---|---|---|---|---|
| | | Sensor Name | Sensor sequence | Sensor Name | Sensor sequence | Sequence | Genome Start site | Genome End site | Genome fragment length |
| CUUAACA CAUUUAC CAACCUA GUGGUG CAACUCA UU (SEQ ID NO: 668) | 9431 | 19A | AAUGAGUUG CACCACUAGG UUGGUAAAU GUGUUAAGG UUAUAGUUA UGAACAGAG GAGACAUAAC AUGAACCUU AACAACAAGG UUAACCUGG CGGCAGCGCA AAAG (SEQ ID NO: 716) | 43B | AAUGAGUUG CACCACUAG GUUGGUAAA UGUGUUAAG GGACUUUAG AACAGAGGA GAUAAAGAU GCUUAACAC AUUGAACCU GGCGGCAGC GCAAAAG (SEQ ID NO: 692) | GGGAGCGGACAA GUUGUCACUUA CGCUCUUAACACA UUUACCAACCUA GUGGUGCAACUC AUUCGGAAUAUG GAGGCUGAGGAA GUUCUAGAGAUG CAAGACUUGUGG CUGCUGCGGAGG UCAGAGAAAGUG ACUAACUGGUUG CAGAGCAACGGA UGGGAUAGGCUC AAACGAAUGG (SEQ ID NO: 740) | 9404 | 9581 | 178 |
| GCGGUAC AGGGGU GUUCGUC UAUAACG ACGUUGA AG (SEQ ID NO: 669) | 2466 | 20A | CUUCAACGUC GUUAUAGAC GAACACCCCU GUACCGCG U AUAGUUAU GAACAGAGG AGACAUAACA UGAACGCGG UAAACCGCGU UAACCUGGC GGCAGCGCAA AAG (SEQ ID NO: 693) | 44B | CUUCAACGU CGUUAUAGA CGAACACCCC UGUACCGCG GACUUUAGA ACAGAGGAG AUAAAGAUG GCGGUACAG GGAAACCUG GCGGCAGCG CAAAAG (SEQ ID NO: 717) | GGGUGCUCGGUG GACUUCUCAAAG AAGGAGACGAGA UGCGGUACAGGA GUGUUCGUCUAU AACGCGUUGAA GCCUGGAGGGAC AGGUACAAGUAC CAUCCUGACUCC CCCGUAGAUUG GCAGCAGCAGUC AAGCAAGCCUGG GAAGAU (SEQ ID NO: 741) | 2429 | 2578 | 150 |
| GAGGCUG AGGAAGU UCUAGAG AUGCAAG ACUUGUG G (SEQ ID NO: 670) | 9476 | 21A | CCACAAGUCU UGCAUCUCU AGAACUUCCU CAGCCUCGU UAUAGUUAU GAACAGAGG AGACAUAACA UGAACGAGG CUAACCUCGU UAACCUGGC GGCAGCGCAA AAG (SEQ ID NO: 694) | 45B | CCACAAGUC UUGCAUCUC UAGAACUUC CUCAGCCUC GGACUUUAG AACAGAGGA GAUAAAGAU GGAGGCUGA GGACAACCU GGCGGCAGC GCAAAAG (SEQ ID NO: 718) | GGGAGUGGUGCA ACUCAUUCGGAA UAUGGAGGCUGA GGAAGUUCUAGA GAUGCAAGACUU GUGGCUGCUGCG GAGGUCAGAGAA AGUGACUAACUG GUUGCAGAGCAA CGGAUGGGAUAG GCUCAAACGAAU GGCAG (SEQ ID NO: 742) | 9451 | 9584 | 134 |
| GGCACAG UGAAGAG CUUGAAA UUCGGU UUGAGGA AU (SEQ ID NO: 671) | 3225 | 22A | AUUCCUCAAA CCGAAUUUCA AGCUCUUCAC UGUGCCGUU AUAGUUAUG AACAGAGGA GACAUAACAU GAACGGCACA AACGCCGUUA ACCUGGCGG CAGCGCAAAA G (SEQ ID NO: 695) | 46B | AUUCCUCAA ACCGAAUUU CAAGCUCUU CACUGUGCC GGACUUUAG AACAGAGGA GAUAAAGAU GGGCACAGU GAAAAACCU GGCGGCAGC GCAAAAG (SEQ ID NO: 719) | GGGCAAUACCAG AGAGGGCUACAG GACCCAAAUGAA AGGGCCAUGGCA CAGUGAAGAGCU UGAAAUUCGGU UGAAAUUCGGU UGAGGAAUGCCC AGGCACUAAGGU CCACGUGGAGGA AACAUGUGGAAC UCUGAGAUCAAC CACUGCAAGC (SEQ ID NO: 743) | 3184 | 3334 | 151 |
| CAUCUAA UGGGAAG GAGAGAG | 6890 | 23A | UAUGGUUGC CCCUCCUCU CUCCUUCCCA | 47B | UAUGGUUGC CCCUCCUCU CUCCUUCCC | GGGAGUAGGUCU UCUGGGCUUGAU UACCGCCAAUGA | 6820 | 6952 | 133 |

TABLE 6 -continued

Sequences of Toehold Switch Sensors and Corresponding Target Sequences in Zika Genome.

| Target sequence in Zika virus genome | Location in genome | A Series Sensors | | B Series Sensors | | Target RNA Fragment Used for Initial Sensor Screening | | | |
|---|---|---|---|---|---|---|---|---|---|
| | | Sensor Name | Sensor sequence | Sensor Name | Sensor sequence | Sequence | Genome Start site | Genome End site | Genome fragment length |
| GAGGGG GCAACCA UA (SEQ ID NO: 672) | | | UUAGAUGGU UAUAGUUAU GAACAGAGG AGACAUAACA UGAACCAUCU AAACAUGGU UAACCUGGC GGCAGCGCAA AAG (SEQ ID NO: 696) | | AUUAGAUGG GACUUUAGA ACAGAGGAG AUAAAGAUG CAUCUAAUG GGAAACCUG GCGGCAGCG CAAAAG (SEQ ID NO: 720) | ACUCGGAUGGUU GGAGAGAACAAA GAGUGACCUAAG CCAUCUAAUGGG AAGGAGAGAGGA GGGGCAACCAU AGGAUUCUCAAU GGACAUUGACCU GCGG (SEQ ID NO: 744) | | | |
| GAUAGGU UUGCACA UGCCCUC AGGUUCU UGAAUGA U (SEQ ID NO: 673) | 9620 | 24A | AUCAUUCAA GAACCUGAG GGCAUGUGC AAACCUAUCG UUAUAGUUA UGAACAGAG GAGACAUAAC AUGAACGAU AGGAACAUC GUUAACCUG GCGGCAGCG CAAAAG (SEQ ID NO: 697) | 48B | AUCAUUCAA GAACCUGAG GGCAUGUGC AAACCUAUC GGACUUUAG AACAGAGGA GAUAAAGAU GGAUAGGUU UGCUAACCU GGCGGCAGC GCAAAAG (SEQ ID NO: 721) | GGGAUAGGCUCA AACGAAUGGCAG UCAGUGGACAUG AUUGCGUUGUGA AGCCAAUUGAUG AUAGGUUUGCAC AUGCCCUCAGGU UCUUGAAUGAUA UGGGAAAAGUUA GGAAGGACACAC AAGAGUGG (SEQ ID NO: 745) | 9561 | 9688 | 128 |

NOTES:
1. The sequence GGG was added to the 5' end of all sensor RNA and RNA fragment sequences for efficient expression by T7 RNA polymerase. If the RNA target sequence began with G or GG, only GG or G, respectively, was added to the 5' end of the sequence. prefix is not shown in the sensor sequences in the table so that the target
2. The GGG RNA be readily identified.
3. The coding sequence of the reporter protein lacZ binding site can was after the switch RNA sequences in the tables.
4. Two Zika virus strains added immediately AY632535) (KU312312, have sufficient sequence homology to be detected using the same switch sensors toehold (27B, 32B).
5. Target RNAs fragments for sensors 7A/3 1B and 11A/35B have a GGGAGAAGG sequence added at the 5' end.
6. Target RNA fragments for sensors 12A/36B have a GGGAGAAG sequence added at the 5' end.

TABLE 7

| | |
|---|---|
| Zika virus from the Americas genome sequence (Accession number: KU312312; 10,374-nts) | ACAGGUUUUAUUUUGGAUUUGGAAACGAGAGUUUCUGGUCAUGAAAAACCCAA AAAAGAAAUCCGGAGGAUUCCGGAUUGUCAAUAUGCUAAAACGCGGAGUAGCC CGUGUGAGCCCCUUUGGGGGCUUGAAGAGGCUGCCAGCCGGACUUCUGCUGGG UCAUGGGCCCAUCAGGAUGGUCUUGGCGAUUCUAGCCUUUUUGAGAUUCACGG CAAUCAAGCCAUCACUGGGUCUCAUCAAUAGAUGGGGUUCAGUGGGGAAAAAA GAGGCUAUGGAAAUAAUAAAGAAGUUCAAGAAAGAUCUGGCUGCUAUGCUGA GAAUAAUCAAUGCUAGGAAGGAGAAGAAGAGACGAGGCGCAGAUACUAGUGU CGGAAUUGUUGGCCUCCUGCUGACCACAGCUAUGGCAGCGGAGGUCACUAGAC GUGGGAGUGCAUACUAUAUGUACUUGGACAGAAACGAUGCUGGGGAGGCCAUA UCUUUUCCAACCACAUUGGGAUGAAUAAGUGUUAUAUACAGAUCAUGGAUCU UGGACACACGUGUGAUGCCACCAUGAGCUAUGAAUGCCCUAUGCUGGAUGAGG GGGUGGAACCAGAUGACGUCGAUUGUUGGUGCAACACGACGUCAACUUGGGUU GUGUACGGAACCUGCCAUCACAAAAAAGGUGAAGCACGGAGAUCUAGAAGAGC UGUGACGCUCCCCUCCCAUUCCACUAGGAAGCUGCAAACGCGGUCGCAAACCU GGUUGGAAUCAAGAGAAUACACAAAGCACUUGAUUAGAGUCGAAAAUUGGAU AUUCAGGAACCCUGGCUUCGCGUUAGCAGCAGCUGCCAUCGCUUGGCUUUUGG GAAGCUCAACGAGCCAAAAAGUCAUAUACUUGGUCAUGAUACUGCUGAUUGCC CCGGCAUACAGCAUCAGGUGCAUAGGAGUCAGCAAUAGGGACUUUGUGGAAGG UAUGUCAGGUGGGACUUGGGUUGAUGUUGUCUUGGAACAUGGAGGUUGUGUC ACUGUAAUGGCACAGGACAAACCGACGUCGACAUAGAGCUGGUUACAACAAC AGUCAGCAACAUGGCGGAGGUAAGAUCCUACUGCUAUGAGGCAUCAAUAUCAG ACAUGGCUUCGGACAGCCGCUGCCCAACACAAGGUGAAGCCUACCUUGACAAG CAAUCAGACACUCAAUAUGUCUGCAAAAGAACGUUAGUGGACAGAGGCUGGGG AAAUGGAUGUGGACUUUUUGGCAAAGGGAGCCUGGUGACAUGCGCUAAGUUU GCAUGCUCCAAGAAAAUGACCGGGAAGAGCAUCCAGCCAGAGAAUCUGGAGUA CCGGAUAAUGCUGUCAGUUCAUGGCUCCCAGCACAGUGGGAUGAUCGUUAAUG ACACAGGACAUGAAACUGAUGAGAAUAGAGCGAAAGUUGAGAUAACGCCCAAU UCACCAAGAGCCGAAGCCACCCUGGGGGGGUUUGGAAGCCUAGGACUUGAUUG UGAACCGAGGACAGGCCUUGACUUUUCAGAUUGUAUUACUUGACUAUGAAUA ACAAGCACUGGCUGGUUCACAAGGAGUGGUUCCACGACAUUCCAUUACCUUGG CACGCUGGGGCAGACACCGGAACUCCACACUGGAACAACAAAGAAGCACUGGU |

TABLE 7 -continued

```
AGAGUUCAAGGACGCACAUGCCAAAAGGCAAACUGUCGUGGUUCUAGGGAGUC
AAGAAGGAGCAGUUCACACGGCCCUUGCUGGAGCUCUGGAGGCUGAGAUGGAU
GGUGCAAAGGGAAGGCUGUCCUCUGGCCACUUGAAAUGUCGCCUGAAAAUGGA
UAAACUUAGAUUGAAGGGCGUGUCAUACUCCUUGUGUACUGCAGCGUUCACAU
UCACCAAGAUCCCGGCUGAAACACUGCACGGGACAGUCACAGUGGAGGUACAG
UACGCAGGGACAGAUGGACCUUGCAAGGUUCCAGCUCAGAUGGCGGUGGACAU
GCAAACUCUGACCCCAGUUGGGAGGUUGAUAACCGCUAACCCCGUAAUCACUG
AAAGCACUGAGAACUCUAAGAUGAUGCUGGAACUUGAUCCACCAUUUGGGGAC
UCUUACAUUGUCAUAGGAGUCGGGGAGAAGAAGAUCACCCACCACUGGUCACAG
GAGUGGCAGCACCAUUGGAAAAGCAUUUGAAGCCACUGUGAGAGGUGCCAAGA
GAAUGGCAGUCUUGGGAGACACAGCCUGGGACUUUGGAUCAGUUGGAGGCGCU
CUCAACUCAUUGGGCAAGGGCAUCCAUCAAAUCUUUGGAGCAGCUUUCAAAUC
AUUGUUUGGAGGAAUGUCCUGGUUCUCACAAAUUCUCAUUGGAACGUUGCUGA
UGUGGUUGGGUCUGAACGCAAAGAAUGGAUCUAUUUCCCUUAUGUGCUUGGCC
UUAGGGGAGUGUUGAUCUUCUAUCCACAGCCGUCUCUGCUGAUGUGGGGUG
CUCGGUGGACUUCUCAAAGAAGGAGACGAGAUGCGGUACAGGGGUGUUCGUCU
AUAACGACGUUGAAGCCUGGAGGGACAGGUACAAGUACCAUCCUGACUCCCCC
CGUAGAUUGGCAGCAGCAGUCAAGCAAGCCUGGGAAGAUGGUAUCUGCGGGAU
CUCCCUCUGUUUCAAGAAUGGAAAACAUCAUGUGGAGAUCAGUAGAAGGGGAGC
UCAACGCAAUCCUGGAAGAGAAUGGAGUUCAACUGACGGUCGUUGUGGGAUCU
GUAAAAAACCCCAUGUGGAGGUCCACAGAGAUUGCCCGUGCCUGUGAACGA
GCUGCCCCACGGCUGGAAGGCUUGGGGGAAAUCGUACUUCGUCAGAGCAGCAA
AGACAAAUAACAGCUUUGUCGUGGAUGGUGACACACUGAAGGAAUGCCCACUC
AAACAUAGAGCAUGGAACAGCUUUCUUGUGGAGGAUCAUGGGUUCGGGUAU
UUCACACUAGUGUCUGGCUCAAGGUUUAGAAGAUUAUUCAUUAGAGUGUGA
UCCAGCCGUUAUUGGAACAGCUGUUAAGGGAAAGGAGGCUGUACACAGUGAUC
UAGGCUACUGGAUUGAGAGUGAGAAGAAUGACACAUGGAGGCUGAAGAGGGC
CCAUCUGAUCGAGAUGAAAACAUGUGAAUGGCCAAAGUCCCCACACAUUGUGGA
CAGAUGGAAUAGAAGAGAGUCUGAUCAUACCCAAGUCUUUAGCUGGGGCCA
CUCAGCCAUCACAAUACCAGAGAGGGCUACAGGACCCAAAUGAAAGGCCAUG
GCACAGUGAAGAGCUUGAAAUUCGGUUUGAGGAAUGCCCAGGCACUAAGGUCC
ACGUGGAGGAAACAUGUGGAACGAGAGGACCAUCUCUGAGAUCAACCACUGCA
AGCGGAAGGGUGAUCGAGGAAUGGUGCUGCAGGGAGUGCACAUGCCCCCACU
GUCGUUCCGGGCUAAAGAUGGCUGUUGGUAUGGAAUGGAGAUAAGGCCCAGGA
AAGAACCAGAAAGCAACUUAGUAAGGUCAAUGGUGACUGCAGGAUCAACUGAU
CACAUGGACCACUUCUCCCUUGGAGUGCUUGUGAUUCUGCUCAUGGUGCAGGA
AGGGUUGAAGAAGAGAAUGACCACAAAGAUCAUCAUAAGCACAUCAAUGGCAG
UGCUGGUAGCUAUGAUCUCGGGAGGAUUUUCAAUGAGUGACCUGGCUAAGCUU
GCAAUUUUGAUGGGUGCCACCUUCGCGGAAAUGAACACUGGAGGAGAUGUAGC
UCAUCUGGCGCUGAUAGCGGCAUUCAAAGUCAGACCAGCGUUGCUGGUAUCUU
UCAUCUUCAGAGCUAAUUGGACACCCCGUGAAAGCAUGCUGCUGGCCUUGGCC
UCGUGUCUUUUGCAAACUGCGAUCUCCGCCUUGGAAGGCGACCUGAUGGUUCU
CAUCAAUGGUUUUGCUUUGGCCUGGUUGGCAAUACGAGCGAUGGUUGUUCCAC
GCACUGAUAACAUCACCUUGGCAAUCCUGGCUGCUCUGACACCACUGGCCCGG
GGCACACUGCUUUGUGGCGUGGAGAGCAGGCCUUGCUACUUGCGGGGGUUUAU
GCUCCUCUCUCUGAAGGGAAAAGGCAGUGUGAAGAAGAACUUACCAUUUGUCA
UGGCCCUGGGACUAACCGCUGUGAGGCUGGUCGACCCCAUCAACGUGGUGGGA
CUGCUGUUGCUCACAAGGAGUGGGAAGCGGAGCUGGCCCCUAGCGAAGUACU
CACAGCUGUUGGCCUGAUAUGCGCAUUGGCUGGAGGGUUCGCCAAGGCAGAUA
UAGAGAUGGCUGGGCCCAUGGCCGCGGUCGGUCUGCUAAUUGUCAGUUACGUG
GUCUCAGGAAAGAGUGUGGACAUGUACAUUGAAAGAGCAGGUGACAUCACAUG
GGAAAAAGAUGCGGAAGUCACUGGAAACAGUCCCCGGCUCGAUGUGGCGCUAG
AUGAGAGUGGUGAUUUCUCCCUGGUGGAGGAUGACGGUCCCCCCAUGAGAGAG
AUCAUACUCAAGGUGGUCCUGAUGACCAUCUGUGGCAUGAACCCAAUAGCCAU
ACCCUUUGCAGCUGGAGCGUGGUACGUAUACGUGAAGACUGGAAAAGGAGUG
GUGCUCUAUGGGAUGUGCCUGCUCCCAAGGAAGUAAAAAAGGGGGAGACCACA
GAUGGAGUGUACAGAGUAAUGACUCGUAGACUGCUAGGUUCAACACAAGUUGG
AGUGGGAGUUAUGCAAGAGGGGGUCUUUCACACUAUGUGGCACGUCACAAAAG
GAUCCGCGCUGAGAAGCGGUGAAGGGAGACUUGAUCCAUACUGGGGAGAUGUC
AAGCAGGAUCUGGUGUCAUACUGUGGUCCAUGGAAGCUAGAUGCCGCCUGGGA
CGGGCACAGCGAGGUGCAGCUCUUGGCCGUGCCCCCCGGAGAGAGAGCGAGGA
ACAUCCAGACUCUGCCCGGAAUAUUUAAGACAAAGGAUGGGGACAUUGGAGCG
GUUUGCGCUGGAUUACCCAGCAGGAACUUCAGGAUCUCCUAUCCUAGACAAGUG
UGGGAGAGUGAUAGGACUUUAUGGCAAUGGGGUCGUGAUCAAAAAUGGGAGU
UAUGUUAGUGCCAUCACCCAAGGGAGGAGGGAGGAAGAGACUCCUGUUGAGUG
CUUCGAGCCUUCGAUGCUGAAGAAGAAGCAGCUACUGUCUUAGACUUGCAUC
CUGGAGCUGGGAAAACCAGGAGAGUUCUUCCUGAAAUAGUCCGUGAAGCCAUA
AAAACAAGACUCCGUACUGUGAUCUUAGCUCCAACCAGGGGUUGUCGCUGCUGA
AAUGGAGGAGGCCCUUAGAGGGCUUCCAGUGCGUUAUAUGACAACAGCAGUCA
AUGUCACCCACUCUGGAACAGAAAUCGUCGACUUAAUGUGCCAUGCCACCUUC
ACUUCGCGUCUACUACAGCCAAUCAGAGUCCCCAACUAUAAUCUGUAUAUUAU
GGAUGAGGCCCACUUCACAGAUCCCUCAAGUAUAGCAGCAAGAGGAUACAUUU
CAACAAGGGUUGAGAUGGGCGAGGCGGCCGCCAUCUUCAUGACCGCCACGCCA
CCAGGAACCCGUGACGCAUUUCCGGACUCCAACUCACCAAUUAUGGACACCGA
AGUGGAAGUCCCAGAGAGCCUGGAGCUCAGGCUUUGAUUGGGUGACGGAUC
AUUCUGGAAAACAGUUUGGUUUGUUCCAAGCGUGAGGAACGGCAAUGAGAUC
GCAGCUUGUCUGACAAAGGCUGGAAACGGGUCAUACAGCUCAGCAGAAAGAC
UUUUGAGACAGAGUUCCAGAAAACAAAACAUCAAGAGUGGGACUUUGUCGUGA
CAACUGACAUUUCAGAGAUGGGCGCCAACUUUAAAGCUGACCGUGUCAUAGAU
UCCAGGAGAUGCCUAAAGCCGGUCAUACUUGAUGGCGAGAGAGUCAUUCUGGC
```

TABLE 7 -continued

```
UGGACCCAUGCCUGUCACACAUGCCAGCGCUGCCCAGAGGAGGGGCGCAUAG
GCAGGAAUCCCAACAAACCUGGAGAUGAGUAUCUGUAUGGAGGUGGGUGCGCA
GAGACUGACGAAGACCAUGCACACUGGCUUGAAGCAAGAAUGCUCCUUGACAA
UAUUUACCUCCAAGAUGGCCUCAUAGCCUCGCUCUAUCGACCUGAGGCCGACA
AAGUAGCAGCCAUUGAGGGAGAGUUCAAGCUUAGGACGGAGCAAAGGAAGACC
UUUGUGGAACUCAUGAAAGAGGGAGAUCUUCCUGUUUGGCUGGCCUAUCAGGU
UGCAUCUGCCGGAAUAACCUACACAGAUAGAAGAUGGUGCUUUGAUGGCACGA
CCAACAACACCAUAAUGGAAGACAGUGUGCCGGCAGAAGUGUGGACCAGACAC
GGAGAGAAAAGAGUGCUCAAACCGAGGUGGAUGGACGCCAGAGUUUGUUCAGA
UCAUGCGGCCCUGAAGUCAUUCAAGGAGUUUGCCGCUGGGAAAAGAGGAGCGG
CUUUUGGAGUGAUGGAAGCCCUGGGAACACUGCCAGGACACAUGACAGAGAGA
UUCCAGGAAGCCAUUGACAACCUCGCUGUGCUCAUGCGGGCAGAGACUGGAAG
CAGGCCUUACAAAGCCGGCGGCCCAAUUGCCGGAGACCCUAGAGACCAUUA
UGCUUUUGGGGUUGCUGGGAACAGUCUCGCUGGGAAUCUUCUUCGUCUUGAUG
AGGAACAAGGGCAUAGGGAAGAUGGGCUUUGGAAUGGUGACUCUUGGGGCCA
GCGCAUGGCUCAUGUGGCUCUCGGAAAUUGAGCCAGCCAGAAUUGCAUGUGUC
CUCAUUGUUGUGUUCCUAUUGCUGGUGGUGCUCAUACCUGAGCCAGAAAAGCA
AAGAUCUCCCCAGGACAACCAAAUGGCAAUCAUCAUCAUGGUAGCAGUAGGUC
UUCUGGGCUUGAUUACCGCCAAUGAACUCGGAUGGUUGGAGAGAACAAAGAGU
GACCUAAGCCAUCUAAUGGGAAGGAGAGAGGAGGGGCAACCAUAGGAUUCUC
AAUGGACAUUGACCUGCGGCCAGCCUCAGCUUGGGCCAUCUAUGCUGCCUUGA
CAACUUUCAUUACCCCAGCCGUCCAACAUGCAGUGACCACCUCAUACAACAACU
ACUCCUUAAUGGCGAUGCCACGCAAGCUGGAGUGUUGUUUGGUAUGGGCAAA
GGGAUGCCAUUCUACGCAUGGGACUUUGGAGUCCCGCUGCUAAUGAUAGGUUG
CUACUCACAAUUAACACCCCUGACCCUAAUAGUGGCCAUCAUUUUGCUCGUGG
CGCACUACAUGUACUUGAUCCCAGGGCUGCAGGCAGCAGCUGCGCGUGCUGCC
CAGAAGAGAACGGCAGCUGGCAUCAUGAAGAACCCUGUUGUGGAUGGAAUAGU
GGUGACUGACAUUGACACAAUGACAAUUGACCCCCAAGUGGAGAAAAGAUGG
GACAGGUGCUACUCAUAGCAGUAGCCGUCUCCAGCGCCAUACUGUCGCGGACC
GCCUGGGGGUGGGGGAGGCUGGGGCCCUGAUCACAGCCGCAACUUCCACUUU
GUGGGAAGGCUCUCCGAACAAGUACUGGAACUCCUCUACAGCCACUUCACUGU
GUAACAUUUUAGGGGAAGUUACUUGGCUGGAGCUUCUCUAAUCUACACAGUA
ACAAGAAACGCUGGCUUGGUCAAGAGACGUGGGGGUGGAACAGGAGAGACCCU
GGGAGAGAAAUGGAAGGCCCGCUUGAACCAGAUGUCGGCCCUGGAGUUCUACU
CCUACAAAAAGUCAGGCAUCACCGAGGUGUGCAGAGAAGAGGCCCGCCGCGCC
CUCAAGGACGGUGUGGCAACGGGAGGCCAUGCUGUGUCCCGAGGAAGUGCAAA
GCUGAGAUGGUUGGUGGAGCGGGGAUACCUGCAGCCCUAUGGAAAGGUCAUUG
AUCUUGGAUGUGGCAGAGGGGCUGGAGUUACUACGCCGCCACCAUCCGCAAA
GUUCAAGAAGUGAAAGGAUACACAAAAGGAGGCCCUGGUCAUGAAGAACCCGU
GUUUGGUGCAAAGCUAUGGGUGGAACAUAGUCCGUCUUAAGAGUGGGGUGGAC
GUCUUUCAUAUGGCGGCUGAGCCGUGUGACACGUUGCUGUGUGACAUAGGUGA
GUCAUCAUCUAGUCCUGAAGUGGAAGAAGCACGGACGCUCAGAGUCCUCUCCA
UGGUGGGGGAUUGGCUUGAAAAAAGACCAGGAGCCUUUUGUAUAAAAGUGUU
GUGCCCAUACACCAGCACUAUGAUGGAAACCCUGGAGCGACUGCAGCGUAGGU
AUGGGGAGGACUGGUCAGAGUGCCACUCUCCCGCAACUCUACACAUGAGAUG
UACUGGGUCUCUGGAGCGAAAAGCAACACCAUAAAAAGUGUGUCCACCACGAG
CCAGCUCCUCUUGGGGCGCAUGGACGGGCCUAGGAGGCCAGUGAAAUAUGAGG
AGGAUGUGAAUCUCGGCUCUGGCACGCGGGCUGUGGUAAGCUGCGCUGAAGCU
CCCAACAUGAAGAUCAUUGGUAACCGCAUUGAAAGGAUCCGCAGUGAGCACGC
GGAAACGUGGUUCUUUGACGAGAACCACCCAUAUAGGACAUGGGCUUACCAUG
GAAGCUAUGAGGCCCCCACACAAGGGUCAGCGUCCUCUCUAAUAAACGGGGUU
GUCAGGCUCCUGUCAAAACCCUGGGAUGUGGUGACUGGAGUCACAGGAAUAGC
CAUGACCGACACCACACCGUAUGGUCAGCAAAGAGUUUUCAAGGAAAAAGUGG
ACACUAGGGUGCCAGACCCCCAAGAAGGCACUCGUCAGGUUAUGACGAUGGUC
UCUUCCUGGUUGUGGAAAGAGCUAGGCAAACACAAACGGCCACGAGUCUGUAC
CAAAGAAGAGUUCAUCAACAAGGUUCGUAGCAAUGCAGCAUUAGGGGCAAUAU
UUGAAGAGGAAAAAGAGUGGAAGACUGCAGUGGAAGCUGUGAACGAUCCAAG
GUUCUGGGCUCUAGUGGACAAGGAAAGAGAGCACCACCUGAGGAGGAGAGUGCC
AGAGUUGUGUGUACAACAUGAUGGGAAAAAGAGAAAAGAAACAAGGGGAAUU
UGGAAAGGCCAAGGGCAGCCGCGCCAUCUGGUAUAUGUGGCUAGGGGCUAGAU
UUCUAGAGUUCGAAGCCCUUGGAUUCUUGAACGAGGAUCACUGGAUGGGGAGA
GAGAACUCAGGAGGUGGUGUUGAAGGGCUGGGAUUACAAAGACUCGGAUAUG
UCCUAGAAGAGAUGAGUCGUAUACCAGGAGGAAGGAUGUAUGCAGAUGACACU
GCUGGCUGGGACACCCGCAUUAGCAGGUUUGAUCUGGAGAAUGAAGCUCUAAU
CACCAACCAAAUGGAGAAAGGGCACAGGGCCUUGGCAUUGGCCAUAAUCAAGU
ACACAUACCAAAACAAAGUGGUAAAGGUCCUUAGACCAGCUGAAAAAGGGAAA
ACAGUUAUGGACAUUAUUUCGAGACAAGACCAAAGGGGGAGCGGAAGAGUUGU
CACUUACGCUCUUAACACAUUUACCAACCUAGUGGUGCAACUCAUUCGGAAUA
UGGAGGCUGAGGAAGUUCUAGAGAUGCAAGACUUGUGGCUGCUGCGGAGGUCA
GAGAAAGUGACUAACUGGUUGCAGAGCAACGGAUGGGAUAGGCUCAAACGAAU
GGCAGUCAGUGGAGAUGAUUGCGUUGUGAAGCCAAUUGAUGAUAGGUUUGCA
CAUGCCCUCAGGUUCUUGAAUGAUAUGGGAAAAGUUAGGAAGGACACACAAGA
GUGGAAACCCUCAACUGGAUGGGACAACUGGGAAGAAGUUCCGUUUUGCUCCC
ACCACUUCAACAAGCUCCAUCUCAAGGACGGGAGGUCCAUUGUGGUUCCCUGC
CGCCACCAAGAUGAACUGAUUGGCCGGGCCCGCGUCUCCCAGGGGGCGGAUG
GAGCAUCCGGGAGACUGCUUGCCUAGCAAAAUCAUAUGCGCAAAUGUGGCAGC
UCCUUUAUUUCCACAGAAGGGACCUCCGACUGAUGGCCAAUGCCAUUUGUUCA
UCUGUGCCAGUUGACUGGGUUCCAACUGGGAGAACUACCGGUCAAUCCAUGG
AAAGGGAGAAUGGAUGACCACUGAAGACAUGCUUGUGGUGUGGAACAGAGUG
UGGAUUGAGGAGAACGACCACAUGGAAGACAAGACCCCAGUUACGAAAUGGAC
```

TABLE 7 -continued

| | |
|---|---|
| | AGACAUUCCCUAUUUGGGAAAAAGGGAAGACUUGUGGUGUGGAUCUCUCAUAG<br>GGCACAGACCGCGCACCACCUGGGCUGAGAACAUUAAAAACACAGUCAACAUG<br>GUGCGCAGGAUCAUAGGUGAUGAAGAAAAGUACAUGGACUACCUAUCCACCCA<br>AGUUCGCUACUUGGGUGAAGAAGGGUCUACACCUGGAGUGCUGUAAGCACCAA<br>UCUUAAUGUUGUCAGGCCUGCUAGUCAGCCACAGCUUGGGGAAAGCUGUGCAG<br>CC (SEQ ID NO: 746) |
| MR 766<br>Zika virus<br>genome,<br>Uganda<br>1947<br>(Accession<br>number:<br>AY632535;<br>10,794-nts) | AGUUGUUGAUCUGUGUGAGUCAGACUGCGACAGUUCGAGUCUGAAGCGAGAGC<br>UAACAACAGUAUCAACAGGUUUAAUUUGGAUUUGGAAACGAGAGUUUCUGGU<br>CAUGAAAAACCCCAAAGAAGAAAUCCGGAGGAUCCGGAUUGUCAAUAUGCUAA<br>AACGCGGAGUAGCCCGUGUAAACCCCUUGGGAGGUUUUGAAGAGGUUGCCAGCC<br>GGACUUCUGCUGGGUCAUGGACCCAUCAGAAUGGUUUUGGCGAUACUAGCCU<br>UUUGAGAUUUACAGCAAUCAAGCCAUCACUGGGCCUUAUCAACAACAUGGGGUU<br>CCGUGGGGAAAAAGAGGCUAUGGAAAUAAUAAAGAAGUUCAAGAAAGAUCU<br>UGCUGCCAUGUUGAGAAUAAUCAAUGCUAGGAAAGAGAGGAAGAGACGUGGC<br>GCAGACACCAGCAUCGGAAUCAUUGGCCUCCUGCUGACUACAGCCAUGGCAGC<br>AGAGAUCACUAGACGCGGGAGUGCAUACUAUGUACUUGGAUAGGAGCGAUG<br>CCGGGAAGGCCAUUUCGUUUGCUACCACAUUGGGAGUGAACAAGUGCCACGUA<br>CAGAUCAUGGACCUCGGGCACAUGUGUGACGCCACCAUGAGUUAUGAGUGCCC<br>UAUGCUGGAUGAGGGAGUGGAACCAGAUGAUGUCGAUUGCUGGUGCAACACGA<br>CAUCAACUUGGGUUGUGUACGGAACCUGCUCACAAAAAAGGUGAGGCACGG<br>CGAUCUAGAAGAGCCGUGACGCUCCCUUCUCACUCUACAAGGAAGUUGCAAAC<br>GCGGUCGCAGACCUGGUUAGAAUCAAGAGAAUACACGAAGCACUUGAUCAAGG<br>UUGAAAACUGGAUAUUCAGGAACCCCGGGUUUGCGCUAGUGGCCGUUGCCAUU<br>GCCUGGCUUUUGGGAAGCUCGACGAGCCAAAAAGUCAUAUACUUGGUCAUGAU<br>ACUGCUGAUUGCCCCGGCAUACAGUAUCAGGUGCAUUGGAGUCAGCAAUAGAG<br>ACUUCGUGGAGGGCAUGUCAGGUGGGACCUGGGUUGAUGUUGUCUUGGAACAU<br>GGAGGCUGCGUUACCGUGAUGGCACAGGACAAGCCAACAGUCGACAUAGAGUU<br>GGUCACGACGACGGUUAGUAACAUGGCCGAGGUAAGAUCCUAUUGCUACGAGG<br>CAUCGAUAUCGGACAUGGCUUCGGACAGUCGUUGCCCAACACAAGGUGAAGCC<br>UACCUUGACAAGCAAUCAGACACUCAAUAUGUCUGCAAAAGAACAUUAGUGGA<br>CAGAGGUUGGGGAAACGGUUGUGGACUUUUUGGCAAAGGGAGCUUGGUGACA<br>UGUGCCAAGUUUACGUGUUCUAAGAAGAUGACCGGGAAGAGCAUUCAACCGGA<br>AAAUCUGGAGUAUCGGAUAAUGCUAUCAGUGCAUGGCUCCCAGCAUAGCGGGA<br>UGAUUGGAUAUGAAACUGACGAAGAUAGAGCGAAAGUCGAGGUUACGCCUAA<br>UUCACCAAGAGCGGAAGCAACCUUGGGAGGCUUUGGAAGCUUAGGACUUGACU<br>GUGAACCAAGGACAGGCCUUGACUUUUCAGAUCUGUAUUACCUGACCAUGAAC<br>AAUAAGCAUUGGUUGGUGCACAAGAGUGGUUUCAUGACAUCCGAUUGCCUUG<br>GCAUGCUGGGGCAGACACCGGAACUCCACACUGGAACAACAAAGAGGCAUUGG<br>UAGAAUUCAAGGAUGCCCACGCCAAGAGGCAAACCGUCGUCGUUCUGGGGAGC<br>CAGGAAGGAGCCGUUCACACGGCUCUCGCUGGAGCUCUAGAGGCUGAGAUGGA<br>UGGUGCAAAGGGAAGGCUGUUCUCUGGCCAUUUGAAAUGCCUAAAAAAUGG<br>ACAAGCUUAGAUUGAAGGGCGUGUCAUAUUCCUUGUGCACUGCGGCAUUCACA<br>UUCACCAAGGUCCCAGCUGAAACACUGCAUGGAACAGUCACAGUGGAGGUGCA<br>GUAUGCAGGGACAGAUGGACCCUGCAAGAUCCCAGUCCAGAUGGCGGUGGACA<br>UGCAGACCCUGACCCCAGUUGGAAGGCUGAUAACCGCCAACCCCGUGAUUACU<br>GAAAGCACUGAGAACUCAAAGAUGAUGUUGGAGCUUGACCCACCAUUUGGGGA<br>UUCUUACAUUGUCAUAGGAGUUGGGGACAAGAAAAUCACCCACCACUGGCAUA<br>GGAGUGGUAGCACCAUCGGAAAGGCAUUUGAGGCCACUGUGAGAGGCGCCAAG<br>AGAAUGGCAGUCCUGGGGGAUACAGCCUGGGACUUUGGAUCAGUCGGGGUGU<br>GUUCAACUCACUGGGGUAAGGGCAUUCACCAGAUUUUUGGAGCAGCCUUCAAAU<br>CACUGUUUGGAGGAAUGUCCUGGUUCUCACAGAUCCUCAUAGGCACGCUGCUA<br>GUGUGGUUAGGUUUGAACACAAAGAAUGGAUCUAUCUCCCUCACAUGCUUGGC<br>CCUGGGGGGAGUGAUGAUCUUCUCUCCACGGCUGUUUCUGCUGACGUGGGGU<br>GCUCAGUGGACUUCUCAAAAAAGGAAACGAGAUGUGGCACGGGGGUAUUCAUC<br>UAUAAUGAUGUUGAAGCUGGAGGGACCGGUACAAGUACCAUCCUGACUCCCC<br>CCGCAGAUUGGCAGCAGCAGUCAAGCAGGCCUGGGAAGAGGGGAUCUGUGGGA<br>UCUCAUCCGUUUCAAGAAUGGAAAACAUCAUGUGGAAAUCAGUAGAAGGGGAG<br>CUCAAUGCUAUCCUAGAGGAGAAUGGAGUUCAACUGACAGUUGUUGUGGGGAUC<br>UGUAAAAACCCCAUGUGGAGAGGUCCACAAAGAUUGCCAGUGCCUGUGAAUG<br>AGCUGCCCCAUGGCUGGAAAGCCUGGGGGAAAUCGUAUUUUGUUAGGGCGGCA<br>AAGACCAACAACAGUUUUGUUGUCGACGGUGACACUGAAGGAAUGUCCGCU<br>UGAGCACAGAGCAUGGAAUAGUUUUCUUGUGGAGGAUCACGGGUUUGGAGUC<br>UUCCACACCAGUGUCUGGCUUAAGGUCAGAGAAGAUUACUCAUUAGAAUGUGA<br>CCCAGCCGUCAUAGGAACAGCUGUUAAGGGAAGGGAGGCCGCGCACAGUGAUC<br>UGGGCUAUUGGAUUGAAAGUGAAAGAAUGACACAUGGAGGCUGAAGAGGGC<br>CCACCUGAUUGAUGAAACAUGAUGGCCAAAGUCUCACAUUGUGGA<br>CAGAUGGAGUAGAAGAAAGUGAUCUUAUCAUACCCAAGUCUUUAGCUGGUCCA<br>CUCAGCCACCACAACACCAGAGAGGGUUACAGAACCCAAGUGAAAGGGCCAUG<br>GCACAGUGAAGAGCUUGAAAUCCGGUUUGAGGAAUGUCCAGGCACCAAGGUUU<br>ACGUGGAGGAGACAUGCGGAACUAGAGGACCAUCUCUGAGAUCAACUACUGCA<br>AGUGGAAGGGUCAUUGAGGAAUGGUGCUGUAGGGAAUGCACAAUGCCCCCACU<br>AUCGUUUCGAGCAAAAGACGGCUGCUGGUAUGGAAUGGAGAUAAGGCCCAGGA<br>AAGAACCAGAGAGCAACUUGUGAGGUCAAUGGUGACAGCGGGGUCAACCGAU<br>CAUAUGGACCACUUCUCUCUUGGAGUGCUUGUGAUUCUACUCAUGGUGCAGGA<br>GGGGUUGAAGAAGAGAAUGACCACAAAGAUCAUCAUGAGCACAUCAAUGGCAG<br>UGCUGGUAGUCAUGAUCUUGGGAGGAUUUUCAAUGAGUGACCUGGCCAAGCUU<br>GUGAUCCUGAUGGGUGCUACUUUCGCAGAAAUGAACACUGGAGGAGAUGUAGC<br>UCACUUGGCAUUGGUAGCGGCAUUUAAAGUCAGACCAGCCUUGCUGGUCUCCU<br>UCAUUUUCAGAGCCAAUUGGACACCCCGUGAGAGCAUGCUGCUAGCCCUGGCU |

TABLE 7 -continued

```
UCGUGUCUUCUGCAAACUGCGAUCUCUGCUCUUGAAGGUGACUUGAUGGUCCU
CAUUAAUGGAUUUGCUUUGGCCUGGUUGGCAAUUCGAGCAAUGGCCGUGCCAC
GCACUGACAACAUCGCUCUACCAAUCUUGGCUGCUCUAACACCACUAGCUCGA
GGCACACUGCUCGUGGCAUGGAGAGCGGGCCUGGCUACUUGUGGAGGGAUCAU
GCUCCUCUCCCUGAAAGGGAAAGGUAGUGUGAAGAAGAACCUGCCAUUUGUCA
UGGCCCUGGGAUUGACAGCUGUGAGGGUAGUAGACCCUAUUAAUGUGGUAGGA
CUACUGUUACUCACAAGGAGUGGGAAGCGGAGCUGGCCCCCUAGUGAAGUUCU
CACAGCCGUUGGCCUGAUAUGUGCACUGGCCGGAGGGUUUGCCAAGGCAGACA
UUGACAUGGCUGGACCCCAUGGCUGCAGUAGGCUUGCUAAUUGUCAGCUAUGUG
GUCUCGGGAAAGAGUGUGGACAUGUACAUUGAAAGAGCAGGUGACAUCACAUG
GGAAAAGGACGCGGAAGUCACUGGAAACAGUCCUCGGCUUGACGUGGCACUGG
AUGAGAGUGGUGACUUCUCCUUGGUAGAGGAAGAUGGUCCACCCAUGAGAGAG
AUCAUACUCAAGGUGGUCCUGAUGGCCAUCUGUGGCAUGAACCCAAUAGCUAU
ACCUUUUGCUGCAGGAGCGUGGUAUGUGUAUGUGAAGACUGGGAAAAGGAGU
GGCGCCCUCUGGGACGUGCCUGCUCCCAAAGAAGUGAAGAAAGGAGAGACCAC
AGAUGGAGUGUACAGAGUGAUGACUCGCAGACUGCUAGGUUCAACACAGGUUG
GAGUGGGAGUCAUGCAAGAGGGAGUCUUCCACACCAUGUGGCACGUUACAAAA
GGAGCCGACUGAGGAGCGGUGAGGGAAGACUUGAUCCAUACUGGGGGGAUGU
CAAGCAGGACUUGGUGUCAUACUGUGGGCCUUGGAAGUUGGAUGCAGCUUGGG
AUGGACUCAGCGAGGUACAGCUUUUGGCCGUACCUCCCGGAGAGAGGGCCAGA
AACAUUCAGACCCUGCCUGGAAUAUUCAAGACAAAGGACGGGGACAUCGGAGC
AGUUGCUCUGGACUACCCUGCAGGGACCUCAGGAUCUCCGAUCCUAGACAAAU
GUGGAAGAGUGAUAGGCUCUAUGGCAAUGGGGUUGUGAUCAAGAAUGGAAG
CUAUGUUAGUGCUAUAACCCAGGGAAAGAGGGAGGAGGAGACUCCGGUUGAAU
GUUUCGAACCCUCGAUGCUGAAGAAGAAGCAGCUAACUGCUUGGAUCUGCAU
CCAGGAGCCGGAAAAACCAGGAGAGUUCUUCCUGAAAUAGUCCGUGAAGCCAU
AAAAAAGAGACUCCGGACAGUGAUCUUGGCACCAACUAGGGUUGUCGCUGCUG
AGAUGGAGGAGGCCUUGAGAGGACUUCCGGUGCGUUACAUGACAACAGCAGUC
AACGUCACCCAUUCUGGGACAGAAAUCGUUGAUUUGAUGUGCCAUGCCACUUU
CACUUCACGCUUACUACAACCCAUCAGAGUCCCUAAUUACAAUCUCAACAUCA
UGGAUGAAGCCCACUUCACAGACCCCUCAAGUAUAGCUGCAAGAGGAUACAUA
UCAACAAGGGUUGAAAUGGGCGAGGCGGCUGCCAUUUUUAUGACUGCCACACC
ACCAGGAACCCGUGAUGCGUUUCCUGACUCUAACUCACCAAUCAUGGACACAG
AAGUGGAAGUCCCAGAGAGAGCCUGGAGCUCAGGCUUUGAUUGGGUGACAGAC
CAUUCUGGGAAAACAGUUUGGUUCGUUCCAAGCGUGAGAAACGGAAAUGAAAU
CGCAGCCUGUCUGACAAAGGCUGGAAAGCGGGUCAUACAGCUCAGCAGGAAGA
CUUUUGAGACAGAAUUUCAGAAAACAAAAAAUCAAGAGUGGGACUUUGUCAU
AACAACUGACAUCUCAGAGAUGGGCGCCAACUUCAAGGCUGACCGGGUCAUAG
ACUCUAGGAGAUGCCUAAAACCAGUCUACUUGAUGGUGAGAGAGUCAUCUUG
GCUGGGCCCAUGCCUGUCACGCAUGCUAGUGCUGCUCAGAGGAGAGGACGUAU
AGGCAGGAACCCUAACAAACCUGGAGAUGAGUACAUGUAUGGAGGUGGGUGUG
CAGAGACUGAUGAAGGCCAUGCACACUGGCUUGAAGCAAGAAUGCUUCUUGAC
AACAUCUACCUCCAGGAUGGCCUCAUAGCCUCGCUCUAUCGGCCUGAGGCCGA
UAAGGUAGCCGCCAUUGAGGGAGAGUUUAAGCUGAGGACAGAGCAAAGGAAG
ACCUUCGUGGAACUCAUGAAGAGAGGAGACCUUCCCGUCUGGCUAGCCUAUCA
GGUUGCAUCUGCCGGAAUAACUUACACAGACAGAAGAUGGUGCUUUUGAUGGCA
CAACCAACAACACCAUAAUGGAAGACAGUGUACCAGCAGAGGUUUGGACAAAG
UAUGGAGAGAAGAGAGUGCUCAAACCGAGAUGGAUGGAUGCUAGGGUCUGUU
CAGACCAUGCGGCCCUGAAGUCGUUCAAAGAAUUCGCCGCUGGAAAAAGAGGA
GCGGCUUUGGGAGUAAUGGAGGCCCUGGGAACACUGCCAGGACACAUGACAGA
GAGGUUUCAGGAAGCCAUUGACAACCUCGCCGUGCUCAUGCGAGCAGAGACUG
GAAGCAGGCCUUAUAAGGCAGCGGCAGCCCAACUGCCGGAGACCCUAGAGACC
AUUAUGCUCUUAGGUUUGCUGGGAACAGUUUCACUGGGGAUCUUCUUCGUCUU
GAUGCGGAAUAAGGGCAUCGGGAAGAUGGGCUUUGGAAUGGUAACCCUUGGG
GCCAGUGCAUGGCUCAUGUGGCUUUCGAAAUUGAACCAGCCAGAAUUGCAUG
UGUCCUCAUUGUUGUGUUUUAUUACUGGUGGUGCUCAUACCCGAGCCAGAGA
AGCAAAGAUCUCCCCAAGAUAACCAGAUGGCAAUUAUCAUCAUGGUGGCAGUG
GGCCUUCUAGGUUUGAUAACUGCAAACGAACUUGGAUGGCUGGAAAGAACAAA
AAAAUGACAUAGCUCAUCUAAUGGGAAGGAGAGAAGAAGGAGCAACCAUGGGA
UUCUCAAUGGACAUUGAUCUGCGGCCAGCCUCCGCCUGGGCUAUCUAUGCCGC
AUUGACAACUCUCAUCACCCCAGCUGUCCAACAUGCGGUAACCACUUCAUACA
ACAACUACUCCUUAAUGGCGAUGGCCACACAAGCUGGAGUGCUGUUUGGCAUG
GGCAAAGGGAUGCCAUUUUAUGCAUGGGGACCUUGGAGUCCCGCUGCUAAUGAU
GGGUUGCUAUUCACAAUUAACACCCCUGACUCUGAUAGUAGCUAUCAUUCUGC
UUGUGGCGCACUACAUGUACUUGAUCCCAGGCCUACAAGCGGCAGCAGCGCGU
GCUGCCCAGAAAAGGACAGCAGCUGGCAUCAUGAAGAAUCCCGUUGUGGAUGG
AAUAGUGGUAACUGACAUUGACACAAUGACAAUAGACCCCCAGGUGGAGAAGA
AGAUGGGACAAGUGUUACUCAUAGCAGUAGCCAUCUCCAGUGCUGUGCUGCUG
CGGACCGCCUGGGGAUGGGGGGAGGCUGGAGCUCUGAUCACAGCAGCGACCUC
CACCUUGUGGGAAGGCUCUCCAAACAAAUACUGGAACUCCUCUACAGCCACCU
CACUGUGCAACAUCUUCAGAGGAAGCUAUCUGGCAGGAGCUUCCCUUAUCUAU
ACAGUGACGAGAAACGCUGGCCUGGUUAAGAGACGUGGAGGUGGGACGGGAGA
GACUCUGGGAGAAGUGGAAAGCUCGUCUGAAUCAGAUGUCGGCCCUGGAGU
UCUACUCUUUAUAAAAAGUCAGGUAUCACUGAAGUGUGUAGAGAGGAGGCUCGC
CGUGCCCUCAAGGAUGGAGUGGCCACAGGAGGACAUGCCGUAUCCCGGGGAAG
UGCAAAGAUCAGAUGGUUGGAGGAGAGAGGAUAUCUGCAGCCCUAUGGGAAG
GUUGUUGACCUCGGAUGUGGCAGAGGGGGCUGGAGCUAUUAUGCCGCCACCAU
CCGCAAAGUGCAGGAGGUGAGAGGAUACACAAAGGGAGGUCCCGGUCAUGAAG
AACCCAUGCUGGUGCAAAGCUAUGGGUGGAACAUAGUUCGUCUCAAGAGUGGA
GUGGACGUCUUCCACAUGGCGGCUGAGCCGUGUGACACACUGCUGUGUGACAU
```

TABLE 7-continued

```
AGGUGAGUCAUCAUCUAGUCCUGAAGUGGAAGAGACACGAACACUCAGAGUGC
UCUCUAUGGUGGGGGACUGGCUUGAAAAAAGACCAGGGGCCUUCUGUAUAAAG
GUGCUGUGCCCAUACACCAGCACUAUGAUGGAAACCAUGGAGCGACUGCAACG
UAGGCAUGGGGGAGGAUUAGUCAGAGUGCCAUUGUGUCGCAACUCCACACAUG
AGAUGUACUGGGUCUCUGGGGCAAAGAGCAACAUCAUAAAAAGUGUGUCCACC
ACAAGUCAGCUCCUCCUGGGACGCAUGGAUGGCCCCAGGAGGCCAGUGAAAUA
UGAGGAGGAUGUGAACCUCGGCUCGGGUACACGAGCUGUGGCAAGCUGUGCUG
AGGCUCCUAACAUGAAAAUCAUCGGCAGGCGCAUUGAGAGAAUCCGCAAUGAA
CAUGCAGAAACAUGGUUUCUUGAUGAAAACCACCCAUACAGGACAUGGGCCUA
CCAUGGGAGCUACGAAGCCCCCACGCAAGGAUCAGCGUCUUCCCUCGUGAACG
GGGUUGUUAGACUCCUGUCAAAGCCUUGGGACGUGGUGACUGGAGUUACAGGA
AUAGCCAUGACUGACACCACACCAUACGGCCAACAAAGAGUCUUCAAAGAAAA
AGUGGACACCAGGGUGCCAGAUCCCCAAGAAGGCACUCGCCAGGUAAUGAACA
UAGUCUCUUCCUGGCUGUGGAAGGAGCUGGGGAAACGCAAGCGGCCACGCGUC
UGCACCAAAGAAGAGUUUAUCAACAAGGUGCGCAGCAAUGCAGCACUGGGAGC
AAUAUUUGAAGAGGAAAAAGAAUGGAAGACGGCUGUGGAAGCUGUGAAUGAU
CCAAGGUUUUGGGCCCUAGUGGAUAGGGAGAGAGAACACCACCUGAGAGGAGA
GUGUCACAGCUGUGUGUACAACAUGAUGGGAAAAAGAGAAAAGAAGCAAGGA
GAGUUCGGGAAAGCAAAAGGUAGCCGCGCCAUCUGGUACAUGUGGUUGGGAGC
CAGAUUCUUGGAGUUUGAAGCCCUUGGAUUCUUGAACGAGGACCAUUGGAUGG
GAAGAGAAAACUCAGGAGGUGGAGUCGAAGGGUUAGGAUUGCAAAGACUUGG
AUACAUUCUAGAAGAAAUGAAUCGGGCACCAGGAGGAAAGAUGUACGCAGAUG
ACACUGCUGGCUGGGACACCCGCAUUAGUAAGUUUGAUCUGGAGAAUGAAGCU
CUGAUUACCAACCAAAUGGAGGAAGGGCACAGAACUCUGGCGUUGGCCGUGAU
UAAAUACACAUACCAAAACAAAGUGGUGAAGGUUCUCAGACCAGCUGAAGGAG
GAAAAACAGUUAUGGACAUCAUUUCAAGACAAGACCAGAGAGGGAGUGGACAA
GUUGUCACUUAUGCUCUCAACACAUUCACCAACUUGGUGGUGCAGCUUAUCCG
GAACAUGGAAGCUGAGGAAGUGUUAGAGAUGCAAGACUUAUGGUUGUUGAGG
AAGCCAGAGAAAGUGACCAGAUGGUUGCAGAGCAAUGGAUGGGAUAGACUCAA
ACGAAUGGCGGUCAGUGGAGAUGACUGCGUUGUGAAGCCAAUCGAUGAUAGGU
UUGCACAUGCCCUCAGGUUCUUGAAUGACAUGGGAAAAGUUAGGAAAGACACA
CAGGAGUGGAAACCCUCGACUGGAUGGAGCAAUUGGGAAGAAGUCCCGUUCUG
CUCCCACCACUUCAACAAGCUGUACCUCAAGGAUGGGAGAUCCAUUGUGGUCC
CUUGCCGCCACCAAGAUGAACUGAUUGGCCGAGCUCGCGUCUCACCAGGGGCA
GGAUGGAGCAUCCGGGAGACUGCCUGUCUUGCAAAAUCAUAUGCGCAGAUGUG
GCAGCUCCUUUAUUUCCACAGAAGAGACCUUCGACUGAUGGCUAAUGCCAUUU
GCUCGGCUGUGCCAGUUGACUGGGUACCAACUGGGAGAACCACCUGGUCAAUC
CAUGGAAAGGGAGAAUGGAUGACCACUGAGGACAUGCUCAUGGUGUGGAAUA
GAGUGUGGAUUGAGGAGAACGACCAUAUGGAGGACAAGACUCCUGUAACAAA
UGGACAGACAUUCCCUAUCUAGGAAAAAGGGAGGACUUAUGGUGUGGAUCCCU
UAUAGGGCACAGACCCCGCACCACUUGGGCUGAAAACAUCAAAGACACAGUCA
ACAUGGUGCGCAGGAUCAUAGGUGAUGAAGAAAAGUACAUGGACUAUCUAUCC
ACCCAAGUCCGCUACUUGGGUGAGGAAGGGUCCACACCCGGAGUGUUGUAAGC
ACCAAUUUUAGUGUUGUCAGGCCUGCUAGUCAGCCACAGUUUGGGGAAAGCUG
UGCAGCCUGUAACCCCCCCAGGAGAAGCUGGGAAACCAAGCUCAUAGUCAGGC
CGAGAACGCCAUGGCACGGAAGAAGCCAUGCUGCCUGUGAGCCCCUCAGAGGA
CACUGAGUCAAAAAACCCCACGCGCUUGGAAGCGCAGGAUGGGAAAGAAGGU
GGCGACCUUCCCCACCCUUCAAUCUGGGGCCUGAACUGGAGACUAGCUGUGAA
UCUCCAGCAGAGGGACUAGUGGUUAGAGGAGACCCCCCGGAAAACGCAAAACA
GCAUAUUGACGUGGGAAAGACCAGAGACUCCAUGAGUUUCCACCACGCUGGCC
GCCAGGCACAGAUCGCCGAACUUCGGCGGCCGGUGUGGGGAAAUCCAUGGUUU
CU (SEQ ID NO: 747)
```

TABLE 8

Sequences of Toehold Switch Sensors Used for Zika RNA Detection

| Toehold Switch Name | Toehold Switch RNA Sequences for Detection of Zika Virus from the Americas (KU312312) | Target Sequence in Zika Virus from the Americas (KU312312) |
|---|---|---|
| 27B_N1 | GGGUUUCGCUCUAUUCUCAUCAGU UUCAUGUCCUGUGUCGGACUUUAG AACAGAGGAGAUAAAGAUGGACAC AGGACACAACCUGGCGGCAGCGCA AAAG (SEQ ID NO: 748) | GACACAGGACAUGAAACUGAUGAGA AUAGAGCGAAA (SEQ ID NO: 758) |
| 27B_N2 | GGGCUCAACUUUCGCUCUAUUCUC AUCAGUUUCAUGUCCGGACUUUAG AACAGAGGAGAUAAAGAUGGGACA UGAAACAACCUGGCGGCAGCGCAA GAAG (SEQ ID NO: 749) | GGACAUGAAACUGAUGAGAAUAGA GCGAAAGUUGAG (SEQ ID NO: 759) |

TABLE 8 -continued

Sequences of Toehold Switch Sensors Used for Zika RNA Detection

| Toehold Switch Name | Toehold Switch RNA Sequences for Detection of Zika Virus from the Americas (KU312312) | Target Sequence in Zika Virus from the Americas (KU312312) |
|---|---|---|
| 27B_N3 | GGGUUAUCUCAACUUUCGCUCUAUUCUCAUCAGUUUCAUGGACUUUAGAACAGAGGAGAUAAAGAUGAUGAAACUGAUAACCUGGCGGCAGCGCAAGAAG (SEQ ID NO: 750) | AUGAAACUGAUGAGAAUAGAGCGAAAGUUGAGAUAA (SEQ ID NO: 760) |
| 27B_N4 | GGGUCGCUCUAUUCUCAUCAGUUUCAUGUCCUGUGUCAUGGACUUUAGAACAGAGGAGAUAAAGAUGAUGACACAGGAAACCUGGCGGCAGCGCAAGAAG (SEQ ID NO: 751) | AUGACACAGGACAUGAAACUGAUGAGAAUAGAGCGA (SEQ ID NO: 761) |
| 27B_N5 | GGGUGGCUUCGGCUCUUGGUGAAUUGGGCGUUAUCUCGGACUUUAGAACAGAGGAGAUAAAGAUGGAGAUAACGCCAACCUGGCGGCAGCGCAAGAAG (SEQ ID NO: 752) | GAGAUAACGCCCAAUUCACCAAGAGCCGAAGCCACC (SEQ ID NO: 762) |
| 32B_N1 | GGGCUGGGAUCAAGUACAUGUAGUGCGCCACGAGCAAAAGGACUUUAGAACAGAGGAGAUAAAGAUGUUUUGCUCGUGUAACCUGGCGGCAGCGCAAAAG (SEQ ID NO: 753) | UUUUGCUCGUGGCGCACUACAUGUACUUGAUCCCAG (SEQ ID NO: 763) |
| 32B_N2 | GGGCCUGCAGCCCUGGGAUCAAGUACAUGUAGUGCGCCGGACUUUAGAACAGAGGAGAUAAAGAUGGGCGCACUACAAACCUGGCGGCAGCGCAAGAAG (SEQ ID NO: 754) | GGCGCACUACAUGUACUUGAUCCCAGGGCUGCAGGC (SEQ ID NO: 764) |
| 32B_N3 | GGGCUGCCGUUCUCUUCUGGGCAGCACGCGCAGCUGCUGGGACUUUAGAACAGAGGAGAUAAAGAUGCAGCAGCUGCGAACCUGGCGGCAGCGCAAGAAG (SEQ ID NO: 755) | CAGCAGCUGCGCGUGCUGCCCAGAAGAGAACGGCAG (SEQ ID NO: 765) |
| 32B_N4 | GGGCAGCCCUGGGAUCAAGUACAUGUAGUGCGCCACGAGGGACUUUAGAACAGAGGAGAUAAAGAUGCUCGUGGCGCAAACCUGGCGGCAGCGCAAGAAG (SEQ ID NO: 756) | CUCGUGGCGCACUACAUGUACUUGAUCCCAGGGCUG (SEQ ID NO: 766) |
| 32B_N5 | GGGAUGCCAGCUGCCGUUCUCUUCUGGGCAGCACGCGCGGACUUUAGAACAGAGGAGAUAAAGAUGGCGCGUGCUGCAACCUGGCGGCAGCGCAAGAAG (SEQ ID NO: 757) | GCGCGUGCUGCCCAGAAGAGAACGGCAGCUGGCAUC (SEQ ID NO: 767) |

We claim:

1. A method of detecting a target nucleic acid in a sample, the method comprising the steps of:
   (a) obtaining nucleic acid from a biological sample obtained from a subject;
   (b) amplifying the nucleic acid using isothermal amplification;
   (c) contacting the amplified nucleic acid to a toehold switch, wherein the toehold switch encodes a reporter protein and comprises one or more single-stranded toehold sequence domains that are complementary to a target nucleic acid or the reverse complement thereof, wherein the contacting occurs under conditions that allow translation of the coding domain in the presence of the target nucleic acid but not in the absence of the target nucleic acid, and detecting the reporter protein as an indicator that the target nucleic acid is present in the amplified nucleic acid of the subject; and
   (d) identifying the target nucleic acid as containing a target protospacer adjacent motif (PAM), wherein identifying comprises:
   (i) amplifying nucleic acid obtained from the biological sample using a reverse primer designed to append the trigger sequence of one or more toehold switch sequence domains;
   (ii) contacting the amplified nucleic acid of (i) to CRISPR/Cas under conditions that allow for sequence-specific cleavage of the contacted nucleic acid by CRISPR/Cas when the target PAM is present in the amplified nucleic acid; and
   (iii) detecting activation of the toehold switch, wherein activation does not occur in the event of CRISPR/Cas-mediated sequence-specific cleavage, thereby indicating the presence of the target PAM.

2. The method of claim 1, wherein the toehold switch comprises one or more single-stranded toehold sequence domains, a fully or partially double-stranded stem domain comprising an initiation codon, a loop domain comprising a ribosome binding site, and a coding domain.

3. The method of claim 2, wherein the toehold and stem domains are complementary in sequence to a naturally occurring RNA.

4. The method of claim 2, wherein the loop domain is complementary in sequence to a non-naturally occurring RNA.

5. The method of claim 1, wherein the target nucleic acid is an RNA specific to a pathogen.

6. The method of claim 1, wherein the pathogen is selected from the group consisting of a virus, bacterium, fungus, and parasite.

7. The method of claim 1, wherein the isothermal amplification is selected from the group consisting of NASBA (nucleic acid sequence-based amplification), loop-mediated isothermal amplification (LAMP), recombinase polymerase amplification (RPA), and helicase-dependent amplification (HAD).

8. The method of claim 1, wherein the biological sample is selected from the group consisting of blood, serum, urine, saliva, tissue, cell, and organ, or a fraction or portion thereof.

9. A method of detecting a target nucleic acid in a sample, the method comprising the steps of:
   (a) obtaining RNA from a biological sample obtained from a subject;
   (b) amplifying the RNA using isothermal amplification;
   (c) contacting the amplified RNA to a toehold switch, wherein the toehold switch encodes a reporter protein and comprises one or more single-stranded toehold sequence domains that are complementary to a target RNA or the reverse complement thereof, wherein the contacting occurs under conditions that allow translation of the coding domain in the presence of the target RNA but not in the absence of the target RNA, and detecting the reporter protein as an indicator that the target RNA is present in the amplified RNA of the subject; and
   (d) identifying the target RNA as containing a target protospacer adjacent motif (PAM), wherein identifying comprises:
   (i) amplifying RNA obtained from the biological sample using a reverse primer designed to append the trigger sequence of one or more toehold switch sequence domains;
   (ii) contacting the amplified RNA of (i) to CRISPR/Cas under conditions that allow for sequence-specific cleavage of the contacted RNA by CRISPR/Cas when the target PAM is present in the amplified RNA; and
   (iii) detecting activation of the toehold switch, wherein activation does not occur in the event of CRISPR/Cas-mediated sequence-specific cleavage, thereby indicating the presence of the target RNA.

10. The method of claim 9, wherein the toehold switch comprises one or more single-stranded toehold sequence domains, a fully or partially double-stranded stem domain comprising an initiation codon, a loop domain comprising a ribosome binding site, and a coding domain.

11. The method of claim 10, wherein the toehold and stem domains are complementary in sequence to a naturally occurring RNA.

12. The method of claim 10, wherein the loop domain is complementary in sequence to a non-naturally occurring RNA.

13. The method of claim 9, wherein the target nucleic acid is an RNA specific to a pathogen.

* * * * *

SEQUENCE LISTING

<160> NUMBER OF SEQ ID NOS: 789

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
tggagtcccg ctgctaatga gtttagagc tagaaatagc aagttaaaat aaggctagtc    60
cgttatcaac ttgaaaagt ggcaccgagt cggtgctttt                         100
```

<210> SEQ ID NO 2
<211> LENGTH: 9
<212> TYPE: PRT
<213> ORGANISM: Unknown
<220> FEATURE:
<223> OTHER INFORMATION: Description of Unknown:
      'LAGLIDADG' homing endonuclease motif sequence

<400> SEQUENCE: 2

Leu Ala Gly Leu Ile Asp Ala Asp Gly
1               5

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtttgaatga attgtaggct tgttatagtt atgttt                             36

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctaatacgac tcactatagg                                               20

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aattctaata cgactcacta tagggagaag g                                  31

<210> SEQ ID NO 6
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guuauaguua ugaacagagg agacauaaca ugaac                              35

<210> SEQ ID NO 7
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggacuuuaga acagaggaga uaaagaug                                      28

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aattctaata cgactcacta tagggagaag gcagtgatct aggctactgg a            51

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aattctaata cgactcacta tagggagaag ggtgccagag ttgtgtgtac a            51

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aattctaata cgactcacta tagggagaag ggcacagtgg gatgatcgtt a            51

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aattctaata cgactcacta tagggagaag gcgggatctc ctctgtttca a            51

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aattctaata cgactcacta tagggagaag gccatcactg ggtctcatca a            51

<210> SEQ ID NO 13
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aattctaata cgactcacta tagggagaag gaatgctgtc agttcatggc tccca        55

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aattctaata cgactcacta tagggagaag gatggtctct tcctggttgt gga         53

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aattctaata cgactcacta tagggagaag ggaccctaat agtggccatc a           51

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aattctaata cgactcacta tagggagaag ggtttggtat gggcaaaggg a           51

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aattctaata cgactcacta tagggagaag ggccatctat gctgccttga caa         53

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aattctaata cgactcacta tagggagaag ggtgattctg ctcatggtgc a           51

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aattctaata cgactcacta tagggagaag ggtttgttcc aagcgtgagg a           51

```
<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aattctaata cgactcacta tagggagaag gagatcaacc actgcaagcg gaa          53

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aattctaata cgactcacta tagggagaag gagtggttcc acgacattcc a            51

<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aattctaata cgactcacta tagggagaag gtggacgcca gagtttgttc aga          53

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aattctaata cgactcacta tagggagaag ggccggaata acctacacag a            51

<210> SEQ ID NO 24
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aattctaata cgactcacta tagggagaag gggctactgg attgagagtg aga          53

<210> SEQ ID NO 25
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aattctaata cgactcacta tagggagaag gcagccagaa ttgcatgtgt cctca        55

<210> SEQ ID NO 26
```

```
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aattctaata cgactcacta tagggagaag gggagcggac aagttgtcac tta          53

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aattctaata cgactcacta tagggagaag ggtgctcggt ggacttctca aagaa        55

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aattctaata cgactcacta tagggagaag gagtggtgca actcattcgg a            51

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aattctaata cgactcacta tagggagaag gcaataccag agagggctac a            51

<210> SEQ ID NO 30
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aattctaata cgactcacta tagggagaag gagtaggtct tctgggcttg a            51

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aattctaata cgactcacta tagggagaag ggctcaaacg aatggcagtc a            51

<210> SEQ ID NO 32
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcccagctaa agacttgggt atga                                            24

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catccagtga tcctcgttca                                                 20

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cctgtcctcg gttcacaatc aa                                              22

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aatctctgtg gacctctcca                                                 20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaggccaaca attccgacac ta                                              22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctgtcctcgg ttcacaatca                                                 20

<210> SEQ ID NO 38
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 38
ccagaacctt ggatcgttca                                          20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ccatccacaa cagggttctt ca                                       22

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
cagccctggg atcaagtaca tgta                                     24

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gcccatacca aacaacactc ca                                       22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gcttagccag gtcactcatt ga                                       22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
aagttggcgc ccatctctga aa                                       22

<210> SEQ ID NO 44
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 44
gttctttcct gggccttatc tcca                                              24

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccttcttgac tccctagaac ca                                                22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atctctctgt catgtgtcct ggca                                              24

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tctgaacaaa ctctggcgtc ca                                                22

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcccagctaa agacttgggt atga                                              24

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgttctctcc aaccatccga                                                   20

<210> SEQ ID NO 50
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 50
gctctgcaac cagttagtca                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atcttcccag gcttgcttga                                               20

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgccattcgt ttgagcctat ccca                                          24

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcagtggttg atctcagaga                                               20

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgcaggtcaa tgtccattga ga                                            22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccactcttgt gtgtccttcc ta                                            22

<210> SEQ ID NO 56
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
aattctaata cgactcacta tagggagaag ggcacagtgg gatgatcgtt a          51

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aattctaata cgactcacta tagggagaag gactctgata gtagctatca             50

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cctgtcctcg gttcacaatc aa                                           22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccatccacaa cgggattctt ca                                           22

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttttccccca cagaacccca tctgttgatg                                   30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atgttgagaa taatcaatgc taggaaggag                                   30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tagtcagcag gagaccaatg attccgatgc                                             30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cacttccacg tctggtaatc tccgctgcca                                             30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccaagtacat gtagtatgca cttccacgtc                                             30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cgtggaagtg catactacat gtacttggac                                             30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggcatttgtt aactcccaag ttggtagcaa                                             30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cacatgtgcc cgagatccat gatctgtaca                                             30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 68
aacaaatgcc atgtacagat catggatctc                                      30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttcctaaata tccagttttc aaccttgatc                                      30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aatcaagaga atacacgaag cacctgatca                                      30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aaggttgaaa actggatatt taggaacccc                                      30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aggcaatggc aacagctgcg agcgcaaacc                                      30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73 cttttttggct cgtcgagctt cccaaaagcc                                     30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
```
aacctccatg ttccaagacg acatcaaccc                                      30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tgtcaactgt tggcttgtcc tgtgccataa                                      30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
caacagttga catagagttg gtcacgacaa                                      30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ttgatgcctc ataacagtag gatcttacct                                      30

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tgtccaccaa tgttcttttg cacacatatt                                      30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ctgtccacca atgttctttt gcacacatat                                      30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cagacaccca atatgtgtgc aaaagaacat					30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
agaacattgg tggacagagg ttggggaaat					30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tcccagtcat cttcttggaa cacgtgaact					30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
atgaaactga cgaaaacaga gcgaaagtcg					30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
taggacttga ttgtgaacca aggacaggcc					30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctttgtgcac caaccagtgc ttgttgttca					30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccggtatctg ccccagcatg ccaaggcaat					30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
cagataccgg aactccacac tggaacaaca                                   30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
ataccggaac tccacactgg aacaacaagg                                   30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
ctagaacaac gacggtttgc ctcttggcgt                                   30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
cctagaacaa cgacggtttg cctcttggcg                                   30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
cggctccttc ctggctccct agaacaacga                                   30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
agaggcaaac cgtcgttgtt ctagggagcc                                   30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 93
ccagcaagag ccgtgtgaac ggctccttcc                                      30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 94
cctccagagc tccagcaaga gccgtgtgaa                                      30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 95
tgtccatttt taagcggcat ttcaaatggc                                      30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 96
cccttcaatc taagcttgtc catttttaag                                      30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 97
cagctgggac cttggtaaat gtgaacgctg                                      30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 98
ccttgtgcac cgcagcgttc acatttacca                                      30

```
<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgtccaccgc catctgggct gggaccttgc                                          30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agggtctgca tgtccaccgc catctgggct                                          30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gggtcagggt ctgcatgtcc accgccatct                                          30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tggcggttat cagcctcccg actggggtca                                          30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ttggcggtta tcagcctccc gactggggtc                                          30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aattctcagt gctttcagta atcacagggt                                          30

<210> SEQ ID NO 105
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cctatgacaa tgtaagaatc cccaaatggt                                      30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggagtggtag caccatcgga aaagcatttg                                      30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtgagaggtg ccaagagaat ggcagttctg                                      30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tgagaggtgc aagagaatg gcagttctgg                                       30

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggggatacag cctgggactt cggatcagtc                                      30

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gggatacagc ctgggacttc ggatcagtcg                                      30

<210> SEQ ID NO 111
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aacagtgatt tgaaagctgc tccaaaaatc                                          30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aaacccaacc acaccagcag cgtgcctatg                                          30

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggttctcaca gatcctcata ggcacgctgc                                          30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctccccccag ggccaagcat gtgagggaga                                          30

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atggatccat ctccctcaca tgcttggccc                                          30

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
caccccacgt cagcagagac agccgtggag                                          30

<210> SEQ ID NO 117
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 117
ccctgggggg agtgatgatc ttcctctcca                                        30

<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
acttctcaaa aagagaaacg agatgtggca                                        30

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119 cccccgcag attggcagca gcagtcaagc                                         30

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tggcagcagc agtcaagcag gcttgggaag                                        30

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gcagcagcag tcaagcaggc ttgggaagag                                        30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
atttccacat gatgttttcc attcttgaaa                                        30

<210> SEQ ID NO 123
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 123
caagaatgga aaacatcatg tggaaatcag                                    30

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
agctcattca caggcactgg caatctttgt                                    30

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
aagcctgggg gaaatcatat tttgtcagag                                    30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtgtgtcacc atcgacaaca aaactgttgt                                    30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tcttctctaa ccttgagcca aacactggtg                                    30

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agtagtcttc tctaaccttg agccaaacac                                    30

<210> SEQ ID NO 129
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 129
tttcccttaa cagctgttcc tatgacggct                                            30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tttcaatcca gtagcccagg tcactgtggg                                            30

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
cactttcaat ccagtagccc aggtcactgt                                            30

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tcactttcaa tccagtagcc caggtcactg                                            30

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ttaagggaaa ggaggccgcc cacagtgacc                                            30

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tcattctttt cactttcaat ccagtagccc                                            30

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 135
gcttgagttc tgtaaccctc tctagtgttg                                   30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tgaaccttgg tgcctggaca ttcctcaaac                                   30

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tagttccgca tgtctcctcc acgtgaacct                                   30

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agagcaactt agtgaggtca atggtgacag                                   30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gcactccaag agagaagtgg tccatgtgat                                   30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tcattatgag cacatcaatg gcagtgctgg                                   30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 141
agtcactcat taaaaatcct cccaggatca                               30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ccttcgcaga aatgaacact ggaggagatg                               30

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
acactggagg agatgtggct cacttggcat                               30

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aattagctct gaaaataaag gagaccagca                               30

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
cacgaggtgt ccaattagct ctgaaaataa                               30

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gagattgcag tttgcaaaag acacgaagcc                               30

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 147
gccaaccagg ccaaagcaaa tccattgacg                                           30

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttgccagagc aatgttgtca gtgcgtggca                                           30

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
cccgaggtac actgctcgtg gcatggagag                                           30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ggttcttctt cacactacct ttccctttca                                           30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tgtggagggt ttatgctcct ctccctgaaa                                           30

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gcagtcaatc ccaaggccat gacaaatggc                                           30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
```
ttgaaagagc aggtgacatc acatgggaaa        30

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tggtctctcc tttttcact tctttgggag        30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aaagaagtga aaaaggaga gaccacagat        30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aagaagtgaa aaaggagag accacagatg        30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctccaacctg tgttgaaccc agcagtctgc        30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
actccaacct gtgttgaacc cagcagtctg        30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gggtatacag agtgatgacc cgcagactgc                                          30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tgatgacccg cagactgctg ggttcaacac                                          30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gcagctcctt ttgtgacgtg ccacatggtg                                          30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
atgtggcacg tcacaaaagg agctgcactg                                          30

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
agcggtgaag ggagacttga tccatactgg                                          30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gcggtgaagg gagacttgat ccatactggg                                          30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gatgtcaagc aggacttagt gtcatactgt                                          30

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
acttagtgtc atactgtggg ccttggaagt                                    30

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gtgcagctct tggcagtacc ccccggagag                                    30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tgcagctctt ggcagtaccc cccggagaga                                    30

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgaatattcc aggcagagtc tgaatgtttc                                    30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tgtctaggat cggggatcct gaagttcctg                                    30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ctatcactct tccgcatttg tctaggatcg                                    30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cctatcactc ttccgcattt gtctaggatc                                    30

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
agaatggaag ctatgttagt gccataaccc                                    30

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ttagtgccat aacccaggga aagagggagg                                    30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
taacccaggg aaagagggag gaggagactc                                    30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggacagttag ctgcttcttc ttcagcatcg                                    30

<210> SEQ ID NO 177
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cgatgctgaa gaagaagcag ctaactgtcc                                    30

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctagtctttc cggctcctgg atgcagatcc                                    30

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ctatttcagg aagaactctc ctagtctttc                                    30

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ccataaaaaa gagactccgc acagtgattt                                    30

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ctgagatgga ggaagccttg agaggacttc                                    30

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atgacaacag cagttaacgt cacccactct                                    30

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tagggactct gatgggttgt aataggcgtg                                    30

<210> SEQ ID NO 184

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttgtaattag ggactctgat gggttgtaat                                              30

<210> SEQ ID NO 185
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tgatgtagag attgtaatta gggactctga                                              30

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gatatgtatc ctcttgcagc tatacttgag                                              30

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cttggaacga accaaactgt tttcccagaa                                              30

<210> SEQ ID NO 188
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tcaggctttg attgggtgac agaccattct                                              30

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gtatgacccg ctttccagcc tttgtcagac                                              30

<210> SEQ ID NO 190
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
aaggctggaa agcgggtcat acaactcagc                                          30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tcagagatgg gcgcgaattt caaagctgac                                          30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cagagatggg cgcgaatttc aaagctgacc                                          30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
atacttgatg gtgagagagt catcttggct                                          30

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccatacatgt actcatctcc aggtttgtta                                          30

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ttgcttcaag ccagtgtgca tggtcttcat                                          30

<210> SEQ ID NO 196
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 196
ctccaggatg gcctcatagc ctcgctctac                                      30

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tcaatggcag ctaccttatc ggcctcaggc                                      30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tagcctcgct ctaccggcct gaggccgata                                      30

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gatgcaacct gataggctag ccaaacggga                                      30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agagtgctca aaccaagatg gatggatgcg                                      30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gagtgctcaa accaagatgg atggatgcga                                      30

<210> SEQ ID NO 202
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 202
attctttgaa cgacttcagg gcagcatgat                                    30

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ccattactcc taaagccact cctctttttcc                                   30

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ggaaaagagg agtggcttta ggagtaatgg                                    30

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ctgggaacat tgccaggaca catgacagag                                    30

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tgcgagcaga gactggaagc aggccttaca                                    30

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ctcttaggct tgttgggaac agtttcgttg                                    30

<210> SEQ ID NO 208
<211> LENGTH: 30
<212> TYPE: DNA
<213> ORGANISM: Artificial Sequence
<220> FEATURE:
```

```
-continued

<223> OTHER INFORMATION: Description of Artificial Sequence: Synthetic
      oligonucleotide

<400> SEQUENCE: 208
tgtcctgggg agatctttgc ttctctggct                                30

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
aggacaacca gatggcaatc atcatcatgg                                30

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
accagatggc aatcatcatc atggtggcag                                30

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
taatgggaag gagagaagaa ggagtaacta                                30

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tgagagttgt cagtgcggca tagatagccc                                30

<210> SEQ ID NO 213
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ggacggctgg ggtgatgaga gttgtcagtg                                30

<210> SEQ ID NO 214
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 214
caactctcat caccccagcc gtccaacacg                                           30

<210> SEQ ID NO 215
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
atgggacttt ggagtcccgc tgctaatga                                            29

<210> SEQ ID NO 216
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
caatgtcagt taccactatt ccatccacaa                                           30

<210> SEQ ID NO 217
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
atttgtttgg agaaccttcc cacaaggtgg                                           30

<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ggtaacttcc tctgaagatg ttgcacagtg                                           30

<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gtcactgtat aaataagaga agcgcctgcc                                           30

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tctcccgttc cacctccacg tctcttgact                                    30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ctggcctagt caagagacgt ggaggtggaa                                    30

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gagtagaact ccagggccga catctgattc                                    30

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aaaagtcagg catcactgaa gtgtgtagag                                    30

<210> SEQ ID NO 224
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
cgcttccccg ggatacagca tgtcctcctg                                    30

<210> SEQ ID NO 225
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ggagtggcca caggaggaca tgctgtatcc                                    30

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gagtggccac aggaggacat gctgtatccc                                    30

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ctgccacatc cgaggtcaac aacctttcca                                    30

<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
taatagctcc aaccccctct gccacatccg                                    30

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gctattatgc cgccaccatc cggaaagtgc                                    30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
attatgccgc caccatccgg aaagtgcagg                                    30

<210> SEQ ID NO 231
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggaaagtgca ggaggtgaaa ggatacacaa                                    30

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232

```
agctttgcac cagcatgggt tcttcatgac                                              30
```

<210> SEQ ID NO 233
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233

```
ctatgtcaca cagcaaggta tcacacggct                                              30
```

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234

```
tagatgatga ctcacctatg tcacacagca                                              30
```

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235

```
tcaagccagt cccccaccat agagagcact                                              30
```

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236

```
ctatggtggg ggactggctt gagaaaagac                                              30
```

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237

```
atggtggggg actggcttga gaaaagaccg                                              30
```

<210> SEQ ID NO 238
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tggtggggga ctggcttgag aaaagaccgg                              30

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ttgagaaaag accgggggcc ttctgtataa                              30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ctgactaatc ctcccccata cctacgttgc                              30

<210> SEQ ID NO 241
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ttgctccaga gacccaatac atctcatgtg                              30

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
actggcctcc tgggaccatc catgcgtccc                              30

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cagcttgcca cagctcgtgt gcccgagccg                              30

<210> SEQ ID NO 244
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tgaaatatga ggaagatgtg aacctcggct                              30

<210> SEQ ID NO 245
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tggcaagctg tgctgaagct cccaacatga                                      30

<210> SEQ ID NO 246
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
cttgtgtggg ggcttcgtag ctcccatggt                                      30

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
aaccatccat acaggacatg ggcctaccat                                      30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ttgacaggag tctaacaacc ccattcacga                                      30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tttgacagga gtctaacaac cccattcacg                                      30

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gtgtccactt tttctttgaa gactctttgt                                      30

<210> SEQ ID NO 251
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ggcgagtgcc ttcttgggga tctggcaccc                                       30

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cacagccagg aagagaccat gttcattgcc                                       30

<210> SEQ ID NO 253
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
caatgaacat ggtctcttcc tggctgtgga                                       30

<210> SEQ ID NO 254
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
acatggtctc ttcctggctg tggaaggagt                                       30

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
atggtctctt cctggctgtg gaaggagttg                                       30

<210> SEQ ID NO 256
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tcatcaacaa ggtgcgcagc aatgcagcac                                       30

```
<210> SEQ ID NO 257
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
caatatttga agaggaaaaa gaatggaaga                                        30

<210> SEQ ID NO 258
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cccaaaacct tggatcattc acagcctcca                                        30

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aagaggaaaa agaatggaag acggccgtgg                                        30

<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
aaggcagccg cgccatctgg tacatgtggt                                        30

<210> SEQ ID NO 261
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
agaatccaag ggcttcaaac tccaagaatc                                        30

<210> SEQ ID NO 262
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tctggtacat gtggttggga gccagattct                                        30

<210> SEQ ID NO 263
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccacctcctg agttttctct tcccatccaa                                           30

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
agacttggat acattctaga agaaatgaat                                           30

<210> SEQ ID NO 265
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gacttggata cattctagaa gaaatgaatc                                           30

<210> SEQ ID NO 266
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
caaacttact aatgcgggtg tcccagccag                                           30

<210> SEQ ID NO 267
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tgtgcccttc ctccatttgg ttggtaatta                                           30

<210> SEQ ID NO 268
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
agaatgaagc cttaattacc aaccaaatgg                                           30

<210> SEQ ID NO 269
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
caaagtggtg aaggtcctca gaccagctga                                         30

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ggaaaacagt tatggacatc atttcaagac                                         30

<210> SEQ ID NO 271
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ccactaagtt ggtaaatgtg ttgagagcat                                         30

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
atctctaaca cttcctcagc ctccatattc                                         30

<210> SEQ ID NO 273
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
attgcactgc aaccatctgg tcactttctc                                         30

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
atgacatggg aaaagttagg aaagacacac                                         30

<210> SEQ ID NO 275
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 275
tgcagcttgt tgaaatggtg ggagcagaac                                      30

<210> SEQ ID NO 276
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
cggccaatca attcatcttg gtggcggcaa                                      30

<210> SEQ ID NO 277
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gccacatctg tgcatatgat tttgctagac                                      30

<210> SEQ ID NO 278
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
accttcgact gatggccaat gctatttgtt                                      30

<210> SEQ ID NO 279
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
cctttccgtg gattgaccag gtggttctcc                                      30

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tccacggaaa gggagaatgg atgactactg                                      30

<210> SEQ ID NO 281
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 281
gagtgtggat tgaggagaac gaccatatgg                                    30

<210> SEQ ID NO 282
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
caccataagt cctccctttt tcccagatag                                    30

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggacagacat cccctatctg ggaaaaaggg                                    30

<210> SEQ ID NO 284
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
cccaagtggt gcggggcctg tgccctataa                                    30

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gcccaagtgg tgcggggcct gtgccctata                                    30

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gacttatggt gtggatccct tatagggcac                                    30

<210> SEQ ID NO 287
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 287
tgtctttgat gttctcagcc caagtggtgc                                           30

<210> SEQ ID NO 288
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gtgtctttga tgttctcagc ccaagtggtg                                           30

<210> SEQ ID NO 289
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
aagaaaaata catggactac ttatccaccc                                           30

<210> SEQ ID NO 290
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ccaggtgtgg acccttcctc acccaagtag                                           30

<210> SEQ ID NO 291
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
acttatccac ccaggtccgc tacttgggtg                                           30

<210> SEQ ID NO 292
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
aacgcggagt agcccgtgtg agcccctttg                                           30

<210> SEQ ID NO 293
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 293
aggctgccag ccggacttct gctgggtcat                                           30

<210> SEQ ID NO 294
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tcttggcgat tctagccttt ttgagattca                                           30

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tggaaataat aaagaagttc aagaaagatc                                           30

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
acctccgctg ccatagctgt ggtcagcagg                                           30

<210> SEQ ID NO 297
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
cacgtctagt gacctccgct gccatagctg                                           30

<210> SEQ ID NO 298
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gcctcctgct gaccacagct atggcagcgg                                           30

<210> SEQ ID NO 299
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 299
acagctatgg cagcggaggt cactagacgt                                    30

<210> SEQ ID NO 300
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
actatatgta cttggacaga aacgatgctg                                    30

<210> SEQ ID NO 301
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tatataacac ttattcatcc ccaatgtggt                                    30

<210> SEQ ID NO 302
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ggggaggcca tatcttttcc aaccacattg                                    30

<210> SEQ ID NO 303
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
atgagctatg aatgccctat gctggatgag                                    30

<210> SEQ ID NO 304
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tgagctatga atgccctatg ctggatgagg                                    30

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 305
ctagatctcc gtgcttcacc tttttttgtga                30

<210> SEQ ID NO 306
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
accgcgtttg cagcttccta gtggaatggg                30

<210> SEQ ID NO 307
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gcgaccgcgt ttgcagcttc ctagtggaat                30

<210> SEQ ID NO 308
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tgcgaccgcg tttgcagctt cctagtggaa                30

<210> SEQ ID NO 309
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
ggaagctgca aacgcggtcg caaacctggt                30

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tacagcatca ggtgcatagg agtcagcaat                30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
acagcatcag gtgcatagga gtcagcaata        30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
agctggttac aacaacagtc agcaacatgg        30

<210> SEQ ID NO 313
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcaaggtagg cttcaccttg tgttgggcag        30

<210> SEQ ID NO 314
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
actccagatt ctctggctgg atgctcttcc        30

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
aagagcatcc agccagagaa tctggagtac        30

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tgctgggagc catgaactga cagcattatc        30

<210> SEQ ID NO 317
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ctaggcttcc aaacccccccc agggtggctt                                30

<210> SEQ ID NO 318
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
caagtcctag gcttccaaac cccccaggg                                  30

<210> SEQ ID NO 319
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
caatcaagtc ctaggcttcc aaaccccccc                                 30

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
aattcaccaa gagccgaagc caccctgggg                                 30

<210> SEQ ID NO 321
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
aggcctgtcc tcggttcaca atcaagtcct                                 30

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
ctatgaataa caagcactgg ctggttcaca                                 30

<210> SEQ ID NO 323
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gccccagcgt gccaaggtaa tggaatgtcg                                 30

```
<210> SEQ ID NO 324
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ggaacaacaa agaagcactg gtagagttca                                       30

<210> SEQ ID NO 325
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
aggacgcaca tgccaaaagg caaactgtcg                                       30

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
catccatctc agcctccaga gctccagcaa                                       30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ccatccatct cagcctccag agctccagca                                       30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gagctctgga ggctgagatg gatggtgcaa                                       30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ccattttcag gcgacatttc aagtggccag                                       30
```

<210> SEQ ID NO 330
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
acgcccttca atctaagttt atccattttc                                     30

<210> SEQ ID NO 331
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gtactgcagc gttcacattc accaagatcc                                     30

<210> SEQ ID NO 332
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
ttcaccaaga tcccggctga aacactgcac                                     30

<210> SEQ ID NO 333
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tcttagagtt ctcagtgctt tcagtgatta                                     30

<210> SEQ ID NO 334
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tttccaatgg tgctgccact cctgtgccag                                     30

<210> SEQ ID NO 335
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
aatgatttga aagctgctcc aaagatttga                                     30

```
<210> SEQ ID NO 336
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
agtccaccga gcaccccaca tcagcagaga                                           30

<210> SEQ ID NO 337
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
atgtggggtg ctcggtggac ttctcaaaga                                           30

<210> SEQ ID NO 338
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
cagaggagat cccgcagata ccatcttccc                                           30

<210> SEQ ID NO 339
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gatcagtaga agggagctc aacgcaatcc                                            30

<210> SEQ ID NO 340
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
caatcctgga agagaatgga gttcaactga                                           30

<210> SEQ ID NO 341
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
aagagaatgg agttcaactg acggtcgttg                                           30

<210> SEQ ID NO 342
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
tccagccgtg gggcagctcg ttcacaggca                                    30

<210> SEQ ID NO 343
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tgcctgtgaa cgagctgccc cacggctgga                                    30

<210> SEQ ID NO 344
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gagcagcaaa gacaaataac agctttgtcg                                    30

<210> SEQ ID NO 345
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
agaaagctgt tccatgctct atgtttgagt                                    30

<210> SEQ ID NO 346
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tctcttctat tccatctgtc cacaatgtgt                                    30

<210> SEQ ID NO 347
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ctctcttcta ttccatctgt ccacaatgtg                                    30

<210> SEQ ID NO 348
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tgtgatggct gagtggccca gctaaagact                                           30

<210> SEQ ID NO 349
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
agtgatctga tcatacccaa gtctttagct                                           30

<210> SEQ ID NO 350
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gccctttcat ttgggtcctg tagccctctc                                           30

<210> SEQ ID NO 351
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
ctcagccatc acaataccag agagggctac                                           30

<210> SEQ ID NO 352
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
gctcttcact gtgccatggc cctttcattt                                           30

<210> SEQ ID NO 353
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
agctcttcac tgtgccatgg ccctttcatt                                           30

<210> SEQ ID NO 354
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 354
catgtttcct ccacgtggac cttagtgcct                                        30

<210> SEQ ID NO 355
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
agcggaaggg tgatcgagga atggtgctgc                                        30

<210> SEQ ID NO 356
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gcggaagggt gatcgaggaa tggtgctgca                                        30

<210> SEQ ID NO 357
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
agggagtgca caatgccccc actgtcgttc                                        30

<210> SEQ ID NO 358
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gggagtgcac aatgccccca ctgtcgttcc                                        30

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tccattccat accaacagcc atctttagcc                                        30

<210> SEQ ID NO 360
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 360
gcaccatgag cagaatcaca agcactccaa                                        30

<210> SEQ ID NO 361
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tgcaccatga gcagaatcac aagcactcca                                        30

<210> SEQ ID NO 362
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
ttggagtgct tgtgattctg ctcatggtgc                                        30

<210> SEQ ID NO 363
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gtggcaccca tcaaaattgc aagcttagcc                                        30

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
agcttgcaat tttgatgggt gccacctccg                                        30

<210> SEQ ID NO 365
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
acgaggccaa ggccagcagc atgctttcac                                        30

<210> SEQ ID NO 366
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 366
cacgaggcca aggccagcag catgctttca                                        30

<210> SEQ ID NO 367
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
ctaattggac accccgtgaa agcatgctgc                                        30

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
aggcggagat cgcagtttgc aaaagacacg                                        30

<210> SEQ ID NO 369
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tgatgagaac catcaggtcg ccttccaagg                                        30

<210> SEQ ID NO 370
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
cgtgtctttt gcaaactgcg atctccgcct                                        30

<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
cattgatgag aaccatcagg tcgccttcca                                        30

<210> SEQ ID NO 372
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 372
ccagtggtgt cagagcagcc aggattgcca                                30

<210> SEQ ID NO 373
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ccttggcaat cctggctgct ctgacaccac                                30

<210> SEQ ID NO 374
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gcaatcctgg ctgctctgac accactggcc                                30

<210> SEQ ID NO 375
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
caatcctggc tgctctgaca ccactggccc                                30

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gtggcgtgga gagcaggcct tgctacttgc                                30

<210> SEQ ID NO 377
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
tggcgtggag agcaggcctt gctacttgcg                                30

<210> SEQ ID NO 378
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gggtcgacca gcctcacagc ggttagtccc             30

<210> SEQ ID NO 379
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ccacgttgat ggggtcgacc agcctcacag             30

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
tcatggccct gggactaacc gctgtgaggc             30

<210> SEQ ID NO 381
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
cagatataga gatggctggg cccatggccg             30

<210> SEQ ID NO 382
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
ccacgtaact gacaattagc agaccgaccg             30

<210> SEQ ID NO 383
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
caccactctc atctagcgcc acatcgagcc             30

<210> SEQ ID NO 384
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 384
tcaccactct catctagcgc cacatcgagc                                      30

<210> SEQ ID NO 385
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
ctctcatggg gggaccgtca tcctccacca                                      30

<210> SEQ ID NO 386
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ggaccacctt gagtatgatc tctctcatgg                                      30

<210> SEQ ID NO 387
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
aggaccacct tgagtatgat ctctctcatg                                      30

<210> SEQ ID NO 388
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
gtggtgctct atgggatgtg cctgctccca                                      30

<210> SEQ ID NO 389
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
gggatgtgcc tgctcccaag gaagtaaaaa                                      30

<210> SEQ ID NO 390
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
```
gatgtgcctg ctcccaagga agtaaaaaag                                           30

<210> SEQ ID NO 391
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
atgtgcctgc tcccaaggaa gtaaaaagg                                            30

<210> SEQ ID NO 392
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
acacaagttg gagtgggagt tatgcaagag                                           30

<210> SEQ ID NO 393
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
cacaagttgg agtgggagtt atgcaagagg                                           30

<210> SEQ ID NO 394
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gatcaagtct cccttcaccg cttctcagcg                                           30

<210> SEQ ID NO 395
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
atccatactg gggagatgtc aagcaggatc                                           30

<210> SEQ ID NO 396
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
ccaagagctg cacctcgctg tgcccgtccc               30

<210> SEQ ID NO 397
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ggtccatgga agctagatgc cgcctgggac               30

<210> SEQ ID NO 398
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
ggatgttcct cgctctctct ccggggggca               30

<210> SEQ ID NO 399
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
ctcttggccg tgccccccgg agagagagcg               30

<210> SEQ ID NO 400
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
tcctttgtct taaatattcc gggcagagtc               30

<210> SEQ ID NO 401
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
caatgtcccc atcctttgtc ttaaatattc               30

<210> SEQ ID NO 402
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
tatttaagac aaaggatggg gacattggag               30

<210> SEQ ID NO 403
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
acttcaggat ctcctatcct agacaagtgt                               30

<210> SEQ ID NO 404
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ctttatggca atggggtcgt gatcaaaaat                               30

<210> SEQ ID NO 405
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gggagttatg ttagtgccat cacccaaggg                               30

<210> SEQ ID NO 406
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
ctaactgtct tagacttgca tcctggagct                               30

<210> SEQ ID NO 407
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
cttcacggac tatttcagga agaactctcc                               30

<210> SEQ ID NO 408
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
caaccagggt tgtcgctgct gaaatggagg                               30

<210> SEQ ID NO 409
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
gttgtcatat aacgcactgg aagccctcta                                    30

<210> SEQ ID NO 410
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gtcgctgctg aaatggagga ggcccttaga                                    30

<210> SEQ ID NO 411
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
gggcctcatc cataatatac agattatagt                                    30

<210> SEQ ID NO 412
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
tccccaacta taatctgtat attatggatg                                    30

<210> SEQ ID NO 413
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ttcctggtgg cgtggcggtc atgaagatgg                                    30

<210> SEQ ID NO 414
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
gaaatgcgtc acgggttcct ggtggcgtgg                                    30

<210> SEQ ID NO 415
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
ccacgccacc aggaacccgt gacgcatttc                                30

<210> SEQ ID NO 416
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
agctccaggc tctctctggg acttccactt                                30

<210> SEQ ID NO 417
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gagcctggag ctcaggcttt gattgggtga                                30

<210> SEQ ID NO 418
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ggaaaaacag tttggtttgt tccaagcgtg                                30

<210> SEQ ID NO 419
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
acaaagtccc actcttgatg ttttgttttc                                30

<210> SEQ ID NO 420
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
tggaatctat gacacggtca gctttaaagt                                30

<210> SEQ ID NO 421

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
catcaagtat gaccggcttt aggcatctcc                                              30

<210> SEQ ID NO 422
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gtgtcataga ttccaggaga tgcctaaagc                                              30

<210> SEQ ID NO 423
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
tgcctatgcg cccctcctc tgggcagcgc                                               30

<210> SEQ ID NO 424
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
ttgggattcc tgcctatgcg cccctcctc                                               30

<210> SEQ ID NO 425
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
cctgtcacac atgccagcgc tgcccagagg                                              30

<210> SEQ ID NO 426
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
ctgtcacaca tgccagcgct gcccagagga                                              30

<210> SEQ ID NO 427
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ctccatacag atactcatct ccaggtttgt                                       30

<210> SEQ ID NO 428
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
aaacctggag atgagtatct gtatggaggt                                       30

<210> SEQ ID NO 429
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
atgaggccat cttggaggta aatattgtca                                       30

<210> SEQ ID NO 430
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
cagccattga gggagagttc aagcttagga                                       30

<210> SEQ ID NO 431
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tcatgaaaag aggagatctt cctgtttggc                                       30

<210> SEQ ID NO 432
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
tgccatcaaa gcaccatctt ctatctgtgt                                       30

<210> SEQ ID NO 433
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 433
ccaacaacac cataatggaa gacagtgtgc                                        30

<210> SEQ ID NO 434
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
tcggtttgag cactcttttc tctccgtgtc                                        30

<210> SEQ ID NO 435
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
agacacggag agaaaagagt gctcaaaccg                                        30

<210> SEQ ID NO 436
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
acttcagggc cgcatgatct gaacaaactc                                        30

<210> SEQ ID NO 437
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ggatggacgc cagagtttgt tcagatcatg                                        30

<210> SEQ ID NO 438
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
gttcagatca tgcggccctg aagtcattca                                        30

<210> SEQ ID NO 439
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 439
cttccagtct ctgcccgcat gagcacagcg                                        30

<210> SEQ ID NO 440
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gaagccattg acaacctcgc tgtgctcatg                                        30

<210> SEQ ID NO 441
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
aagccattga caacctcgct gtgctcatgc                                        30

<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
tctctagggt ctccggcaat tgggccgccg                                        30

<210> SEQ ID NO 443
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
agactggaag caggccttac aaagccgcgg                                        30

<210> SEQ ID NO 444
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tgccggagac cctagagacc attatgcttt                                        30

<210> SEQ ID NO 445
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 445
ccggagaccc tagagaccat tatgcttttg                                         30

<210> SEQ ID NO 446
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
tctggctcag gtatgagcac caccagcaat                                         30

<210> SEQ ID NO 447
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
ttgttctctc caaccatccg agttcattgg                                         30

<210> SEQ ID NO 448
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tctttgttct ctccaaccat ccgagttcat                                         30

<210> SEQ ID NO 449
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ccctcctctc tccttcccat tagatggctt                                         30

<210> SEQ ID NO 450
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450 gttgcccct cctctctcct tcccattaga                                          30

<210> SEQ ID NO 451
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 451
gtgacctaag ccatctaatg ggaaggagag          30

<210> SEQ ID NO 452
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
acctaagcca tctaatggga aggagagagg          30

<210> SEQ ID NO 453
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
ctaagccatc taatgggaag gagagaggag          30

<210> SEQ ID NO 454
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
taagccatct aatgggaagg agagaggagg          30

<210> SEQ ID NO 455
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
gccgcaggtc aatgtccatt gagaatccta          30

<210> SEQ ID NO 456
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
gcatagatgg cccaagctga ggctggccgc          30

<210> SEQ ID NO 457
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gggtaatgaa agttgtcaag gcagcataga                                          30

<210> SEQ ID NO 458
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
gttggacggc tggggtaatg aaagttgtca                                          30

<210> SEQ ID NO 459
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
ccatcgccat taaggagtag ttgttgtatg                                          30

<210> SEQ ID NO 460
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
tgcgccacga gcaaaatgat ggccactatt                                          30

<210> SEQ ID NO 461
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
agtacatgta gtgcgccacg agcaaaatga                                          30

<210> SEQ ID NO 462
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
ctcgtggcgc actacatgta cttgatccca                                          30

<210> SEQ ID NO 463
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
cagcagctgc gcgtgctgcc cagaagagaa                                    30

<210> SEQ ID NO 464
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
atgtcagtca ccactattcc atccacaaca                                    30

<210> SEQ ID NO 465
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
ttgaccccca agtggagaaa aagatgggac                                    30

<210> SEQ ID NO 466
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466 cccccaccc ccaggcggtc cgcgacagta                                     30

<210> SEQ ID NO 467
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tgatcagggc cccagcctcc ccccaccccc                                    30

<210> SEQ ID NO 468
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tcgcggaccg cctggggtg gggggaggct                                     30

<210> SEQ ID NO 469
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
cgcggaccgc ctgggggtgg ggggaggctg                                     30

<210> SEQ ID NO 470
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cccacaaagt ggaagttgcg gctgtgatca                                     30

<210> SEQ ID NO 471
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tcccacaaag tggaagttgc ggctgtgatc                                     30

<210> SEQ ID NO 472
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tcggagagcc ttcccacaaa gtggaagttg                                     30

<210> SEQ ID NO 473
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
tctacagcca cttcactgtg taacattttt                                     30

<210> SEQ ID NO 474
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
ctacagccac ttcactgtgt aacatttta                                      30

<210> SEQ ID NO 475
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
taatctacac agtaacaaga aacgctggct 30

<210> SEQ ID NO 476
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
acaagaaacg ctggcttggt caagagacgt 30

<210> SEQ ID NO 477
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
caagaaacgc tggcttggtc aagagacgtg 30

<210> SEQ ID NO 478
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
agagacgtgg gggtggaaca ggagagaccc 30

<210> SEQ ID NO 479
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
ggttcaagcg ggccttccat ttctctccca 30

<210> SEQ ID NO 480
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
tggttcaagc gggccttcca tttctctccc 30

<210> SEQ ID NO 481
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
gaacaggaga gaccctggga gagaaatgga 30

<210> SEQ ID NO 482
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
agaactccag ggccgacatc tggttcaagc                                           30

<210> SEQ ID NO 483
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tagaactcca gggccgacat ctggttcaag                                           30

<210> SEQ ID NO 484
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
ttgtaggagt agaactccag ggccgacatc                                           30

<210> SEQ ID NO 485
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
tgcacacctc ggtgatgcct gactttttgt                                           30

<210> SEQ ID NO 486
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
tctactccta caaaaagtca ggcatcaccg                                           30

<210> SEQ ID NO 487
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
gggcgcggcg ggcctcttct ctgcacacct                                           30

<210> SEQ ID NO 488
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
ccgttgccac accgtccttg agggcgcggc                                      30

<210> SEQ ID NO 489
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
cccgttgcca caccgtcctt gagggcgcgg                                      30

<210> SEQ ID NO 490
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
cccgccgcgc cctcaaggac ggtgtggcaa                                      30

<210> SEQ ID NO 491
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
ctcagctttg cacttcctcg ggacacagca                                      30

<210> SEQ ID NO 492
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
ggaagtgcaa agctgagatg gttggtggag                                      30

<210> SEQ ID NO 493
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gaagtgcaaa gctgagatgg ttggtggagc                                      30

```
<210> SEQ ID NO 494
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
ctttgcacca acacgggttc ttcatgacca                                        30

<210> SEQ ID NO 495
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
atatgaaaga cgtccacccc actcttaaga                                        30

<210> SEQ ID NO 496
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
tatgggtgga acatagtccg tcttaagagt                                        30

<210> SEQ ID NO 497
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
atgggtggaa catagtccgt cttaagagtg                                        30

<210> SEQ ID NO 498
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
tcatcatcta gtcctgaagt ggaagaagca                                        30

<210> SEQ ID NO 499
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499 ctttttcaa gccaatcccc caccatggag                                         30

<210> SEQ ID NO 500
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
ctggtctttt ttcaagccaa tcccccacca                                            30

<210> SEQ ID NO 501
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
tccagggttt ccatcatagt gctggtgtat                                            30

<210> SEQ ID NO 502
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
cctcccccat acctacgctg cagtcgctcc                                            30

<210> SEQ ID NO 503
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
agcgactgca gcgtaggtat gggggaggac                                            30

<210> SEQ ID NO 504
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
agacccagta catctcatgt gtagagttgc                                            30

<210> SEQ ID NO 505
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
gagacccagt acatctcatg tgtagagttg                                            30

<210> SEQ ID NO 506
<211> LENGTH: 30
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
ggagctggct cgtggtggac acactttta                                30

<210> SEQ ID NO 507
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ctaggcccgt ccatgcgccc caagaggagc                               30

<210> SEQ ID NO 508
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
agtgtgtcca ccacgagcca gctcctcttg                               30

<210> SEQ ID NO 509
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
acgagccagc tcctcttggg gcgcatggac                               30

<210> SEQ ID NO 510
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
acgggcctag gaggccagtg aaatatgagg                               30

<210> SEQ ID NO 511
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
gaggaggatg tgaatctcgg ctctggcacg                               30

<210> SEQ ID NO 512
<211> LENGTH: 30
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 512
aggaggatgt gaatctcggc tctggcacgc    30

<210> SEQ ID NO 513
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 513
tccgcgtgct cactgcggat cctttcaatg    30

<210> SEQ ID NO 514
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 514
aacatgaaga tcattggtaa ccgcattgaa    30

<210> SEQ ID NO 515
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 515
accgcattga aaggatccgc agtgagcacg    30

<210> SEQ ID NO 516
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 516
tagcttccat ggtaagccca tgtcctatat    30

<210> SEQ ID NO 517
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 517
ataggacatg ggcttaccat ggaagctatg    30

<210> SEQ ID NO 518
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 518
acaggagcct gacaaccccg tttattagag                                            30

<210> SEQ ID NO 519
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
tcagcgtcct ctctaataaa cggggttgtc                                            30

<210> SEQ ID NO 520
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ttgtcaggct cctgtcaaaa ccctgggatg                                            30

<210> SEQ ID NO 521
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
tttgctgacc atacggtgtg gtgtcggtca                                            30

<210> SEQ ID NO 522
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
aaactctttg ctgaccatac ggtgtggtgt                                            30

<210> SEQ ID NO 523
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
ccttgaaaac tctttgctga ccatacggtg                                            30

<210> SEQ ID NO 524
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 524
ccacaccgta tggtcagcaa agagttttca                                    30

<210> SEQ ID NO 525
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
atgctcataa cctgacgagt gccttcttgg                                    30

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
atcaacaagg ttcgtagcaa tgcagcatta                                    30

<210> SEQ ID NO 527
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tcaacaaggt tcgtagcaat gcagcattag                                    30

<210> SEQ ID NO 528
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
tacacacaac tctggcactc tcctctcagg                                    30

<210> SEQ ID NO 529
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
aacatgatgg gaaaaagaga aagaaacaa                                     30

<210> SEQ ID NO 530
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 530
acatgatggg aaaaagagaa aagaaacaag                                              30

<210> SEQ ID NO 531
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
aaagagaaaa gaaacaaggg gaatttggaa                                              30

<210> SEQ ID NO 532
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
aaaagaaaca agggggaattt ggaaaggcca                                             30

<210> SEQ ID NO 533
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gccacatata ccagatggcg cggctgccct                                              30

<210> SEQ ID NO 534
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ggcagccgcg ccatctggta tatgtggcta                                              30

<210> SEQ ID NO 535
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
gcagccgcgc catctggtat atgtggctag                                              30

<210> SEQ ID NO 536
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
cttggattct tgaacgagga tcactggatg                                    30

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
gagagaactc aggaggtggt gttgaagggc                                    30

<210> SEQ ID NO 538
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
cttcctcctg gtatacgact catctcttct                                    30

<210> SEQ ID NO 539
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ctagaagaga tgagtcgtat accaggagga                                    30

<210> SEQ ID NO 540
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
gacactgctg gctgggacac ccgcattagc                                    30

<210> SEQ ID NO 541
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
ctaatcacca accaaatgga gaaagggcac                                    30

<210> SEQ ID NO 542
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 542
taatcaccaa ccaaatggag aaagggcaca                                            30

<210> SEQ ID NO 543
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ggtatgtgta cttgattatg gccaatgcca                                            30

<210> SEQ ID NO 544
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ccactttgtt ttggtatgtg tacttgatta                                            30

<210> SEQ ID NO 545
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
gctggtctaa ggacctttac cactttgttt                                            30

<210> SEQ ID NO 546
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
gttatggaca ttatttcgag acaagaccaa                                            30

<210> SEQ ID NO 547
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
ctagagatgc aagacttgtg gctgctgcgg                                            30

<210> SEQ ID NO 548
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
```

```
actaactggt tgcagagcaa cggatgggat                                        30
```

<210> SEQ ID NO 549
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549

```
ggttcttgaa tgatatggga aaagttagga                                        30
```

<210> SEQ ID NO 550
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550

```
acacacaaga gtggaaaccc tcaactggat                                        30
```

<210> SEQ ID NO 551
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551

```
ggaaccacaa tggacctccc gtccttgaga                                        30
```

<210> SEQ ID NO 552
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552

```
caccacttca acaagctcca tctcaaggac                                        30
```

<210> SEQ ID NO 553
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553

```
cacttcaaca agctccatct caaggacggg                                        30
```

<210> SEQ ID NO 554
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
cccggccaat cagttcatct tggtggcggc                                      30

<210> SEQ ID NO 555
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
ccctgccgcc accaagatga actgattggc                                      30

<210> SEQ ID NO 556
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
cctgccgcca ccaagatgaa ctgattggcc                                      30

<210> SEQ ID NO 557
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
tgattggccg ggcccgcgtc tctccagggg                                      30

<210> SEQ ID NO 558
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
gcatatgatt ttgctaggca agcagtctcc                                      30

<210> SEQ ID NO 559
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
agctgccaca tttgcgcata tgattttgct                                      30

<210> SEQ ID NO 560
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
atcagtcgga ggtcccttct gtggaaataa                                      30

<210> SEQ ID NO 561
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
caaatgtggc agctccttta tttccacaga                                      30

<210> SEQ ID NO 562
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
aaatgtggca gctcctttat ttccacagaa                                      30

<210> SEQ ID NO 563
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
acagatgaac aaatggcatt ggccatcagt                                      30

<210> SEQ ID NO 564
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
gaacccagtc aactggcaca gatgaacaaa                                      30

<210> SEQ ID NO 565
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ctctgttcca caccacaagc atgtcttcag                                      30

<210> SEQ ID NO 566
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
aatagggaat gtctgtccat ttcgtaactg                                      30

<210> SEQ ID NO 567
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
aaatagggaa tgtctgtcca tttcgtaact                                      30

<210> SEQ ID NO 568
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
tgttgactgt gttttttaatg ttctcagccc                                     30

<210> SEQ ID NO 569
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
tcttcaccca agtagcgaac ttgggtggat                                      30

<210> SEQ ID NO 570
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
cactcccacg tctagtgacc tccactgcca                                      30

<210> SEQ ID NO 571
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
cttctagatc tccgtgcttc acctttttg                                       30

<210> SEQ ID NO 572
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
ttcctgaata tccaattttc gactctaatc                                      30

```
<210> SEQ ID NO 573
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573 cttttggct cgttgaactt cccaaaagcc                                   30

<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
tgtcgacagc cggtttgtcc tgtgccatta                                  30

<210> SEQ ID NO 575
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
gttgtgttac cgtaatggca caggacaaac                                  30

<210> SEQ ID NO 576
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
taagatccta ttgctatgag gcatcaatat                                  30

<210> SEQ ID NO 577
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
caggacatga aactgatgag aatagagcga                                  30

<210> SEQ ID NO 578
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
cagccgggat cttggtgaat gtgaacgctg                                  30

<210> SEQ ID NO 579
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
tgtccaccgc catctgagct ggaaccttgc                                            30

<210> SEQ ID NO 580
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
ggttctcaca aattctcatt ggaacgttgc                                            30

<210> SEQ ID NO 581
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
acttctcaaa gaaggaaacg agatgcggta                                            30

<210> SEQ ID NO 582
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
gcagcagcag tcaagcaagc ctgggragat                                            30

<210> SEQ ID NO 583
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
tttggccatt cacatgtttt catctcgatc                                            30

<210> SEQ ID NO 584
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
caaaggtggc acccatcaaa attgcaagct                                            30

<210> SEQ ID NO 585
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
gagatcgcag tttgcagaag acacgaagcc                                          30

<210> SEQ ID NO 586
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586 tgcgggggt tcatgcttct ctctctgaag                                           30

<210> SEQ ID NO 587
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587 ggggttcat gcttctctct ctgaagggga                                           30

<210> SEQ ID NO 588
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
gcggtgagtc ccaaggccat gacaaatggt                                          30

<210> SEQ ID NO 589
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
tatgcgcgtt ggccggaggg ttcgccaagg                                          30

<210> SEQ ID NO 590
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
ctggaaacag tccccggctc gatgtggcac                                          30

<210> SEQ ID NO 591
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 591
gcggatcctt ttgtgacgtg ccacatagtg                                       30

<210> SEQ ID NO 592
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
actctcctgg ttttcccagc tccaggatgc                                       30

<210> SEQ ID NO 593
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
atgacaacag cagtcaatgt cacccattct                                       30

<210> SEQ ID NO 594
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
agtccgggaa tgcgtcacgg gttcctggtg                                       30

<210> SEQ ID NO 595
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
gagtccggga atgcgtcacg ggttcctggt                                       30

<210> SEQ ID NO 596
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
tcggtgtcca taattggtga gttggagtcc                                       30

<210> SEQ ID NO 597
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 597
acaccataat ggaagacagt gtgccggcag                                         30

<210> SEQ ID NO 598
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
gcaatgttcc cagggcttcc atcactccaa                                         30

<210> SEQ ID NO 599
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
ttggagtgat ggaagccctg ggaacattgc                                         30

<210> SEQ ID NO 600
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
accaaatggc aatcatcatc atgatagcag                                         30

<210> SEQ ID NO 601
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
caactttcat caccccagcc gtccaacatg                                         30

<210> SEQ ID NO 602
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
atgggacttt ggagtcccgc tgctaatga                                          29

<210> SEQ ID NO 603
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 603
ccctaaaaat gttacacagt gaagtggctg                                      30

<210> SEQ ID NO 604
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ctggcttggt caagagacgt gggggtggaa                                      30

<210> SEQ ID NO 605
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
gagtagaact ctagggccga catctggttc                                      30

<210> SEQ ID NO 606
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
cttcagcgca gcttaccaca gcccgcgtgc                                      30

<210> SEQ ID NO 607
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
tctggtatat gtggctaggg gctagattcc                                      30

<210> SEQ ID NO 608
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tcgttcaaga atccaagggc ttcgaactcc                                      30

<210> SEQ ID NO 609
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 609
tcacttacgc tcttaataca ttcaccaacc            30

<210> SEQ ID NO 610
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
gctatgaatg ccctatgctg gatgaggggg            30

<210> SEQ ID NO 611
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
ctaggcttcc aaacccccccc agggtggctt            30

<210> SEQ ID NO 612
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
aattcaccaa gagccgaagc caccctgggg            30

<210> SEQ ID NO 613
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
tcttagagtt ctcagtgctt tcagtgatta            30

<210> SEQ ID NO 614
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
tttccaatgg tgctgccact cctgtgccag            30

<210> SEQ ID NO 615
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 615
aggcttgctt gactgctgct gccaatctac                              30

<210> SEQ ID NO 616
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
caggcttgct tgactgctgc tgccaatcta                              30

<210> SEQ ID NO 617
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
acaagtacca tcctgactcc ccccgtagat                              30

<210> SEQ ID NO 618
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
gctcttcact gtgccatggc cctttcattt                              30

<210> SEQ ID NO 619
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
agctcttcac tgtgccatgg ccctttcatt                              30

<210> SEQ ID NO 620
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
agcagaatca caagcactcc aagggagaag                              30

<210> SEQ ID NO 621
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 621
aggcggagat cgcagtttgc aaaagacacg                                30

<210> SEQ ID NO 622
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
cacgcactga taacatcacc ttggcaatcc                                30

<210> SEQ ID NO 623
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
ttcttcacac tgccttttcc cttcagagag                                30

<210> SEQ ID NO 624
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
gggtcgacca gcctcacagc ggttagtccc                                30

<210> SEQ ID NO 625
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
ttggcgaacc ctccagccaa tgcgcatatc                                30

<210> SEQ ID NO 626
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
tggcgctaga tgagagtggt gatttctccc                                30

<210> SEQ ID NO 627
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
acggtccccc catgagagag atcatactca 30

<210> SEQ ID NO 628
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
tatttaagac aaaggatggg gacattggag 30

<210> SEQ ID NO 629
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
caaccagggt tgtcgctgct gaaatggagg 30

<210> SEQ ID NO 630
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
atgaggccat cttggaggta aatattgtca 30

<210> SEQ ID NO 631
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
gctccgtcct aagcttgaac tctccctcaa 30

<210> SEQ ID NO 632
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gttcagatca tgcggccctg aagtcattca 30

<210> SEQ ID NO 633
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
cccagcaacc ccaaaagcat aatggtctct           30

<210> SEQ ID NO 634
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
cccaggacaa ccaaatggca atcatcatca           30

<210> SEQ ID NO 635
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
gggtaatgaa agttgtcaag gcagcataga           30

<210> SEQ ID NO 636
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
gttggacggc tggggtaatg aaagttgtca           30

<210> SEQ ID NO 637
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
ccatcgccat taaggagtag ttgttgtatg           30

<210> SEQ ID NO 638
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
tagcacctgt cccatctttt tctccacttg           30

<210> SEQ ID NO 639
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
gtagcacctg tcccatcttt ttctccactt           30

<210> SEQ ID NO 640
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
tcggagagcc ttcccacaaa gtggaagttg                                    30

<210> SEQ ID NO 641
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
ggaaggcccg cttgaaccag atgtcggccc                                    30

<210> SEQ ID NO 642
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
cccgccgcgc cctcaaggac ggtgtggcaa                                    30

<210> SEQ ID NO 643
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
ggaagtgcaa agctgagatg gttggtggag                                    30

<210> SEQ ID NO 644
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
gaagtgcaaa gctgagatgg ttggtggagc                                    30

<210> SEQ ID NO 645
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
cgtttattag agaggacgct gacccttgtg                                    30

<210> SEQ ID NO 646
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
cttttcccca tcatgttgta cacacaactc                                30

<210> SEQ ID NO 647
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
ccctgccgcc accaagatga actgattggc                                30

<210> SEQ ID NO 648
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
cctgccgcca ccaagatgaa ctgattggcc                                30

<210> SEQ ID NO 649
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
gggctgagaa cattaaaaac acagtcaaca                                30

<210> SEQ ID NO 650
<211> LENGTH: 36
<212> TYPE: RNA
<213> ORGANISM: Zika virus

<400> SEQUENCE: 650
uugagaguga gaagaaugac caugggaggc ugaaga                         36

<210> SEQ ID NO 651
<211> LENGTH: 36
<212> TYPE: RNA
<213> ORGANISM: Zika virus

<400> SEQUENCE: 651
augaugggaa aagagaaaa gaaacaaggg gaauuu                          36

<210> SEQ ID NO 652
<211> LENGTH: 36
<212> TYPE: RNA
<213> ORGANISM: Zika virus

<400> SEQUENCE: 652
gacacaggac augaaacuga ugagaauaga gcgaaa        36

<210> SEQ ID NO 653
<211> LENGTH: 36
<212> TYPE: RNA
<213> ORGANISM: Zika virus

<400> SEQUENCE: 653
uggaaaacau cauguggaga ucaguagaag gggagc        36

<210> SEQ ID NO 654
<211> LENGTH: 36
<212> TYPE: RNA
<213> ORGANISM: Zika virus

<400> SEQUENCE: 654
ggggaaaaaa gaggcuaugg aaauaauaaa gaaguu        36

<210> SEQ ID NO 655
<211> LENGTH: 36
<212> TYPE: RNA
<213> ORGANISM: Zika virus

<400> SEQUENCE: 655
gauaacgccc aauucaccaa gagccgaagc cacccu        36

<210> SEQ ID NO 656
<211> LENGTH: 36
<212> TYPE: RNA
<213> ORGANISM: Zika virus

<400> SEQUENCE: 656
uugaagagga aaaagagugg aagacugcag uggaag        36

<210> SEQ ID NO 657
<211> LENGTH: 36
<212> TYPE: RNA
<213> ORGANISM: Zika virus

<400> SEQUENCE: 657
uuuugcucgu ggcgcacuac auguacuuga ucccag        36

<210> SEQ ID NO 658
<211> LENGTH: 36
<212> TYPE: RNA
<213> ORGANISM: Zika virus

<400> SEQUENCE: 658
uugcuacuca caauuaacac cccugacccu aauagu        36

<210> SEQ ID NO 659
<211> LENGTH: 36
<212> TYPE: RNA
<213> ORGANISM: Zika virus

<400> SEQUENCE: 659
accaccucau acaacaacua cuccuuaaug gcgaug        36

<210> SEQ ID NO 660
<211> LENGTH: 36
<212> TYPE: RNA
<213> ORGANISM: Zika virus

```
<400> SEQUENCE: 660
accacaaaga ucaucauaag cacaucaaug gcagug                              36

<210> SEQ ID NO 661
<211> LENGTH: 36
<212> TYPE: RNA
<213> ORGANISM: Zika virus

<400> SEQUENCE: 661
agacagaguu ccagaaaaca aaacaucaag aguggg                              36

<210> SEQ ID NO 662
<211> LENGTH: 36
<212> TYPE: RNA
<213> ORGANISM: Zika virus

<400> SEQUENCE: 662
ugcacaaugc ccccacuguc guuccgggcu aaagau                              36

<210> SEQ ID NO 663
<211> LENGTH: 36
<212> TYPE: RNA
<213> ORGANISM: Zika virus

<400> SEQUENCE: 663
gacaccggaa cuccacacug gaacaacaaa gaagca                              36

<210> SEQ ID NO 664
<211> LENGTH: 36
<212> TYPE: RNA
<213> ORGANISM: Zika virus

<400> SEQUENCE: 664
guuugccgcu gggaaaagag gagcggcuuu uggagu                              36

<210> SEQ ID NO 665
<211> LENGTH: 36
<212> TYPE: RNA
<213> ORGANISM: Zika virus

<400> SEQUENCE: 665
ggcagaagug uggaccagac acggagagaa aagagu                              36

<210> SEQ ID NO 666
<211> LENGTH: 36
<212> TYPE: RNA
<213> ORGANISM: Zika virus

<400> SEQUENCE: 666
cugaucgaga ugaaaacaug ugaauggcca aagucc                              36

<210> SEQ ID NO 667
<211> LENGTH: 36
<212> TYPE: RNA
<213> ORGANISM: Zika virus

<400> SEQUENCE: 667
gagccagaaa agcaaagauc uccccaggac aaccaa                              36

<210> SEQ ID NO 668
<211> LENGTH: 36
<212> TYPE: RNA
<213> ORGANISM: Zika virus
```

-continued

<400> SEQUENCE: 668
cuuaacacau uuaccaaccu aguggugcaa cucauu                              36

<210> SEQ ID NO 669
<211> LENGTH: 36
<212> TYPE: RNA
<213> ORGANISM: Zika virus

<400> SEQUENCE: 669
gcgguacagg gguguucguc uauaacgacg uugaag                              36

<210> SEQ ID NO 670
<211> LENGTH: 36
<212> TYPE: RNA
<213> ORGANISM: Zika virus

<400> SEQUENCE: 670
gaggcugagg aaguucuaga gaugcaagac uugugg                              36

<210> SEQ ID NO 671
<211> LENGTH: 36
<212> TYPE: RNA
<213> ORGANISM: Zika virus

<400> SEQUENCE: 671
ggcacaguga agagcuugaa auucgguuug aggaau                              36

<210> SEQ ID NO 672
<211> LENGTH: 36
<212> TYPE: RNA
<213> ORGANISM: Zika virus

<400> SEQUENCE: 672
caucuaaugg gaaggagaga ggagggggca accaua                              36

<210> SEQ ID NO 673
<211> LENGTH: 36
<212> TYPE: RNA
<213> ORGANISM: Zika virus

<400> SEQUENCE: 673
gauagguuug cacaugcccu cagguucuug aaugau                              36

<210> SEQ ID NO 674
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 674
ucuucagccu ccauguguca uucuucucac ucucaaguua uaguuaugaa cagaggagac    60
auaacaugaa cuugagaaac caaguuaacc uggcggcagc gcaaaag                 107

<210> SEQ ID NO 675
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 675
aaauuccccu uguuucuuuu cucuuuuucc caucauguua uaguuaugaa cagaggagac    60
auaacaugaa caugaugaac cauguuaacc uggcggcagc gcaaaag                 107

<210> SEQ ID NO 676
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 676
uuucgcucua uucucaucag uuucaugucc ugugucguua uaguuaugaa cagaggagac    60
auaacaugaa cgacacaaac gucguuaacc uggcggcagc gcaaaag                 107

<210> SEQ ID NO 677
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 677
gcuccccuuc uacugaucuc cacaugaugu uuuccaguua uaguuaugaa cagaggagac    60
auaacaugaa cuggaaaaac ccaguuaacc uggcggcagc gcaaaag                 107

<210> SEQ ID NO 678
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 678
aacuucuuua uuauuuccau agccucuuuu uuccccguua uaguuaugaa cagaggagac    60
auaacaugaa cggggaaaac cccguuaacc uggcggcagc gcaaaag                 107

<210> SEQ ID NO 679
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 679 agggguggcuu cggcucuugg ugaauugggc guuaucguua uaguuaugaa cagaggagac    60
auaacaugaa cgauaacaac aucguuaacc uggcggcagc gcaaaag                 107

<210> SEQ ID NO 680
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 680
cuuccacugc agucuuccac ucuuuuuccu cuucaaguua uaguuaugaa cagaggagac    60
auaacaugaa cuugaagaac caaguuaacc uggcggcagc gcaaaag    107

<210> SEQ ID NO 681
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 681
cugggaucaa guacauguag ugcgccacga gcaaaaguua uaguuaugaa cagaggagac    60
auaacaugaa cuuuugcaac aaaguuaacc uggcggcagc gcaaaag    107

<210> SEQ ID NO 682
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 682
acuauuaggg ucagggguguu uaauugugag uagcaaguua uaguuaugaa cagaggagac    60
auaacaugaa cuugcuaaac caaguuaacc uggcggcagc gcaaaag    107

<210> SEQ ID NO 683
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 683
caucgccauu aaggaguagu uguuguauga ggugguguua uaguuaugaa cagaggagac    60
auaacaugaa caccaccaac gguguuaacc uggcggcagc gcaaaag    107

<210> SEQ ID NO 684
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 684
cacugccauu gaugugcuua ugaugaucuu ugugguguua uaguuaugaa cagaggagac    60
auaacaugaa caccacaaac gguguuaacc uggcggcagc gcaaaag    107

<210> SEQ ID NO 685
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 685
cccacucuug auguuuuguu uucuggaacu cugucuguua uaguuaugaa cagaggagac    60
auaacaugaa cagacagaac ucuguuaacc uggcggcagc gcaaaag    107

<210> SEQ ID NO 686

<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 686
aucuuuagcc cggaacgaca guggggcau ugugcaguua aguuaugaa cagaggagac      60 auaacaugaa cugcacaaac gcaguuaacc uggcggcagc gcaaaag                 107

<210> SEQ ID NO 687
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 687
ugcuucuuug uuguccagu guggaguucc ggugucguua uaguuaugaa cagaggagac    60
auaacaugaa cgacaccaac gucguuaacc uggcggcagc gcaaaag                 107

<210> SEQ ID NO 688
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 688
acuccaaaag ccgcuccucu uucccagcg gcaaacguua uaguuaugaa cagaggagac    60
auaacaugaa cguuugcaac aacguuaacc uggcggcagc gcaaaag                 107

<210> SEQ ID NO 689
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 689
acucuuuucu cuccgugucu gguccacacu ucugccguua uaguuaugaa cagaggagac    60
auaacaugaa cggcagaaac gccguuaacc uggcggcagc gcaaaag                 107

<210> SEQ ID NO 690
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 690
ggacuuuggc cauucacaug uuuucaucuc gaucagguua uaguuaugaa cagaggagac    60
auaacaugaa ccugaucaac cagguuaacc uggcggcagc gcaaaag                 107

<210> SEQ ID NO 691
<211> LENGTH: 107
<212> TYPE: RNA
<213> ORGANISM: Artificial Sequence
<220> FEATURE:

<223> OTHER INFORMATION: Description of Artificial Sequence: Synthetic
polynucleotide

<400> SEQUENCE: 691
uugguugucc uggggagauc uuugcuuuuc uggcucguua uaguuaugaa cagaggagac    60
auaacaugaa cgagccaaac cucguuaacc uggcggcagc gcaaaag                 107

<210> SEQ ID NO 692
<211> LENGTH: 107
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 692
aaugaguugc accacuaggu ugguaaaugu guuaagguua uaguuaugaa cagaggagac    60
auaacaugaa ccuuaacaac aagguuaacc uggcggcagc gcaaaag                 107

<210> SEQ ID NO 693
<211> LENGTH: 107
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 693
cuucaacguc guuauagacg aacaccccug uaccgcguua uaguuaugaa cagaggagac    60
auaacaugaa cgcgguaaac cgcguuaacc uggcggcagc gcaaaag                 107

<210> SEQ ID NO 694
<211> LENGTH: 107
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 694
ccacaagucu ugcaucucua gaacuuccuc agccucguua uaguuaugaa cagaggagac    60
auaacaugaa cgaggcuaac cucguuaacc uggcggcagc gcaaaag                 107

<210> SEQ ID NO 695
<211> LENGTH: 107
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 695
auuccucaaa ccgaauuuca agcucuucac ugugccguua uaguuaugaa cagaggagac    60
auaacaugaa cggcacaaac gccguuaacc uggcggcagc gcaaaag                 107

<210> SEQ ID NO 696
<211> LENGTH: 107
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 696

```
uaugguugcc cccuccucuc uccuucccau uagaugguua uaguuaugaa cagaggagac    60
auaacaugaa ccaucuaaac augguuaacc uggcggcagc gcaaaag                 107

<210> SEQ ID NO 697
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 697
aucauucaag aaccugaggg caugugcaaa ccuaucguua uaguuaugaa cagaggagac    60
auaacaugaa cgauaggaac aucguuaacc uggcggcagc gcaaaag                 107

<210> SEQ ID NO 698
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
ucuucagccu ccaugugca uucuucucac ucucaaggac uuuagaacag aggagauaaa     60
gauguugaga gugaguaacc uggcggcagc gcaaaag                            97

<210> SEQ ID NO 699
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
aaauuccccu uguuucuuuu cucuuuuucc caucauggac uuuagaacag aggagauaaa    60
gaugaugaug ggaaaaaacc uggcggcagc gcaaaag                            97

<210> SEQ ID NO 700
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
uuucgcucua uucucaucag uuucaugucc ugucggac uuuagaacag aggagauaaa      60
gauggacaca ggacacaacc uggcggcagc gcaaaag                            97

<210> SEQ ID NO 701
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
gcuccccuuc uacugaucuc cacaugaugu uuuccaggac uuuagaacag aggagauaaa    60 gaugugggaaa acaucaaacc uggcggcagc gcaaaag                           97
```

<210> SEQ ID NO 702
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
aacuucuuua uuauuuccau agccucuuuu uucccggac uuuagaacag aggagauaaa      60
gaugggggaa aaagaaacc uggcggcagc gcaaaag                               97

<210> SEQ ID NO 703
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703 agggugggcuu cggcucuugg ugaauugggc guuaucggac uuuagaacag aggagauaaa    60
gauggauaac gcccauaacc uggcggcagc gcaaaag                              97

<210> SEQ ID NO 704
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
cuuccacugc agucuuccac ucuuuuuccu cuucaaggac uuuagaacag aggagauaaa     60
gauguugaag aggaaaaacc uggcggcagc gcaaaag                              97

<210> SEQ ID NO 705
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
cugggaucaa guacauguag ugcgccacga gcaaaggac uuuagaacag aggagauaaa      60
gauguuuugc ucguguaacc uggcggcagc gcaaaag                              97

<210> SEQ ID NO 706
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
acuauuaggg ucaggggugu uaauugugag uagcaaggac uuuagaacag aggagauaaa     60
gauguugcua cucacuaacc uggcggcagc gcaaaag                              97

<210> SEQ ID NO 707
<211> LENGTH: 97

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
caucgccauu aaggaguagu uguuguauga ggugguggac uuuagaacag aggagauaaa    60
gaugaccacc ucauauaacc uggcggcagc gcaaaag    97

<210> SEQ ID NO 708
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
cacugccauu gaugugcuua ugaugaucuu ugugguggac uuuagaacag aggagauaaa    60
gaugaccaca aagauaaacc uggcggcagc gcaaaag    97

<210> SEQ ID NO 709
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
cccacucuug auguuuuguu uucuggaacu cugucuggac uuuagaacag aggagauaaa    60
gaugagacag aguuccaacc uggcggcagc gcaaaag    97

<210> SEQ ID NO 710
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
aucuuuagcc cggaacgaca guggggggcau ugugcaggac uuuagaacag aggagauaaa    60
gaugugcaca augccgaacc uggcggcagc gcaaaag    97

<210> SEQ ID NO 711
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
ugcuucuuug uuguuccagu guggaguucc ggugucggac uuuagaacag aggagauaaa    60
gauggacacc ggaacaaacc uggcggcagc gcaaaag    97

<210> SEQ ID NO 712
<211> LENGTH: 97
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 712
acuccaaaag ccgcuccucu uucccagcg gcaaacggac uuuagaacag aggagauaaa    60
gaugguuugc cgcugcaacc uggcggcagc gcaaaag                            97

<210> SEQ ID NO 713
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
acucuuuucu cuccgugucu gguccacacu ucugccggac uuuagaacag aggagauaaa    60
gaugggcaga aguguaaacc uggcggcagc gcaaaag                            97

<210> SEQ ID NO 714
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
ggacuuuggc cauucacaug uuuucaucuc gaucagggac uuuagaacag aggagauaaa    60
gaugcugauc gagaugaacc uggcggcagc gcaaaag                            97

<210> SEQ ID NO 715
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
uugguugucc uggggagauc uuugcuuuuc uggcucggac uuuagaacag aggagauaaa    60
gauggagcca gaaaagaacc uggcggcagc gcaaaag                            97

<210> SEQ ID NO 716
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
aaugaguugc accacuaggu ugguaaaugu guuaagggac uuuagaacag aggagauaaa    60
gaugcuuaac acauugaacc uggcggcagc gcaaaag                            97

<210> SEQ ID NO 717
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
cuucaacguc guuauagacg aacaccccug uaccgcggac uuuagaacag aggagauaaa      60
gauggcggua cagggaaacc uggcggcagc gcaaaag                              97

<210> SEQ ID NO 718
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
ccacaagucu ugcaucucua gaacuuccuc agccucggac uuuagaacag aggagauaaa      60
gauggaggcu gaggacaacc uggcggcagc gcaaaag                              97

<210> SEQ ID NO 719
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
auuccucaaa ccgaauuuca agcucuucac ugugccggac uuuagaacag aggagauaaa      60
gaugggcaca gugaaaaacc uggcggcagc gcaaaag                              97

<210> SEQ ID NO 720
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
uaugguugcc cccuccucuc uccuucccau uagaugggac uuuagaacag aggagauaaa      60
gaugcaucua augggaaacc uggcggcagc gcaaaag                              97

<210> SEQ ID NO 721
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
aucauucaag aaccugaggg caugugcaaa ccuaucggac uuuagaacag aggagauaaa      60
gauggauagg uuugcuaacc uggcggcagc gcaaaag                              97

<210> SEQ ID NO 722
<211> LENGTH: 167
<212> TYPE: RNA
<213> ORGANISM: Zika virus

<400> SEQUENCE: 722
gggcagugau cuaggcuacu ggauugagag ugagaagaau gacacaugga ggcugaagag      60
ggcccaucug aucgagauga aaacauguga auggccaaag ucccacacau uguggacaga     120
uggaauagaa gagagugauc ugaucauacc caagucuuua gcugggc                   167

```
<210> SEQ ID NO 723
<211> LENGTH: 160
<212> TYPE: RNA
<213> ORGANISM: Zika virus

<400> SEQUENCE: 723
gggugccaga guugugugua caacaugaug ggaaaaagag aaaagaaaca aggggaauuu    60
ggaaaggcca agggcagccg cgccaucugg uauauguggc uaggggcuag auuucuagag   120
uucgaagccc uuggauucuu gaacgaggau cacuggaugg                         160

<210> SEQ ID NO 724
<211> LENGTH: 150
<212> TYPE: RNA
<213> ORGANISM: Zika virus

<400> SEQUENCE: 724
gggccagcac agugggauga ucguuaauga cacaggacau gaaacugaug agaauagagc    60
gaaaguugag auaacgccca auucaccaag agccgaagcc acccuggggg gguuuggaag   120
ccuaggacuu gauugugaac cgaggacagg                                    150

<210> SEQ ID NO 725
<211> LENGTH: 150
<212> TYPE: RNA
<213> ORGANISM: Zika virus

<400> SEQUENCE: 725
gggcgggauc uccucuguuu caagaaugga aaacaucaug uggagaucag uagaagggga    60
gcucaacgca auccuggaag agaauggagu ucaacugacg gucguugugg gaucuguaaa   120
aaaccccaug uggagagguc cacagagauu                                    150

<210> SEQ ID NO 726
<211> LENGTH: 168
<212> TYPE: RNA
<213> ORGANISM: Zika virus

<400> SEQUENCE: 726
gggccaucac uggucucau caauagaugg gguucagugg ggaaaaaaga ggcuauggaa     60
auaauaaaga aguucaagaa agaucuggcu gccaugcuga gaauaaucaa ugcuaggaag   120
gagaagaaga gacgaggcgc agauacuagu gucggaauug uuggccuc                168

<210> SEQ ID NO 727
<211> LENGTH: 171
<212> TYPE: RNA
<213> ORGANISM: Zika virus

<400> SEQUENCE: 727
gggaaugcug ucaguucaug gcucccagca cagugggaug aucguuaaug acacaggaca    60
ugaaacugau gagaauagag cgaaaguuga gauaacgccc aauucaccaa gagccgaagc   120
cacccugggg ggguuuggaa gccuaggacu ugauugugaa ccgaggacag g            171

<210> SEQ ID NO 728
<211> LENGTH: 201
<212> TYPE: RNA
<213> ORGANISM: Zika virus

<400> SEQUENCE: 728
gggagaagga uggucucuuc cugguugugg aaagagcuag gcaaacacaa acggccacga    60
```

```
gucuguacca aagaagaguu caucaacaag guucguagca augcagcauu aggggcaaua      120
uuugaagagg aaaaagagug gaagacugca guggaagcug ugaacgaucc aagguucugg      180
gcucuagugg acaaggaaag a                                                201

<210> SEQ ID NO 729
<211> LENGTH: 137
<212> TYPE: RNA
<213> ORGANISM: Zika virus

<400> SEQUENCE: 729
gggcugaccc uaauaguggc caucauuuug cucguggcgc acuacaugua cuugauccca      60
gggcugcagg cagcagcugc gcgugcugcc cagaagagaa cggcagcugg caucaugaag      120
aacccuguug uggaugg                                                    137

<210> SEQ ID NO 730
<211> LENGTH: 153
<212> TYPE: RNA
<213> ORGANISM: Zika virus

<400> SEQUENCE: 730
ggguuuggua ugggcaaagg gaugccauuc uacgcauggg acuuuggagu cccgcugcua      60
augauagguu gcuacucaca auuaacaccc cugacccuaa uaguggccau cauuuugcuc      120
guggcgcacu acauguacuu gaucccaggg cug                                  153

<210> SEQ ID NO 731
<211> LENGTH: 176
<212> TYPE: RNA
<213> ORGANISM: Zika virus

<400> SEQUENCE: 731
gggccaucua ugcugccuug acaacuuuca uuaccccagc cguccaacau gcagugacca      60
ccucauacaa caacuacucc uuaauggcga uggccacgca agcuggagug uuguuuggua      120
ugggcaaagg gaugccauuc uacgcauggg acuuuggagu cccgcugcua augaua          176

<210> SEQ ID NO 732
<211> LENGTH: 191
<212> TYPE: RNA
<213> ORGANISM: Zika virus

<400> SEQUENCE: 732
gggagaaggg ugauucugcu cauggugcag gaagggguuga agaagagaau gaccacaaag     60
aucaucauaa gcacaucaau ggcagugcug guagcuauga uccugggagg auuuucaaug     120
agugaccugg cuaagcuugc aauuuugaug ggugccaccu ucgcggaaau gaacacugga     180
ggagauguag c                                                          191

<210> SEQ ID NO 733
<211> LENGTH: 231
<212> TYPE: RNA
<213> ORGANISM: Zika virus

<400> SEQUENCE: 733
gggagaaggg uuuguuccaa gcugaggaa cggcaaugag aucgcagcuu gucugacaaa      60
ggcuggaaaa cgggucauac agccucagcag aaagacuuuu gagacagagu uccagaaaac    120
aaaacaucaa gaguggggacu uugucgugac aacugacauu ucagagaugg cgccaacuu     180 uaaagcugac cgugucauag auuccaggag augccuaaag ccggucauac u              231
```

<210> SEQ ID NO 734
<211> LENGTH: 132
<212> TYPE: RNA
<213> ORGANISM: Zika virus

<400> SEQUENCE: 734
gggagaucaa ccacugcaag cggaagggug aucgaggaau ggugcugcag ggagugcaca 60
augcccccac ugucguuccg ggcuaaagau ggcuguuggu auggaaugga gauaaggccc 120
aggaaagaac ca 132

<210> SEQ ID NO 735
<211> LENGTH: 158
<212> TYPE: RNA
<213> ORGANISM: Zika virus

<400> SEQUENCE: 735
gggagugguu ccacgacauu ccauuaccuu ggcacgcugg ggcagacacc ggaacuccac 60
acuggaacaa caaagaagca cugguagagu ucaaggacgc acaugccaaa aggcaaacug 120
ucgugguucu agggagucaa gaaggagcag uucacacg 158

<210> SEQ ID NO 736
<211> LENGTH: 132
<212> TYPE: RNA
<213> ORGANISM: Zika virus

<400> SEQUENCE: 736
ggguggacgc cagaguuugu ucagaucaug cggcccugaa gucauucaag gaguuugccg 60
cugggaaaag aggagcggcu uuuggaguga uggaagcccu gggaacacug ccaggacaca 120
ugacagagag au 132

<210> SEQ ID NO 737
<211> LENGTH: 157
<212> TYPE: RNA
<213> ORGANISM: Zika virus

<400> SEQUENCE: 737
gggcugccgg aauaaccuac acagauagaa gauggugcuu ugauggcacg accaacaaca 60
ccauaaugga agacagugug ccggcagaag uguggaccag acacggagag aaaagagugc 120
ucaaaccgag guggauggac gccagaguuu guucaga 157

<210> SEQ ID NO 738
<211> LENGTH: 155
<212> TYPE: RNA
<213> ORGANISM: Zika virus

<400> SEQUENCE: 738
gggcuacugg auugagagug agaagaauga cacauggagg cugaagaggg cccaucugau 60
cgagaugaaa acaugugaau ggccaaaguc ccacacauug uggacagaug gaauagaaga 120
gagugaucug aucauaccca agucuuuagc ugggc 155

<210> SEQ ID NO 739
<211> LENGTH: 176
<212> TYPE: RNA
<213> ORGANISM: Zika virus

<400> SEQUENCE: 739

```
gggcagccag aauugcaugu guccucauug uuguguuccu auugcuggug gugcucauac    60
cugagccaga aaagcaaaga ucuccccagg acaaccaaau ggcaaucauc aucaugguag   120
caguaggucu ucugggcuug auuaccgcca augaacucgg augguuggag agaaca       176

<210> SEQ ID NO 740
<211> LENGTH: 178
<212> TYPE: RNA
<213> ORGANISM: Zika virus

<400> SEQUENCE: 740
gggagcggac aaguugucac uuacgcucuu aacacauuua ccaaccuagu ggugcaacuc    60
auucggaaua uggaggcuga ggaaguucua gagaugcaag acuuggggcu gcugcggagg   120
ucagagaaag ugacuaacug guugcagagc aacggauggg auaggcucaa acgaaugg    178

<210> SEQ ID NO 741
<211> LENGTH: 150
<212> TYPE: RNA
<213> ORGANISM: Zika virus

<400> SEQUENCE: 741
gggugcucgg uggacuucuc aaagaaggag acgagaugcg guacaggggu guucgucuau    60
aacgacguug aagccuggag ggacagguac aaguaccauc cugacucccc ccguagauug   120
gcagcagcag ucaagcaagc cugggaagau                                     150

<210> SEQ ID NO 742
<211> LENGTH: 137
<212> TYPE: RNA
<213> ORGANISM: Zika virus

<400> SEQUENCE: 742
gggaguggug caacucauuc ggaauaugga ggcugaggaa guucuagaga ugcaagacuu    60
guggcugcug cggaggucag agaaagugac uaacgguug cagagcaacg gauggauag   120 gcucaaacga auggcag                                                   137

<210> SEQ ID NO 743
<211> LENGTH: 154
<212> TYPE: RNA
<213> ORGANISM: Zika virus

<400> SEQUENCE: 743
gggcaauacc agagagggcu acaggaccca aaugaaaggg ccauggcaca gugaagagcu    60
ugaaauucgg uuugaggaau gcccaggcac uaagguccac guggaggaaa caugggaac   120 gagaggacca ucucugagau caaccacugc aagc                                154

<210> SEQ ID NO 744
<211> LENGTH: 136
<212> TYPE: RNA
<213> ORGANISM: Zika virus

<400> SEQUENCE: 744
gggaguaggu cuucgggcu ugauuaccgc caaugaacuc ggaugguugg agagaacaaa    60
gagugaccua agccaucuaa ugggaaggag agaggagggg gcaaccauag gauucucaau   120
ggacauugac cugcgg                                                    136

<210> SEQ ID NO 745
<211> LENGTH: 128
```

```
<212> TYPE: RNA
<213> ORGANISM: Zika virus

<400> SEQUENCE: 745
gggauaggcu caaacgaaug gcagucagug gagaugauug cguugugaag ccaauugaug    60
auagguuugc acaugcccuc agguucuuga augauauggg aaaaguuagg aaggacacac   120
aagagugg                                                            128

<210> SEQ ID NO 746
<211> LENGTH: 10374
<212> TYPE: RNA
<213> ORGANISM: Zika virus

<400> SEQUENCE: 746
acagguuuua uuuuggauuu ggaaacgaga guuucgguc augaaaaacc caaaaaagaa    60
auccggagga uuccggauug ucaauaugcu aaaacgcgga guagcccgug ugagcccuu   120
uggggggcuug aagaggcugc cagccggacu ucugcugggu caugggccca ucaggaugggu  180
cuuggcgauu cuagccuuuu ugagauucac ggcaaucaag ccaucacugg gucucaucaa   240
uagauggggu ucagggggga aaaagaggc uauggaaaua auaaagaagu caagaaaga    300
ucuggcugcc augcugagaa uaaucaaugc uaggaaggag aagaagagac gaggcgcaga   360
uacuagguc ggaauuguug gccuccugcu gaccacagcu auggcagcgg aggucacuag   420
acgugggagu gcauacuaua uguacuugga cagaaacgau gcuggggagg ccauaucuuu   480
uccaaccaca uugggauga auaaguguua uauacagauc auggaucuug acacacgug    540
ugaugccacc augagcuaug aaugcccuau gcuggaugag ggguggaac cagaugacgu   600
cgauuguug gcgaacacga cgucaaccuug gguuguguac ggaaccugcc aucacaaaaa   660
aggugaagca cggagaucua aagagcugu gacgcucccc ucccauucca cuaggaagcu   720
gcaaacgcgg ucgcaaaccu gguugaauc aagagaauac acaaagcacu ugauuagaagu  780
cgaaaauugg auauucagga acccuggcuu cgcguuagca gcagcugcca ucgcuuggcu   840
uuugggaagc ucaacgagcc aaaaagucau uacuuggguc augauacugc ugauugcccc   900
ggcauacagc aucaggugca uaggagucag caauagggac uuuguggaag uaugucagg   960
ugggacuugg guugauguug ucuuggaaca uggagguugu gucacuguaa uggcacagga  1020
caaaccgacu gucgacauag agcugguuac aacaacaguc agcaacaugg cggaggaag  1080
auccuacugc uaugaggcau caauaucaga cauggcuucg gacagccgcu gcccaacaca  1140
agugaagcc uaccuugaca agcaaucaga cacucaauau gucugcaaaa gaacguuagu  1200
ggacagaggc uggggaaaug gaugguggac uuuuggcaaa gggagccugg ugacaugcgc  1260
uaaguuugca ugcucaagg aaaugaccgg gaagagcauc cagccagaga ucuggagua  1320
ccggauaaug cugucaguuc augcuccca gcacagggg augaucguua augacacagg  1380
acaugaaacu gaugaaaua gagcgaaagu ugagauaacg cccaauucac caagagccga  1440
agccaccucug gggggguuug aagccuagg acuugauugu gaaccgagga caggccuuga  1500
cuuuucagau uuguauuacu ugacuauaa uaacaagcac uggcugguuc acaaggagug  1560
guuccacgac auuccauuac cuggcacgc uggggcagac accggaacuc cacacuggaa  1620
caacaaagaa gcacugguag aguucaagga cgcacaugcc aaaggcaaaa cugucguggu  1680
ucuagggagu caagaaggag caguucacac ggcccuugcu ggagcucugg aggcugauau  1740
ggauggugca aagggaaggc ugccucucgg ccacuugaaa ugucgccuga aaauggauaa  1800
```

-continued

| | |
|---|---|
| acuuagauug aagggcgugu cauacuccuu guguacugca gcguucacau ucaccaagau | 1860 |
| cccggcugaa acacugcacg ggacagucac aguggaggua caguacgcag ggacagaugg | 1920 |
| accuugcaag guuccagcuc agauggcggu ggacaugcaa acucugaccc caguugggag | 1980 |
| guugauaacc gcuaaccccg uaaucacuga aagcacugag aacucuaaga ugaugcugga | 2040 |
| acuugaucca ccauuugggg acucuuacau ugucauagga gucggggaga agaagaucac | 2100 |
| ccaccacugg cacaggagug gcagcaccau uggaaaagca uuugaagcca cugugagagg | 2160 |
| ugccaagaga auggcagucu ugggagacac agccugggac uuuggaucag uuggaggcgc | 2220 |
| ucucaacuca uugggcaagg gcauccauca aaucuuugga gcagcuuuca aaucauuguu | 2280 |
| uggaggaaug uccugguucu cacaaauucu cauuggaacg uugcugaugu gguugggucu | 2340 |
| gaacgcaaag aauggaucua uuucccuuau gugcuuggcc uuaggggag uuugaucuu | 2400 |
| cuuauccaca gccgucucug cugauguggg gugcucggug gacuucucaa agaaggagac | 2460 |
| gagaugcggu acaggggugu ucgucuauaa cgacguugaa gccugg aggg acagguacaa | 2520 |
| guaccauccu gacucccccc guagauuggc agcagcaguc aagcaagccu ggaagaugg | 2580 |
| uaucugcggg aucuccucug uuucaagaau ggaaaacauc augugga gau caguagaagg | 2640 |
| ggagcucaac gcaauccugg aagagaaugg aguucaacug acggucguug ugggaucugu | 2700 |
| aaaaaacccc augugga gag guccacagag auugcccgug ccugugaacg agcugcccca | 2760 |
| cggcuggaag gcuggggga aaucguacuu cgucagagca gcaaagacaa auaacagcuu | 2820 |
| ugucguggau ggugacacac ugaaggaaug cccacucaaa cauagagcau ggaacagcuu | 2880 |
| ucuuguggag gaucauggu ucggggaauu ucacacuagu gucuggcuca agguuagaga | 2940 |
| agauuauuca uuagagugug auccagccgu uauuggaaca gcuguuaagg gaaaggaggc | 3000 |
| uguacacagu gaucuaggcu acuggauuga gagugagaag aaugacacau ggaggcugaa | 3060 |
| gagggcccau cugaucgaga ugaaaacaug ugaauggcca aagucccaca cauguggac | 3120 |
| agauggaaua gaagagagug aucgaucau acccaagucu uuagcuggc cacucagcca | 3180 |
| ucacaauacc agagagggcu acaggaccca aaugaaaggg ccauggcaca gugaagagcu | 3240 |
| ugaaauucgg uuugaggaau gcccaggcac uaagguccac guggaggaaa caugggaac | 3300 |
| gagaggacca ucucugagau caaccacugc aagcggaagg gugaucgagg aauggugcug | 3360 |
| cagggagugc acaaugcccc cacugucguu ccgggcuaaa gauggcuguu gguauggaau | 3420 |
| ggagauaagg cccaggaaag aaccagaaag caacuuagua aggucaaugg ugacugcagg | 3480 |
| aucaacugau cacauggacc acuucccccu uggagcuu ugauucgc ucauggugca | 3540 |
| ggaagggu ug aagaagagaa ugaccacaaa gaucaucaua agcacaucaa uggcagugcu | 3600 |
| gguagcuaug auccgggag gauuuucaau gaguga cug gcuaagcuug caauuuugau | 3660 |
| gggugccacc uucgcggaaa ugaacacugg aggagaugua gcucaucugg cgcugauagc | 3720 |
| ggcauucaaa gucagaccag cguugcuggu aucuuucauc uucagagcua auuggacacc | 3780 |
| ccgugaaagc augcugcugg ccuuggccuc ugucuuuug caaacugcga ucuccgccuu | 3840 |
| ggaaggcgac cugauggu uc ucaucaaugg uuuugcuuug gccugguugg caauacgagc | 3900 |
| gaugguuguu ccacgcacug auaacaucac cuuugcaauc cuggcugcuc ugacaccacu | 3960 |
| ggccccgggc acacugcuug uggcguggag agcaggccuu gcuacuugcg ggggguuuau | 4020 |
| gcuccucucu cugaagggaa aaggcagugu gaagaagaac uuaccauug ucauggcccu | 4080 |
| gggacuaacc gcugugaggc uggucgaccc caucaacgug guggacgc uguugcucac | 4140 |
| aaggagugg g aagcggagcu ggccccuag cgaaguacuc acagcuguug gccugauaug | 4200 |

```
cgcauuggcu ggagggyuucg ccaaggcaga uauagagaug gcugggccca uggccgcggu    4260
cggucugcua auugucaguu acguggucuc aggaaagagu guggacaugu acauugaaag    4320
agcaggugac aucacauggg aaaaagaugc ggaagucacu ggaaacaguc cccggcucga    4380
uguggcgcua gaugagagug gugauuucuc ccugguggag gaugacgguc ccccaugag     4440 agagaucaua cucaaggugg uccugaugac caucuguggc augaacccaa uagccauacc    4500
cuuugcagcu ggagcgguggu acguauacgu gaagacugga aaaaggagug gugcucuaug   4560
ggaugugccu gcucccaagg aaguaaaaaa gggggagacc acagauggag guacagagu    4620 aaugacucgu agacugcuag guucaacaca aguuggagug ggaguuaugc aagagggggu    4680
cuuucacacu augugggcacg ucacaaaagg auccgcgcug agaagcggug aagggagacu   4740
ugauccauac uggggagaug ucaagcagga ucugguguca acuggguguc caugcaagcu    4800
agaugccgcc ugggacgggc acagcgaggu gcagcucuug gccgugcccc cggagagag    4860 agcgaggaac auccagacuc ugcccggaau auuuaagaca aaggauggg acauuggagc    4920 gguugcgcug gauuacccag caggaacuuc aggaucuccu auccuagaca agugugggag   4980
aguagaugga cuuuauggca auggggucgu gaucaaaaau gggaguuaug uuagugccau    5040
cacccaaggg aggagggagg aagagacucc uguugagugc uucgagccuu cgaugcugaa    5100
gaagaagcag cuaacugucu uagacuugca uccuggagcu gggaaaaacca ggagaguucu   5160 uccugaaaua guccgugaag ccauaaaaac aagacccgu acugaucu uagcuccaac      5220 cagguugucuc gcugcugaaa uggaggaggc ccuuagaggg cuuccagugc guuauaugac    5280
aacagcaguc aaugucaccc acucggaaca gaaaacucuc gacuuaaugu gccaugccac    5340
cuucacuucg cgucuacuac agccaaucag aguccccaac uauaaucugu auauuuugga    5400
ugaggcccac uucacagauc ccucaaguau agcagcaaga ggauucauuu caacaagggu    5460 ugagauggc gaggcggccg ccaucuucau gaccgccacg ccaccaggaa cccgugacgc     5520
auuuccggac uccaacucac caauuaugga caccgaagug gaaguccag agagagccug    5580 gagcucaggc uuugauuggg ugacggauca uucugaaaaa acaguuuggu uuguccaag    5640 cguagaggaac ggcaaugaga ucgcagcuug ucugacaaag gcuggaaaac ggggucauaca   5700 gcucagcaga aagacuuuug agacagaguu ccagaaaaca aaacaucaag aguggacuu     5760 ugucgugaca acugacauuu cagaugauggg cgccaacuu aaagcugacc cgucauaga    5820 uuccaggaga ugccuaaagc cggcauacu ugaugggcgag agagucauuc uggcuggacc    5880
caugccuguc acacaugcca gcgcugccca gaggaggggg cgcauaggca ggaaucccaa    5940
caaaccugga gaugaguauc uguauggagg ugggguggca gagacugacg aagaccaugc    6000
acacuggcuu gaagcaagaa ugcuccuuga caauauuuac cuccaagaug gccucauagc    6060
cucgcucuau cgaccugagg ccgacaaagu agcagccauu gagggagagu ucaagcuuag    6120
gacggagcaa aggaagaccu uuguggaacu caugaaaaga ggagaucuuc cugauuggcu   6180
ggccuaucag guugcaucug ccggaauaac cuacacagau agaagauggu gcuuugaugg    6240
cacgaccaac aacaccauaa uggaagacag ugugccggca gaaguggga ccagacacgg    6300 agagaaaaga gugcucaaac cgagguggau ggacgccaga guuugucag aucaugcggc     6360 ccugaaguca uucaaggagu uugccgcugg gaaaagagga gcggcuuuug gagugaugga    6420
agcccuggga acacugccag acacaugac agagagauuc caggaagcca uugacaaccu    6480
cgcugugcuc augcgggcag agacuggaag caggccuuac aaagccgcgg cggcccaauu   6540
```

```
gccggagacc cuagagacca uuaugcuuuu ggguugcug ggaacagucu cgcugggaau    6600
cuucuucguc uugaugagga acaagggcau agggaagaug ggcuuuggaa uggugacucu    6660
uggggccagc gcauggcuca uguggcucuc ggaaauugag ccagccagaa uugcaugugu    6720
ccucauuguu uguuccuau ugcugguggu gcucauaccu gagccagaaa agcaaagauc    6780
uccccaggac aaccaaaugg caaucaucau cauggu agca guaggucuuc ugggcuugau    6840
uaccgccaau gaacucggau gguuggagag aacaaagagu gaccuaagcc aucuaauggg    6900
aaggagagag gagggggcaa ccauaggauu ucaauggac auugaccugc ggccagccuc    6960
agcuugggcc aucuaugcug ccugacaac uuucauuacc ccagccguc aacaugcagu    7020 gaccaccuca uacaacaacu acuccuuaau ggcgauggcc acgcaagcug gaguguuguu    7080
ugguaugggc aagggaugc cauucuacgc augggacuuu ggaguccgc ugcuaaugau    7140 agguugcuac ucacaauuaa cacccccgac ccuaauagug gccaucauuu ugcucgugc    7200 gcacuacaug uacuugaucc cagggcugca ggcagcagcu gcgcgugcug cccagaagag    7260
aacggcagcu ggcaucauga agaacccugu gugggaugga auagggguga cugacauuga    7320
cacaaugaca auugaccccc aaguggagaa aaagauggga caggugcuac ucauagcagu    7380
agccgucucc agcgccauac gucgcggac cgccuggggg ugggggagg cuggggcccu    7440 gaucacagcc gcaacuucca cuuugug gga aggcucuccg aacaaguacu ggaacuccuc    7500
uacagccacu ucacgugua acauuuuag gggaaguuac uugcuggag cuucucuaau    7560 cuacacagua acaagaaacg cuggcuuggu caagagacgu gggggugaa caggagagac    7620 ccugggagag aaauggaagg cccgcuugaa ccagaugucg gcccuggagu cuacuccua    7680 caaaaaguca ggcaucaccg aggugugcag agaagaggcc cgccgcgccc ucaaggacgg    7740
uguggcaacg ggaggccaug cugugucccg aggaagugca aagcugagau gguuggugga    7800
gcggggauac cugcagcccu auggaaaggu cauugaucuu ggauguggca gggggcug    7860 gaguuacuac gccgccacca uccgcaaagu ucaagaagug aaaggauaca caaaaggagg    7920
cccuggucau gaagaacccg uguggugca agcuauggg uggaacauag uccgucuuaa    7980 gagugggug gacgucuuuc auauggcggc ugagccgugu gacacguugc ugugugacau    8040
aggugaguca ucaucuaguc cugaagugga agaagcacgg acgcucagag uccucuccau    8100 gguggggau uggcuugaaa aaagaccagg agccuuuugu auaaaagugu gugcccaua    8160 caccagcacu augauggaaa cccuggagcg acugcagcgu agguauggg gaggacuggu    8220 cagagugcca cucucccgca acucuacaca ugagauguac ugggucucug agcgaaaag    8280 caacaccaua aaaagugugu ccaccacgag ccagcccuc uuggggcgca uggacgggcc    8340
uaggaggcca gugaaauaug aggaggaugu gaaucucggc ucuggcacgc gggcuguggu    8400
aagcugcgcu gaagcuccca caugaagau cauugguaac cgcauugaaa ggaucccgcag    8460 ugagcacgcg gaaacguggu ucuuugacga gaaccaccca uauaggacau gggcuuacca    8520
uggaagcuau gaggccccca cacaagggue agcguccucu cuaauaaacg ggguugcag    8580 gcuccuguca aaacccuggg auguggugac uggagucaca ggaauagcca ugaccgacac    8640
cacaccguau ggucagcaaa gaguuucuaa ggaaaaagug gacacuaggg uccagaccc    8700 ccaagaaggc acucgucagg uuaugagcau ggucucuucc ugguugugga agagcuagg    8760 caaacacaaa cggccacgag ucuguaccaa agaagaguuc aucaacaagg uucuagcaa    8820 ugcagcauua ggggcaauau uugaaggga aaaagaguu aagacugcag ggaagcugu    8880 gaacgaucca agguucuggg cucuagugga caaggaaaga gagcaccacc ugagaggaga    8940
```

```
gugccagagu ugugaguaca acaugauggg aaaaagagaa aagaaacaag gggaauuugg    9000
aaaggccaag ggcagccgcg ccaucuggua uauguggcua ggggcuagau uucuagaguu    9060
cgaagcccuu ggauucuuga acgaggauca cuggaugggg agagagaacu caggaggugg    9120
uguugaaggg cugggauuac aaagacucgg auaugcccua agagagauga gucguauacc    9180
aggaggaagg auguaugcag augacacugc uggcugggac acccgcauua gcagguuuga    9240
ucuggagaau gaagcucuaa ucaccaacca aauggagaaa gggcacaggg ccuuggcauu    9300
ggccauaauc aaguacacau accaaaacaa aguggaaaag guccuuagac cagcugaaaa    9360
agggaaaaca guuauggaca uuauuucgag acaagaccaa aggggggagcg acaaguugu    9420 cacuuacgcu cuuaacacau uuaccaaccu aguggugcaa cucauucgga auauggaggc    9480
ugaggaaguu cuagagaugc aagacuugug gcugcugcgg aggucagaga agugacuaa     9540 cugguugcag agcaacggau gggauaggcu caaacgaaug gcagucagug agaugauug     9600 cguugugaag ccaauugaug auagguuugc acaugcccuc agguucuuga augauauggg    9660
aaaaguuagg aaggacacac aagagugaa acccucaacu ggaugggaca acugggaaga    9720
aguuccguuu ugcuccccacc acuucaacaa gccucaucuc aaggacggga gguccauugu    9780
gguucccugc cgccaccaag augaacugau uggccgggcc cgcgucucuc caggggcggg    9840
auggagcauc cgggagacug cuugccuagc aaaaucauau gcgcaaaugu ggcagcuccu    9900
uuauuuccac agaagggacc uccgacugau ggccaaugcc auuuguucau cugugccagu    9960
ugacuggguu ccaacuggga aacuaccug gucaauccau ggaaagggag aauggaugac    10020
cacugaagac augcuugugg uguggaacag agugggauu gaggagaacg accacaugga    10080
agacaagacc ccaguuacga aauggacaga cauucccuau uugggaaaaa gggaagacuu    10140 gugugugga ucucucauag ggcacagacc gcgcaccacc uggcugaga acauuaaaaa    10200 cacagucaac augugcgca ggaucauagg ugaugaagaa aaguacaugg acuaccauc    10260 cacccaaguu cgcuacuugg gugaagaagg gucuacaccu ggagugcugu aagcaccaau    10320
cuuaauguug ucaggccugc uagucagcca cagcuugggg aaagcugugc agcc         10374
```

<210> SEQ ID NO 747
<211> LENGTH: 10794
<212> TYPE: RNA
<213> ORGANISM: Zika virus

<400> SEQUENCE: 747

```
aguuguugau cugugugagu cagacugcga caguucgagu cugaagcgag agcuaacaac      60
aguaucaaca gguuuaauuu ggauuuggaa acgagaguuu cuggucauga aaaccccaa     120 agaagaaauc cggaggaucc ggauugcaa uaugcuaaaa cgcggaguag cccguguaaa    180
ccccuuggga gguuugaaga ggugccagc cggacuucug cugggucaug acccaucag     240 aauguuuug cgauacuag ccuuuuugag auuuacagca aucaagccau cacugggccu     300
uaucaacaga uggggguuccg uggggaaaaa agaggcuaug gaaauaauaa agaaguucaa    360
gaaagaucuu gcugccaugu ugagaauaau caaugcuagg aaagagagga agagacgugg    420
cgcagacacc agcaucggaa ucauuggccu ccugcugacu acagccaugg cagcagagau    480
cacuagacgc gggagugcau acuacaugua cuuggauagg agcgaugccg ggaaggccau    540
uucguuugcu accacauugg gagugaacaa gugccacgua cagaucaugg accucgggca    600
caugugugac gccaccauga guuaugagug cccuaugcug gaugagggag uggaaccaga    660
```

-continued

```
ugaugucgau ugcuggugca acacgacauc aacuuggguu guguacggaa ccugucauca      720
caaaaaaggu gaggcacggc gaucuagaag agccgugacg cucccuucuc acucuacaag      780
gaaguugcaa acgcggucgc agaccugguu agaaucaaga gaauacacga agcacuugau      840
caagguugaa aacuggauau ucaggaaccc cggguuugcg cuaguggccg uugccauugc      900
cuggcuuuug ggaagcucga cgagccaaaa agucauauac uuggucauga uacugcugau      960
ugccccggca uacaguauca ggugcauugg agucagcaau agagacuucg uggagggcau     1020 gucaggugggg accugguug auguugucuu ggaacaugga ggcugcguua ccgugauggc     1080
```

```
cagugaucug ggcuauugga uugaaaguga aaagaaugac acauggaggc ugaagagggc    3120
ccaccugauu gagaugaaaa caugugaaug gccaaagucu cacacauugu ggacagaugg    3180
aguagaagaa agugaucuua ucauacccaa gucuuuagcu gguccacuca gccaccacaa    3240
caccagagag gguuacagaa cccaagugaa agggccaugg cacagugaag agcuugaaau    3300
ccgguuugag gaauguccag gcaccaaggu uuacguggag gagacaugcg gaacuagagg    3360
accaucucug agaucaacua cugcaagugg aagggucauu gaggaauggu gcuuaggga    3420 augcacaaug cccccacuau cguuucgagc aaaagacggc ugcugguaug gaauggagau    3480
aaggcccagg aaagaaccag agagcaacuu agugaggucu auggugacag cgggucaac    3540 cgaucauaug gaccacuucu cucuuggagu gcuugugauu cuacucaugg ugcaggaggg    3600
guugaagaag agaaugacca caaagaucau caugagcaca ucaauggcag cgcugguagu    3660
caugaucuug ggaggauuuu caaugaguga ccuggccaag cuugugaucc ugaugggugc    3720
uacuuucgca gaaaugaaca cuggaggaga guagcucac uuggcauugg uagcggcauu    3780
uaaagucaga ccagccuugc uggucuccuu cauuuucaga gccaauugga caccccguga    3840
gagcaugcug cuagcccugg cuucgugucu ucugcaaaacu gcgaucucug cucuugaagg    3900
ugacuugaug guccucauua auggauuugc uuuggccugg uuggcaauuc gagcaauggc    3960
cgugccacgc acugacacaa ucgcucuacc aaucuuggcu gcucuaacac cacuagcucg    4020
aggcacacug cucguggcau ggagcgggg ccuggcuacu uguggaggga ucaugcuccu    4080
cucccugaaa ggaaaggua gugugaagaa gaaccugcca uuugucaugg cccugggauu    4140
gacagcugug agggguaguag acccuauuaa uguggaaga cuacuguuac ucacaaggag    4200
ugggaagcgg agcuggcccc cuagugaagu ucucacagcc guuggccuga uaugugcacu    4260
ggccggaggg uuugccaagg cagacauuga gauggcugga cccauggcug caguaggcuu    4320
gcuaauugug agcuaugugg ucucgggaaa gagugggac auguacauug aaagagcagg    4380
ugacaucaca ugggaaaagg acgcggaagu cacuggaaac aguccucggc uugacguggc    4440
acuggaugag aguggugacu ucuccuuggu agaggaagau ggccacccca ugagagagau    4500
cauacucaag guggucccuga uggccaucug uggcaugaac ccaauagcua uaccuuuugc    4560
ugcaggagcg ugguauguguu augugaagac ugggaaaagg aguggcgccc ucgggacgu    4620 gccugcuccc aaagaaguga gaaaggaga gaccacagau ggagugaca gagugaugac    4680 ucgcagacug cuagguucaa cacagguugg aguggaguc augcaagagg gagucuucca    4740 caccauguagg cacguuacaa aaggagccgc acugaggagc ggugagggaa gacuugaucc    4800 auacugggg gaugucaagc aggacuuggu gucauacugu gggccuugga aguuggaugc    4860
agcuugggau ggacucagcg agguacagcu uuuggccgua ccuccggag agagggccag    4920 aaacauucag acccugccug gaauauucaa gacaaaggac ggggacaucg gagcaguugc    4980
ucuggacuac ccugcaggga ccucaggauc uccgauccua gacaaaugug aagagugau    5040 aggacucuau ggcaauggg uugugaucaa gaauggaagc uauguuagug cuauaaccca    5100
gggaaagagg aggaggaga cuccgguuga auguuucgaa cccucgaugc ugaagaagaa    5160
gcagcuaacu gucuuggauc ugcauccagg agccggaaaa accaggagag uucuuccuga    5220 aauagccgu gaagccauaa aaaagagacu ccggacagug aucuuggcac caacuagggu    5280
ugucgcugcu gagauggagg aggccuugag aggacuccgg gugcguuaca ugacaacagc    5340
agucaacguc acccauucug gacagaaauu cguugauuug augugccaug ccacuuucac    5400
```

-continued

```
uucacgcuua cuacaacccca ucagaguccc uaauuacaau cucaacauca uggaugaagc    5460
ccacuucaca gaccccucaa guauagcugc aagaggauac auaucaacaa ggguugaaau    5520
gggcgaggcg gcugccauuu uuaugacugc cacaccacca ggaacccgug augcguuucc    5580
ugacucuaac ucaccaauca uggacacaga aguggaaguc ccagagagag ccuggagcuc    5640
aggcuuugau ugggugacag accauucugg gaaaacaguu gguucguuc caagcgugag     5700
aaacggaaau gaaaucgcag ccugucugac aaaggcugga aagcgagguca uacagcucag    5760
caggaagacu uuugagacag aauuucagaa aacaaaaaau caagaguggg acuuugucau    5820
aacaacugac aucucagaga ugggcgccaa cuucaaggcu gaccgggucu uagacucuag    5880
gagaugccua aaaccaguca uacuugaugg ugagagaguc aucuuggcug ggcccaugcc    5940
ugucacgcau gcuagugcug cucagaggag aggacguaua ggcaggaacc cuaacaaacc    6000
uggagaugag uacauguaug gagguggugu gcagagacu gaugaaggcc augcacacug      6060
gcuugaagca agaaugcuuc uugcaacau cuaccuccag gauggccuca uagcccucgcu    6120
cuaucggccu gaggccgaua agguagccgc cauugaggga gaguuuaagc ugaggacaga    6180
gcaaaggaag accuucgugg aaacucaugaa gagaggagac cuucccgucu ggcuagccua    6240
ucagguugca ucugccggaa uaacuuacac agacagaaga uggugcuuug auggcacaac    6300
caacaacacc auaauggaag acaguguacc agcagagguu uggacaaagu auggagagaa    6360
gagagugcuc aaaccgagau ggauggaugc uagggucugu ucagaccaug cggcccugaa    6420
gucguucaaa gaauucgccg cuggaaaaag aggagcggcu uugggaguaa uggaggcccu    6480
gggaacacug ccaggacaca ugacagagag guuucaggaa gccauugaca ccucgccgu     6540
gcucaugcga gcagagacug aagcaggcc uuauaaggca gcggcagccc aacugccgga    6600
gacccuagag accauuaugc ucuuagguuu gcugggaaca guuucacugg ggaucuucuu    6660
cgucuugaug cggaauaagg gcaucgggaa gaugggcuuu ggaauggua cccuuggggc     6720
cagugcaugg cucaugugge uuucggaaau ugaaccagcc agaauugcau gugccucau     6780
uguuguguuu uuauuacugg uggugcucau acccgagcca gagaagcaaa gaucucccca    6840
agauaaccag auggcaauua ucaucauggu ggcagugggc cuucuagguu ugauaacugc    6900
aaacgaacuu ggauggcugg aaagaacaaa aaaugacaua gcucaucuaa ugggaaggag    6960
agaagaagga gcaaccaugg gauucucaau ggacauugau cugcggccag ccuccgccug    7020
ggcuaucuau gccgcauuga caacucucau caccccagcu guccaacaug cgguaaccac    7080
uucauacaac aacucacccu uaauggcgau ggccacacaa gcuggagugc guuuggcau     7140
gggcaaaggg augccauuua ugcauggga ccuuggaguc ccgcugcuaa ugaugggguug    7200
cuauucacaa uuaacaccc ugacucugau aguagcuauc auucgcuug ggcgcacua       7260
cauguacuug uccccaggcc uacaagcggc agcagcgcgu gcugcccaga aaggacagc     7320
agcuggcauc augaagaauc ccguguggga uggaauagug guaacugaca uugacacaau    7380
gacaauagac cccaggugg agaagaagau gggacaagug uuacucauag caguagccau    7440
cuccagugcu gugcugcugc ggaccgcccug ggaugggg gaggcuggag cucugaucac     7500
agcagcgacc uccaccuugu ggaaggcuc uccaaacaaa uacuggaacu ccucuacagc    7560
caccucacug ugcaacaucu ucagaggaag cuaucggca ggagcuucc uuaucuauac     7620
agugacgaga aacgcuggcc ugguuaagag acguggaggu gggacgggag agacucuggg    7680
agagaagugg aaagcucguc ugaaucgau gucggcccug gaguucuacu cuuauaaaaa    7740
gucagguauc acugaagugu guagagagga ggcucgccgu gcccucaagg auggaguggc    7800
```

-continued

| | |
|---|---|
| cacaggagga caugccguau cccggggaag ugcaaagauc agauggunugg aggagagagg | 7860 |
| auaucugcag cccuauggga agguuguuga ccucggaugu ggcagagggg gcuggagcua | 7920 |
| uuaugccgcc accauccgca aagugcagga ggugagagga uacacaaagg gagguccegg | 7980 |
| ucaugaagaa cccaugcugg ugcaaagcua ugggguggaac auaguucguc ucaagagugg | 8040 |
| aguggacguc uuccacaugg cggcugagcc gugugacacu cugcugugug acauagguga | 8100 |
| gucaucaucu aguccugaag uggaagagac acgaacacuc agagugcucu cuauggugg | 8160 |
| ggacuggcuu gaaaaaagac caggggccuu cuguauaaag gugcugugcc cauacaccag | 8220 |
| cacuaugaug gaaccaugg agcgacugca acguaggcau gggggaggau uagucagagu | 8280 |
| gccauugugu cgcaacucca cacaugagau guacuggguc ucuggggcaa agagcaacau | 8340 |
| cauaaaaagu guguccacca caagucagcu ccuccuggga cgcauggaug gccccaggag | 8400 |
| gccagugaaa uaugaggagg augugaaccu cggcucgggu acacgagcug uggcaagcug | 8460 |
| ugcugaggcu ccuaacauga aaaucaucgg caggcgcauu gagagaaucc gcaaugaaca | 8520 |
| ugcagaaaca ugguuucuug augaaaacca cccauacagg acaugggccu accaugggag | 8580 |
| cuacgaagcc cccacgcaag gaucagcguc uucccucgug aacggggunug unuagacuccu | 8640 |
| gucaaagccu ugggacgugg ugacuggagu uacaggaaua gccaugacug acaccacacc | 8700 |
| auacggccaa caaagagucu ucaaagaaaa aguggcacc agggugccag auccccaaga | 8760 |
| aggcacucgc caggunauga acauagucuc uuccuggcug uggaaggagc uggggaaacg | 8820 |
| caagcggcca cgcgucugca ccaaagaaga guuuaucaac aaggugcgca gcaaugcagc | 8880 |
| acugggagca auauuugaag aggaaaaaga auggaagacg gcugunggaag cugugaauga | 8940 |
| uccaaggunu uggggcccuag uggauaggga gagagaacac caccgagag gagaguguca | 9000 |
| cagcugugug uacaacauga uggggaaaaag agaaaagaag caaggagagu ucgggaaagc | 9060 |
| aaaagguagc cgcgccaucu gguacagugug guugggagcc agauucuugg aguuugaagc | 9120 |
| ccuuggauuc uugaacgagg accauuggau gggaagagaa aacucaggag guggagucga | 9180 |
| agggunuagga uugcaaagac uuggauacau ucuagaagaa augaaucggg caccaggagg | 9240 |
| aaagauguac gcagaugaca cugcuggcug ggacacccgc auuaguaagu uugaucggga | 9300 |
| gaaugaagcu cugauuacca accaaauggga ggaagggcac agaacucugg cguuggccgu | 9360 |
| gauuaaauac acauaccaaa acaaagguggu gaagguucuc agaccagcug aaggaggaaa | 9420 |
| aacaguuaug gacaucauuu caagacaaga ccagagaggg aguggacaag uugucacuua | 9480 |
| ugcucucaac acauucacca acuuggggu gcagcuuauc cggaacaugg aagcugagga | 9540 |
| aguguuagag augcaagacu uaugguugu gaggaagcca gagaaaguga ccagaugguu | 9600 |
| gcagagcaau ggaugggaua gacucaaacg aauggcgguc agugagaug acugcguugu | 9660 |
| gaagccaauc gaugauaggu uugcacaugc ccucagguuc uugaaugaca ugggaaaagu | 9720 |
| uaggaaagac acacaggagu ggaaacccuc gacuggaugg agcaauuggg aagaaguccc | 9780 |
| guucugcucc caccacuuca caaagcugua ccucaaggau gggagaucca uuguggucec | 9840 |
| uugccgccac caagaugaac ugauuggccg agcucgcguc ucaccagggg caggauggag | 9900 |
| cauccgggag acugccuguc uugcaaauc auaugcgcag auggcagc ccuuuauuu | 9960 |
| ccacagaaga gaccuucgac ugauggcuaa ugccauuugc ucggcugugc caguugacug | 10020 |
| gguaccaacu gggagaacca ccugucaau ccauggaaag ggagaaugga ugaccacuga | 10080 |
| ggacaugcuc auggugugga auagagugug gauugaggag aacgaccaua uggaggacaa | 10140 |

```
gacuccugua caaaaaugga cagacauucc cuaucuagga aaaagggagg acuuaugguu    10200
uggaucccuu auagggcaca gaccccgcac cacuugggcu gaaaacauca aagacacagu    10260
caacauggug cgcaggauca uaggugauga agaaaaguac auggacuauc uauccaccca    10320
aguccgcuac uugggugagg aagggucccac acccggagug uuguaagcac caauuuuagu    10380
guugucaggc cugcuaguca gccacaguuu ggggaaagcu gugcagccug uaaccccccc    10440
aggagaagcu gggaaaccaa gcucauaguc aggccgagaa cgccauggca cggaagaagc    10500
caugcugccu gugagccccu cagaggacac ugagucaaaa aaccccacgc gcuuggaagc    10560
gcaggauggg aaaagaaggu ggcgaccuuc cccacccuuc aaucuggggc cugaacugga    10620
gacuagcugu gaaucuccag cagagggacu aguguagga ggagacccc cggaaaacgc    10680 aaaacagcau auugacgugg gaaagaccag agacuccaug aguuuccacc acgcuggccg    10740
ccaggcacag aucgccgaac uucggcggcc gguguggga aauccaugu uucu          10794
```

<210> SEQ ID NO 748
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 748

```
ggguuucgcu cuauucucau caguuucaug uccugugucg gacuuuagaa cagaggagau    60
aaagauggac acaggacaca accuggcggc agcgcaaaag                         100
```

<210> SEQ ID NO 749
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 749

```
gggcucaacu uucgcucuau ucucaucagu uucauguccg gacuuuagaa cagaggagau    60
aaagauggga caugaaacaa ccuggcggca gcgcaagaag                         100
```

<210> SEQ ID NO 750
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 750

```
ggguuaucuc aacuuucgcu cuauucucau caguuucaug gacuuuagaa cagaggagau    60
aaagaugaug aaacugauaa ccuggcggca gcgcaagaag                         100
```

<210> SEQ ID NO 751
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 751

```
gggucgcucu auucucauca guuucauguc cugugucaug gacuuuagaa cagaggagau    60
```
aaagaugaug acacaggaaa ccuggcggca gcgcaagaag                                  100

<210> SEQ ID NO 752
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
ggguggcuuc ggcucuuggu gaauugggcg uuaucucgga cuuuagaaca gaggagauaa           60
agauggagau aacgccaacc uggcggcagc gcaagaag                                   98

<210> SEQ ID NO 753
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 753
gggcugggau caaguacaug uagugcgcca cgagcaaaag gacuuuagaa cagaggagau           60
aaagauguuu ugcucgugua accggcggc agcgcaaaag                                 100

<210> SEQ ID NO 754
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
gggccugcag cccugggauc aaguacaugu agugcgccgg acuuuagaac agaggagaua           60
aagaugggcg cacuacaaac cuggcggcag cgcaagaag                                  99

<210> SEQ ID NO 755
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 755
gggcugccgu ucucuucugg gcagcacgcg cagcugcugg gacuuuagaa cagaggagau           60
aaagaugcag cagcugcgaa ccuggcggca gcgcaagaag                                100

<210> SEQ ID NO 756
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 756
gggcagcccu gggaucaagu acauguagug cgccacgagg gacuuuagaa cagaggagau           60
aaagaugcuc guggcgcaaa ccuggcggca gcgcaagaag                                100

-continued

```
<210> SEQ ID NO 757
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 757
gggaugccag cugccguucu cuucugggca gcacgcgcgg acuuuagaac agaggagaua     60
aagauggcgc gugcugcaac cuggcggcag cgcaagaag                            99

<210> SEQ ID NO 758
<211> LENGTH: 36
<212> TYPE: RNA
<213> ORGANISM: Zika virus

<400> SEQUENCE: 758
gacacaggac augaaacuga ugagaauaga gcgaaa                               36

<210> SEQ ID NO 759
<211> LENGTH: 36
<212> TYPE: RNA
<213> ORGANISM: Zika virus

<400> SEQUENCE: 759
ggacaugaaa cugaugagaa uagagcgaaa guugag                               36

<210> SEQ ID NO 760
<211> LENGTH: 36
<212> TYPE: RNA
<213> ORGANISM: Zika virus

<400> SEQUENCE: 760
augaaacuga ugagaauaga gcgaaaguug agauaa                               36

<210> SEQ ID NO 761
<211> LENGTH: 36
<212> TYPE: RNA
<213> ORGANISM: Zika virus

<400> SEQUENCE: 761
augacacagg acaugaaacu gaugagaaua gagcga                               36

<210> SEQ ID NO 762
<211> LENGTH: 36
<212> TYPE: RNA
<213> ORGANISM: Zika virus

<400> SEQUENCE: 762
gagauaacgc ccaauucacc aagagccgaa gccacc                               36

<210> SEQ ID NO 763
<211> LENGTH: 36
<212> TYPE: RNA
<213> ORGANISM: Zika virus

<400> SEQUENCE: 763
uuuugcucgu ggcgcacuac auguacuuga ucccag                               36

<210> SEQ ID NO 764
<211> LENGTH: 36
<212> TYPE: RNA
<213> ORGANISM: Zika virus
```

```
<400> SEQUENCE: 764
ggcgcacuac auguacuuga ucccagggcu gcaggc                                36

<210> SEQ ID NO 765
<211> LENGTH: 36
<212> TYPE: RNA
<213> ORGANISM: Zika virus

<400> SEQUENCE: 765
cagcagcugc gcgugcugcc cagaagagaa cggcag                                36

<210> SEQ ID NO 766
<211> LENGTH: 36
<212> TYPE: RNA
<213> ORGANISM: Zika virus

<400> SEQUENCE: 766
cucguggcgc acuacaugua cuugauccca gggcug                                36

<210> SEQ ID NO 767
<211> LENGTH: 36
<212> TYPE: RNA
<213> ORGANISM: Zika virus

<400> SEQUENCE: 767
gcgcgugcug cccagaagag aacggcagcu ggcauc                                36

<210> SEQ ID NO 768
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
taatacgact cactataggg                                                  20

<210> SEQ ID NO 769
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
cttcagcctc cagtacagcg                                                  20

<210> SEQ ID NO 770
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
gttcccacgg agaatccgac                                                  20

<210> SEQ ID NO 771
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 771
tttcaagaat ggaaaacatc                                                     20

<210> SEQ ID NO 772
<211> LENGTH: 53
<212> TYPE: DNA
<213> ORGANISM: Zika virus

<400> SEQUENCE: 772
gcgggatctc ctctgtttca agaatggaaa acatcatgtg gagatcagta gaa               53

<210> SEQ ID NO 773
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
gatctcctct gtttcaagaa                                                     20

<210> SEQ ID NO 774
<211> LENGTH: 53
<212> TYPE: DNA
<213> ORGANISM: Zika virus

<400> SEQUENCE: 774
agatggtatc tgcgggatct cctctgtttc aagaatggaa acatcatgt gga                53

<210> SEQ ID NO 775
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
tggagtcccg ctgctaatga                                                     20

<210> SEQ ID NO 776
<211> LENGTH: 53
<212> TYPE: DNA
<213> ORGANISM: Zika virus

<400> SEQUENCE: 776
ttatgcatgg gactttggag tcccgctgct aatgatgggt tgctactcac aat               53

<210> SEQ ID NO 777
<211> LENGTH: 347
<212> TYPE: DNA
<213> ORGANISM: Zika virus

<400> SEQUENCE: 777
tggtgacatg cgctaagttt gcatgctcca agaaaatgac cgggaagagc atccagccag        60
agaatctgga gtaccggata atgctgtcag ttcatggctc ccagcacagt gggatgatcg       120
ttaatgacac aggacatgaa actgatgaga atagagcgaa agttgagata cgcccaatt        180 caccaagagc cgaagccacc ctgggggggt tggaagcct aggacttgat tgtgaaccga       240
```

```
ggacaggcct tgactttcca gatttgtatt acttgactat gaataacaag cactggctgg    300
ttcacaagga gtggttccac gacattccat taccttggca cgctggg                  347
```

<210> SEQ ID NO 778
<211> LENGTH: 232
<212> TYPE: DNA
<213> ORGANISM: Dengue virus

<400> SEQUENCE: 778

```
tattgacgtg tgccaagttc aagtgtgtga caaaactaga aggaaagata gttcaatatg    60
aaaacctaaa atattcagtg atagtcactg tccacactgg ggaccagcac caggtgggaa   120
acgagactac agaacatgga acaattgcga ccataacacc tcaagctccc acgtcggaaa   180
tacagctgac cgactacgga gccctcacat tggactgctc acctagaaca gg           232
```

<210> SEQ ID NO 779
<211> LENGTH: 334
<212> TYPE: DNA
<213> ORGANISM: Zika virus

<400> SEQUENCE: 779

```
agctggagtg ttgtttggta tgggcaaagg gatgccattc tacgcatggg actttggagt    60
cccgctgcta atgataggtt gctactcaca attaacaccc ctgacccctaa tagtggccat  120 cattttgctc gtggcgcact acatgtactt gatcccaggg ctgcaggcag cagctgcgcg   180
tgctgcccag aagagaacgg cagctggcat catgaagaac cctgttgtgg atggaatagt   240
ggtgactgac attgacacaa tgacaattga cccccaagtg gagaaaaaga tgggacaggt   300
gctactcata gcagtagccg tctccagcgc cata                                334
```

<210> SEQ ID NO 780
<211> LENGTH: 334
<212> TYPE: DNA
<213> ORGANISM: Dengue virus

<400> SEQUENCE: 780

```
ggcagctata ttgatgggac ttgacaaggg atggccaata tcgaagatgg acataggagt    60
tccacttctc gccttagggt gctattccca ggtgaaccca ttgacactga cagcggcggt   120
gttgatgtta gtggctcatt atgccataat tggaccagga ctgcaagcaa aggccactag   180
agaagctcaa aaaaggacag cggccggaat aatgaaaaat ccaaccgtag acgggattgt   240
tgcaatagac ttggatcctg tggtttatga tacaaaattt gaaaaacagc taggccaaat   300
aatgttactg atactttgta catcacagat cctc                                334
```

<210> SEQ ID NO 781
<211> LENGTH: 32
<212> TYPE: DNA
<213> ORGANISM: Zika virus

<400> SEQUENCE: 781

```
ctgcgcgtgc tgcccagaag agaacggcag ct                                   32
```

<210> SEQ ID NO 782
<211> LENGTH: 32
<212> TYPE: DNA
<213> ORGANISM: Zika virus

<400> SEQUENCE: 782

```
cagcgcgtgc tgcccagaag agaacagcag ct                                     32

<210> SEQ ID NO 783
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
cttcagcctc cagtacagcg cgg                                               23

<210> SEQ ID NO 784
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
gttcccacgg agaatccgac ggg                                               23

<210> SEQ ID NO 785
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
ctgcgatgtc ggtttccgcg agg                                               23

<210> SEQ ID NO 786
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
tggaagatca ggatatgtgg cgg                                               23

<210> SEQ ID NO 787
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
ttaacgcctc gaatcagcaa cgg                                               23

<210> SEQ ID NO 788
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
gcgcgtcgtg attagcgccg tgg                                               23
```

```
<210> SEQ ID NO 789
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
gttttagagc tagaaatagc aagttaaaat aaggctagtc cgttatcaac ttgaaaaagt        60
ggcaccgagt cggtgctttt                                                   80
```